US011980606B2

(12) United States Patent
Trikha et al.

(10) Patent No.: US 11,980,606 B2
(45) Date of Patent: May 14, 2024

(54) USE OF MARIZOMIB FOR THE TREATMENT OF CENTRAL NERVOUS SYSTEM (CNS) CANCERS

(71) Applicant: Celgene International II Sàrl, Couvet (CH)

(72) Inventors: Mohit Trikha, La Jolla, CA (US); Nancy Levin, La Jolla, CA (US); Ann Maclaren, La Jolla, CA (US)

(73) Assignee: Celgene International II Sàrl, Couvet (CH)

( * ) Notice: Subject to any disclaimer, the term of this patent is extended or adjusted under 35 U.S.C. 154(b) by 362 days.

(21) Appl. No.: 17/094,495

(22) Filed: Nov. 10, 2020

(65) Prior Publication Data

US 2021/0169851 A1 Jun. 10, 2021

Related U.S. Application Data

(62) Division of application No. 15/611,614, filed on Jun. 1, 2017, now abandoned.

(60) Provisional application No. 62/491,943, filed on Apr. 28, 2017, provisional application No. 62/490,528, filed on Apr. 26, 2017, provisional application No. 62/471,321, filed on Mar. 14, 2017, provisional application No. 62/424,178, filed on Nov. 18, 2016, provisional application No. 62/418,466, filed on Nov. 7, 2016, provisional application No. 62/374,136, filed on Aug. 12, 2016, provisional application No. 62/362,845, filed on Jul. 15, 2016, provisional application No. 62/349,491, filed on Jun. 13, 2016, provisional application No. 62/344,194, filed on Jun. 1, 2016.

(51) Int. Cl.
*A61K 39/00* (2006.01)
*A61K 31/407* (2006.01)
*A61K 31/495* (2006.01)
*A61K 39/395* (2006.01)
*A61N 5/10* (2006.01)
*C07K 16/22* (2006.01)
*C07K 16/28* (2006.01)

(52) U.S. Cl.
CPC .......... *A61K 31/407* (2013.01); *A61K 31/495* (2013.01); *A61K 39/3955* (2013.01); *A61K 39/39558* (2013.01); *A61N 5/10* (2013.01); *C07K 16/22* (2013.01); *C07K 16/2896* (2013.01); *A61K 2039/545* (2013.01); *A61N 2005/1098* (2013.01); *C07K 2317/21* (2013.01); *C07K 2317/24* (2013.01); *C07K 2317/73* (2013.01)

(58) Field of Classification Search
CPC .......... A61K 39/3955; A61K 39/39558; A61K 2039/545; A61N 5/10; C07K 16/22; C07K 16/2896
See application file for complete search history.

(56) References Cited

U.S. PATENT DOCUMENTS

| | | | |
|---|---|---|---|
| 7,144,723 B2 | 12/2006 | Fenical et al. |
| 7,179,834 B2 | 2/2007 | Fenical et al. |
| 7,276,530 B2 | 10/2007 | Potts et al. |
| 7,572,606 B1 | 8/2009 | Lam et al. |
| 7,824,698 B2 | 11/2010 | Potts et al. |
| 8,003,802 B2 | 8/2011 | Ling et al. |
| 8,067,616 B2 | 11/2011 | Ling et al. |
| 8,168,803 B2 | 5/2012 | Palladino et al. |
| 8,222,289 B2 | 7/2012 | Fenical et al. |
| 8,394,816 B2 | 3/2013 | Ghobrial et al. |
| 8,772,724 B2 | 5/2014 | Anderson et al. |
| 10,011,814 B2 | 7/2018 | Lam et al. |
| 2002/0128228 A1 | 9/2002 | Hwu |
| 2008/0280968 A1 | 11/2008 | Palladino |
| 2009/0148445 A1 | 6/2009 | Bonavida et al. |
| 2015/0065781 A1 | 3/2015 | Bais et al. |
| 2020/0085789 A1 | 3/2020 | Trikha et al. |
| 2023/0181534 A1 | 6/2023 | Trikha et al. |

FOREIGN PATENT DOCUMENTS

| | | |
|---|---|---|
| WO | 2007120801 A2 | 10/2007 |
| WO | 2007130404 A1 | 11/2007 |
| WO | 2008124699 A1 | 10/2008 |
| WO | 2009140287 A1 | 11/2009 |
| WO | 2017210463 A1 | 12/2017 |
| WO | 2018169740 A1 | 9/2018 |

OTHER PUBLICATIONS

Clinical Trials.Gov NCT02330562, first post Jan. 5, 2015 (Year: 2015).*
Ammirati et al (J Clin Neurosci 21:633-637, Apr. 2014 (Year: 2014).*
Potts et al (Curr Cancer Drug Targets, 2011 (Year: 2011).*
VAL083 clinical trial, start date, Jan. 2017 (Year: 2017).*
Stupp et al, New England J Med 352:987-996, 2005 (Year: 2005).*
Hatanpaa et al, Neoplasia, 12: 675-684, 2010 (Year: 2010).*
International Search Report and Written Opinion received for PCT Application No. PCT/US2017/035504, dated Oct. 20, 2017, 15 Pages.
Anonymous (Oct. 11, 2016) "Study of Marizomib With Temozolomide and Radiotherapy in Patients with Newly Diagnosed Brain Cancer", Retrieved from: https://clinicaltrials.gov/ct2/history/NCT02903069?V View#StudyPage Top, 7 Pages.
Bota et al. (2016) "Investigation of Pharmacodynamic and Predictive Biomarkers to Define Response to Proteasome Inhibitor Marizomib in Glioma", Cancer Research, 76(Suppl. 14):3069.

(Continued)

*Primary Examiner* — Lei Yao
(74) *Attorney, Agent, or Firm* — Mintz Levin Cohn Ferris Glovsky and Popeo, P.C.

(57) ABSTRACT

The present disclosure relates to treatment of central nervous system (CNS) cancers (e.g., malignant glioma, glioblastoma, or CNS-multiple myeloma) using marizomib. The disclosure further relates to uses of synergistic combinations of marizomib with additional therapeutic agents such as bevacizumab, daratumumab, temozolomide, pomalidomide, and radiotherapy.

8 Claims, 96 Drawing Sheets

(56) References Cited

OTHER PUBLICATIONS

Clinical Leader (Nov. 18, 2016) "Triphase Accelerator Corporation Announces Full Enrollment Results Of Its Phase 1 Trial Of Marizomib And Bevacizumab In Malignant Glioma", retrieved from: https://www.clinicalleader.com/doc/triphase-accelerator-corporation-its-phase-marizomib-in-malignant-glioma-0001, 2 Pages.

Desisto et al. (Nov. 2017) "Abstracts from the 22nd Annual Scientific Meeting and Education Day of the Society for Neuro-Oncology, Nov. 16-19, 2017", Neuro-Oncology, 324 Pages.

Di et al. (Dec. 17, 2015) "Marizomib Activity as a Single Agent in Malignant Gliomas: Ability to Cross the Blood-brain Barrier", Neuro Oncology, 18(6):840-848.

Harrison et al. (Sep. 15, 2016) "Phase I Clinical Trial of Marizomib (NPI-0052) in Patients with Advanced Malignancies Including Multiple Myeloma", Clinical Cancer Research, 22(18):4559-4566.

Inman et al. (Jul. 13, 2016) "Improved Optune System Approved for Glioblastoma Multiforme", retrieved from: https://www.curetoday.com/articles/improved-optune-system-approved-for-glioblastoma-multiforme, 2 Pages.

Kubicek et al. (2009) "Phase I Trial Using Proteasome Inhibitor Bortezomib and Concurrent Temozolomide and Radiotherapy for Central Nervous System Malignancies", International Journal of Radiation Oncology, Biology, Physics, 74(2):433-439.

Lin et al. (Dec. 9, 2016) "Bevacizumab in High-grade Glioma Patients Following Intraparenchymal Hemorrhage", Neuro Oncology, 4(1):24-28.

Manton et al. (Jan. 25, 2016) "Induction of Cell Death by the Novel Proteasome Inhibitor Marizomib in Glioblastoma In Vitro and In Vivo", Scientific Reports, 6:18953 (13 Pages).

Mattes et al. (Jan. 2009) "The Proteasome Inhibitor NPI-0052 Targets Glioma Stem Cells And Radiosensitizes Glioblastomas In-vitro and In-vivo", Journal of Investigative Medicine, 57(1):120.

Vlashi et al. (Feb. 2010) "Differential Effects of the Proteasome Inhibitor NPI-0052 against Glioma Cells", Translational Oncology, 3(1):50-55.

Yu et al. (Feb. 2016) "Efficacy and Safety of Bevacizumab for the Treatment of Glioblastoma", Experimental and Therapeutic Medicine, 11(2):371-380.

\* cited by examiner

FIG. 40

| Best Response | # Responses | Efficacy Evaluable (N=33) | ITT (N=36) |
|---|---|---|---|
| CR (1) + PR$_{CR}$* (4) + PR (11) | 16 | 48% | 44% |
| SD (including 2 unconfirmed PR) | 11 | 33% | 31% |
| PD | 6 | 18% | 17% |
| NE | 3 | NA | 8% |

FIG. 41

| Study | Treatment | 6 mo PFS | | | 9 mo PFS | | | 12 mo PFS | | |
|---|---|---|---|---|---|---|---|---|---|---|
| | | All Pts | Unmethylated | Methylated | All Pts | Unmethylated | Methylated | All Pts | Unmethylated | Methylated |
| MRZ+BEV-108 (n=36) | MRZ+BEV | 34% | 36% | 29% | 24% | 26% | 15% | 10% | 10% | 0% |
| Taal (BELOB, n=50) | BEV Monotherapy | 16% | 8% | 33% | 8% | 0% | 22% | 2% | 0% | 4% |
| Field (CABARET, n=62) | | 18% | NR | NR | 6% | NR | NR | 2% | NR | NR |
| Heiland (Freiburg, Germany, n=18) | | 12% | 10% | 38% | 0% | 0% | 22% | 0% | 0% | 10% |
| Wick (EORTC 26101 P2, n=274) | | 14% | 10% | 25% | 9% | 10% | 9% | 8% | 10% | 9% |

| Study | Treatment | 6 mo OS | | | 9 mo OS | | | 12 mo OS | | |
|---|---|---|---|---|---|---|---|---|---|---|
| | | All Pts | Unmethylated | Methylated | All Pts | Unmethylated | Methylated | All Pts | Unmethylated | Methylated |
| MRZ+BEV-108 | MRZ+BEV | 75% | 55% | 78% | 60% | 45% | 78% | 39% | 15% | 67% |
| Taal (BELOB) | BEV Monotherapy | 62% | 50% | 83% | 45% | 12% | 67% | 26% | 8% | 56% |
| Field (CABARET) | | 61% | NR | NR | 39% | NR | NR | 24% | NR | NR |
| Heiland (Freiburg, Germany) | | 18% | 25% | 58% | 30% | 12% | 40% | 10% | 12% | 24% |

FIG. 42
| Treatment | | |
|---|---|---|
| DISEASE HISTORY | Surgical Resection | 16 May 2015 |
| | TMZ+RT | 23 Jun – 04 Aug 2015 |
| | TMZ (5 day 150 mg/m²) | 09 Sept 2015 – 22 Mar 2016 |
| | Surgeries | 30 Mar & 13 Apr 2016 |
| | TMZ (5 day 150 mg/m²) | 16 May – 09 Aug 2016 |
| | Baseline MRI | 703 mm² |
| | DEX at baseline | 3 mg QD |
| | C1D1 Date | 18 Aug 2016 |
| ON STUDY | C2D15 MRI | 328 mm² |
| | DEX at assessment | 2 mg QD |
| | MRI Date | 12 Oct 2016 |
| | C4D15 MRI | 285 mm² |
| | DEX at assessment | 4 mg QD |
| | MRI Date | 6 Dec 2016 |
| | C6D15 MRI | 255 mm² |
| | DEX at assessment | 4 mg QD |
| | MRI Date | 28 Jan 2017 |
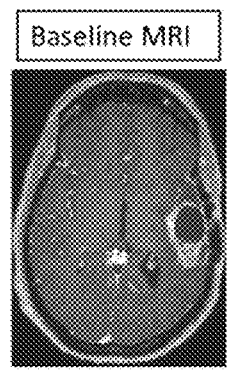 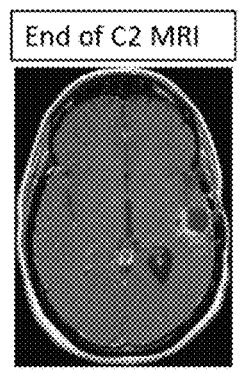
Baseline MRI | End of C2 MRI

FIG. 43

| | Treatment | Date |
|---|---|---|
| DISEASE HISTORY | Surgical Resection | 21 Dec 2015 |
| | TMZ+RT | 27 Jan – 10 Mar 2016 |
| | TMZ (5 day) | 14 Apr – 18 Apr 2016 |
| | Surgical Resection | 23 May 2016 |
| ON STUDY | Baseline MRI | 506 mm$^2$ |
| | DEX at baseline | 2 mg |
| | C1D1 Date | 24 Jun 2016 |
| | C2D15 MRI | 800 mm$^2$ |
| | DEX at assessment | 0 mg |
| | C2D15 Date | 15 Aug 2016 |
| | Surgery | 6 Sept 2016 |

FIG. 44

| Treatment | Date |
|---|---|
| Surgical Resection | 05 Dec 2015 |
| TMZ+RT | 11 Jan – 22 Feb 2016 |
| TMZ (5 day 150 mg/m$^2$) | 09 Mar – 13 Mar 2016 |
| TMZ (5 day 200 mg/m$^2$) | 07 Apr – 02 Aug 2016 |
| MRI | 24 Jun 2016 (1147 mm$^2$) |
| MRI | 26 Jul 2016 (1862 mm$^2$) |
| Novo TTF + TMZ | 18 Jun – 23 Aug 2016 |
| Baseline MRI | 2184 mm$^2$ |
| DEX at baseline | 2 mg |
| C1D1 Date | 26 Aug 2016 |
| Unscheduled MRI | 2849 mm$^2$ |
| DEX at assessment | 0 mg |
| Unscheduled MRI Date | 21 Sep 2016 |
| Surgery | 04 Oct 2016 |

(Rows 1–10: DISEASE HISTORY / ON STUDY; rows 11–14: ON STUDY)

USE OF MARIZOMIB FOR THE TREATMENT OF CENTRAL NERVOUS SYSTEM (CNS) CANCERS

CROSS REFERENCE TO RELATED APPLICATIONS

This application is a divisional application of U.S. application Ser. No. 15/611,614, filed on Jun. 1, 2017, which claims priority to and the benefit of U.S. Provisional Patent Application No. 62/344,194, filed Jun. 1, 2016; U.S. Provisional Patent Application No. 62/349,491, filed Jun. 13, 2016; U.S. Provisional Patent Application No. 62/362,845, filed Jul. 15, 2016; U.S. Provisional Patent Application No. 62/374,136, filed Aug. 12, 2016; U.S. Provisional Patent Application No. 62/418,466, filed Nov. 7, 2016; U.S. Provisional Patent Application No. 62/424,178, filed Nov. 18, 2016; U.S. Provisional Patent Application No. 62/471,321, filed Mar. 14, 2017; U.S. Provisional Patent Application No. 62/490,528, filed Apr. 26, 2017; and U.S. Provisional Patent Application No. 62/491,943, filed Apr. 28, 2017, the contents of each of which are hereby incorporated by reference in their entirety.

FIELD OF THE INVENTION

The present invention relates to treatment of central nervous system (CNS) cancers (e.g., malignant glioma, glioblastoma, primary CNS lymphoma, or CNS-multiple myeloma) using marizomib alone or in combination with additional therapeutic agents.

BACKGROUND OF THE INVENTION

Marizomib is an irreversible proteasome inhibitor.

Gliomas account for about 80% of primary malignant tumors in the central nervous system (CNS), with WHO Grade IV malignant glioma (G4 MG; including glioblastoma and gliosarcoma) constituting the majority of gliomas, and are essentially incurable. Currently only surgical resection and radiotherapy (RT) with concomitant and adjuvant temozolomide (TMZ) are standard-of-care treatment strategies for newly diagnosed G4 MG. However, resistance to chemotherapy and radiotherapy results in a high recurrence rate, with median survival of ~15-16 months. Since no survival advantage has been demonstrated for the addition of bevacizumab (BEV) to temozolomide and radiotherapy in newly diagnosed G4 MG, alternative promising investigational agents need to be tested.

Targeting the proteasome has been used for the treatment of multiple myeloma (MM), and preclinical evidence suggests that targeting the proteasome in glioma cells shows significant anti-tumor activity. Importantly, preclinical evidence demonstrates that proteasome inhibition sensitizes GBM cell lines to irradiation and to temozolomide. Further, the combination of bortezomib (BTZ, one of three proteasome inhibitors [PI] currently approved for the treatment of MM) with temozolomide resulted in synergistic glioblastoma cell death in vitro, and bortezomib reduces glioma cell survival in vitro in cell lines sensitive and resistant to temozolomide. Despite the activity against GBM cells in vitro, bortezomib does not cross the blood brain barrier, and thus has proven ineffective in treatment of GBM in animal models and in the clinic.

Central nervous system-multiple myeloma (CNS-MM) is a rare manifestation of extra-medullary disease with few therapeutic options. Its prevalence is increasing as anti-myeloma therapies become more effective at treating systemic disease, highlighting the urgent unmet clinical need in this patient population.

Accordingly, there is an unmet need for proteasome inhibitors capable of crossing the blood-brain barrier for the treatment of brain cancers (e.g., malignant glioma, glioblastoma, or CNS-multiple myeloma).

SUMMARY OF THE INVENTION

The present disclosure teaches marizomib, alone or in combination with additional therapeutic agents for the treatment of CNS cancers. As set forth herein, marizomib is capable of inhibiting all three domains of the proteasome (i.e., the chymotrypsin-like (CT-L); trypsin-like (T-L); and caspase-like (C-L) domains). Without wishing to be bound by theory, the present disclosure teaches that repeated dosage with marizomib can also overcome compensatory hyperactivation of the C-L and T-L domains of the proteasome.

In one aspect, the present disclosure provides a method of treating a CNS-cancer comprising administering to a subject in need thereof an effective amount of marizomib and bevacizumab.

In some embodiments, the CNS-cancer is a glioma. In some embodiments, the glioma is grade IV malignant glioma. In some embodiments, the glioma is glioblastoma. In some embodiments, the glioma is newly diagnosed. In some embodiments, the glioma is relapsed or refractory. In some embodiments, the promoter of the subject's gene encoding $O^6$-methylguanine-DNA methyltransferase is unmethylated. In some embodiments, the promoter of the subject's gene encoding $O^6$-methylguanine-DNA methyltransferase is less than 8% methylated. In some embodiments, subject's EGFR is normal. In some embodiments, the subject's EGFR is altered. In some embodiments, the subject's EGFR alteration is amplified EGFR, mutated EGFR, EGFRVII positive, or a combination thereof.

In another aspect, the present disclosure provides a method of treating a CNS-cancer comprising administering to a subject in need thereof an effective amount of marizomib and temozolomide.

In some embodiments, the CNS-cancer is a glioma. In some embodiments, the glioma is grade IV malignant glioma. In some embodiments, the glioma is glioblastoma. In some embodiments, the glioma is newly diagnosed. In some embodiments, the glioma is relapsed or refractory. In some embodiments, the method further comprises administering to the subject radiotherapy. In some embodiments, the combination of marizomib and temozolomide is synergistic.

In another aspect, the present disclosure provides a method of treating a CNS-cancer comprising administering to a subject in need thereof an effective amount of marizomib, temozolomide and radiotherapy.

In another aspect, the present disclosure provides a method of treating a central nervous system hematological cancer in a subject in need thereof, comprising administering to the subject an effective amount of marizomib.

In some embodiments, the central nervous system cancer is newly diagnosed. In some embodiments, the central nervous system hematologic cancer is central nervous system multiple myeloma, central nervous system leukemia, central nervous system myelodysplastic syndrome or central nervous system lymphoma. In some embodiments, the central nervous system-hematologic cancer originates from the central nervous system. In some embodiments, the central nervous system-hematologic cancer originates in the blood and metastasizes to the central nervous system. In some embodiments, the subject suffers from relapsed or refractory central nervous system-hematologic cancer. In some embodiments, the central nervous system-hematologic cancer affects the meninges. In some embodiments, the method further comprises administering to the subject an additional therapeutic agent. In some embodiments, the additional therapeutic agent can cross the blood-brain barrier. In some embodiments, the additional therapeutic agent is an anti-CD38 antibody, pomalidomide, or any combination thereof. In some embodiments, the anti-CD38 antibody is daratumumab. In some embodiments, the combination therapy with the additional therapeutic agent is synergistic.

In another aspect, the present disclosure provides a method of treating central nervous system multiple myeloma comprising administering to a subject in need thereof an effective amount of marizomib.

In another aspect, the present disclosure provides a method of treating a central nervous system multiple myeloma comprising administering to a subject in need thereof an effective amount of marizomib and daratumumab.

In another aspect, the present disclosure provides a method of treating a central nervous system multiple myeloma comprising administering to a subject in need thereof an effective amount of marizomib and pomalidomide.

In one aspect, the present disclosure teaches a method of treating a central nervous system cancer in a subject in need thereof, comprising administering to the subject an effective amount of marizomib.

In one aspect, the present disclosure teaches a method of treating a central nervous system hematological cancer in a subject in need thereof, comprising administering to the subject an effective amount of marizomib.

In one aspect, the present disclosure teaches a method of treating a glioma in a subject in need thereof, comprising administering to the subject an effective amount of marizomib.

In one aspect, the present disclosure teaches a method of treating glioma comprising administering to a subject in need thereof an effective amount of marizomib, temozolomide, and radiotherapy.

In one aspect, the present disclosure teaches a method of treating glioma comprising administering to a subject in need thereof an effective amount of marizomib and radiotherapy.

In one aspect, the present disclosure teaches a method of treating glioma comprising administering to a subject in need thereof an effective amount of marizomib and bevacizumab.

In one aspect, the present disclosure teaches a method of treating central nervous system multiple myeloma comprising administering to a subject in need thereof an effective amount of marizomib and an anti-CD38 antibody.

In one aspect, the present disclosure teaches a method of treating central nervous system multiple myeloma comprising administering to a subject in need thereof an effective amount of marizomib and daratumumab.

In one aspect, the present disclosure teaches a method of treating central nervous system multiple myeloma comprising administering to a subject in need thereof an effective amount of marizomib and pomalidomide.

In one aspect, the present disclosure teaches a pharmaceutical composition comprising marizomib for the treatment of central nervous system cancer.

In one aspect, the present disclosure teaches the use of marizomib in the manufacture of a medicament for the treatment of central nervous system cancer.

In one aspect, the present disclosure teaches the use of marizomib for the treatment of central nervous system cancer.

In one aspect, the present disclosure teaches a method of treating a central nervous system-hematologic cancer in a subject in need thereof, comprising administering to the subject an effective amount of daratumumab.

In one aspect, the present disclosure teaches a method of treating central nervous system multiple myeloma in a subject in need thereof, comprising administering to the subject an effective amount of daratumumab.

In another aspect, the present disclosure provides a pharmaceutical composition comprising marizomib for the treatment of central nervous system cancer. Another aspect of the disclosure is directed to pharmaceutical compositions comprising marizomib, a further therapeutic agent and a pharmaceutically acceptable carrier. The pharmaceutical acceptable carrier may further include an excipient, diluent, or surfactant. The additional therapeutic agent can be an anti-CD38 antibody (e.g., daratumumab), pomalidomide, bevacizumab, temozolomide, or any combination thereof.

Another aspect of the disclosure provides the use of marizomib and an additional therapeutic agent for use in treating a CNS cancer. The additional therapeutic agent can be an anti-CD38 antibody (e.g., daratumumab), pomalidomide, bevacizumab, temozolomide, or any combination thereof.

Another aspect of the disclosure provides the use of marizomib and an additional therapeutic agent in the manufacture of a medicament for use in treating a CNS cancer. The additional therapeutic agent can be an anti-CD38 antibody (e.g., daratumumab), pomalidomide, bevacizumab, temozolomide, or any combination thereof.

BRIEF DESCRIPTION OF THE FIGURES

FIG. 40 shows a chart of the RANO response rate for the combination of MRZ and BEV.

FIG. 41 shows a chart comparing marizomib monotherapy with bevacizumab in recurrent glioblastoma.

FIG. 42 shows a chart depicting the history of MRZ monotherapy for a patient (101-0511).

FIG. 43 shows a chart depicting the history of MRZ monotherapy for a patient (101-0503).

FIG. 44 shows a chart depicting the history of MRZ monotherapy for a patient (101-0513).

DETAILED DESCRIPTION OF THE INVENTION

Figure 1:
FIG. 1 shows an MRI image of the head of the subject in Example 1, Case 1 prior to treatment with marizomib.

The present disclosure teaches the use of marizomib, alone or in combination with additional therapeutic agents, for the treatment of CNS cancers. In some embodiments, marizomib can be used in combination with, for instance, temozolomide and/or radiotherapy and/or bevacizumab for the treatment of glioma (e.g., grade IV malignant glioma). In some embodiments, marizomib can be used in combination with, for instance, an anti-CD38 antibody (e.g., daratumumab) or an additional therapeutic agent such as pomalidomide for the treatment of CNS-hematological cancers such as CNS-multiple myeloma.

In one or more embodiments of any of the above-aspects, the central nervous system cancer is newly diagnosed.

In some embodiments, the central nervous system hematologic cancer is central nervous system multiple myeloma, central nervous system leukemia, central nervous system myelodysplastic syndrome or central nervous system lymphoma. In some embodiments, the central nervous system-hematologic cancer originates from the central nervous system. In some embodiments, the central nervous system-hematologic cancer originates in the blood and metastasizes to the central nervous system. In some embodiments, the subject suffers from relapsed or refractory central nervous system-hematologic cancer. In some embodiments, the central nervous system-hematologic cancer affects the meninges.

In some embodiments, the central nervous system cancer is glioma. In some embodiments, the glioma is grade IV malignant glioma. In some embodiments, the central nervous system cancer is glioblastoma.

In some embodiments of any of the above aspects, the method of treating a central nervous system cancer further comprises administering to the subject an additional therapeutic agent. In some embodiments, the additional therapeutic agent can cross the blood-brain barrier. In some embodiments, the additional therapeutic agent is an anti-CD38 antibody, daratumumab, pomalidomide, bevacizumab, temozolomide, radiotherapy, or any combination thereof. In some embodiments, the treatment comprises an effective amount of a combination of marizomib and temozolomide. In some embodiments, the treatment further comprises administering radiotherapy. In some embodiments, the combination therapy with the additional therapeutic agent is synergistic.

Definitions

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

"Cancer" can be understood as abnormal or unregulated cell growth within a patient.

A hematologic cancer is understood as a cancer of the blood and can include acute and chronic leukemias, lymphomas, multiple myeloma and myelodysplastic syndromes As used herein, "central nervous system" is understood to mean the complex of nerve tissues that controls the activities of the body. The central nervous system is understood to comprise the brain and spinal cord.

As used herein, "marizomib," also abbreviated as "MRZ," is understood as a proteasome inhibitor. Marizomib is an irreversible proteasome inhibitor that has demonstrated promising anti-myeloma activity in highly refractory MM-patients that has the structure:

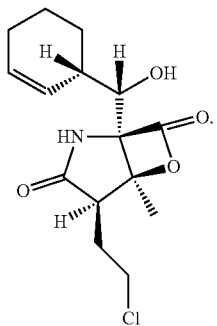

The definition of marizomib is understood to include marizomib as well as pharmaceutically acceptable salts, prodrugs, solvates, hydrates, tautomers, or isomers thereof. In specific embodiments, the term marizomib refers to Compound 1 or a pharmaceutically acceptable salt thereof. Without wishing to be bound by theory, marizomib is a proteasome inhibitor with unique features compared to other proteasome inhibitors. For example, marizomib inhibits all three catalytic activities of the proteasome and is capable of crossing the blood brain barrier (BBB). Without wishing to be bound by theory, several studies have demonstrated that marizomib localizes to the CNS and significantly inhibits proteasome activity in the brain. Radiolabeled marizomib has shown 30% CNS biodistribution compared with blood levels in rats. Marizomib can elicit a significant anti-tumor effect in a rodent model of malignant glioma. Additionally, pharmacological inhibition of proteasome activity using marizomib has been observed in primate brains. Without wishing to be bound by theory, marizomib has also shown promising anti-tumor activity in malignant glioma using weekly dosing and has been well tolerated. Without wishing to be bound by theory, the clinical activity of marizomib in MM as well as its ability to penetrate and be retained in the CNS suggest that it can be used as a potential therapeutic agent for CNS-MM.

As used herein, "daratumumab" is an anti CD38 antibody.
As used herein, "TMZ" means temozolomide.
As used herein, "RT" means radiotherapy.
As used herein, "BEV" means bevacizumab.
As used herein, "RP2D" means recommended phase 2 dose.
As used herein, "primary CNS cancers" refers to CNS cancers that begin in the central nervous system and are substantially confined to the central nervous system.
As used herein, "secondary CNS cancers" refers to CNS cancers (e.g., CNS-MM) that originate outside the central nervous system (e.g., in the blood or bone marrow) and progress (e.g., metastasize) to the central nervous system.

As used herein, "MGMT" is understood as O 6-methyl-guanine-DNA methyltransferase (also known as $O^6$ methyl-guanine-DNA methyltransferase; AGT, and AGAT). In some embodiments, the promoter of the gene encoding MGMT can be methylated. Without wishing to be bound by theory, methylation of the promoter of the gene encoding MGMT is generally a predictor of a better prognosis for patients with malignant glioma (e.g., grade IV malignant glioma).

As used herein, "OS" is understood to mean overall survival. OS is understood as the number of months from the date of first dose of study drug to date of death due to any cause.

As used herein, "PFS" is understood to mean progression free survival. PFS is understood as the number of months between first does of study drug to first evidence of disease progression or death.

As used herein, "CR" is understood to mean complete response.

As used herein, "PR" is understood to mean partial response.

As used herein, "SD" is understood to mean stable disease.

As sued herein, "PD" is understood to mean progressive disease.

As used herein, "EGFR" is understood to mean Epidermal growth factor receptor.

As used herein, "IV" means intravenous.

As used herein, "IMWG-URC" is understood to mean International Myeloma Working Group Uniform response criteria.

In some embodiments, the response definitions are different depending on the type of cancer (e.g., myeloma or glioma). For myeloma, a complete response is understood as no detectable serum or urine M-protein (Myeloma protein); disappearance of any soft tissue plasmacytomas and <5% plasma cells in the bone marrow. A very good partial response (VGPR) is understood as ≥90% reduction of tumor measurement from baseline measurement. A partial response (PR) is understood as ≥50% reduction of tumor measurement from baseline measurement. Stable disease (SD) is understood to apply to patients who do not meet the criteria for CR, VGPR, or PD. Progressive disease (PD) is understood as increase in tumor of ≥25% from lowest response value. For gliomas, complete repose (CR) requires all of the following: complete disappearance of all enhancing measurable and nonmeasurable disease sustained for at least 4 weeks; no new lesions; stable or improved nonenhancing (T2/FLAIR) lesions; patients must be off corticosteroids (or on physiologic replacement doses only); and stable or improved clinically. Partial response (PR) is understood as ≥50% decrease compared with baseline in the sum of products of perpendicular diameters of all measurable enhancing lesions sustained for at least 4 weeks; no progression of nonmeasurable disease; no new lesions; stable or improved nonenhancing (T2/FLAIR) lesions on same or lower dose of corticosteroids compared with baseline scan; the corticosteroid dose at the time of the scan evaluation should be no greater than the dose at time of baseline scan; and stable or improved clinically. Stable disease (SD) requires all of the following: does not qualify for complete response, partial response, or progression; stable nonenhancing (T2/FLAIR) lesions on same or lower dose of corticosteroids compared with baseline scan. Progressive disease (PD) is defined by any of the following: ≥25% increase in sum of the products of perpendicular diameters of enhancing lesions compared with the smallest tumor measurement obtained either at baseline (if no decrease) or best response, on stable or increasing doses of corticosteroids; significant increase in T2/FLAIR nonenhancing lesion on stable or increasing doses of corticosteroids compared with baseline scan or best response after initiation of therapy not caused by comorbid events (e.g., radiation therapy, demyelination, ischemic injury, infection, seizures, postoperative changes, or other treatment effects); any new lesion; clear clinical deterioration not attributable to other causes apart from the tumor (e.g., seizures, medication adverse effects, complications of therapy, cerebrovascular events, infection) or changes in corticosteroid dose; failure to return for evaluation as a result of death or deteriorating condition; or clear progression of nonmeasurable disease.

CNS Cancer Indications

The present disclosure provides for the use of marizomib for the treatment of CNS cancers. In some embodiments, the CNS cancers are CNS hematological cancers. In some embodiments, the CNS cancers are gliomas such as grade IV malignant glioma.

CNS Hematological Cancers

The present disclosure provides the use of marizomib for the treatment of hematological cancer (e.g., MM) with central nervous system involvement (e.g., CNS-MM or primary CNS lymphoma PCNSL). In some embodiments, the present disclosure provides for the treatment of patients with relapsed, refractory CNS-MM and meningeal brain involvement. One of skill in the art will recognize that cancers such as multiple myeloma are considered blood cancers which do not necessarily interact with the central nervous system. However, without wishing to be bound by theory, in some embodiments the central nervous system can serve as a "sanctuary site" for diseased plasma cells (e.g., upon systemic treatment), leading to a CNS-hematological cancer (e.g., CNS-MM). Accordingly, the present disclosure teaches marizomib for the treatment of CNS-hematological cancers. In some embodiments, this is a result of marizomib's ability to cross the blood-brain barrier.

Without wishing to be bound by theory, the outcome of therapy for multiple myeloma (MM) patients has significantly improved with the introduction of immunomodulatory drugs proteasome inhibitors (PIs), and more recently, monoclonal antibodies. However, in some embodiments, extra-medullary relapse including CNS involvement continues to confer poor prognosis.

Without wishing to be bound by theory, recent myeloma therapies can change the biology of myeloma disease progression, and the central nervous system can be a sanctuary site for plasma cells, leading to CNS-hematological cancers. Without wishing to be bound by theory, the outcome of therapy for non-CNS-MM patients has improved. In contrast, CNS involvement still confers a poor prognosis. In some embodiments, CNS-myeloma is terminal in many patients (e.g., with a median survival of about 4 months). In some cases, median survival can be as short as 2 months. Without wishing to be bound by theory, conventional therapies can fail to treat CNS-myeloma because they cannot cross the blood-brain barrier.

Without wishing to be bound by theory, CNS-MM is a rare manifestation (e.g., about 1-3% of MM cases) of extra-medullary disease in MM patients, which is increasing in prevalence as the treatment of systemic disease becomes more effective. It can be characterized by the presence of neoplastic plasma cells in the cerebrospinal fluid (CSF) and lepto-meningeal involvement. Without wishing to be bound by theory, the neurological symptoms usually do not correlate with MIll findings, which can be normal, nor with the extent of plasmacytosis. CNS-MM can be a terminal event in the majority of patients, with a median survival of less than four months (e.g., median survival can be about 2-4 months). Without wishing to be bound by theory, this may be related to a lack of effective intrathecal therapy (IT) and the limited activity of radiotherapy (RT), as well as to the limited availability of systemic therapies, which cross the blood-brain barrier.

In some embodiments, the present disclosure provides for treatment of patients who have suffered CNS relapse of MM after allogenic hematopoietic stem cell transplant. In some embodiments, the relapse can occur after progression on multiple lines of therapy, for example in the setting of extra-medullary disease. In some embodiments, the disease can be substantially confined to the CNS. In other words, the present disclosure can be used to treat both primary and secondary CNS cancers (e.g., CNS-MM).

In some embodiments, the present disclosure provides for treatment of patients with few (e.g., substantially no) remaining therapeutic options. For instance, a patient may have been treated with chemotherapy (e.g., IT chemotherapy), and/or radiation (e.g., cranio-spinal radiation). In some embodiments, prior treatment has resulted in minimal or transient improvement followed by deterioration and/or persistent symptoms.

As set forth in Example 1 below, marizomib was administered to seven patients for the treatment of CNS-MM. Without wishing to be bound by theory, no CNS adverse events were identified in this patient population. Without wishing to be bound by theory, five of seven patients achieved at least a partial response, with two patients achieving a complete response. Without wishing to be bound by theory, four of seven patients achieved survival greater than four months, which exceeds the median survival for CNS-MM. Without wishing to be bound by theory, one patient has been treated for 13 months and has achieved complete resolution of the disease.

As set forth in Example 1 below, treatment of CNS-MM (e.g., refractory CNS-MM) patients with marizomib resulted in clinical improvement, e.g., a reduction in CSF plasmacytosis (Case 1) or eradication of the disease (Case 2). In some embodiments, treatment of CNS-MM patients can result in radiologic improvements in leptomeningeal disease, and/or improvement in quality of life.

Figure 2:
FIG. 2 shows an MM image of the head of the subject in Example 1, Case 1 two months after beginning treatment with Marizomib.
Figure 3:
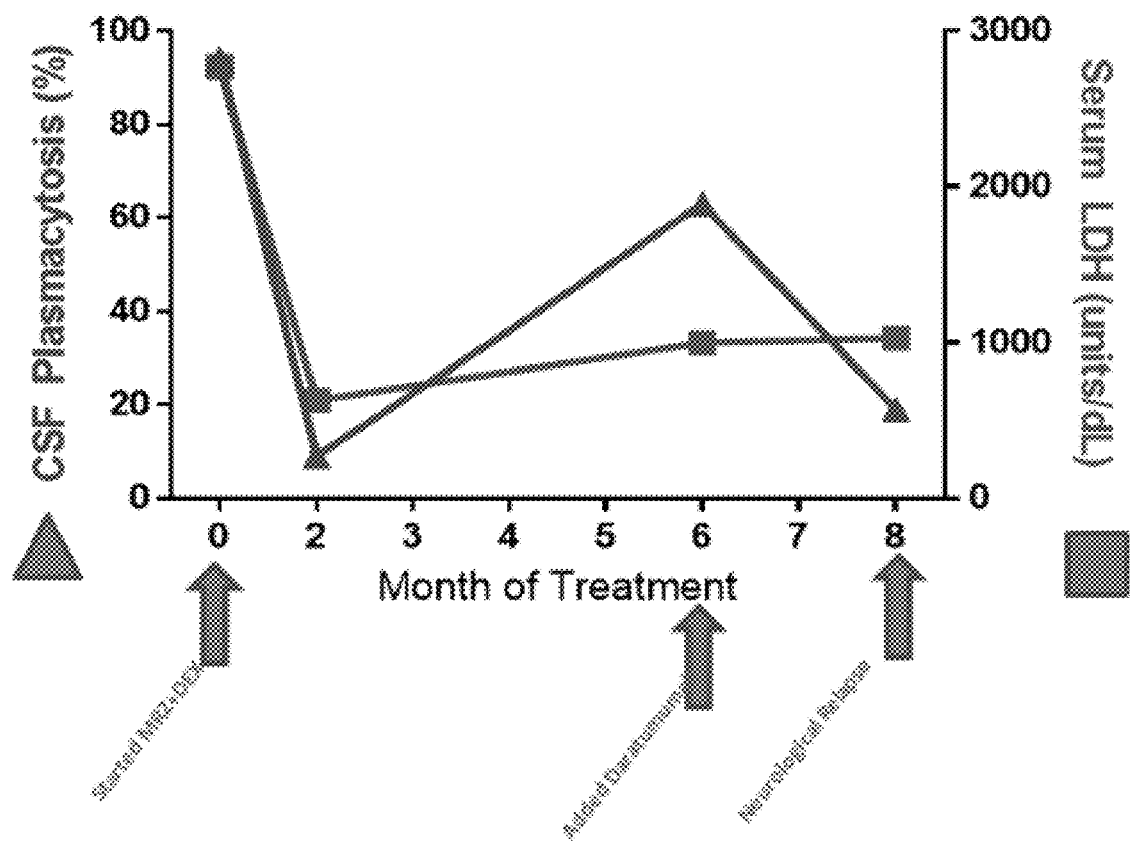
FIG. 3 shows a plot of the percent CSF plasmacytosis (triangle) and serum LDL (square) as a function of time for the subject in Example 1, Case 1.

As set forth in Example 1, Case 1, a patient with multiple myeloma with CNS progression presented with multiple lesions in the brain despite years of treatment for CNS-MM (FIG. 1). However, after treatment with marizomib for two months, the lesions were largely absent (FIG. 2) and the patient's disease was held in check with either MRZ alone for 4 months or MRZ combined with daratumumab for an additional 2 months. Example 1 (e.g., Case 1) demonstrates that marizomib is an effective therapy for multiple myeloma with brain involvement, including in relapsed or refractory patients who have previously received therapy. FIG. 3 shows a plot of the percent CSF plasmacytosis and serum LDL as a function of time for the subject in Example 1, Case 1

Figure 4:
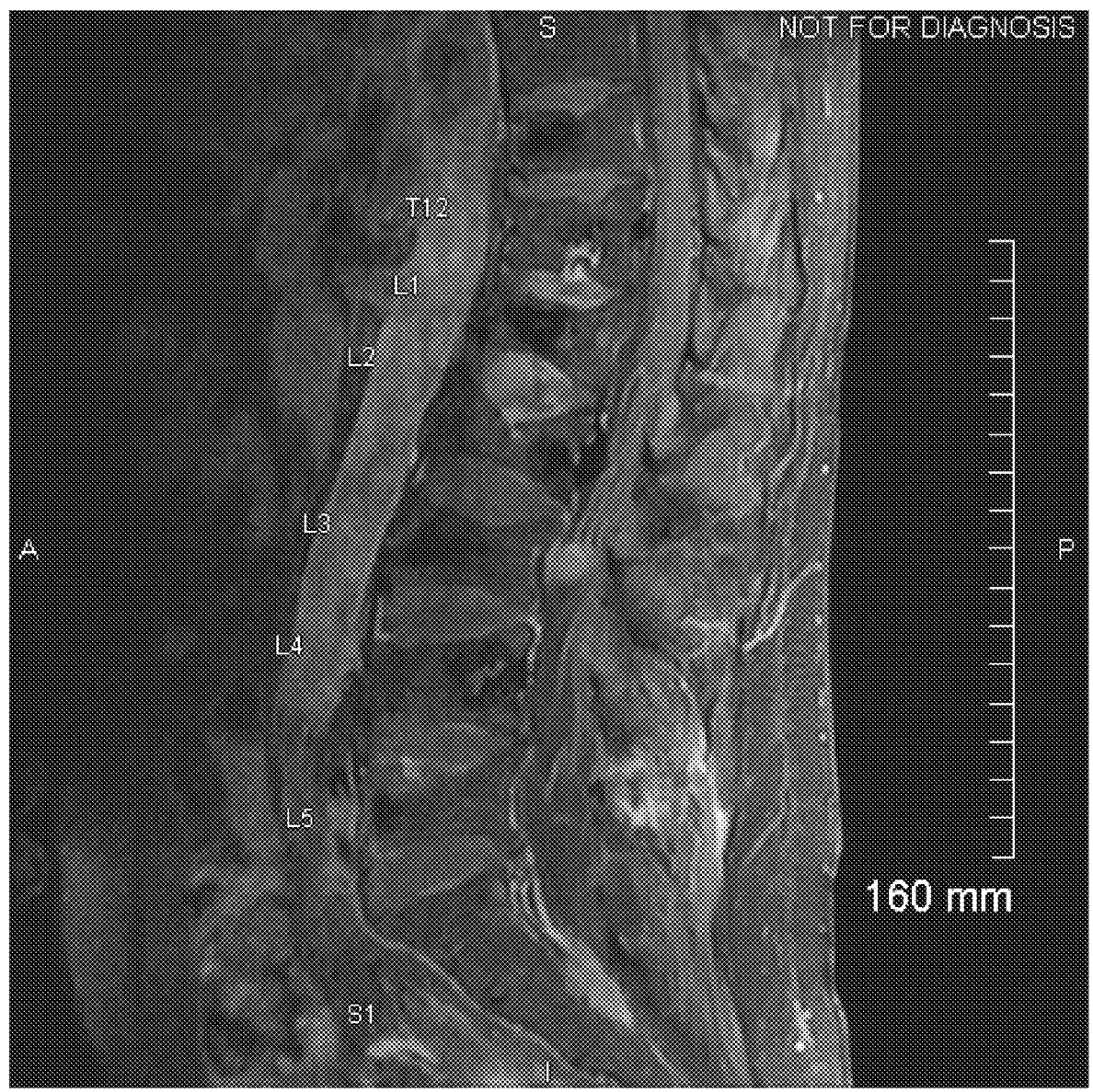
FIG. 4 shows an MM image of the lumbar spine of the subject of Example 1, Case 2 prior to treatment with marizomib.
Figure 5:
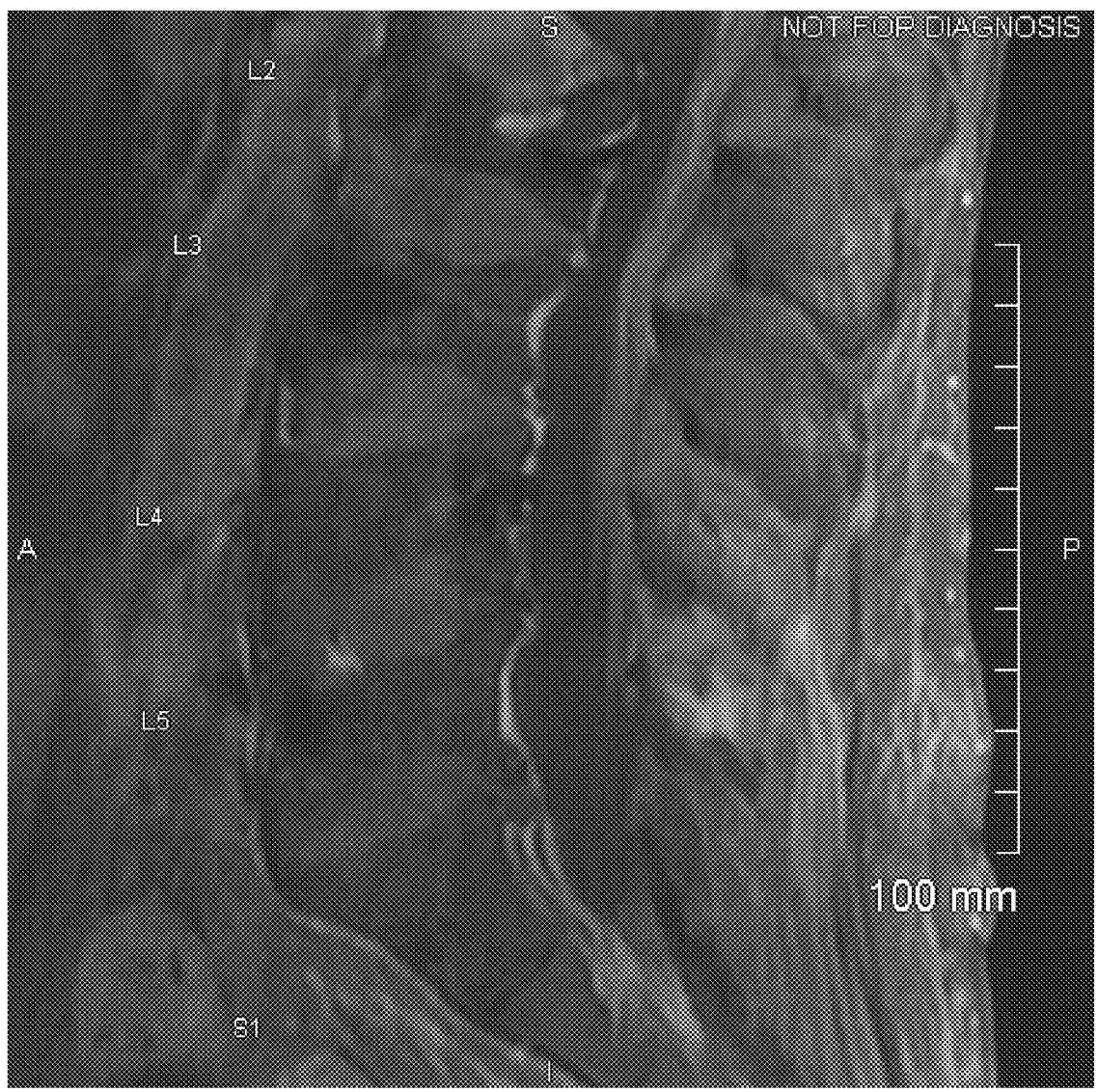
FIG. 5 shows an MM image of the lumbar spine of the subject of Example 1, Case 2 two months after beginning treatment with marizomib.
Figure 6:
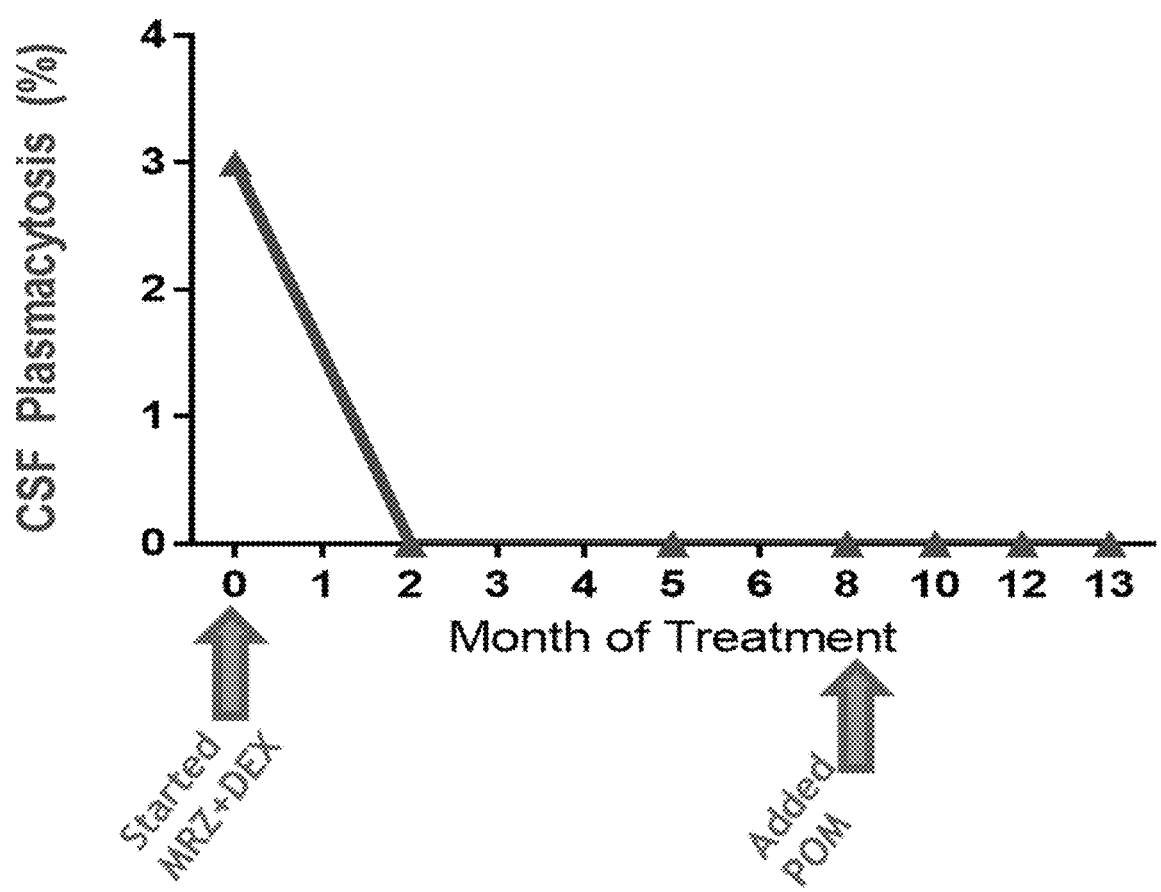
FIG. 6 shows a plot of the percent CSF plasmacytosis of the subject of Example 1, Case 2 as a function of time.

Additionally, as set forth in Case 2, marizomib is an effective therapy for patients who have multiple myeloma with spinal involvement. For example, FIG. 4 shows an MRI of a patient showing abnormal epithelial soft tissue around the spine, confirming CNS-MM, prior to treatment with marizomib. After two months of treatment with marizomib, the tissue around the spine has returned to normal as set forth in FIG. 5. This patient's disease continues to be undetectable in the CNS after 7 months of MRZ therapy. FIG. 6 shows a plot of this patient's CSF plasmacytosis as a function of time.

Gliomas

Example 2 teaches a Phase 1b, open-label, 3+3, dose-escalation followed by dose-expansion study in patients with newly diagnosed glioma grade IV malignant glioma (G4 MG) including glioblastoma and gliosarcoma, who have not previously received any local or systemic therapy for their grade IV malignant glioma. The study examines the effect of the addition of marizomib to standard of care treatment utilizing two study arms: Concomitant Treatment in which marizomib is combined with temozolomide and radiotherapy (TMZ+RT) and Adjuvant Treatment in which marizomib is combined with temozolomide. The study was conducted in two Stages. In Stage 1 (Dose-Escalation): 3 to 6 evaluable patients per marizomib dose cohort were enrolled in each study arm. In Stage 2 (Dose-Expansion): a minimum of 12 and up to approximately 18 additional evaluable patients were enrolled in a cohort in which Concomitant Treatment is followed by Adjuvant Treatment to confirm the maximum tolerated dose (MTD) for each treatment regimen as determined in the Dose-Escalation (Stage 1), and to assess preliminary activity of the recommended phase 2 dose. A total of approximately 48 patients were enrolled in Stages 1 and 2 combined. Patients were not enrolled in more than 1 marizomib dose cohort per arm.

Example 3 sets forth a Phase 1 open-label dose-escalation clinical trial evaluating the safety, pharmacokinetics, and efficacy of marizomib and bevacizumab to treat a CNS cancer. The patients were bevacizumab naive and had had no prior anti-angiogenic or proteasome inhibitor therapy. As set forth in Example 3, the combination of marizomib and bevacizumab demonstrated good tolerability and promising signs of efficacy in recurrent glioma patients. The most common adverse events related to study drugs included fatigue, nausea, headache, vomiting, hypertension, and hallucinations. The most common marizomib related adverse events of Grade 3 or greater were hallucination and headache. There were relatively few study treatment related serious adverse events. The majority of recurrent glioblastoma patients (i.e., $25/31$) derived a clinical benefit from the combination therapy of marizomib and bevacizumab (FIG. 5). For five patients, the tumor area decreased to 0 mm² by MM on greater than or equal to 2 Mill scans. Three of the 36 patients enrolled remain on study. The RANO response was 42% in efficacy evaluable patients and 39% in ITT patients. Without wishing to be bound by theory, the marizomib and bevacizumab pharmacokinetic parameters were found to be consistent with previous trials. As set forth in Example 3, the combination of marizomib and bevacizumab was well-tolerated in patients, with no dose-limiting toxicities at 0.8 mg/m². After repeated dosing, marizomib was able to overcome compensatory hyperactivation of proteasome subunits, resulting in pan-subunit inhibition.

Marizomib Monotherapy and Combination Therapy

In some embodiments, the present disclosure provides for the treatment of CNS-hematologic cancers using a combination of marizomib and an additional therapeutic agent.

Any of the combination therapies described herein can be used in the treatment of any of the CNS cancer indications described herein. For example, in some embodiments, CNS-hematological cancers such as CNS-multiple myeloma can be treated with a combination of marizomib and an anti-CD-38 antibody such as daratumumab. Similarly, CNS-multiple myeloma can be treated with a combination of marizomib and/or temozolomide and/or bevacizumab. Likewise, gliomas can be treated using a combination of marizomib and an anti-CD-38 antibody such as daratumumab. Similarly, gliomas can be treated with a combination of marizomib and/or temozolomide and/or bevacizumab Marizomib Monotherapy In some embodiments, marizomib can be used as a single therapeutic agent for monotherapy for any of the CNS cancers described herein. In some embodiments, marizomib monotherapy can be used to treat any of the CNS cancers described herein (e.g., CNS hematological cancers, gliomas, or glioblastomas). In some embodiments, marizomib monotherapy is used to treat CNS-hematological cancers. In some embodiments, marizomib monotherapy is used to treat gliomas (e.g, grade IV malignant glioma). In some embodiments, marizomib monotherapy is used to treat glioblastomas.

In some embodiments, marizomib can be administered as a single therapeutic agent at a dose of between about 0.1 to about 1.2 mg/m². For example, marizomib can be administered at a dose of about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.05, about 1.1, about 1.15, or about 1.2 mg/m². In some embodiments, marizomib can be administered daily, twice a week, weekly, or every two weeks. In some embodiments, marizomib is administered by IV injection (e.g., over a course of between about 1 minute and about 1 hour, e.g., about 10 minutes). In some embodiments, treatment with marizomib can be administered for between about 1 week and about 8 weeks. For instance, marizomib can be administered for about 1 week, about 2 weeks, about 3 weeks, about 4 weeks, about 5 weeks, about 6 weeks, about 7 weeks, or about 8 weeks.

In some embodiments, marizomib can be administered at a dose of about 0.7 mg/m² every week with an IV infusion (e.g., about 10 min infusion time). In some embodiments, marizomib can be administered at a dose of about 0.8 mg/m² every week with an IV infusion (e.g., about 10 min infusion time). In some embodiments, marizomib can be administered at a dose of about 0.7 mg/m² every week for about 4 weeks with an IV infusion (e.g., about 10 min infusion time). In some embodiments, marizomib can be administered at a dose of about 0.8 mg/m² every week for about 4 weeks with an IV infusion (e.g., about 10 min infusion time).

For instance, in some embodiments, a patient can be administered marizomib at a dose of about 0.55 mg/m² for the first two cycles and administered marizomib subsequent doses at about 0.7 mg/m². Marizomib can be administered weekly.

Marizomib and Dexamethasone

In some embodiments, marizomib can be administered in combination with dexamethasone. For example, the dosage schedule of marizomib can be the same or different than the dosing schedule of marizomib monotherapy. In some embodiments, marizomib monotherapy can be used to treat any of the CNS cancers described herein (e.g., CNS hematological cancers, gliomas, or glioblastomas). In some embodiments, marizomib monotherapy is used to treat CNS-hematological cancers.

For instance, in some embodiments, a patient can be administered marizomib at a dose of about 0.55 mg/m² for the first two cycles and administered marizomib subsequent doses at about 0.7 mg/m². Marizomib can be administered weekly. In some embodiments, the dosage regimen can further include administration of dexamethasone at a dose of about 1-50 mg (e.g., about 1 mg, about 5 mg, about 10 mg, about 15 mg, about 20 mg, about 25 mg, about 30 mg, about 35 mg, about 40 mg, about 45 mg, or about 50 mg). In some embodiments, dexamethasone can be dosed higher for treatment of CNS cancers than for the treatment of peripheral cancers (e.g., to reduce inflammation and/or pressure in the CNS). For instance, dexamethasone can be administered daily, weekly, twice a week, or every two weeks. For example, dexamethasone can be administered on days 1, 2, 8, 9, 15 and 16.

Marizomib and Pomalidomide

In some embodiments, marizomib can be co-administered with pomalidomide. Marizomib can be co-administered with pomalidomide and dexamethasone, or marizomib can be co-administered with pomalidomide without dexamethasone. For example, the dosage schedule of marizomib can be the same or different than the dosing schedule of marizomib monotherapy. Similarly, if administered with dexamethasone, the dosage schedule of dexamethasone can be the same or different than the dosing schedule of marizomib+dexamethasone combination therapy.

For instance, pomalidomide can be administered daily, weekly, twice a week, or every two weeks.

For example, in some embodiments, pomalidomide can be administered at a dose of about 1 to 5 mg (e.g., about 1 mg, about 2 mg, about 3 mg, about 4 mg, or about 5 mg). For instance, pomalidomide can be administered on day 1 and day 21 of a dosage regimen. For instance, in some embodiments, marizomib can be administered at a dose of about 0.8 mg/m$^2$, pomalidomide can be administered at a dose of about 4 mg, and dexamethasone can be administered at a dose of about 20 mg.

Marizomib and Lenalidomide

In some embodiments, marizomib can be co-administered with lenalidomide. Marizomib can be co-administered with lenalidomideand dexamethasone, or marizomib can be co-administered with lenalidomide without dexamethasone. For example, the dosage schedule of marizomib can be the same or different than the dosing schedule of marizomib monotherapy. Similarly, if administered with dexamethasone, the dosage schedule of dexamethasone can be the same or different than the dosing schedule of marizomib+dexamethasone combination therapy.

For instance, lenalidomidecan be administered daily, weekly, twice a week, or every two weeks.

For example, in some embodiments, lenalidomidecan be administered at a dose of about 1 to 50 mg (e.g., about 1 mg, about 5 mg, about 10 mg, about 15 mg, about 20 mg, about 25 mg, about 30 mg) about 35 mg, about 40 mg, about 55 mg, or about 50 mg). For instance, lenalidomidecan be administered on day 1 and day 21 of a dosage regimen. For instance, in some embodiments, marizomib can be administered at a dose of about 0.8 mg/m$^2$, lenalidomidecan be administered at a dose of about 4 mg, and dexamethasone can be administered at a dose of about 20 mg.

Marizomib and Anti-CD38 Antibodies

In some embodiments, marizomib can be co-administered with an anti-CD38 antibody (e.g., daratumumab or Isatuximab). Marizomib can be co-administered with the anti-CD38 antibody and dexamethasone, or marizomib can be co-administered with the anti-CD38 antibody without dexamethasone. Marizomib can be co-administered with the anti-CD38 antibody and pomalidomide, or marizomib can be co-administered with the anti-CD38 antibody without pomalidomide. For example, the dosage schedule of marizomib can be the same or different than the dosing schedule of marizomib monotherapy. Similarly, if administered with dexamethasone, the dosage schedule of dexamethasone can be the same or different than the dosing schedule of marizomib+dexamethasone combination therapy.

For instance, the anti-CD38 antibody (e.g., daratumumab) can be administered daily, weekly, twice a week, or every two weeks.

For example, in some embodiments, daratumumab can be administered at a dose of about 16 mg/m$^2$. For instance, daratumumab can be administered once every week of a dosage regimen.

Without wishing to be bound by theory, the disappearance of CD38 from the malignant plasma cells after the addition of daratumumab, as set forth in Example 1 suggests that the daratumumab may also cross the blood-brain barrier. Accordingly, the present disclosure provides for a combination therapy using both marizomib and an anti-CD38 antibody (e.g., daratumumab) for the treatment of CNS-hematologic cancer (e.g., CNS-MM).

Marizomib and Temozolomide

As set forth in Example 2, a combination of marizomib and temozolomide can be effective at treating glioma (e.g., grade IV malignant glioma). Additionally, as set forth in Example 2, a combination of marizomib, radiotherapy and temozolomide can be effective at treating glioma (e.g., grade IV malignant glioma). Alternatively, in some embodiments Example 2 teaches that a combination of marizomib and radiotherapy can be effective at treating glioma (e.g., grade IV malignant glioma).

Accordingly, as set forth in Example 2, without wishing to be bound by theory, proteasome inhibition (PI) can sensitize glioma cells to TMZ and RT, thus providing a novel therapeutic strategy for newly diagnosed grade IV malignant glioma (ndG4MG). Marizomib is an irreversible, brain-penetrant, pan-proteasome inhibitor which demonstrates anti-glioma activity preclinically and has been evaluated in ndG4MG patients in combination with concomitant temozolomide (TMZ)+radiotherapy (RT) and adjuvant TMZ. The phase 1 study was 3+3 MRZ dose-escalation (0.55, 0.7, 0.8, and 1.0 mg/m$^2$) in separate concomitant and adjuvant treatment arms, followed by dose-expansion at the recommended phase 2 dose in concomitant MRZ+TMZ+RT followed by adjuvant MRZ+TMZ treatment. Marizomib is administered IV (10 min infusion) on days 1, 8, 15, 29, and 36 with RT (total dose 60 Gy) and TMZ (75 mg/m$^2$, PO QD) of the 42 day concomitant treatment; MRZ is administered on days 1, 8 and 15 of each 28 day cycle in adjuvant treatment with TMZ (150 mg/m$^2$, PO QDX5, increased to 200 mg/m$^2$ in cycle 2+ if tolerated). Tumor response was measured at the beginning and end of the concomitant treatment, and every other cycle during adjuvant treatment, by RANO criteria; MRZ and TMZ PK were evaluated on concomitant treatment days 1-2 and 8-9. Three patients have completed each of the first three concomitant treatment cohorts (MRZ 0.55, 0.7, and 0.8 mg/$^2$) with no dose-limiting toxicities (DLTs). Three patients were enrolled in the first (0.55 mg/m$^2$), 6 in the second (0.7 mg/m$^2$) due to a DLT (fatigue) in one patient, and 3 in the third (0.8 mg/m$^2$) adjuvant treatment cohort. The mean age for the 20 patients (60% male) included in the interim analysis was 55 yrs. The most common treatment-related AEs (≥4 pts) were: fatigue, nausea, vomiting, decreased appetite, dizziness (related to TMZ and/or MRZ), and hallucination (MRZ-related); three Grade 3 SAEs (fatigue, hallucination, and vomiting, all MRZ-related), and two Grade 2 SAEs (nausea, confusional state, MRZ-related). One adjuvant cohort 2 patient (0.7 mg/m$^2$) had DLT (fatigue); no other DLTs have occurred. Seventeen of the 20 patients included in the interim analysis remain on study: of the 9 concomitant patients, 7 had entered adjuvant treatment with the longest being in adjuvant cycle 7; of the 11 adjuvant patients, the longest on treatment are in cycles 7 and 9.

Further, dosing has been initiated for the 4th dose cohorts (1.0 mg/m$^2$) for both concomitant and adjuvant treatment. Without wishing to be bound by theory, the data demonstrate that the combination of MRZ with standard of care in ndG4MG is well tolerated and can provide therapeutic benefit in this unmet need.

For example, the dosage schedule of marizomib can be the same or different than the dosing schedule of marizomib monotherapy. In some embodiments, marizomib can be administered at a dosage of between about 0.1 and 1.2 mg/m$^2$. For instance, marizomib can be administered at a dosage of about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.05, about 1.1, about 1.15, or about 1.2 mg/m$^2$.

In some embodiments, temozolomide is administered at a dose of between about 0.1 and 1 mg/kg. For instance, temozolomide can be administered at a dosage of about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 1 mg/kg.

In some embodiments, temozolomide can be dosed between about 50 and about 100 mg/m$^2$. For instance, temozolomide can be dosed at about 55, about 60, about 65, about 70, about 75, about 80, about 85, about 90, or about 100 mg/m$^2$. For instance, temozolomide can be dosed at about 75 mg/m$^2$ (e.g., for about 40 or about 42 days, PO).

In some embodiments, temozolomide can be administered in a range of about 150-200 mg/m$^2$ (e.g., about 150, about 155, about 160, about 165, about 170, about 175, about 180, about 185, about 190, about 195, or about 200 mg/m$^2$. In some embodiments, this dosage can be administered for 5 days (e.g., PO) within a 28-day treatment cycle.

In some embodiments, temozolomide can be dosed daily at range of about 40-100 mg/m$^2$ (e.g., about 40, about 45, about 50, about 55, about 60, about 65, about 70, about 75, about 80, about 85, about 90, about 95, or about 100 mg/m$^2$). In some embodiments this dose is administered daily (e.g., for between about 21 and 365 days). In some embodiments, temozolomide can be dosed in alternating cycles (e.g., 1-week dosed, 1-week off dose).

In some embodiments, temozolomide can be administered daily, weekly, twice a week, or every two weeks. In some embodiments, temozolomide is administered every two weeks.

In some embodiments, treatment with the combination of marizomib and temozolomide can last between about 1 and about 8 weeks. For instance, treatment with marizomib and temozolomide can last about 1 week, about 2 weeks, about 3 weeks, about 4 weeks, about 5 weeks, about 6 weeks, about 7 weeks, or about 8 weeks.

In some embodiments of the present disclosure, the combination of marizomib with temozolomide can be synergistic. In some embodiments of the present disclosure, the combination of marizomib with radiotherapy can be synergistic. In some embodiments of the present disclosure, the combination of marizomib with temozolomide and radiotherapy can be synergistic.

Accordingly, as set forth in Example 2, for concomitant treatment, the present disclosure provides for administration of marizomib, temozolomide and radiotherapy substantially simultaneously. Without wishing to be bound by theory, in some embodiments all three therapies can work together. In some embodiments, radiotherapy can add to the effect seen with the administration of marizomib and/or temozolomide.

For adjuvant treatment, as set forth in Example 2, the present disclosure provides for administration of marizomib and temozolomide substantially simultaneously. In some embodiments, the marizomib can add to the effect of temozolomide. In some embodiments, the temozolomide can add to the effect of the marizomib.

In some embodiments, the present disclosure also provides for the administration of marizomib and radiotherapy substantially simultaneously.

In some embodiments, radiotherapy can be administered 5 days per week. In some embodiments, radiotherapy is administered for six weeks. In some embodiments, the total dose is about 60 Gy (e.g., 60 Gy is the total dosage after 30 treatments over 6 weeks).

Marizomib and Bevacizumab

In some embodiments, marizomib and bevacizumab can be used in combination to treat a CNS cancer. In some embodiments, the cancer is glioma. In some embodiments, the cancer is glioblastoma. The cancer can be, for instance, grade I, grade II, grade III, or grade IV malignant glioblastoma. In some embodiments, the patients are in first or second relapse.

For example, the dosage schedule of marizomib can be the same or different than the dosing schedule of marizomib monotherapy. In some embodiments, marizomib can be administered at a dosage of between about 0.1 and 1.2 mg/m$^2$. For instance, marizomib can be administered at a dosage of about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.05, about 1.1, about 1.15, or about 1.2 mg/m$^2$.

In some embodiments, marizomib can be administered daily, weekly, twice a week, or every two weeks. In some embodiments, marizomib is administered weekly.

In some embodiments, bevacizumab is administered at a dose of between about 0.1 and 1 mg/kg. For instance, bevacizumab can be administered at a dosage of about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 1 mg/kg.

In some embodiments, bevacizumab can be administered daily, weekly, twice a week, or every two weeks. In some embodiments, bevacizumab is administered every two weeks.

In some embodiments, treatment with the combination of marizomib and bevacizumab can last between about 1 and about 8 weeks. For instance, treatment with marizomib and bevacizumab can last about 1 week, about 2 weeks, about 3 weeks, about 4 weeks, about 5 weeks, about 6 weeks, about 7 weeks, or about 8 weeks.

In some embodiments, marizomib can be administered at a dose of about 0.55 mg/m$^2$ every week while simultaneously administering bevacizumab every two weeks at a dose of about 10 mg/kg. In some embodiments, the treatment last about 4 weeks. In some embodiments, marizomib can be administered at a dose of about 0.7 mg/m$^2$ every week while simultaneously administering bevacizumab every two weeks at a dose of about 10 mg/kg. In some embodiments, the treatment last about 4 weeks. In some embodiments, marizomib can be administered at a dose of about 0.8 mg/m$^2$ every week while simultaneously administering bevacizumab every two weeks at a dose of about 10 mg/kg. In some embodiments, the treatment last about 4 weeks.

In some embodiments, marizomib can be administered once weekly for 5 total doses over 6 weeks in combination with radiotherapy and temozolomide. For example, for concomitant therapy in newly diagnosed GBM, a dosage regimen can include 75 mg/m² TMZ QD PO for 42 days, 60 GY RT total dose delivered 5 d/wk for 6 wks).

In some embodiments, marizomib can be administered once weekly for 3 weeks on a 28-day cycle in combination with temozolomide. For example, for adjuvant therapy in newly diagnosed GBM, a dosage regimen can include 150-200 mg/m² for 5 days PO, over a 28-day cycle);

In some embodiments, marizomib can be combined with concomitant or adjuvant standard of care at 0.55, 0.7, 0.8, 1.0 mg/m² marizomib.

Example 3 teaches the treatment of malignant glioma using marizomib and bevacizumab included three dose escalation cohorts plus an expansion cohort, for a total of 36 recurrent glioma patients receiving MRZ on days 1, 8, and 15, with standard dose of bevacizumab (BEV at 10 mg/kg) on days 1 and 15, of a 28-day cycle. The MRZ+BEV combination was well tolerated with no dose limiting toxicity at 0.8 mg/m², which was the highest dose of MRZ was evaluated in this study.

The Response Rate (by Response Assessment in Neuro-Oncology (RANO) criteria) was 42% (14/33) in efficacy evaluable patients, with 34% of patients achieving six months progression-free survival (PFS) and 55% achieving nine months overall survival (OS). The 6 and 9 months PFS in patients with unmethylated promoter of the gene encoding MGMT—which can be a marker of poor prognosis and resistance to standard-of-care in glioblastoma—were 34% and 23%, respectively. These data are comparable to PFS in all patients (34% PFS 6 months, 22% PFS 9 months).

Accordingly, the present disclosure teaches the treatment of a glioma (e.g., grade IV malignant glioma or glioblastoma) in patients with unmethylated promoter of the gene encoding MGMT. As used herein, "unmethylated" MGMT promoter is understood to mean less than about 8% methylation of the promoter of the gene encoding MGMT. For example, the patient can have about 8% methylation, about 7% methylation, about 6% methylation, about 5% methylation, about 4% methylation, about 3% methylation, about 2% methylation, about 1% methylation, or substantially no methylation. The extent of methylation can be measured by a technique known in the art (e.g., pyrosequencing). In some embodiments, one of skill in the art can recognize that an MGMT promoter may have greater than about 8% methylation and still be considered "unmethylated."

In some embodiments, a constitutively active variant of EGFRvIII can be an indicator of poor prognosis (e.g., for glioblastoma). Accordingly, in some embodiments the present disclosure teaches treatment of patients (e.g., glioblastoma patients) who have a constitutively active variant of EGFRvIII.

In some cases, these glioblastomas can be difficult to treat. Overall survival appears to be higher in the unmethylated MGMT promoter patients treated with MRZ+BEV in comparison with reported OS in recurrent glioma patients receiving BEV monotherapy. The 9 months OS in unmethylated MGMT promoter patients was 44%, with data collection continuing for most patients. Without wishing to be bound by theory, this result suggests a consequential response in this study population.

In an ongoing Phase 2 (MRZ monotherapy) portion of the study, a total of 15 recurrent glioma patients have been enrolled, receiving 0.8 mg/m² MRZ on days 1, 8, and 15 of a 28-day cycle. MRZ monotherapy in these patients resulted in a partial remission in 1 patient, and stable disease in 2 additional patients, demonstrating activity of MRZ as a single agent. Based on these data, the study will continue enrollment up to 30 total patients. Without wishing to be bound by theory, MRZ is generally well tolerated in combination with BEV and as monotherapy. The most common study treatment-related adverse events across both phases of the study included fatigue, headache, nausea, diarrhea, dysphonia, hypertension, vomiting, hallucination and weakness.

Figure 31:
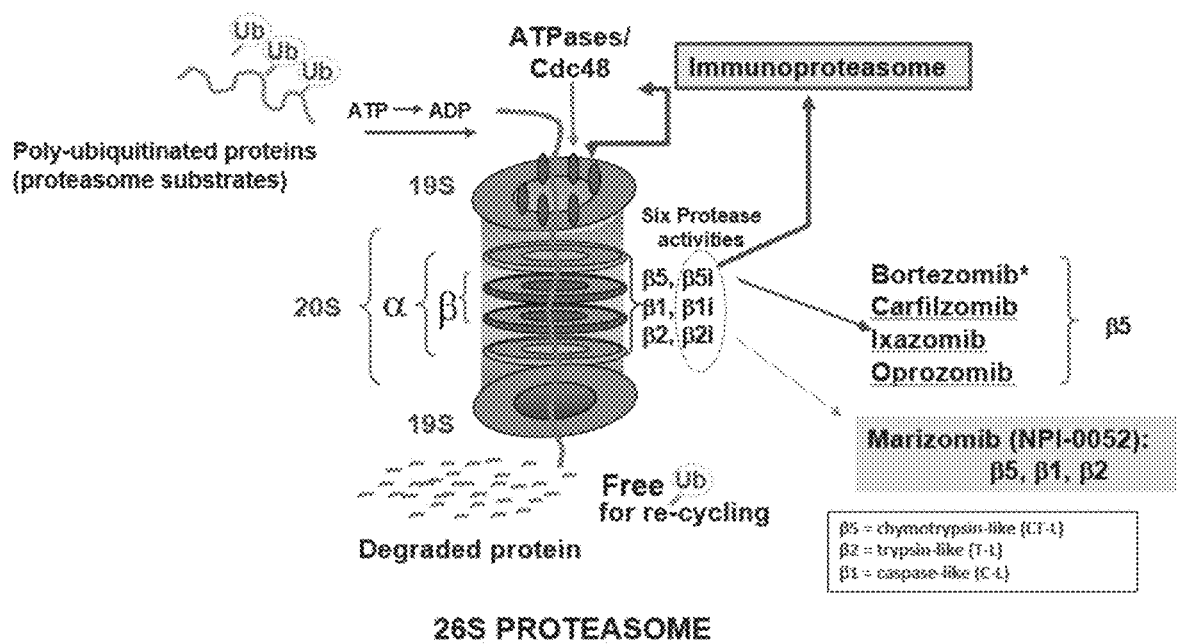
FIG. 31 shows the activity of marizomib as a first-in-class pan-proteasome inhibitor.

FIG. 31 shows the activity of marizomib as a first-in-class pan-proteasome inhibitor.

Figure 32:
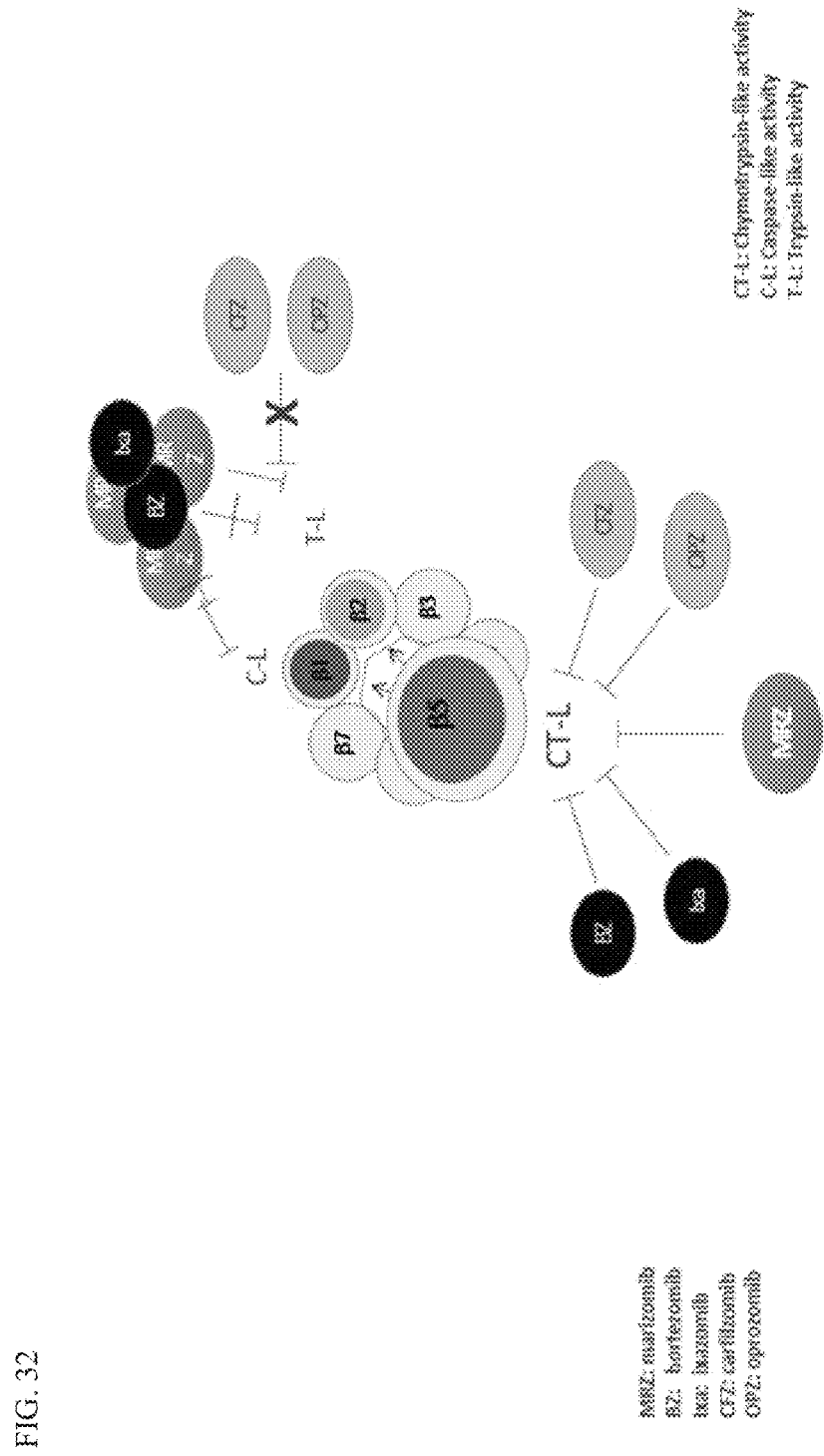
FIG. 32 shows that marizomib overcomes compensatory hyperactivation of tripsin-like (T-L) and caspase-like (C-L) proteasome subunits.

FIG. 32 shows that marizomib overcomes compensatory hyperactivation of tripsin-like (T-L) and caspase-like (C-L) proteasome subunits.

Figure 33A:
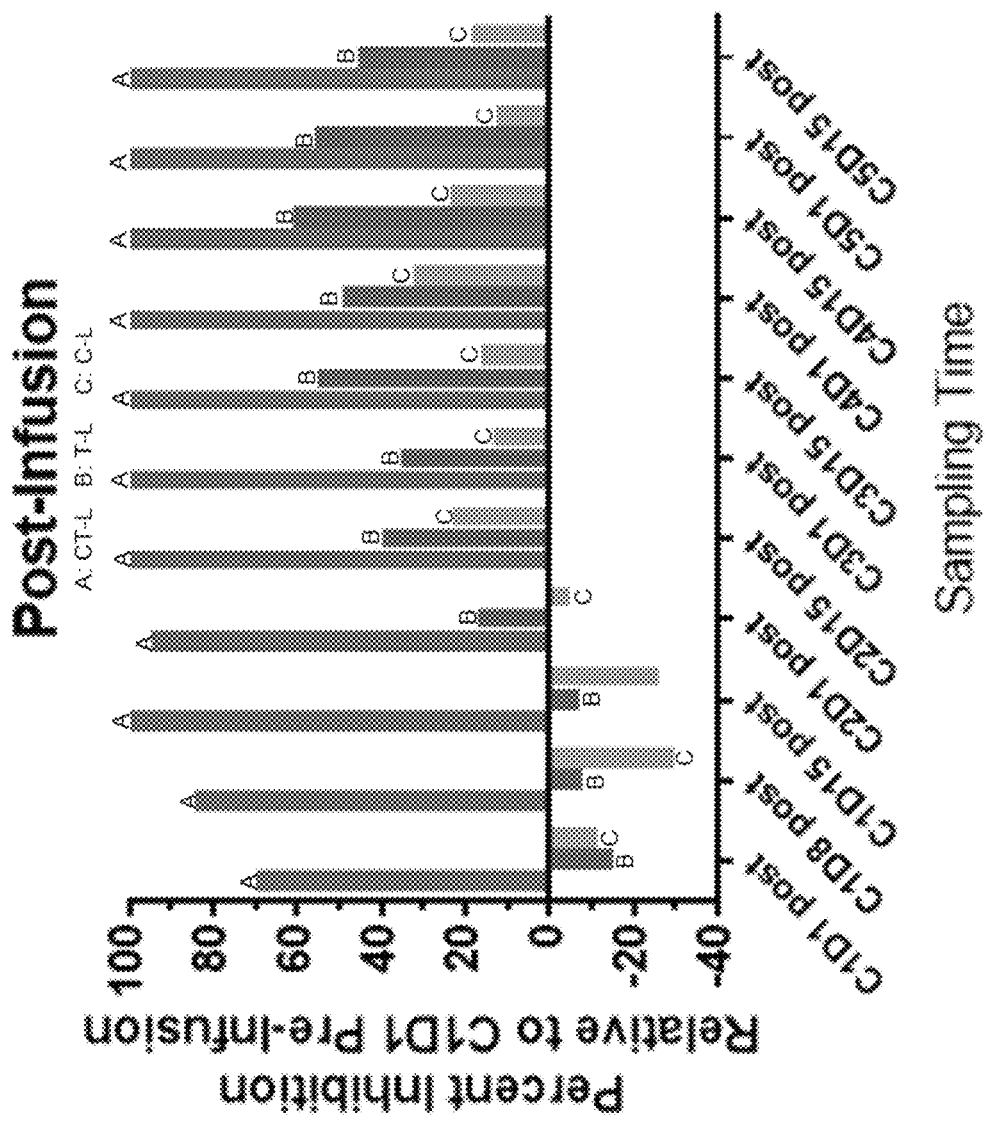
FIG. 33A shows plots demonstrating the packed whole blood proteasome inhibition of marizomib and bevacizumab for patient 101-0101 (partial response) post-infusion.
Figure 33B:
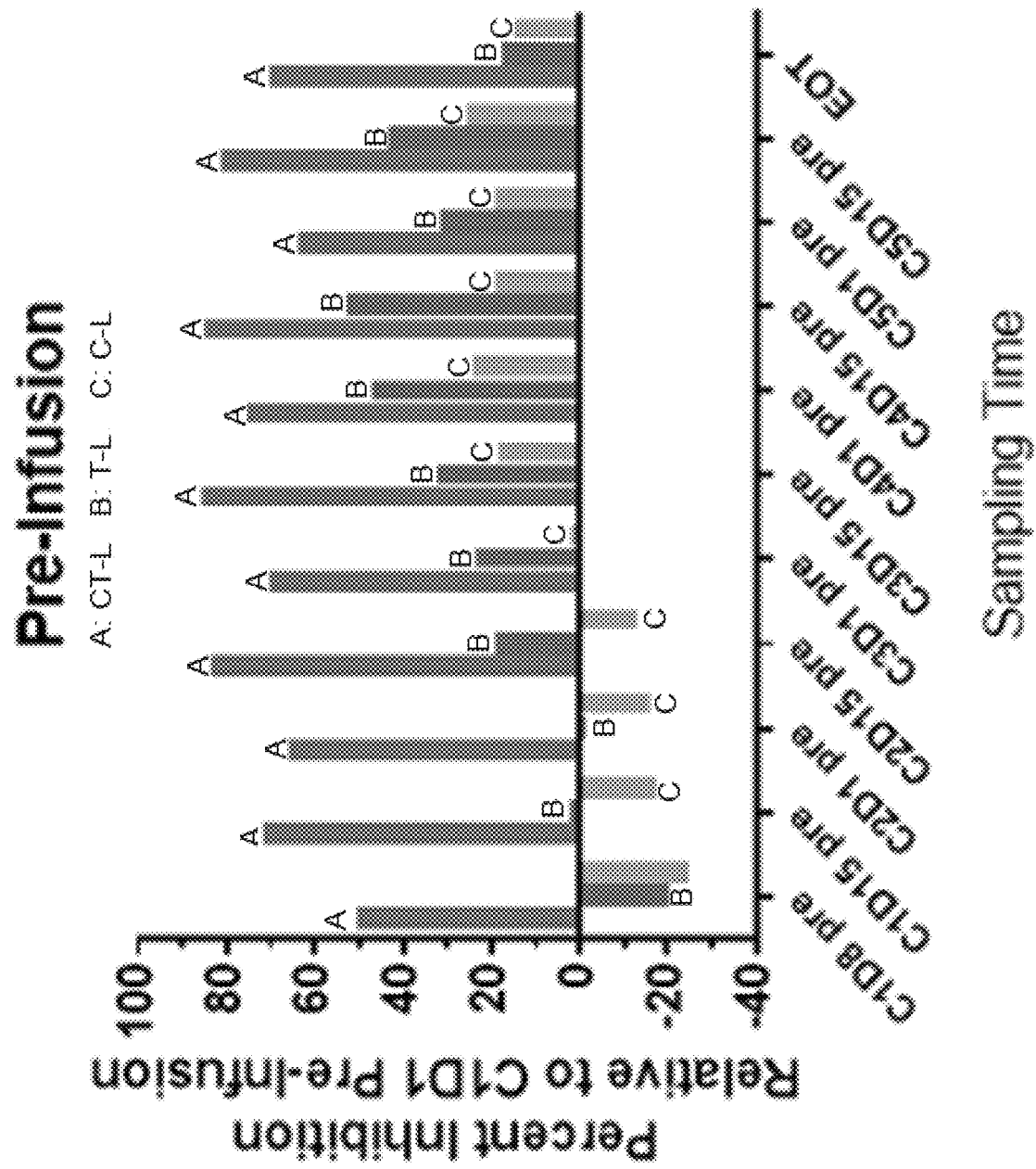
FIG. 33B shows plots demonstrating the packed whole blood proteasome inhibition of marizomib and bevacizumab for patient 101-0101 (partial response) pre-infusion.

FIGS. 33A and B show plots demonstrating the packed whole blood proteasome inhibition of marizomib and bevacizumab for patient 101-0101 (partial response). For each timepoint, the bars are in the order: (i) chymotrypsin-like; (ii) trypsin-like; and (iii) caspase-like. As shown in FIG. 33, there is initial hyperactivation of T-L and C-L proteasome domains, followed by evolving pan-proteasome subunit inhibition. In some embodiments, this is evident pre- and post-infusion. As shown in FIG. 33A, complete (100%) inhibition of the CT-L domain was found after cycle 1 in packed whole blood (PWB). As shown in FIG. 33B, patients exhibited sustained (e.g., 60-80%) inhibition of the CT-L domain in packed whole blood (PWB) up to two weeks after marizomib dosing.

Figure 34A:
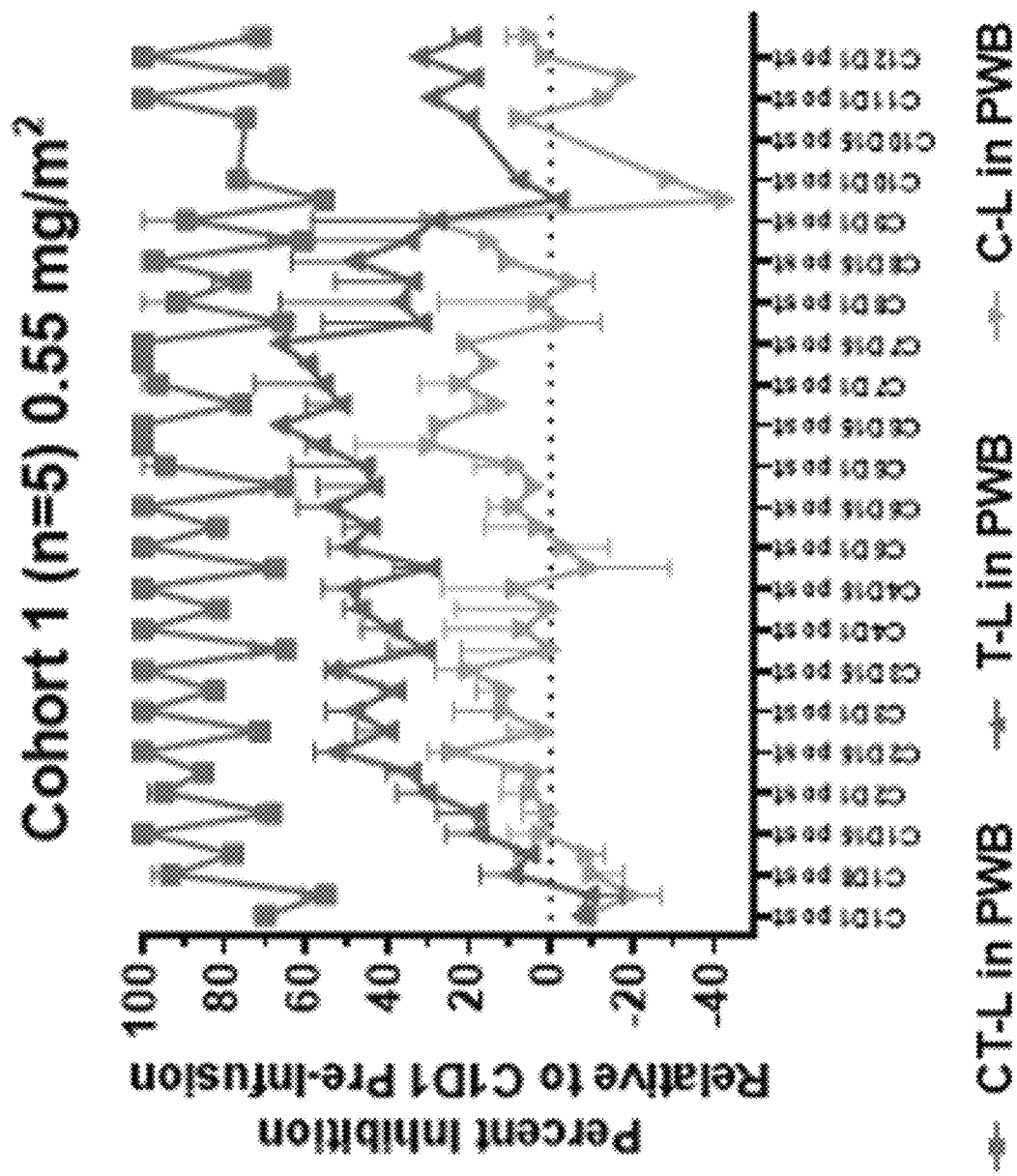
FIG. 34A shows plots demonstrating the dose-related proteasome subunit inhibition in packed whole blood for the combination of marizomib and bevacizumab in cohort 1 (0.55 mg/m$^2$).
Figure 34B:
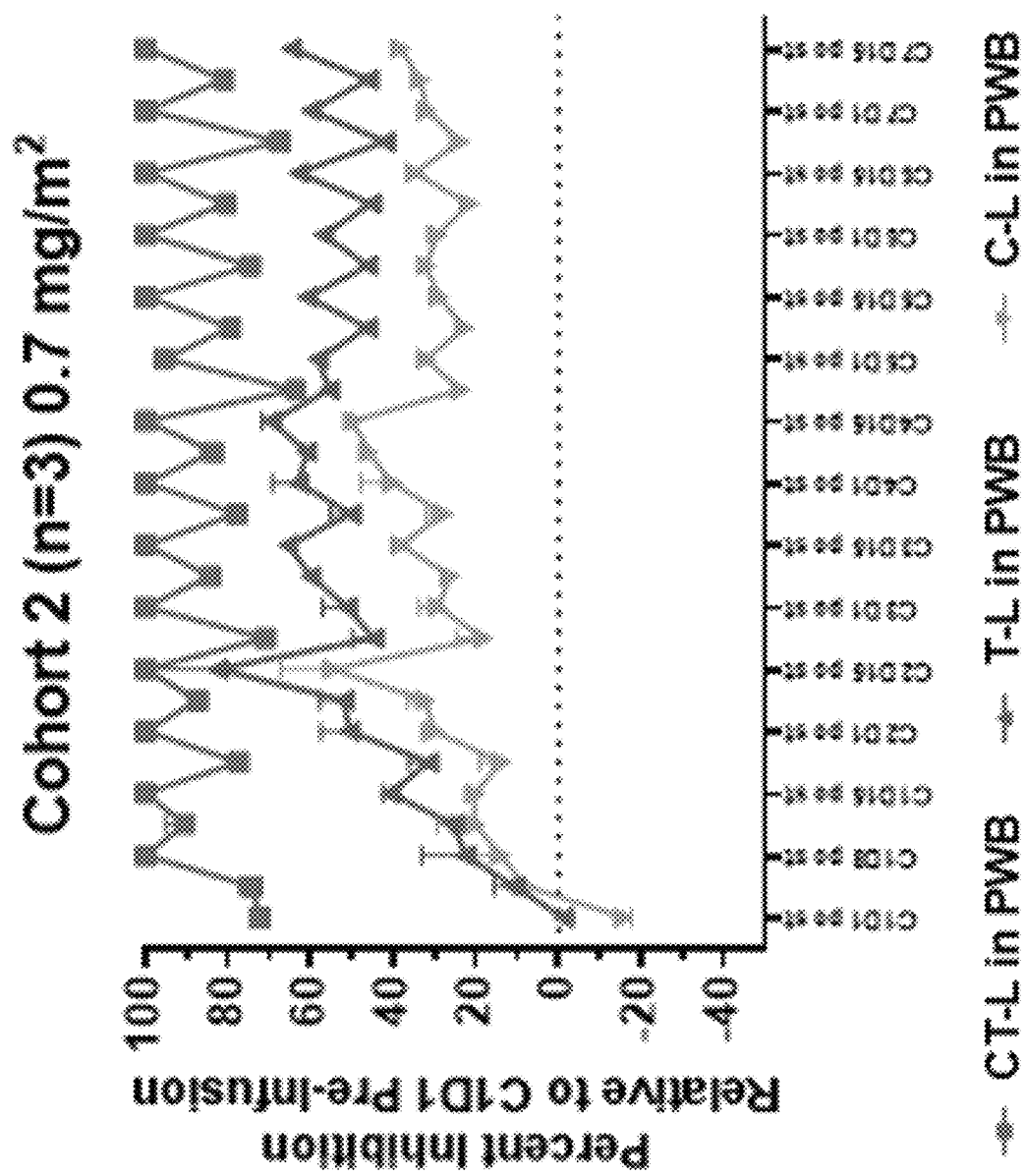
FIG. 34B shows plots demonstrating the dose-related proteasome subunit inhibition in packed whole blood for the combination of marizomib and bevacizumab in cohort 2 (0.7 mg/m$^2$).
Figure 34C:
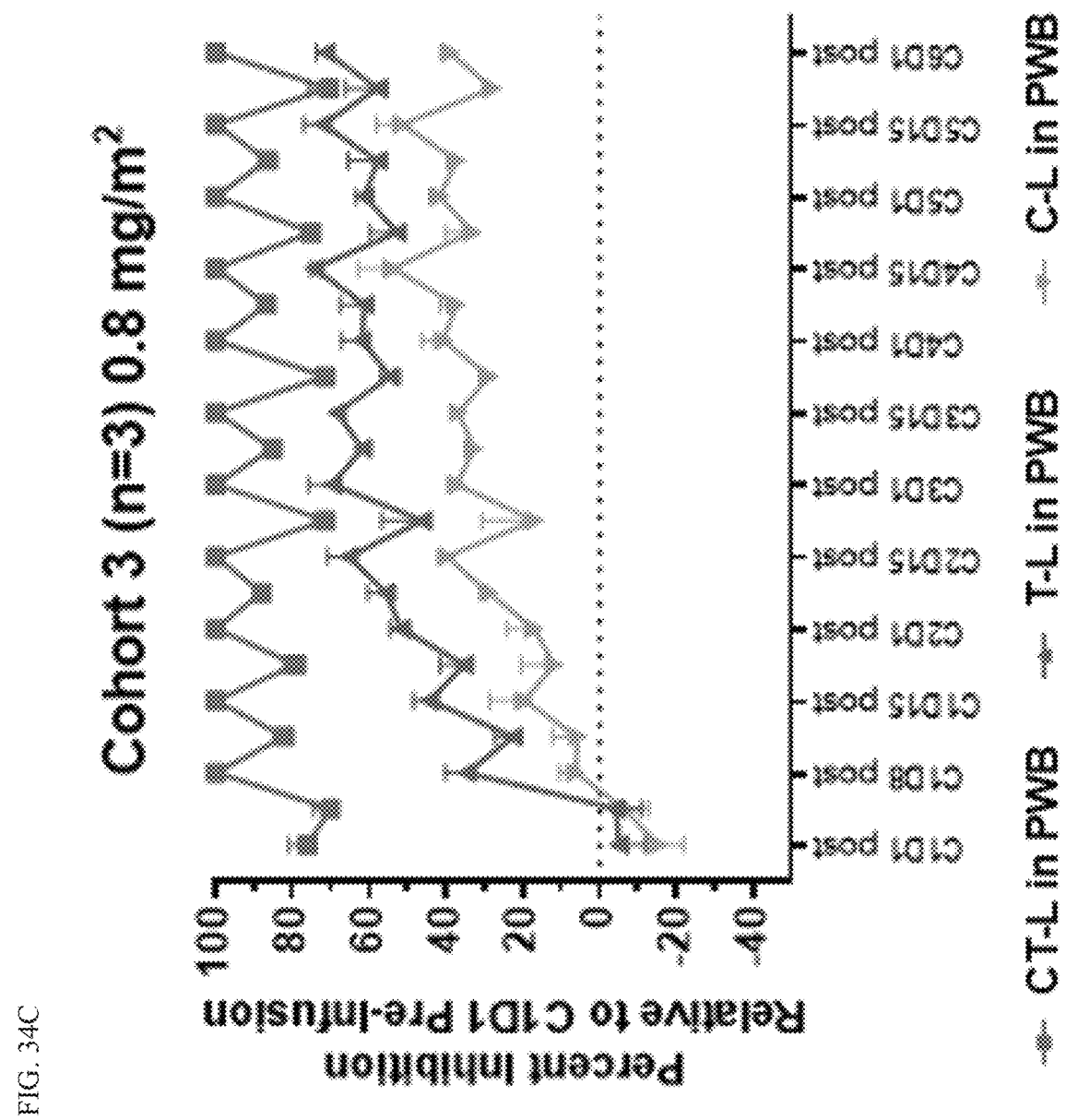
FIG. 34C shows plots demonstrating the dose-related proteasome subunit inhibition in packed whole blood for the combination of marizomib and bevacizumab in cohort 3 (0.8 mg/m$^2$).

FIGS. 34A-C shows plots demonstrating the dose-related proteasome subunit inhibition in packed whole blood for the combination of marizomib and bevacizumab. As shown in FIG. 34, 100% inhibition of CT-L post infusion on C1D8 was observed in cohorts 2 and 3, and on C1D15 in cohort 1. The observed T-L maximum inhibition was about 60% in all cohorts. Maximum T-L inhibition was achieved earlier in cohorts 2 and 3 (e.g., about cycle 3) than in cohort 1 (e.g., about cycle 6). The C-L maximum inhibition was about 30% in cohort 1, and about 40% in cohorts 2 and 3. Hyperactivation of T-L and C-L was apparent in cohort 1, and was less pronounced in cohorts 2 and 3. FIG. 33A shows the percent inhibition for cohort 1, FIG. 33B shows the percent inhibition for cohort 2, and FIG. 33C shows the percent inhibition for cohort 3.

Figure 35:
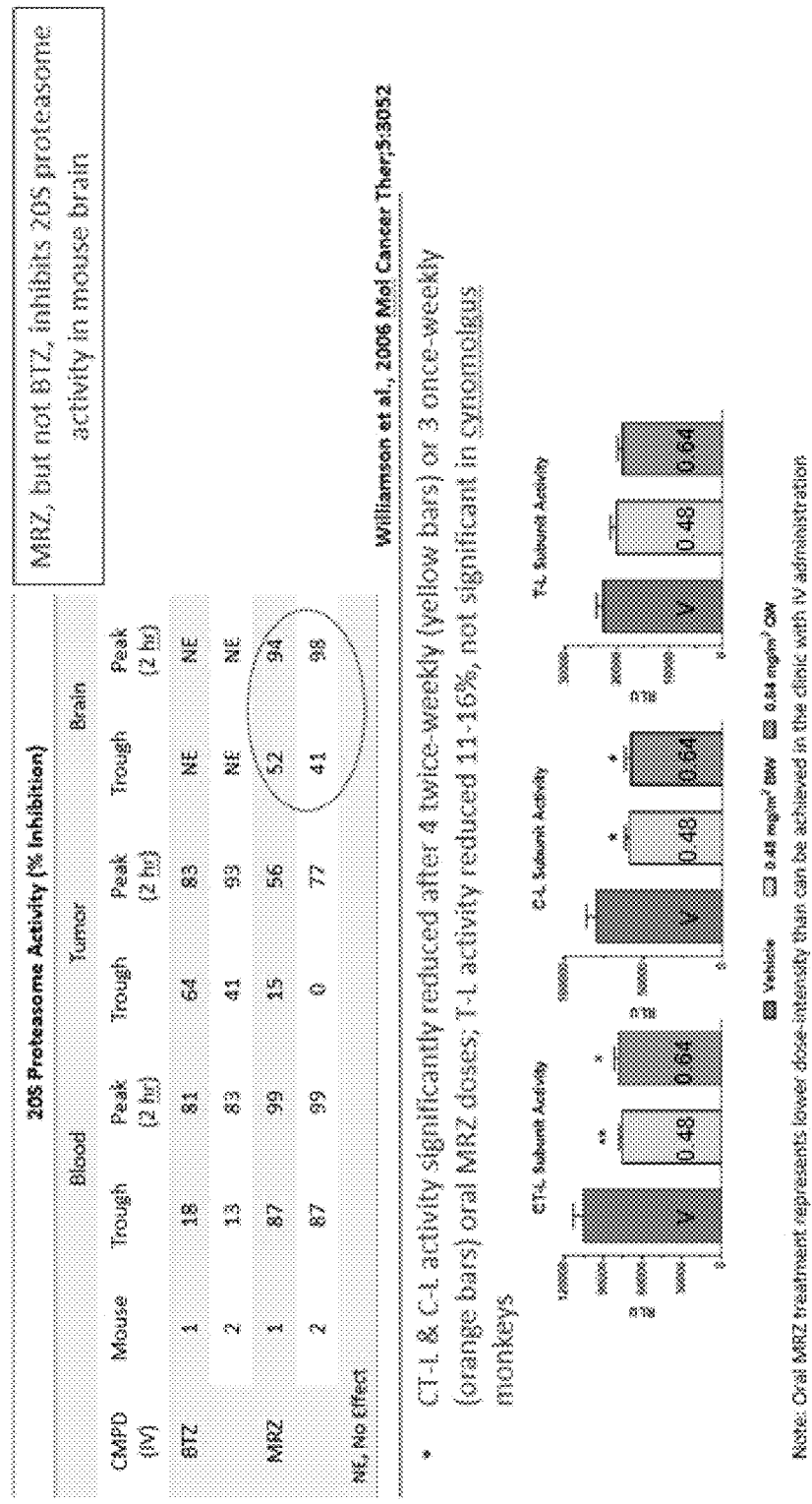
FIG. 35 shows that marizomib inhibits proteasome activity in the mouse and monkey brain.

FIG. 35 shows that marizomib inhibits proteasome activity in the mouse and monkey brain.

Figure 36:
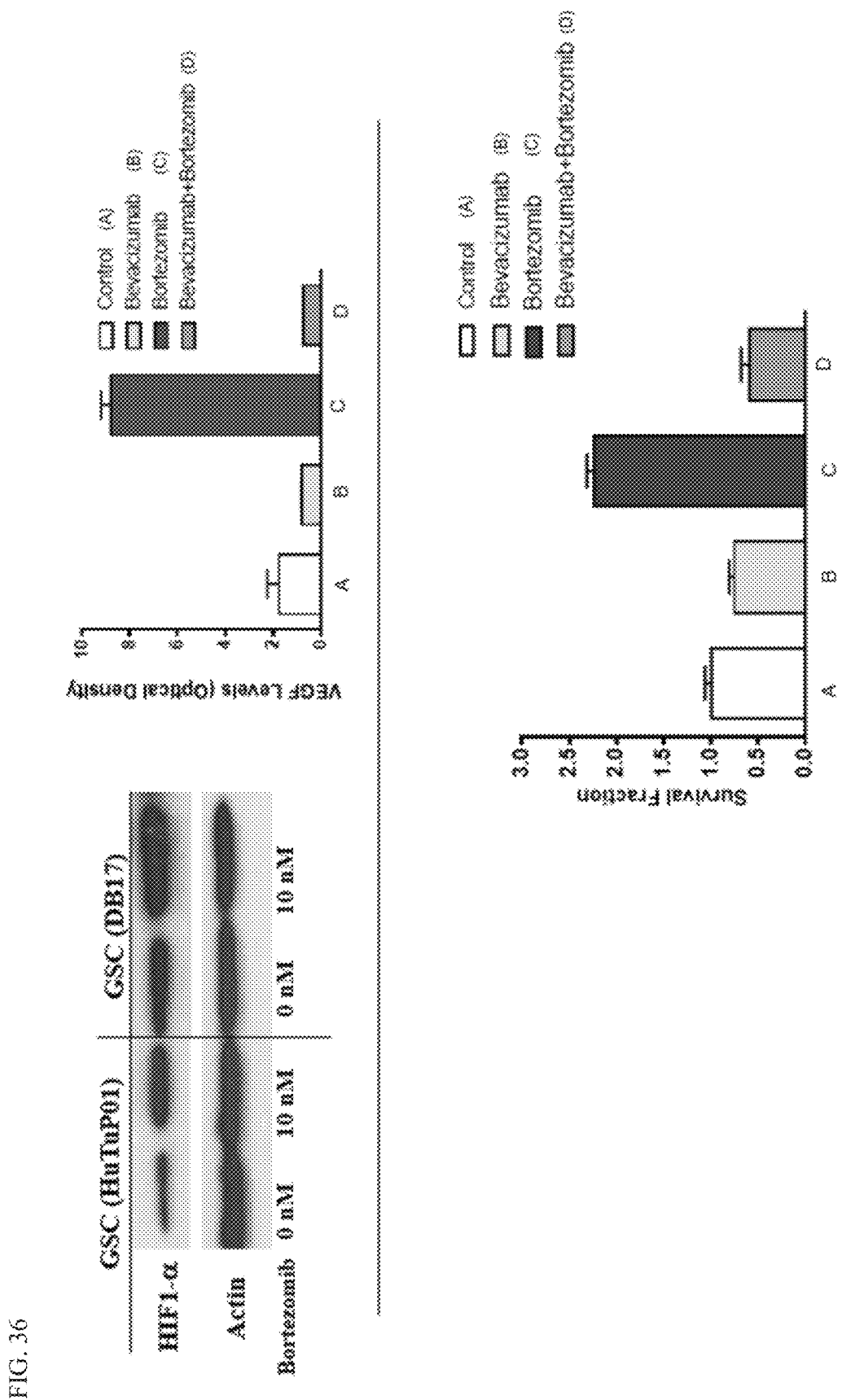
FIG. 36 shows that bortezomib induces HIF1-α and VEGF levels in malignant glioma stem-like cells.

FIG. 36 shows that bortezomib induces HIF1-α and VEGF levels in malignant glioma stem-like cells.

Figure 37:
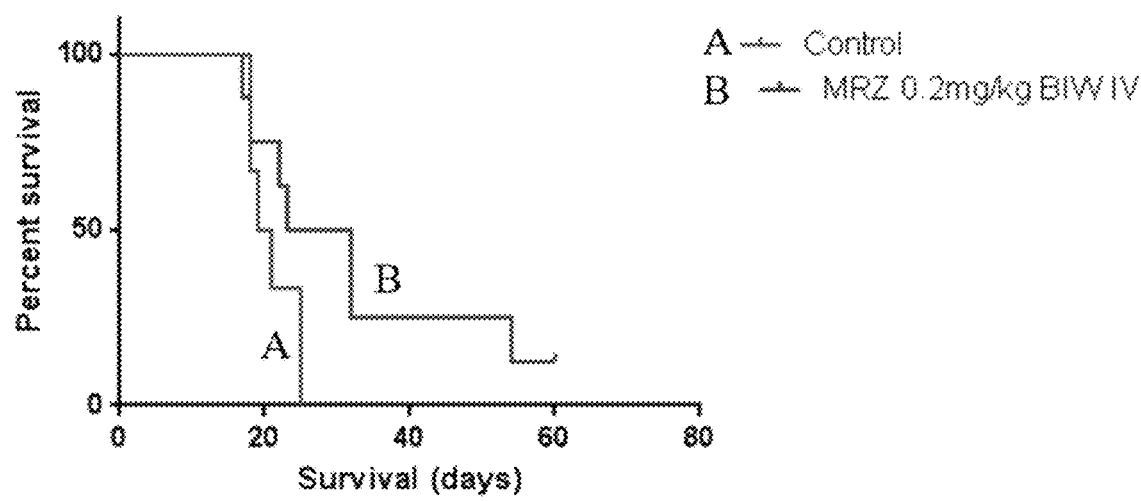
FIG. 37 shows a plot of survival for patients treated with MRZ in intracranial GBM xenograft model.

FIG. 37 shows a plot of survival for patients treated with MRZ in intracranial GBM xenograft model.

Figure 38:
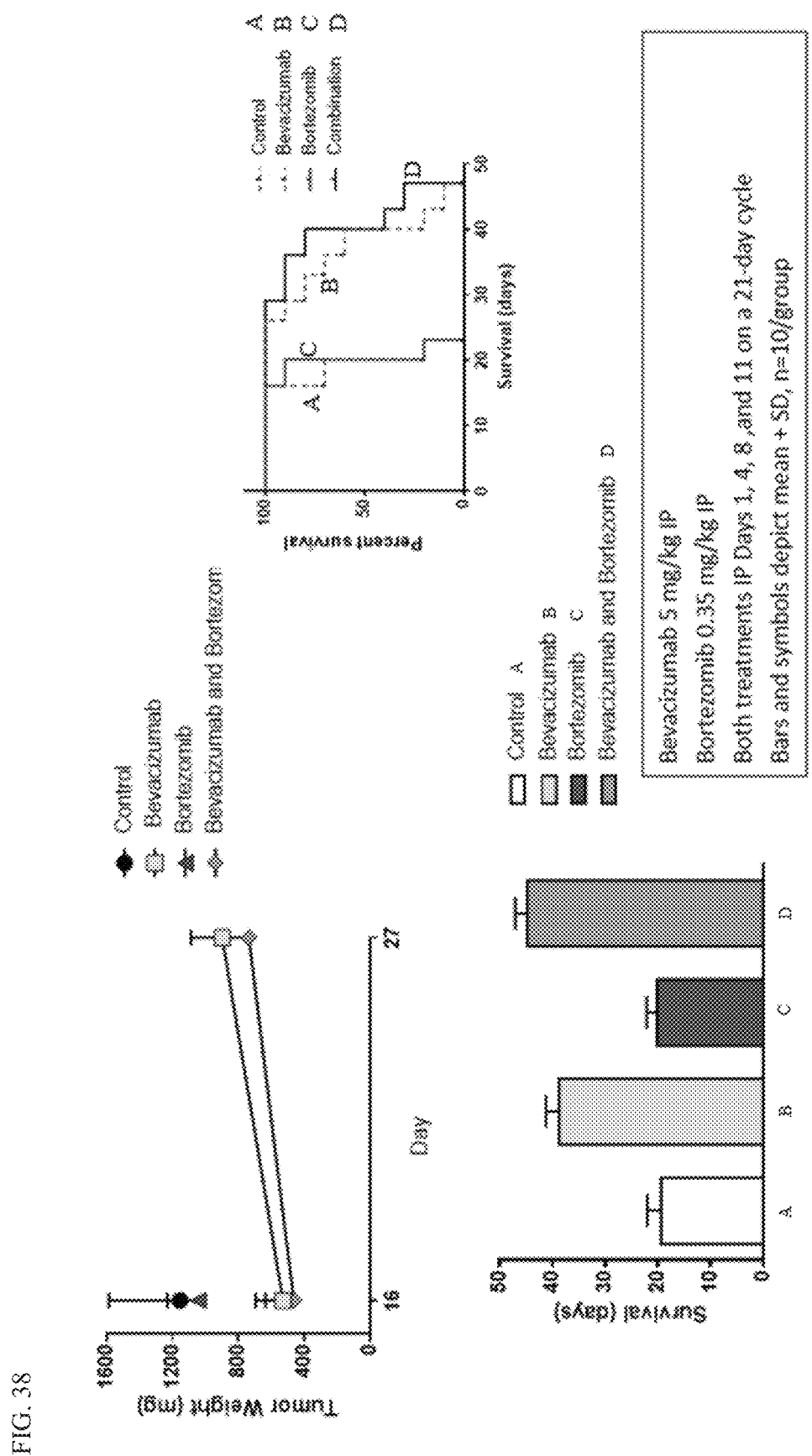
FIG. 38 shows the results of a study combining bortezomib and bevacizumab in a D54-MG tumor xenograft model.

FIG. 38 shows the results of a study combining bortezomib and bevacizumab in a D54-MG tumor xenograft model.

Figure 39:
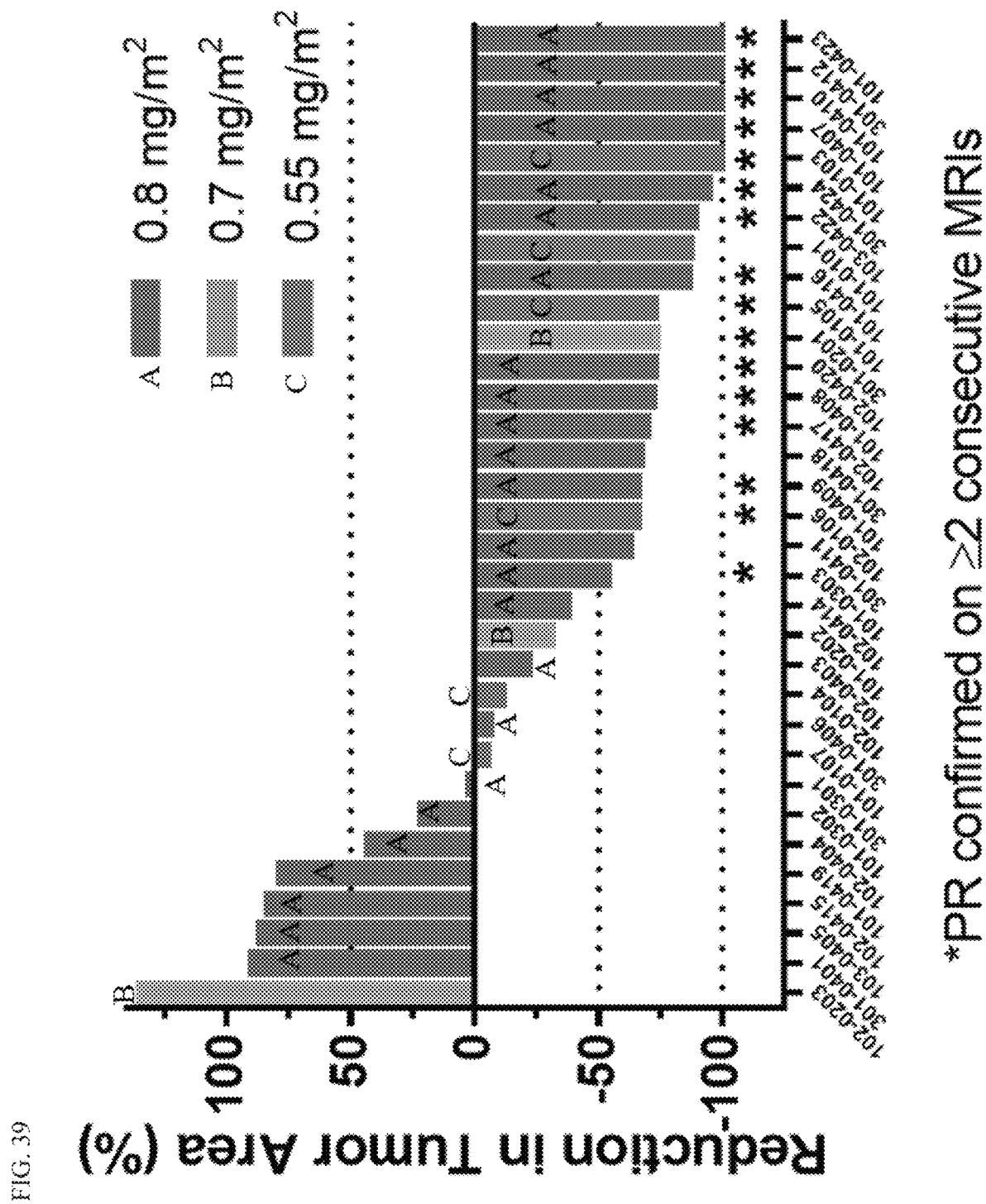
FIG. 39 shows a plot of the tumor response rate by RANO for patients treated with MRZ and BEV.
Figure 45:
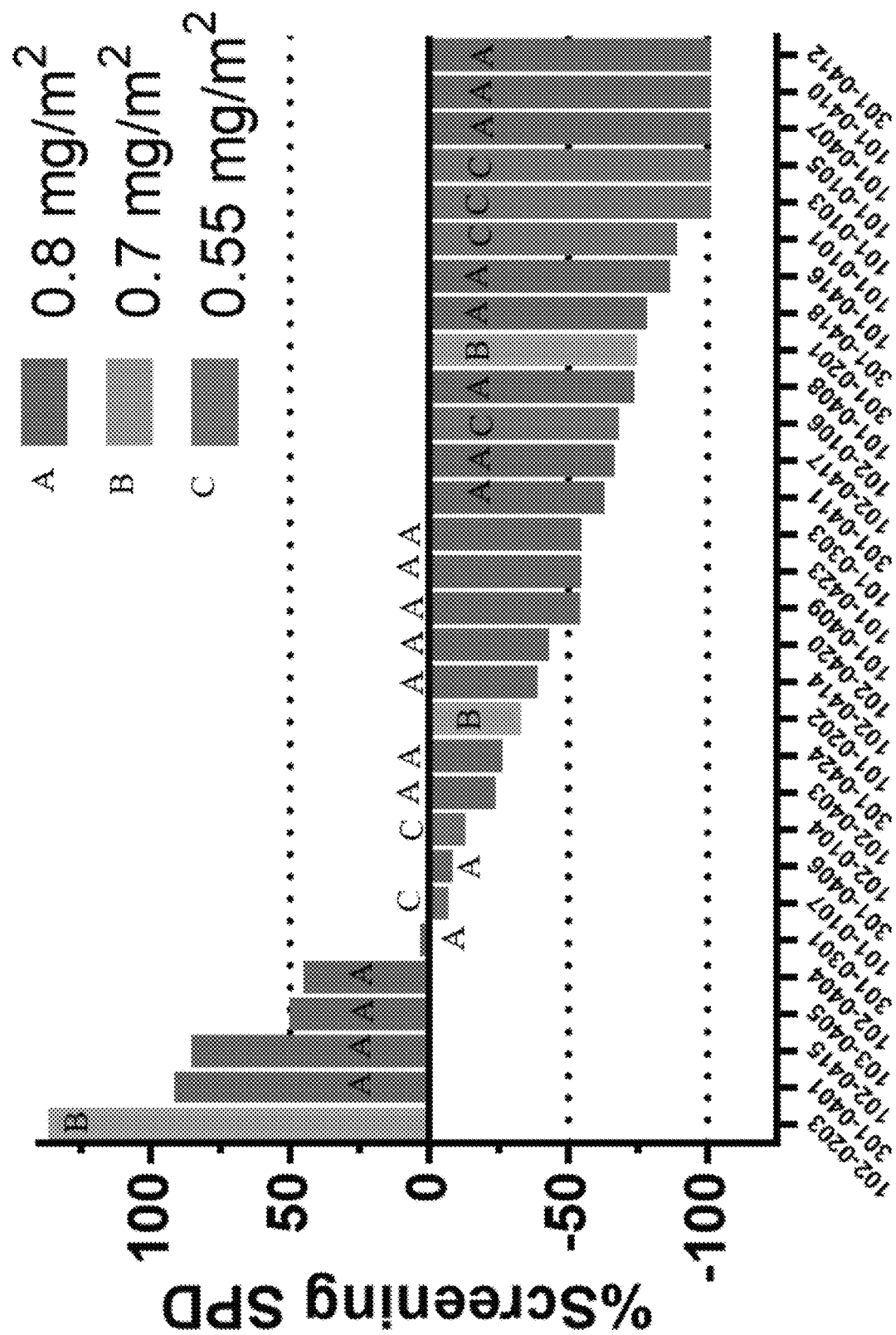
FIG. 45 shows the best response by RANO for patients treated with MRZ and BEV as set forth in Example 5.

FIG. 39 shows a plot of the tumor response rate by RANO for patients treated with MRZ and BEV.

FIG. 40 shows a chart of the RANO response rate for the combination of MRZ and BEV.

FIG. 41 shows a chart comparing marizomib monotherapy with bevacizumab in recurrent glioblastoma.

FIG. 42A shows a chart depicting the history of MRZ monotherapy for a patient (101-0511).

FIG. 43 shows a chart depicting the history of MRZ monotherapy for a patient (101-0503).

FIG. 44 shows a chart depicting the history of MRZ monotherapy for a patient (101-0513).

Routes of Administration

Any of the compounds disclosed herein (e.g., marizomib, bevacizumab, temozolomide, daratumumab) can be administered by any number of conventional techniques known in the art. These modes include systemic or local administration such as oral, intravenous, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Pharmaceutical Compositions

In some embodiments, the present disclosure provides for pharmaceutical compositions comprising marizomib and at least one additional therapeutic agent. For instance, the additional therapeutic agent can be an anti-CD38 antibody (e.g., daratumumab), pomalidomide, bevacizumab, temozolomide, or any combination thereof. For instance, in some embodiments the present disclosure provides a pharmaceutical composition comprising marizomib and daratumumab. In some embodiments the present disclosure provides a pharmaceutical composition comprising marizomib and pomalidomide. In some embodiments the present disclosure provides a pharmaceutical composition comprising marizomib and bevacizumab. In some embodiments the present disclosure provides a pharmaceutical composition comprising marizomib and temozolomide. Illustrative pharmaceutical compositions are tablets and gelatin capsules comprising a Compound of the Disclosure (i.e., marizomib and an additional therapeutic agent) and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions comprising marizomib and an additional therapeutic agent can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compositions can be also formulated as a suppository that can be prepared from fatty emulsions or suspensions; using polyalkylene glycols such as propylene glycol, as the carrier.

The disclosed compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of marizomib and the additional therapeutic agent or agents by weight or volume.

EXAMPLES

Example 1: Treatment of CNS-Myeloma Using Marizomib

This example sets forth seven case studies in which CNS-MM (i.e., multiple myeloma with CNS involvement) was treated using marizomib alone or in combination with other agents.

Case 1: Treatment of IgA Kappa Multiple Myeloma with CNS Progression Using Marizomib A 32-year-old man presented with severe back pain leading to diagnosis of IgA kappa MM in February 2008. At presentation, he had 70% plasma cells in the bone marrow with a complex karyotype (deletion of 13q and 17p, and gain of 1q). He received 4 cycles of cytoxan, bortezomib and dexamethasone (CyBorD), followed by melphalan and autologous stem cell transplantation (ASCT) achieving a very good partial response (VGPR). Thalidomide and bortezomib maintenance was continued for one year, followed by daily thalidomide (50 mg). In May 2010, his disease progressed and he received lenalidomide and dexamethasone with no response. Subsequent CyBorD treatment resulted in a partial response. In March 2011 he received a second ASCT followed in August 2011 with an allogeneic HCT from a matched sibling after non-myeloablative conditioning (melphalan and fludarabine). Graft-versus-host disease (GVHD) prophylaxis consisted of mycophenolate mofetil and tacrolimus; he had limited chronic sclerodermatous lesions on the skin achieving a complete remission. In March 2014, he presented with a non-secretory relapse with multiple active lytic bony lesions on PET/CT (kappa restricted plasma cells on biopsy) and received carfilzomib, pomalidomide, and dexamethasone, achieving a negative PET before relapsing with a pathologic fracture (left humerus) requiring placement of a rod and radiation in March 2015. Three cycles of panobinostat and bortezomib were received with no response, and subsequent development of plasmacytomas with multiple fractures in the ribs requiring radiotherapy for pain control.

In June 2015, he presented with severe headaches, numbness of the chin, and visual changes. Mill suggested leptomeningeal lesions and the CSF was positive for kappa-restricted plasma cells with elevated protein and normal glucose (Table 1). He started IT chemotherapy (methotrexate 12 mg, cytarabine 50 mg, and prednisone 100 mg) twice weekly for 4 weeks, with worsening neurological symptoms (headaches, double vision, and inability to walk) followed by cranio-spinal radiation (5000 cGy) and continued weekly IT chemotherapy. He had a transient clinical improvement, with rapid deterioration and worsening neurological symptoms, including hoarseness, difficulty swallowing, double vision requiring an eye patch, and he was unable to walk without support. He received further localized radiation to the brain and IT therapy was increased to three times weekly, with no response. Mill now showed additional lesions (FIG. 1).

Beginning in October of 2015, he received marizomib on compassionate use protocol at 0.5 mg/m$^2$ over 10 minutes weekly×3; cycle repeated every 4 weeks for 2 cycles and then the dose was increased to 0.7 mg/m$^2$, at which time he demonstrated rapid and sustained clinical improvement. Although CSF plasmacytosis persisted at a low level (99% reduction), serum LDH decreased. In February 2016, five months after initiating marizomib therapy, he had an enlarged axillary lymph node, which on histology revealed an extramedullary plasmacytoma with CD38+ plasma cells. Daratumumab (16 mg/kg weekly×2 months) was added with continued marizomib. Neurologically, there were further improvements observed; he was able to remove the eye patch with resolution of the double vision and became fully ambulatory. No adverse events were reported. An MM image of the patient's head two months after beginning treatment with marizomib is shown in FIG. 2. The patient experienced partial response and resolution of neurological symptoms for five months. However, by April 2016, six months after completion of marizomib therapy this clinical picture deteriorated with worsening of neurological symptoms and more bony fractures. Interestingly, CSF plasma cells at this time remained negative for CD38. The patient elected to stop therapy and was referred to hospice for comfort care. FIG. 3 shows a plot of the percent CSF plasmacytosis (triangle) and Serum LDL (square) as a function of time.

The progression of the patients' disease and treatment is summarized in Table 1.

TABLE 1

Disease Progression and Therapeutic Intervention of for Case 1

| CNS-MM | Diagnosis | 2 months | 3 months |
|---|---|---|---|
| Symptoms | Headache Chin numbness | Minimal Improvement | Worsening: Double vision, inability to talk |
| CSF | | | |
| Total Protein | 103 | 50 | 109 |
| Plasmacytosis | 20% | 10% | 94% |
| Flow cytometry | +CD138/38 | + | + |
| Serum LDH (units/dL) | 500 | 1900 | 2770 |
| Therapy | IT | Craniospinal XRT | Marizomib + Dexamethasone |

TABLE 1-continued

Disease Progression and Therapeutic Intervention of for Case 1

| CNS-MM | 4-7 months | 8 months | 10 months + |
|---|---|---|---|
| Symptoms | Complete Resolution of symptoms | Axillary LN Cytoplasmic Kappa with surface expression of CD138/38/56 | Worsening Neurological & systemic |
| CSF | | | |
| Total Protein | 59 | 60 | 100 |
| Plasmacytosis | 9% | 63% | 19% |
| Flow cytometry | + | + | CD138+/38− (lost expression of CD38) |
| Serum LDH (units/dL) | 630 | 1000 | 1032 |
| Therapy | Marizomib + Dexamethasone + Added Daratumumab (at 8 months) | | |

TABLE 2

Treatment Regimen for Case 1

| Cycle | IV MRZ (mg/m$^2$) | IV Daratumumab (mg/kg, weekly) | Oral DEX (mg) |
|---|---|---|---|
| 1-2 | 0.55 | 0 | 20 |
| 3-5 | 0.7 | 0 | |
| 6-7 | 0.7 | 16 | |

Case 2: Treatment of IgG Lambda Multiple Myeloma with CNS Progression Using Marizomib A 52-year-old man was diagnosed with IgG lambda MINI (ISS III) in February 2009. He presented with back pain related to vertebral compression fracture. A bone marrow biopsy showed 90% involvement with lambda restricted plasma cells. This patient had high risk cytogenetics including hypodiploidy, and deletion of chromosomes 13, 14, 17, 18 and 22. He received three cycles of lenalidomide, bortezomib and dexamethasone (RVD) followed by high dose melphalan and ASCT, achieving a VGPR. With high-risk disease, he underwent matched sibling allo-HCT in December 2009 after non-myeloablative conditioning (total body irradiation 200 cGy). GVHD prophylaxis consisted of mycophenolate and cyclosporine; immunosuppression was stopped by August 2010 and he started lenalidomide (10 mg/day) maintenance (March 2010). He achieved a stringent CR for 5 years at which point lenalidomide maintenance was discontinued (March 2015).

In November 2015, a biochemical progression was documented (monoclonal protein IgG lambda in the serum at 0.28 g/dl). The patient was asymptomatic so no treatment was offered. In January 2016, he presented with weakness and numbness of hands with inability to write and perform fine motor functions. He rapidly developed loss of balance, gait incoordination and increasing pain in his lower back. On neurological examination he had perineal/saddle anesthesia, but no bowel or bladder incontinence. Serum monoclonal protein at that time increased to 0.41 g/dl. CNS involvement was confirmed with the MRI of the spine showing new abnormal enhancing epidural soft tissue (FIG. 4). Lumbar puncture confirmed CNS MM with detection of plasma cells (Table 2). He received craniospinal irradiation (5000 cGy) with pomalidomide and dexamethasone which was associated with minimal improvement in the back pain but persistent weakness of the hands and saddle anesthesia. He received 1 dose of intrathecal methotrexate with persistent CNS symptoms.

Marizomib was given on compassionate use protocol (see above) at 0.7 mg/m² as a 10 min IV infusion on days 1, 8 and 15 along with dexamethasone on a 28 day Cycle. After 2 cycles of marizomib, the patient's clinical symptoms disappeared; with sustained complete resolution of CSF plasmacytosis and CSF monoclonal spike. MM spine showed improvement in epidural enhancement. The patient continues to do well and is currently undergoing the 4th cycle of treatment with sustained resolution of saddle anesthesia and no further signs of cauda equina symptoms. FIG. 5 shows an MRI image of the patient's lumbar spine two months after beginning treatment with marizomib. No adverse events or serious adverse events were observed. This patient's disease continues to be undetectable in the CNS after 7 months of MRZ therapy. FIG. 6 shows a plot of the percent CSF plasmacytosis of the subject of Example 1, Case 2 as a function of time.

The progression of the patient's disease and treatment is summarized in Table 3.

TABLE 3

Disease progression and Therapeutic Intervention for Case 2

| CNS-MM (IgG lambda) | Diagnosis | 2 months | 3-6 months | |
|---|---|---|---|---|
| Symptoms | Hand/arm weakness Ataxia Sexual symptoms | Minimal Improvement | Complete resolution of symptoms | Patient currently on third cycle of Marizomib + dexamethasone and doing well. |
| CSF | | | | |
| Total Protein | 195 | 30 | 35 | |
| Flow cytometry | +CD138/38 cells | NA | — | |
| M protein | 33% | 3% | — | |
| Therapy | Crainospinal XRT | IT | Marizomib + dexamethasone | |

TABLE 4

Treatment Regimen for Case 2

| Cycle | IV MRZ (mg/m²) | Oral POM (mg, D 1-21) | Oral DEX (mg) |
|---|---|---|---|
| 1-7 | 0.7 | 0 | 10 |
| 8+ | 0.7 | 4 | |

Case 3: Treatment of IgA Kappa Multiple Myeloma with Marizomib

A 46 year old female was diagnosed with IgA kappa multiple myeloma in 2010. Her original therapy was Velcade followed by ASCT. In 2014 she presented with right radicular pain in her right leg and neurological symptoms in her right arm which led to a diagnosis of meningeal myelomatosis. Intrathecal radiotherapy cleared her CSF and was followed with pomalidomide therapy. In July 2014 she had an allogeneic stem cell transplant and was subsequently placed on pomalidomide maintenance. In June 2016 she presented with pain in her right lower spine radiating to her leg and MRI suggested CNS recurrence. The patient received a pulse of steroids and radiation therapy.

In July 2016, marizomib was given on compassionate use protocol at 0.8 mg/m² as a 10 min IV infusion on days 1, 8 and 15 along with dexamethasone on a 28 day Cycle. Pomalidomide was also given at 4 mg daily on days 1 through days 21. After 2 cycles of marizomib, the patient's CSF M-protein markers reduced and she tolerated treatment well.

Figure 7:
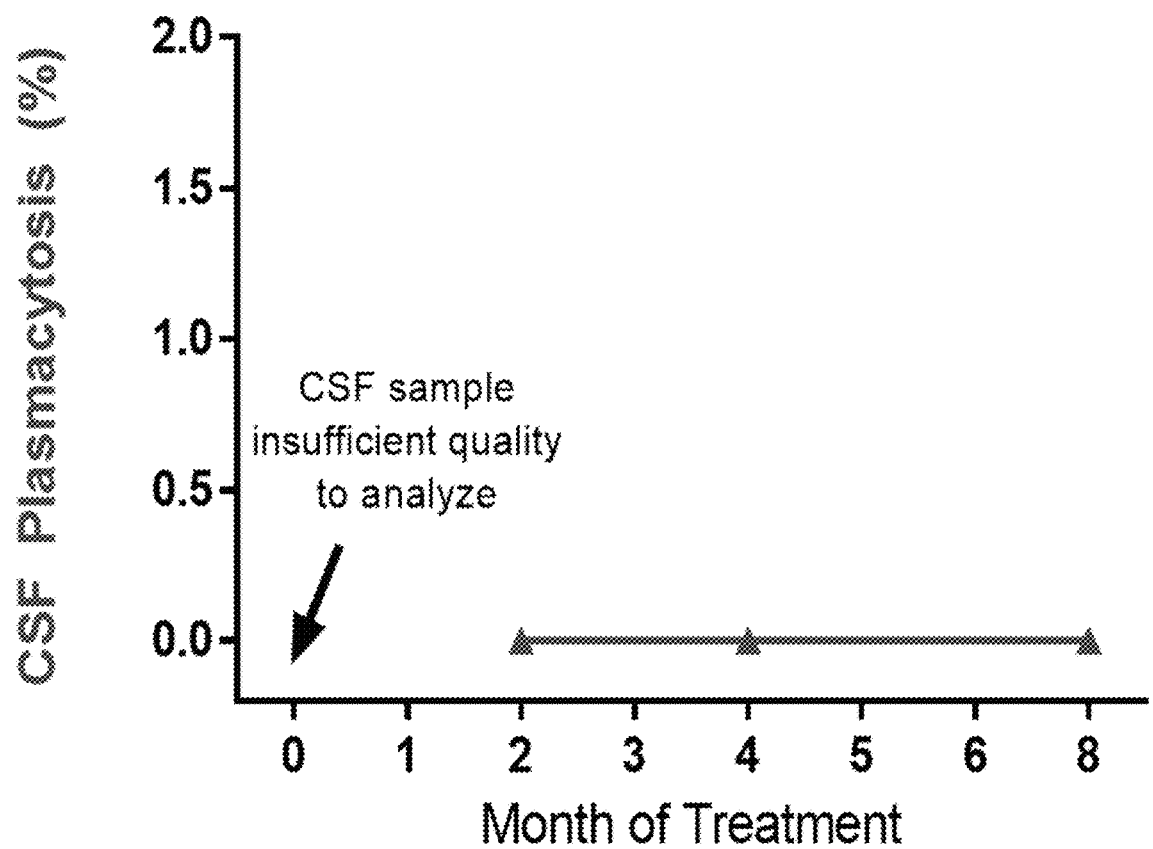
FIG. 7 shows a plot of the percent CSF plasmacytosis of the subject of Example 1, Case 3 as a function of time.

The patient has had undetectable CSF plasmacytosis since C3D1 (day 1 of the third 28-day cycle of marizomib therapy). No detectable serum markers and no FDG-avid (fluorodeoxyglucose-avid) lesions on PET or CT scans were identified. There was insufficient cellular material in the CSF to test via flow cytometry prior to MRZ treatment. The patient has completed cycle 8 of treatment and continues to tolerate treatment with resolution of clinical symptoms. A grade 1 adverse event was reported (shortness of breath) after cycle 6. A medi-port infection on right chest was observed, and the port was removed. The patient has an ongoing complete response with no evidence of active disease and continues to tolerate treatment well. FIG. 7 shows the patient's CSF plasmacytosis as a function of time.

TABLE 5

Dosage Regimen for Case 3

| Cycle | IV MRZ (mg/m²) | Oral POM (mg, D 1-21) | Oral DEX (mg) |
|---|---|---|---|
| 1-8+ | 0.8 | 4 | 20 |

Case 4: Treatment of Multiple Myeloma with CNS Progression Using Marizomib

A 71 year old patient was initially diagnosed in 2010. The patient was treated with ASCT following velcade induction. The patient relapsed in 2013 and was subsequently treated with thalidomide, lenalidomide, velcade and carfilzomib. The patient was refractory to all of these therapies. In 2016 the patient presented with double vision and the MRI demonstrated lesions in the clivus and orbits of the skull. Analysis of the CSF revealed myeloma plasma cells in this compartment further demonstrating progression of myeloma into the CNS.

In August 2016, marizomib was given on compassionate use protocol at 0.7 mg/m² as a 10 min IV infusion on days 1, 8 and 15 along with dexamethasone on a 28 day Cycle. Pomalidomide was dosed at 4 mg daily on days 1 through days 21. The patient has currently completed two cycles of therapy and results are pending on their disease status.

The patient had a partial response at the end of cycle 2. Following cycle 3, the patient experienced subsequent disease progression. The treatment was well-tolerated with no adverse events reported.

TABLE 6

| | Dosage Regimen for Case 4 | | |
| --- | --- | --- | --- |
| Cycle | IV MRZ (mg/m$^2$) | Oral POM (mg, D 1-21) | Oral DEX (mg) |
| 1-3 | 0.7 | 4 | 20 |

Case 5: Progression Following First Marizomib Dose

A 57-year old female presented with multiple myeloma with multiple extramedullary plasmycytosmas to the neck and brain with mass effects. Treatments included 3 cycles of palliative cranio-spinal radiation, stem cell transplantation, and stem cell boost with persistent CNS symptoms.

The patient was dosed once with marizomib and had a recurrent pleural effusion following dosing and was hospitalized. The patient discontinued use due to disease progression. The pleural effusion was identified as a serious adverse event.

TABLE 7

| | Dosage Regimen for Case 5 | |
| --- | --- | --- |
| Cycle | IV MRZ (mg/m$^2$) | Oral DEX (mg) |
| 1 | 0.7 | 20 mg |

Case 6: Partial Response Ongoing at 5 Months

A 39-year old female presented with multiple myeloma in October 2012. Treatment included RVD, ASCT, BTZ/POM/Lo-Dex. The patient presented with relapse to CNS in January 2016. Treatment included a high dose of steroids, IT-chemotherapy, and Daratumumab with continued CSF plasmacytosis.

Figure 8:
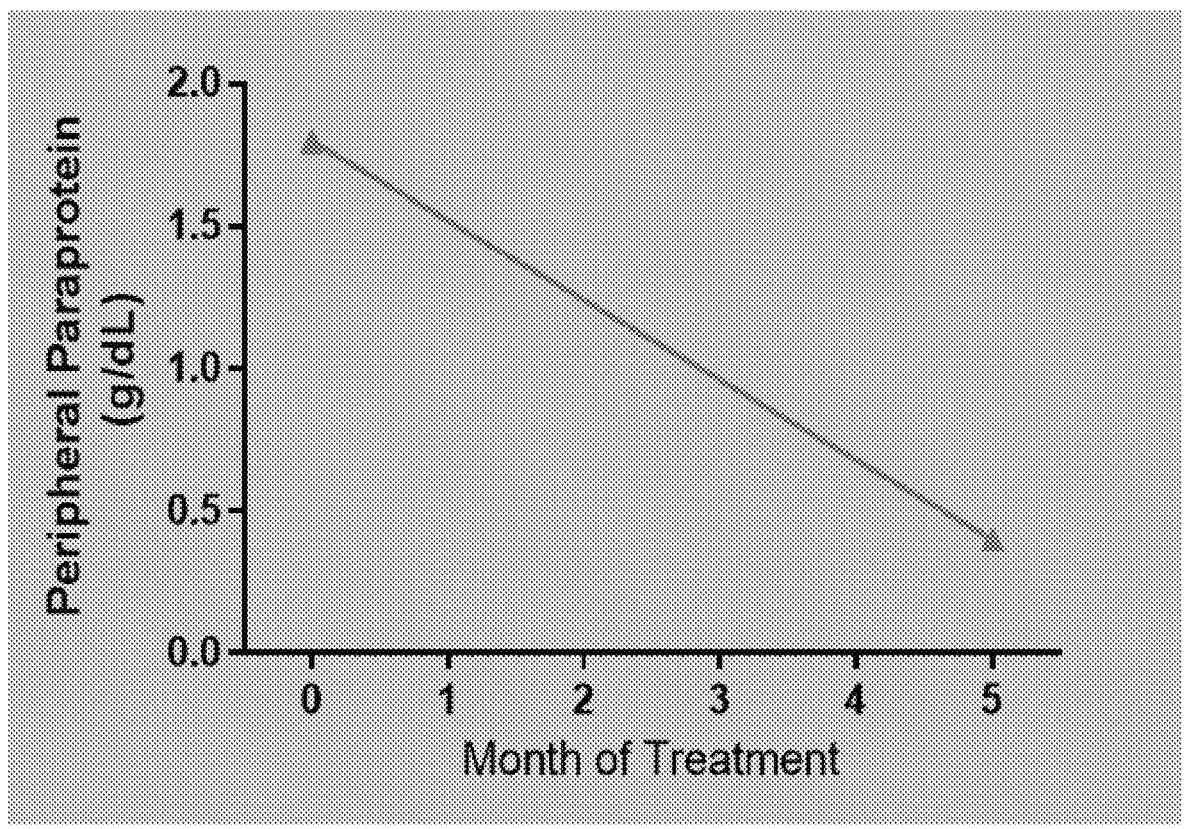
FIG. 8 shows a plot of the peripheral paraprotein of the subject of Example 1, Case 6 as a function of time.

The patient was treated with marizomib, oral pomalidomide, and oral dexamethasone. The patient showed a durable partial response. The patient showed a 77% reduction in systemic paraprotein (baseline: 1.8 g/dL to 0.4 g/dL). An MRI of the brain and spine demonstrated a resolution of CNS disease. There was a grade 2 adverse event: reactivation of a plantar wart, possibly related to marizomib. The patient has had an ongoing systemic partial response after 5 months of treatment and diseae resolution by MRI. FIG. 8 shows the concentration of peripheral paraprotein (g/dL) for this patient as a function of time.

TABLE 8

| | Dosage Regimen for Case 6 | | |
| --- | --- | --- | --- |
| Cycle | IV MRZ (mg/m$^2$) | Oral POM (mg, D 1-21) | Oral DEX (mg) |
| 1-5+ | 0.7 | 4 | 20 |

Case 7: Progressive Disease after 2 Months

A 39-year old man presented with multiple myeloma with plasmacytoma in March 2014. Treatment included VCD, ASCT, BTZ/POM/Lo-Dex. The patient presented with relapse to CNS in December 2016 with lesions in the spinal canal (T10T11) and left orbital/frontal involvement. Treatment included high-dose steroid and XRT (radiotherapy).

The patient experienced extensive progression while on MRZ/Revlimid/Dex. No adverse events or safety concerns were noted. The patient had progressive disease at the end of cycle 2 assessment.

TABLE 9

| | Dosage Regimen for Case 7 | | |
| --- | --- | --- | --- |
| Cycle | IV MRZ (mg/m$^2$) | Oral LEN, (mg, D 1-D 21) | Oral DEX (mg) |
| 1-2 | 0.7 | 25 | 10 |

Summary: Response Rate in CNS-Myeloma Patients

Figure 9:
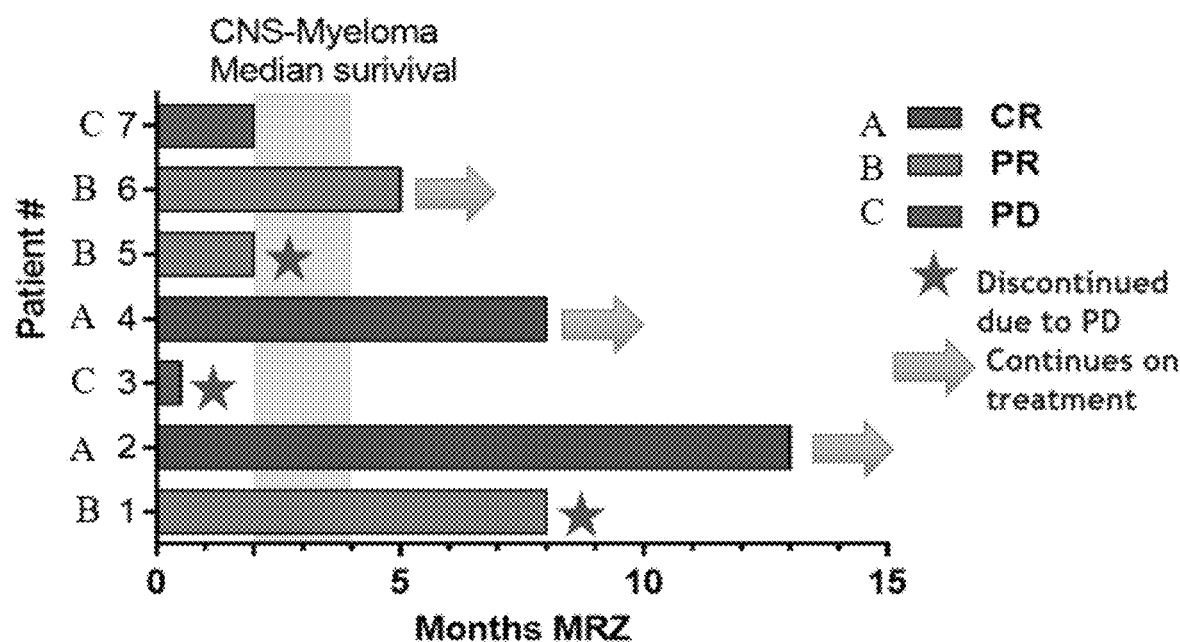
FIG. 9 shows an IMWG Response Assessment of Systemic Disease for each of the cases presented in Example 1.

FIG. 9 shows an IMWG (international myeloma working group) Response Assessment of Systemic Disease for each of the cases presented in this example. The overall response rate was 5/7, with 3 partial responses and 2 complete responses. All patients had systemic disease with CNS involvement. Marizomib treatment resulted in systemic responses as per IMWG response criteria in addition to neurological improvements.

TABLE 10

| | Summary of Results of CNS-MM Studies | |
| --- | --- | --- |
| Case # | IMWG Assessment Systemic Disease | Neurological Assessment |
| 1 | PR | Reduction of CSF plasma cells (90% C2D1) |
| 2 | CR | Stable remission by MRI No CSF plasma cells detected from C3 onwards |
| 3 | CR | No evidence of FDG-avid lesions on PET/CT since C3 |
| 4 | PR | Transient improvement through C2 with progression during C3 |
| 5 | PD | N.D. |
| 6 | PR | Complete resolution of central disease in brain and spine by MRI |
| 7 | PD | N.D. |

TABLE 11

| | | Summary of CNS-Myeloma Compassionate Use Patients | | |
| --- | --- | --- | --- | --- |
| Case # | Start Date | Current Cycle/Status | Response | Safety |
| 1 | October 2015 | Discontinued on C7 | Rapid and sustained clinical and neurologic improvement by C2: Reduction in CSF plasmacytosis and serum LDH | MRZ was well tolerated with no adverse events reported |

TABLE 11-continued

Summary of CNS-Myeloma Compassionate Use Patients

| Case # | Start Date | Current Cycle/Status | Response | Safety |
|---|---|---|---|---|
| 5 | April 2016 | Discontinued C1 | Resolution of double vision Patient became fully ambulatory Pleural effusion following C1D1 treatment, non-evaluable | AE due to PD, unrelated to MRZ |
| 2 | February 2016 | Ongoing C13 | CR by serology; stable remission by MRI | No concerning AEs |
| 3 | July 2016 | Ongoing C8 | CR - no evidence of active disease: No detectable serum marker and no FDG-avid lesions on PET/CT M-protein undetectable since Sep. 15, 2016. PET/CT was repeated Dec. 27, 2016 and still showed no evidence of lesions | Grade 1 shortness of breath Dec. 15, 2016, mediport infection on R chest (port removed) |
| 4 | August 2016 | Discontinued on C3 | Best response PR with PD after C3 | Tolerated treatment well |
| 6 | November 2016 | Ongoing C5 | Best Response to date PR: Paraprotein decrease from 18 g/L to 4 g/L MRI of brain and spine demonstrate resolution of central disease | Overall, no safety concerns. Grade 2 Viral reactivation of a plantar wart/verruca possibly related to MRZ. |
| 7 | December 2016 | Discontinued on C2 | "Extensive progression while on MRd" | No AEs or safety concerns |

As set forth herein, 7 patients were treated under single patient compassionate use protocols with MRZ for CNS-myeloma. Marizomib was well-tolerated. No CNS-adverse events were reported. Five of 7 patients showed at least a partial response. One patient has been on the study for 13 months with complete resolution of both systemic CNS disease. Another patient has completed nine cycles of treatment with a systemic complete response and resolution of CNS disease.

Example 2—Phase 1B, Multicenter, Open-Label Study of Marizomib Combined with Temozolomide and Radiotherapy in Patients with Glioma Objectives
Primary Objectives To determine the maximum tolerated dose (MTD) and RP2D of MRZ in combination with TMZ+RT (Concomitant Treatment). Accordingly, for concomitant treatment, the present disclosure provides for administration of MRZ, TMZ and RT substantially simultaneously. Without wishing to be bound by theory, in some embodiments all three therapies can work together. In some embodiments, RT can add to the effect seen with the administration of MRZ and/or TMZ.

To determine the MTD and RP2D of MRZ in combination with TMZ (Adjuvant Treatment). Accordingly, for adjuvant treatment, the present disclosure provides for administration of MRZ and TMZ substantially simultaneously. In some embodiments, the MRZ can add to the effect of TMZ. In some embodiments, the TMZ can add to the effect of the MRZ.

In some embodiments, the present disclosure also provides for the administration of MRZ and RT substantially simultaneously.

Secondary Objectives

To evaluate the safety of the combination of MRZ+TMZ+RT (Concomitant Treatment).

To evaluate the safety of the combination of MRZ+TMZ (Adjuvant Treatment).

To confirm the R2PD of MRZ in an expanded group of patients who receive MRZ, TMZ, and RT as part of Concomitant Treatment and who continue on to Adjuvant Treatment with MRZ and TMZ.

To evaluate activity of the combination of MRZ+TMZ (+RT in Concomitant Treatment): e.g., (i) Progression-Free Survival (PFS); (ii) Overall Survival (OS).

Exploratory Objectives

To evaluate Response Rate (RR using RANO 2010 criteria) during Adjuvant Treatment.

To evaluate the pharmacokinetics (PK) of MRZ and TMZ when administered in combination in the patient population.

To evaluate baseline tumor proteasome activity, gene signature and transcriptional profiling using pre-study, archived tissue samples, pending methodologic feasibility assessments.

To evaluate neurological coordination assessment using the Scale for the Assessment and Rating for Ataxia (SARA).

Study Design

This is a Phase 1b, open-label, 3+3, dose-escalation followed by dose-expansion study in patients with newly diagnosed G4 MG who have not previously received any local or systemic therapy for their G4 MG. The study will examine the effect of the addition of MRZ to standard of care treatment utilizing two study arms: Concomitant Treatment in which MRZ will be combined with TMZ+RT and Adjuvant Treatment in which MRZ will be combined with TMZ. The study will be conducted in two Stages. In Stage 1 (Dose-Escalation): 3 to 6 evaluable patients per MRZ dose cohort will be enrolled in each study arm. In Stage 2 (Dose-Expansion): a minimum of 12 and up to approximately 18 additional evaluable patients will be enrolled in a cohort in which Concomitant Treatment is followed by Adjuvant Treatment to confirm the MTD for each treatment regimen as determined in the Dose-Escalation (Stage 1), and to assess preliminary activity of the RP2D. A total of approximately 48 patients will be enrolled in Stages 1 and 2 combined. Patients may not be enrolled in more than 1 MRZ dose cohort per arm.

Study Treatments

TMZ will be provided by the Investigator via prescription to patients who are enrolled into the Stage 1 and Stage 2 portions of this Phase 1 study.

Stage 1

Concomitant Treatment

Concomitant Treatment consists of a 6 week (42 day) treatment period, followed by a 4 (−1) week break from treatments. All patients will receive intravenous (IV) MRZ infusion on Days 1, 8, 15, 29, and 36 as a 10 minute infusion. IV hydration will be given prior to the infusion. Focal RT will be administered once daily, 5 days/week, for 30 doses over 6 weeks to a total dose of 60 Gy, starting on Day 1. TMZ will be administered once daily, 7 days/week, for 6 weeks, starting on Day 1, at a dose of 75 mg/m$^2$. Patients who complete Concomitant Treatment may continue on to Adjuvant Treatment.

Adjuvant Treatment

All patients will receive IV MRZ infusion on Days 1, 8, and 15 as a 10 minute infusion, in 28-day cycles. IV hydration will be given prior to the infusion. TMZ will be administered daily for 5 consecutive days, starting on Day 1 of Cycle 1 (C1D1), at a dose of 150 mg/m$^2$. If tolerated in Cycle 1, the TMZ dose will be increased on Day 1 of Cycle 2 (C2D1) to a dose of 200 mg/m$^2$.

Stage 2

All patients will be treated with Concomitant Treatment of MRZ+TMZ+RT using the MRZ RP2D determined in Stage 1 followed by Adjuvant Treatment of MRZ+TMZ using the RP2D determined in Stage 1. MRZ will be administered as a 10-minute, IV infusion on Days 1, 8, 15, 29, and 36 of the Concomitant Treatment, and on Days 1, 8, and 15 of every 28-day Cycle of Adjuvant Treatment. IV hydration will be given prior to each MRZ infusion.

Patients will receive up to 12 cycles of MRZ+TMZ during Adjuvant Treatment, unless discontinued for disease progression, unacceptable toxicity, withdrawal of consent, or termination of the study. Adjuvant Treatment continuation with MRZ after 12 cycles may be decided upon in discussions between the sponsor and the investigator. In the event that one drug (TMZ or MRZ) is discontinued for reasons other than disease progression, the other will then continue as a single agent.

Dose-Limiting Toxicity

The purpose of Stage 1 of this Phase 1b trial is to determine the MTD for MRZ. Per the TMZ Prescribing Information 2015, the only Grade 3 to 4 adverse events related to TMZ (±RT) with an incidence >5% was fatigue. Grade 3 to 4 hematologic laboratory abnormalities were lymphopenia, thrombocytopenia, neutropenia, and leukopenia; which occur at ≥10% incidence. Dose reductions or interruptions of TMZ for toxicity will follow the dosing guidelines as defined in the TMZ label.

TMZ dose reduction or interruption as directed by TMZ Prescribing Information 2015 will not necessarily constitute a dose-limiting toxicity (DLT) with respect to MRZ. Across clinical studies, the incidence of neutropenia and thrombocytopenia with MRZ has been low, and only infrequently of Grade 3 or higher. Therefore, adverse events (AEs), in particular myelotoxicity, will be considered a DLT for MRZ if the effect is above and beyond that expected for TMZ+RT (Concomitant Treatment) or TMZ (Adjuvant Treatment).

For the dose-escalation (Stage 1) portion of the trial, DLT is defined as the occurrence of any of the following AEs related to MRZ during the assessment period (Days 1 through 42 (+14 day window) during the Concomitant Treatment dosing period, or during Cycle 1 for Adjuvant Treatment), using National Cancer Institute Common Terminology Criteria for Adverse Events version 4.03 (NCI-CTCAE v 4.03) to determine severity:

Grade 4 myelotoxicity that does not reduce to ≤Grade 3 within two weeks of onset despite adequate supportive therapy.

Grade 3 or 4 non-hematological toxicity (excluding alopecia) lasting for more than 4 days despite adequate supportive therapy or preventing the next scheduled dose from being administered within 4 days of scheduled day; for Grade 3 fatigue to be considered a DLT, it must be present for more than 7 days.

To be evaluable for DLT determination, patients without DLT must receive at least the following minimum number of doses of each required treatment:

Concomitant Treatment: 5 doses of MRZ, 37 doses of TMZ, and 27 RT doses, within 56 days.

Adjuvant Treatment: 3 doses of MRZ, 5 doses of TMZ, within 5 (+1) wks.

During dose-escalation, patients without a DLT who do not meet these dosing minimums will be replaced to facilitate evaluation of the MTD.

Stage 1 Dose-Escalation

Patients who have completed screening procedures and meet all eligibility criteria may be enrolled into the study.

A 3+3 design will be used to define the MTD for MRZ in combination with TMZ and RT in Concomitant Treatment, and to define the MTD for MRZ in combination with TMZ in Adjuvant Treatment.

MRZ dosing will begin at 0.55 mg/m$^2$ once weekly (Cohort 1). Additional dose cohorts are planned as shown below (Table-12):

TABLE 12

Dose Cohorts for the Concomitant and Adjuvant Treatment in Stage 1 (Dose-Escalation)

| Cohort | Concomitant Treatment IV MRZ Days 1, 8, 15, 29, and 36 | Adjuvant Treatment IV MRZ Days 1, 8, and 15 (28-day cycle) |
| --- | --- | --- |
| −1 | 0.4 mg/m$^2$ | 0.4 mg/m$^2$ |
| 1 | 0.55 mg/m$^2$ | 0.55 mg/m$^2$ |
| 2 | 0.7 mg/m$^2$ | 0.7 mg/m$^2$ |
| 3 | 0.8 mg/m$^2$ | 0.8 mg/m$^2$ |
| 4 | 1.0 mg/m$^2$ | 1.0 mg/m$^2$ |
| 5 | 1.2 mg/m$^2$ | 1.2 mg/m$^2$ |

A minimum of 3 patients will be enrolled into a cohort, at the doses shown in Table-12 above. Dose-Escalation will proceed as follows:

If none of the first 3 evaluable patients in a dose cohort experience a DLT during the 6-week Concomitant Treatment dosing period or during Cycle 1 for the Adjuvant Treatment, then enrollment into the next higher dose cohort can be initiated.

If 1 of the first 3 evaluable patients in a dose cohort experiences a DLT during the 6-week Concomitant Treatment dosing period or during Cycle 1 for the Adjuvant Treatment, then an additional 3 patients will be enrolled into the same cohort.

If ⅙ evaluable patients in the expanded 6-patient cohort experiences a DLT during the 6-week Concomitant Treatment dosing period or during Cycle 1 for the Adjuvant Treatment, then the next higher dose cohort can be tested and enrollment of the next 3 patients at the next higher dose level can be initiated.

If ≥⅔ evaluable patients in the expanded 6-patient cohort experience a DLT during the 6-week Concomitant Treatment dosing period or during Cycle 1 for the Adjuvant Treatment, then the MTD has been exceeded and no further dose escalation will occur.

A cohort of reduced MRZ at 0.4 mg/m$^2$ will be initiated if the initial dose (0.55 mg/m$^2$) is associated with a DLT in ≥2 patients. If the 0.4 mg/m$^2$ dose level of MRZ is tolerated (DLT in ≤1 patient), then higher doses of MRZ (between 0.4 and 0.55 mg/m$^2$) may be evaluated, depending on review of the safety information by the Investigators and Sponsor, or this dose level may be considered as the PR2D.

If the MRZ dose at 1.2 mg/m$^2$ does not result in DLT, then a higher dose may be explored or this dose will be considered as the RP2D after review of the safety information by the Investigators and Sponsor.

The MTD is defined as the highest dose level where DLT is not observed in at least 2 patients in the same cohort during the 6-week Concomitant Treatment dosing period or during Cycle 1 for the Adjuvant Treatment. Intermediate dosing levels, or alternate infusion durations, may be explored if indicated. The RP2D is the MTD unless safety information suggests a lower RP2D.

Teleconferences between Sponsor and the clinical study sites will occur at least every other week to discuss safety. Additional teleconferences will be scheduled at the end of each cohort to decide on the MRZ dose of the next cohort. Once the RP2D has been identified, a cohort of 12 to 18 additional evaluable patients will be treated at the RP2D (approximately 48 patients for the entire study) to further confirm the safety and to assess preliminary activity for the combination treatment in both the Concomitant and Adjuvant Treatment dosing protocols.

Number of Patients

Stage 1: Up to 36 evaluable patients, 18 per arm will be enrolled in the study at multiple centers.

Stage 2: Approximately 12 to 18 evaluable patients will be enrolled in the study at multiple centers.

The total number of patients in the study will be approximately 48.

Study Parameters

The study population includes patients with newly diagnosed G4 MG (including glioblastoma and gliosarcoma). The eligibility criteria are the same for both Stage 1 and Stage 2 portions of the trial except where noted.

Inclusion Criteria

Concomitant Treatment and Adjuvant Treatment

Patients must meet the following criteria to be eligible for study participation:
1. Understand and voluntarily sign and date an informed consent document prior to any study related assessments/procedures.
2. Males and females of age ≥18 years at the time of signing of the informed consent document.
3. Histologically confirmed newly diagnosed G4 MG.
4. Karnofsky Performance Status (KPS) score ≥70%.
5. For Concomitant Treatment: Prior tumor resection or biopsy up to 8 weeks prior to first MRZ dose.
6. For Adjuvant Treatment: Patients must complete RT and TMZ therapy, and then have a MRI documenting stable disease prior to starting study treatment.
7. For Concomitant Treatment: All AEs resulting from surgery must have resolved to NCI-CTCAE (v. 4.03) Grade ≤1.
8. For Adjuvant Treatment: All AEs resulting from surgery and prior RT and TMZ chemotherapy must have resolved to NCI-CTCAE (v. 4.03) Grade ≤1 (except for laboratory parameters outlined below).
9. Stable or decreasing dose of corticosteroids over 14 days prior to first MRZ dose.
10. For Concomitant Treatment: No prior treatment with MRZ or any other PIs, including BTZ, carfilzomib (CFZ), or ixazomib (IXZ).
11. For Adjuvant Treatment: No prior treatment with BTZ, CFZ, or IXZ.
12. No investigational agent within 4 weeks prior to first dose of study drug.
13. Adequate hematological, renal, and hepatic function (assessment performed within 14 days prior to study treatment):
    Absolute neutrophil count ≥1.5×10$^9$/L
    Platelets ≥100×10$^9$/L
    Serum creatinine, Total serum bilirubin ≤1.5× upper limit of laboratory normal (ULN)
    Aspartate Serine Transaminase (AST), Aspartate Leucine Transaminase ALT, Alkaline Phosphatase (ALP) ≤2.5×ULN
14. Patients with a history of seizures must be on a stable dose of anti-epileptic drugs (AEDs) for 7 days prior to enrollment.
15. Absence of known HIV infection, chronic hepatitis B or hepatitis C infection; absence of any other serious medical conditions which could interfere with oral medication intake.
16. Subjects with archival tumor tissue suitable for measurement of proteasome activity (e.g., fresh frozen tissue) and biomarker status (e.g., formalin fixed paraffin embedded slides) must give permission to access and test the tissue. Subjects without archival tumor tissue are eligible for the Dose-Escalation stage, but not the Dose-Expansion stage of the study.
17. For women of child-bearing potential and for men with partners of childbearing potential, patient must agree to take contraceptive measures for duration of treatments and for one month after last study treatment.
18. Willing and able to adhere to the study visit schedule and other protocol requirements.

Exclusion Criteria

Concomitant Treatment and Adjuvant Treatment

Patients with any of the following will be excluded from participation in the study:
1. Co-medication or concomitant therapy that may interfere with study results, e.g., immuno-suppressive agents other than corticosteroids.
2. History of thrombotic or hemorrhagic stroke or myocardial infarction within 6 months.
3. Chemotherapy or other anti-tumor treatment for brain tumor (other than the therapies required by the inclusion criteria of this protocol).
4. Pregnant or breast feeding.
5. Uncontrolled intercurrent illness including, but not limited to, ongoing or active infection requiring IV antibiotics & psychiatric illness/social situations that would limit compliance with study requirements, or disorders associated with significant immunocompromised state.
6. Known other previous/current malignancy requiring treatment within ≤3 years except for limited disease treated with curative intent, such as in situ prostate cancer, intracapsular renal cancer, cervical carcinoma in situ, squamous or basal cell skin carcinoma, and superficial bladder carcinoma 7. Any comorbid condition that confounds the ability to interpret data from the study as judged by the Investigator or Medical Monitor.

Length of Study Participation

Patients enrolled in the Concomitant Treatment should complete this treatment arm (MRZ+TMZ+RT) and then continue onto the Adjuvant Treatment (MRZ+TMZ) for up to up to 12 cycles, unless discontinued for disease progression, unacceptable toxicity, withdrawal of consent, or termination of the study. Patients enrolled in continuation Adjuvant Treatment should continue MRZ+TMZ treatment for up to 12 cycles. Patients enrolled in the expansion stage, should enroll in the Concomitant Treatment and continue onto the Adjuvant Treatment for up to 12 cycles of MRZ+ TMZ. Continuation with MRZ after 12 cycles may be decided upon in discussions between the sponsor and the investigator. In the event that one drug (TMZ or MRZ) is discontinued for reasons other than disease progression, the other drug will then continue as a single agent. For patients who discontinue study drug for reasons other than disease progression, whenever possible, tumor assessment will continue as per protocol until disease progression. After disease progression, patients will be followed for survival and the start of first new anti-GBM therapy and its outcome.

Investigational Product/Background Therapy Route/Regimen

Stages 1 and 2

MRZ will be provided by Sponsor and administered IV over 10 minutes. Volume of administration will vary based on assigned dose (Table-13) and patient body surface area (BSA). To mitigate the possibility of renal dysfunction, patients will receive 250 mL of normal saline administered for 30 minutes prior to the MRZ infusion. The lyophilized drug product vial contains 2 mg API and 60 mg sucrose bulk excipient. Diluent vials contain 55% propylene glycol, 5% ethanol, and 40% citrate buffer pH 5 (20 mL fill; 10 mL intended for use).

TMZ will be provided or prescribed by Institution and administered orally. Dose amounts vary based on BSA, and capsules will be provided for accurate dosing based on the TMZ Prescribing Information 2015. RT will also be provided by Institution.

Procedures

Study visits and procedures will be performed as outlined in Table 13 and Table 14. The study will consist of Screening, Baseline, Treatment, and Follow-up periods.

Screening

The screening period may not exceed a 28-day period (with a 3 day window for logistical reasons) prior to start of study treatment. After informed consent is obtained, Screening demographics, medical (and cancer) history, and concomitant medications (including cancer treatments) should be obtained. The Screening MM scan with contrast, after surgical resection or biopsy, and tumor pathology assessments with consent to acquire and test archival tumor tissue samples, should be obtained within 14 (+3) days prior to study treatment.

Baseline

All Baseline procedures and assessments including physical examination including Karnofsky Performance Status (KPS), neurological evaluation, neurological coordination assessment using the Scale for the Assessment and Rating of Ataxia (SARA), vital signs measurement, electrocardiogram (ECG), and laboratory tests are to be conducted within 7 (+1) days prior to study treatment.

Treatment

Patients on Concomitant Treatment will be treated for 42 (+14) days unless discontinued earlier for disease progression, unacceptable toxicity, withdrawal of consent, or termination of the study. During Concomitant Treatment, assessment will include Mill scans at the end of week 10 (−1 week).

Patients on Adjuvant Treatment will continue TMZ through 12 cycles unless discontinued earlier for disease progression, unacceptable toxicity, withdrawal of consent, or termination of the study. During Adjuvant Treatment, assessment will include MM scans at the end of Cycle 2 and every even numbered Cycle (±7 days) using RANO 2010 criteria for assessment. Responses (complete response [CR] and partial response [PR]) should be confirmed by repeat scans performed 4 weeks (±2 days) later. Functional status using the KPS and neurological coordination assessment using the SARA will be assessed regularly. Patients who discontinue study drug for reasons other than disease progression whenever possible will continue tumor assessment as per protocol schedule until progression or initiation of new therapy against G4 MG.

End-of-Treatment Visit

Patients will be followed for safety for 28 (+7) days after discontinuation of trial therapy. The End of Treatment (EOT) visit should occur 7 to 28 days (+7) after the last study treatment. If the EOT visit occurs less than 28 days after the last study treatment, the patient should be contacted to assess for ongoing or new AEs.

Post Treatment Follow-up

All patients will be followed in the long-term survival follow-up period for as long as they are alive or until the study is terminated to determine survival and start of first subsequent anti-malignant glioma regimens (regimen, start and end date, and treatment outcome). Long-term follow-up will occur every 3 months (±7 days) after the End-of-Treatment visit. Telephone contact or publicly available data will be sufficient to document survival status. Study MRI scans will continue in the post treatment follow-up period until disease progression or initiation of new GBM therapy.

Overview of Assessments

Activity (Efficacy) Assessments

Tumor response, including progressive disease, will be assessed with MRI following completion of Concomitant Treatment at the end of Week 10 (−1 week), and during Adjuvant Treatment every 2 cycles (at the end of each even-numbered Cycle of therapy), and during post treatment follow up, according to the RANO 2010 criteria. Specific efficacy assessments are:

Radiographic Response
Progression-Free Survival (PFS)
Overall Survival (OS)

Pharmacokinetic Assessments: Concomitant Treatment only, Stage 1 Dose—Escalation Only

MRZ

Blood samples will be taken pre-dose, immediately prior to the end of infusion, and then 5 and 60 minutes post-infusion on Day 1; and pre-dose and immediately prior to end of infusion, and then 2, 5, 15, 30, 45, and 60 minutes post-infusion on Day 8. PK parameters ($C_{max}$, $T_{max}$, $t_{1/2}$, $AUC_{0-t}$, $AUC_{0-inf}$, CL, $V_d$) will be estimated by non-compartmental analysis.

TMZ

Pre-dose and 1 hr post-dose, and 24 hrs post-dose (prior to the next TMZ dose), serum samples will be taken on Day 1 and Day 8 to assess TMZ peak and trough levels.

Tumor Biomarker Assessments (Exploratory) At the discretion of the Sponsor, assessment of pre-treatment proteasome activity, genomic analysis and transcriptional profiling in flash-frozen and/or formalin fixed paraffin embedded, archived patient tumor sample tissue. These assessments will proceed pending the outcome of methodologic feasibility studies.

Statistical Analysis

Overview

Stage 1 (Dose-Escalation)

A 3+3 design will be utilized to determine the MTD of MRZ for MRZ+TMZ+RT in Concomitant Treatment, and the MTD of MRZ for MRZ+TMZ in Adjuvant Treatment. The MTD will be the RP2D unless safety review suggests a lower dose for the RP2D.

Stage 2 (Dose-Expansion)

After RP2D has been determined in the dose-escalation part of the study, 12-18 (approximately 48 patients for the entire study) additional evaluable patients will be treated at the RP2D to confirm the safety and assess the preliminary activity for the combination of MRZ+TMZ (+RT in Concomitant Treatment). Summaries will be provided for each dose-escalation cohort and treatment arm in Stage 1, the dose-expansion cohort in Stage 2, the pooled MTD/RP2D treated patients (Stage 1 plus Stage 2), and for the total study population. Patients in Concomitant Treatment of Stage 1 may also participate in the Adjuvant Treatment of Stage 1; these patients will be counted once in the pooled group and the total group.

Activity

Tumor response, progression-Free survival (PFS), and overall survival (OS) will be assessed. Tumor response will be assessed by the Investigators using RANO 2010 criteria. The best confirmed response, Response Rate (partial response or better), PFS, and OS will be summarized for patients who received at least 5 doses of MRZ in the Concomitant Treatment phase and had at least 1 post-dose tumor evaluation, or at least 1 dose of MRZ and had at least 1 post-dose tumor evaluation in the Adjuvant Treatment phase.

Safety

All patients will be evaluated for safety analysis if they receive at least one dose of MRZ. The safety data will be presented in individual listings and summary tables, including frequency tables for AEs and frequency and shift tables for laboratory variables.

Pharmacokinetics (PK)

The following PK parameters ($C_{max}$, $T_{max}$, $t_{1/2}$, $AUC_{0-t}$, $AUC_{0-inf}$, $CL$, $V_d$) for MRZ will be calculated using standard non-compartmental analysis. Blood concentrations and computed PK parameters for MRZ will be listed and summarized by cohort (mean, geometric mean, standard deviation, coefficient of variation, minimum, maximum and number of observations). Patient population for PK will be all patients who received at least one dose of either study drug and had at least one post-infusion sample analyzed. Select PK parameters will be determined by non-compartmental analysis for TMZ.

Karnofsky Performance Status Scale

| Activity Level | Score |
| --- | --- |
| Normal, no complaints | 100 |
| Able to carry on normal activity; minor signs or symptoms of disease | 90 |
| Normal activity with effort | 80 |
| Unable to carry on normal activity or perform active work; cares for self | 70 |
| Requires occasional assistance but is able to care for most own needs | 60 |
| Requires considerable assistance and frequent medical care | 50 |
| Disabled; requires special medical care and assistance | 40 |
| Severely disabled; hospitalization indicated although death not imminent | 30 |
| Very sick; hospitalized and requires active supportive care. | 20 |
| Moribund; fatal processes progressing rapidly | 10 |
| Dead | 0 |

Oxford Textbook of Palliative Medicine, Oxford University Press. 109, 1993.
Schag CC, Heinrich RL, Ganz PA. Karnofsky preformance status revisited: reliability, validity, and guidelines.
J Clin Oncol Mar; 2(3): 187-93, 1984

Scale for the Assessment and Rating of Ataxia (SARA)

Gait

Proband is asked (1) to walk at a safe distance parallel to a wall including a half-turn (turn around to face the opposite direction of gait) and (2) to walk in tandem heels to toes) without support. Scores are given below:

0 Normal, no difficulties in walking, turning and walking tandem (up to one misstep allowed)

1 Slight difficulties, only visible when walking 10 consecutive steps in tandem

2 Clearly abnormal, tandem walking>10 steps not possible

3 Considerable staggering, difficulties in half-turn, but without support

4 Marked staggering, intermittent support of the wall required

5 Severe staggering, permanent support of one stick or light support by one arm required 6 Walking>10 m only with strong support (two special sticks or stroller or accompanying person)

7 Walking<10 m only with strong support (two special sticks or stroller or accompanying person)

8 Unable to walk, even supported

Stance

Proband is asked to stand (1) in natural position, (2) with feet together in parallel (big toes touching each other) and (3) in tandem (both feet on one line, no space between heel and toe). Proband does not wear shoes, eyes are open. For each condition, three trials are allowed. Best trial is rated. Scores are given below:

0 Normal, able to stand in tandem for >10 s

1 Able to stand with feet together without sway, but not in tandem for >10 s

2 Able to stand with feet together for >10 s, but only with sway

3 Able to stand for >10 s without support in natural position, but not with feet together 4 Able to stand for >10 s in natural position only with intermittent support 5 Able to stand >10 s in natural position only with constant support of one arm 6 Unable to stand for >10 s even with constant support of one arm)

Sitting

Proband is asked to sit on an examination bed without support of feet, eyes open and anus outstretched to the front. Scores are given below:

0 Normal, no difficulties sitting >10 sec

1 Slight difficulties, intermittent sway

2 Constant sway, but able to sit >10 s without support

3 Able to sit for >10 s only with intermittent support
4 Unable to sit for >10 s without continuous support Speech Disturbance Speech is assessed during normal conversation. Scores are given below:
0 Normal
1 Suggestion of speech disturbance
2 Impaired speech, but easy to understand
3 Occasional words difficult to understand
4 Many words difficult to understand
5 Only single words understandable
6 Speech unintelligible/anarthria Finger Chase: Rated Separately for Each Side Proband sits comfortably. If necessary, support of feet and trunk is allowed. Examiner sits in front of proband and performs 5 consecutive sudden and fast pointing movements in unpredictable directions in a frontal plane, at about 50% of proband's reach. Movements have an amplitude of 30 cm and a frequency of 1 movement every 2 s. Proband is asked to follow the movements with his index finger, as fast and precisely as possible. Average performance of last 3 movements is rated.
0 No dysmetria
1 Dysmetria, under/overshooting target <5 cm
2 Dysmetria, under/overshooting target <15 cm
3 Dysmetria, under/overshooting target >15 cm
4 Unable to perform 5 pointing movements Nose-Finger Test: Rated Separately for Each Side Proband sits comfortably. If necessary, support of feet and trunk is allowed. Proband is asked to point repeatedly with his index finger from his nose to examiner's finger which is in front of the proband at about 90% of proband's reach. Movements are performed at moderate speed. Average performance of movements is rated according to the amplitude of the kinetic tremor.
0 No tremor
1 Tremor with an amplitude <2 cm
2 Tremor with an amplitude <5 cm
3 Tremor with an amplitude >5 cm
4 Unable to perform 5 pointing movements Fast Alternating Hand Movements: Rated Separately for Each Side Proband sits comfortably. If necessary, support of feet and trunk is allowed. Proband is asked to perform 10 cycles of repetitive alternation of pro- and supinations of the band on his/her thigh as fast and as precise as possible. Movement is demonstrated by examiner at a speed of approx. 10 cycles within 7 s. Exact times for movement execution have to be taken.
0 Normal, no irregularities (performs <10 s)
1 Slightly irregular (performs <10 s)
2 Clearly irregular, single movements difficult to distinguish or relevant interruptions, but performs <10 s
3 Very irregular, single movements difficult to distinguish or relevant interruptions, performs >10 s
4 Unable to complete 10 cycles Heel-Shin Slide: Rated Separately for Each Side Proband lies on examination bed, without sight of his legs. Proband is asked to lift one leg, point with the heel to the opposite knee, slide down along the shin to the ankle, and lay the leg back on the examination bed. The task is performed 3 times. Slide-down movements should be performed within 1 s. If proband slides down without contact to shin in all three trials, rate 4.
0 Normal
1 Slightly abnormal, contact to shin maintained
2 Clearly abnormal, goes off shin up to 3 times daring 3 cycles
3 Severely abnormal, goes off shin 4 or more times during 3 cycles
4 Unable to perform the task Response Assessment for High Grade Gliomas (RANO CRITERIA)

| Criterion | CR | PR | SD | PD |
|---|---|---|---|---|
| TI gadolinium enhancing disease | None | ∃ 50% ↓ | <50% ↓ but <25% ↑ | ∃ 25% ↑* |
| T2/FLAIR | Stable or ↓ | Stable or ↓ | Stable or ↓ | ↑* |
| New lesion | None | None | None | Present* |
| Corticosteroids | None | Stable or ↓ | Stable or ↓ | NA† |
| Clinical status | Stable or ↑ | Stable or ↑ | Stable or ↑ | ↓* |
| Requirement for response | All | All | All | Any* |

Abbreviations:
RANO, Response Assessment in Neuro-Oncology;
CR, complete response;
PR, partial response;
SD, stable disease;
PD, progressive disease;
FLAIR, fluid-attenuated inversion recovery;
NA, not applicable.
*Progression occurs when this criterion is present.
†Increase in corticosteroids alone will not be taken into account in determining progression in the absence of persistent clinical deterioration.

TABLE 13a

Schedule of Assessments and Procedures, Concomitant Treatment

| | Assessment | | | | | |
|---|---|---|---|---|---|---|
| | Screening[1] | Baseline[1] | Week Number* | | | |
| Study Week | −4 to −1 | −1 | 1 | 2 | 3 | 4 |
| Window | Day −28(−3) | Day −7(−1) | +/−3 days per week; total treatment 42 (+14) days | | | |
| Informed consent | X | | | | | |
| Medical History/Demog | X | | | | | |
| Concomitant medications | X | X | X | X | X | X |
| Physical examination, height[2] | | X | | | | |
| Targeted physical, weight, BSA[2] | | X | X | | | |
| Karnofsky Performance Status (KPS)[3] | | X | X | | | |

TABLE 13a-continued

Schedule of Assessments and Procedures, Concomitant Treatment

| | Assessment | | | | | |
|---|---|---|---|---|---|---|
| | Screening[1] | Baseline[1] | Week Number* | | | |
| Study Week | −4 to −1 | −1 | 1 | 2 | 3 | 4 |
| Neurological examination and assessment, SARA[4] | | X | X | | | |
| Safety assessment[5] | | | X | X | X | X |
| Vital signs (HR, temp, BP)[6] | | X | X | X | X | X |
| ECG[7] | | X | | | | |
| Complete Blood Count, Differential, Platelets[8] | | X | X | X | X | X |
| Serum Chemistry[9] | | X | X | X | X | X |
| PT/PTT[10] | | X | | | | |
| Urinalysis[11] | | X | | | | |
| Marizomib infusion with hydration[12] | | | X (Day 1) | X (Day 8) | X (Day 15) | |
| Radiotherapy[13] | | | X (QD * 5) | X (QD * 5) | X (QD * 5) | X (QD * 5) |
| Temozolomide[14] | | | X (QD * 7) | X (QD * 7) | X (QD * 7) | X (QD * 7) |
| Blood PK sampling (MRZ)[15] | | | X | | | |
| Plasma PK sampling (TMZ)[16] | | | X (Day 1) | X (Day 8) | | |
| Pregnancy test[17] | | X | | | | |
| Tumor measurement[18] | X (−14 to −1) | | | | | |
| Tumor proteasome activity[19] | X | | | | | |
| Tumor & blood gene signature profiling[20] | X | | | | | |
| Survival and subsequent therapy | | | | | | |

TABLE 13b

Schedule of Assessments and Procedures, Concomitant Treatment, Continued

| | Assessment | | | | | | | |
|---|---|---|---|---|---|---|---|---|
| | Week Number* | | | | | | End of | Post Treatment Follow- |
| Study Week | 5 | 6 | 7 | 8 | 9 | 10 | Treatment[21] | up[22] |
| Window | +/−3 days per week; total treatment 42 (+14) days | | | | | | +7 | ±7 |
| Informed consent | | | | | | | | |
| Medical History/Demog | | | | | | | | |
| Concomitant medications | X | X | X | X | X | X | X | X |
| Physical examination, height[2] | | | | | | | | |
| Targeted physical, weight, BSA[2] | X | | | | | | X | |
| Karnofsky Performance Status (KPS)[3] | X | | | X | | | X | |
| Neurological examination and assessment, SARA[4] | X | | | X | | | X | |
| Safety assessment[5] | X | X | | X | | | X | |
| Vital signs (HR, temp, BP)[6] | X | X | | X | | | X | |
| ECG[7] | | | | | | | | |

TABLE 13b-continued

Schedule of Assessments and Procedures, Concomitant Treatment, Continued

| | Assessment | | | | | | | |
|---|---|---|---|---|---|---|---|---|
| | Week Number* | | | | | | End of | Post Treatment Follow- |
| Study Week | 5 | 6 | 7 | 8 | 9 | 10 | Treatment[21] | up[22] |
| Complete Blood Count, Differential, Platelets[8] | X | X | | X | | | X | |
| Serum Chemistry[9] | X | X | | X | | | X | |
| PT/PTT[10] | | | | | | | | |
| Urinalysis[11] | | | | | | | X | |
| Marizomib infusion with hydration[12] | X (Day 29) | X (Day 36) | | | | | | |
| Radiotherapy[13] | X (QD * 5) | X (QD * 5) | | | | | | |
| Temozolomide[14] | X (QD * 7) | X (QD * 7) | | | | | | |
| Blood PK sampling (MRZ)[15] | | | | | | | | |
| Plasma PK sampling (TMZ)[16] | | | | | | | | |
| Pregnancy test[17] | | | | | | | X | |
| Tumor measurement[18] | | | | | X | | X | X |
| Tumor proteasome activity [19] | | | | | | | | |
| Tumor & blood gene signature profiling[20] | | | | | | | | |
| Survival and subsequent therapy | | | | | | | | X |

*Unless otherwise indicated, each assessment or procedure is once during the indicated week number (+/−3 days). Total concomitant treatment week = 42 days (+14 days).

1. After informed consent is obtained, screening demographics, medical history, concomitant medications, tumor pathology assessments, and consent to acquire and test archival tumor tissue samples should be obtained within 28 days prior to the start of treatment; screening radiographic/tumor assessments should be obtained within 14 days prior to study treatment; and baseline procedures and tests should be performed within 7 days prior to study treatment.
2. Height measured at baseline only. Physical examination is a complete physical as per institutional guidelines (genitourinary examination not required unless there are related signs or symptoms) at baseline, but thereafter as directed by signs and symptoms (targeted physical examination).
3. Functional assessment using the Karnofsky Performance Status (KPS) is to be completed at baseline, at the beginning of weeks 1, 5, and 8, and at the end of treatment.
4. Neurological examination, including the evaluation of coordination to be performed at baseline, at the beginning of weeks 1, 5, and 8, and at the end of treatment using the scale for the assessment and rating of ataxia (SARA). Tests to be performed within 48 hours of scheduled dosing, except prior to Week 1, which can be done within 7 days prior to dosing.
5. Refer to standard methods for reporting procedures and adverse events for hallucinations.
6. Vital Signs: (blood pressure, heart rate, and temperature) during the Concomitant Treatment portion of the study at baseline, on Day 1 of weeks 1, 2, 3, 5, and 6 immediately before the marizomib infusion and approximately 10 (±2) minutes, 30 (±5) minutes and 1 hour (±5 minutes) following the marizomib infusion, and at the beginning of week 8. For both the Concomitant and Adjuvant Treatment portions of the study vital signs are also collected as part of the physical examination.
7. ECG: Eligibility ECGs must be performed within 7 days prior to Day 1 of week 1. Additional ECGs should be obtained if clinically indicated.
8. Hemoglobin (Hgb), hematocrit (Hct), red blood cell (RBC) count, white blood cell (WBC) count with differential, and platelets. Hematology tests to be performed within 7 days prior Week 1 dosing, on Day 1 of weeks 2, 3, 4, 5, 6, and 8, and at the end of treatment visit. Tests to be performed within 48 hours of scheduled dosing, except prior to Week 1, which can be done within 7 days prior to dosing. A decrease in absolute neutrophil count ($\geq 0.5$ and $<1.5 \times 10^9$/L) or platelets ($\geq 10$ and $<100 \times 10^9$/L) will result in temozolomide dose interruption until absolute neutrophil count is $>1.5 \times 10^9$/L or platelets are $>100 \times 10^9$/L. Temozolomide will be discontinued if absolute neutrophil count is $<0.5 \times 10^9$/L or platelet count $<10 \times 10^9$/L.
9. Sodium, potassium, chloride, bicarbonate, calcium, magnesium, glucose, BUN, serum creatinine, uric acid, ALT, AST, alkaline phosphatase, total protein, albumin, and total bilirubin. Chemistry to be performed within 7 days prior Week 1 dosing, on Day 1 of weeks 2, 3, 4, 5, 6, and 8, and at the end of treatment visit. Tests to be performed within 48 hours of scheduled dosing, except prior to Week 1, which can be done within 7 days prior to dosing. Minimum criterion to continue weekly marizomib infusion on Day 1 of each week: creatinine ≤1.5×ULN.
10. [Prothrombin time (PT) or International Normalized Ratio (INR)] and [partial thromboplastin time (PTT) or activated PTT (aPTT)]. May be performed more often if clinically indicated.
11. Urinalysis: protein, blood, glucose, pH; microscopic (RBC, WBC, casts) if abnormal urinalysis. Urinalysis performed within 72 hours of scheduled dosing, except prior to Week 1, which can be done within 7 days prior to dosing.
12. IV marizomib infusion over 10 minutes. The volume of infusate will vary per patient depending on dose and BSA. Patients will receive 250 mL normal saline over approximately 30 minutes prior to the marizomib infusion. At the discretion of the Investigator, pre-hydration can be increased or additional normal saline can be given after the marizomib infusion is complete. Patients are to be encouraged to maintain good oral hydration during the study (e.g., 2 liters per day, as considered appropriate by the Investigator).
13. Focal radiotherapy (RT) (60 Gy administered in 30 fractions of 2 Gy each) include the tumor bed or resection site with a 2 to 3 cm margin administered 5 days/week for 6 weeks.
14. Temozolomide (TMZ) administered per package insert daily (75 mg/m$^2$) for 42 days during the Concomitant Treatment up to 56 days if all of the following conditions are met: absolute neutrophil count is >1.5× 10$^9$/L, platelet count >100×10$^9$/L, and NCI-CTCAE, Version 4.03 nonhematological toxicity is ≤Grade 1 (except for alopecia, nausea, and vomiting). No dose reductions are recommended during Concomitant Treatment; however, temozolomide should be interrupted or discontinued during Concomitant Treatment according to the hematological and nonhematological toxicity criteria (see Footnote 9 above).
15. Blood PK Sampling (marizomib) (dose-escalation only): On Day 1 of Week 1, marizomib samples will be obtained before treatment, just prior to end of marizomib infusion, and at 5 and 60 minutes after the infusion. On Day 1 of Week 2 (Day 8), marizomib samples will be obtained before treatment, just prior to the end of marizomib infusion, and 2, 5, 15, 30, 45, and 60 minutes after the infusion. Every effort should be made to collect samples at the prescribed times, but deviations up to 10% of the time point are allowed. Additional samples may be collected if the patient experiences a potentially drug-related serious adverse event.
16. Blood PK temozolomide Sampling (dose-escalation only). On Day 1 of Week 1 (D1) and on Day 1 of Week 2 (D8), temozolomide samples will be obtained before treatment, and 60 minutes after the dose and 24 hrs after the dose (prior to the Day 9 temozolomide dose). Every effort should be made to collect samples at the prescribed times, but deviations up to 10% of the time point are allowed.
17. Pregnancy test (serum or urine) to be performed at Baseline, End-of-Treatment visit, and more frequently if clinically indicated.
18. Tumor assessment: Baseline tumor assessments are to be made within 14 days prior to Day 1 of Week 1 and during Week 10 (−1 week) (during the rest period between Concomitant and Adjuvant treatment). The Week 10 MRI must be interpreted before the patient can start Adjuvant Treatment. Response should be assessed per RANO criteria. If a patient is determined to have an overall disease response of CR, PR, or SD, the patient can proceed to Adjuvant treatment. If tumor assessments have not been performed in the 4 weeks prior to the End-of Treatment Visit, then tumor assessments are to be done at the End-of Treatment Visit (if progression not already documented), and subsequently until progression or initiation of new therapy for G4 MG.
19. For patients with flash-frozen, GBM tumor tissue, assessment of pre-treatment proteasome activity levels will be performed.
20. For patients with archived formalin fixed paraffin embedded slides of GBM tumor, genomic analysis and transcriptional profiling will be conducted. A blood sample may also be collected in these patients so comparisons can be made between germ line and tumor mutations.
21. The EOT visit should occur 7 to 28 days (+7) after the last study treatment. If the EOT visit occurs less than 28 days after the last study treatment, the patient should be contacted to assess for ongoing or new adverse events at 28 (+7) days. Patients who do not go on to the Adjuvant Treatment arm, and have drug-related adverse events of Grade ≥2 observed at the EOT assessment should be followed-up at least monthly until the adverse event has resolved to Grade 1, the event is believed to be chronic or patient receives other anti-cancer therapy.
22. Post Treatment Follow-up visits for patients who do not go on to the Adjuvant Treatment may be made in person or other means of communication. Purpose of the follow-up, which should occur every 3 months (±14 days), is to determine survival and the start of first new anti-GBM treatment and its outcome. Publicly available data sources may be used for ascertaining survival status. If the patient did not have progressive disease at the time of the End-of-Treatment Visit, results of MRI scans done as part of standard of care will be collected. MM scans will continue in the post treatment follow-up period until disease progression or initiation of new GBM therapy Adjuvant Treatment All patients will receive IV marizomib infusion on Days 1, 8, and 15 as a 10 minute infusion, in 28-day cycles. IV hydration will be given prior to the infusion. Temozolomide will be administered daily for 5 consecutive days, starting on Day 1 of Cycle 1 (C1D1), at a dose of 150 mg/m$^2$. If tolerated in Cycle 1, the temozolomide dose will be increased on Day 1 of Cycle 2 (C2D1) to a dose of 200 mg/m$^2$.

Stage 2

All patients will be treated with Concomitant Treatment of marizomib+temozolomide+radiotherapy using the marizomib recommended phase 2 dose determined in Stage 1 followed by Adjuvant Treatment of marizomib+temozolomide using the recommended phase 2 dose determined in Stage 1. Marizomib will be administered as a 10-minute, IV infusion on Days 1, 8, 15, 29, and 36 of the Concomitant Treatment, and on Days 1, 8, and 15 of every 28-day Cycle of Adjuvant Treatment. IV hydration will be given prior to each marizomib infusion.

Patients will receive up to 12 cycles of marizomib+ temozolomide during Adjuvant Treatment, unless discontinued for disease progression, unacceptable toxicity, withdrawal of consent, or termination of the study. Adjuvant Treatment continuation with marizomib after 12 cycles may be decided upon in discussions between the sponsor and the investigator. In the event that one drug (temozolomide or marizomib) is discontinued for reasons other than disease progression, the other will then continue as a single agent. Tables 14a and 14b show a schedule of assessments and procedures for adjuvant treatment TABLE 14a Schedule of Assessments and Procedures, Adjuvant Treatment

| Study Week | Screening[1] −4 to −1 | Baseline[1] −1 | Cycle 1* | | | | Cycle 2* | | | |
|---|---|---|---|---|---|---|---|---|---|---|
| | | | Day 1 | Day 8 | Day 15 | Day 22 | Day 1 | Day 8 | Day 15 | Day 22 |
| Window | Up to Day −28 (−3) | Up to Day −7(−1) | | | | | | | | |
| Informed consent | X | | | | | | | | | |
| Medical history/Demographics | X | | | | | | | | | |
| Concomitant medications | X | X | X | X | X | X | X | X | | |
| Physical examination, height [2] | | X | | | | | | | | |
| Targeted physical, weight, BSA [2] | | X | X | | | | X | | | |
| Karnofsky Performance Status (KPS) [3] | | X | X | | | | X | | | |
| Neurological examination and assessment, SARA [4] | | X | X | | | | X | | | |
| Safety assessment [5] | | | X | X | X | X | X | X | X | |
| Vital signs (HR, temp, BP) [6] | | X | X | X | X | X | X | X | X | |
| ECG [7] | | X | | | | | | | | |
| Complete Blood Count, Differential, Platelets [8] | | X | | | X | | | | X | |
| Serum Chemistry [9] | | X | | | X | | | | X | |
| PT/PTT [10] | | X | | | | | | | | |
| Urinalysis[11] | | X | X | | | | X | | | |
| Marizomib infusion with hydration [12] | | | X | X | X | X | X | X | X | |
| Temozolomide [13] | | | X (QD * 5) | | | | X (QD * 5) | | | |
| Pregnancy test [14] | | X | | | | | | | | |
| Tumor measurement [15] | X (−14 to −1) | | | | | | | | | X |
| Tumor proteasome activity [16] | X | | | | | | | | | |
| Tumor and blood gene signature profiling [17] | X | | | | | | | | | |
| Survival and subsequent therapy | | | | | | | | | | |

TABLE 14b

Schedule of Assessments and Procedures, Adjuvant Treatment, Continued

| Study Week | Cycle 3+* | | | | End of Treatment [18] | Post Treatment Follow-up [19] |
|---|---|---|---|---|---|---|
| | Day 1 | Day 8 | Day 15 | Day 22 | | |
| Window | | | | | +7 | ±7 |
| Informed consent | | | | | | |
| Medical history/Demographics | | | | | | |
| Concomitant medications | X | X | X | | X | X |
| Physical examination, height [2] | | | | | | |
| Targeted physical, weight, BSA [2] | X | | | | X | |

TABLE 14b-continued

Schedule of Assessments and Procedures, Adjuvant Treatment, Continued

| Study Week | Cycle 3+* Day 1 | Day 8 | Day 15 | Day 22 | End of Treatment [18] | Post Treatment Follow-up [19] |
|---|---|---|---|---|---|---|
| Karnofsky Performance Status (KPS) [3] | X | | | | X | |
| Neurological examination and assessment, SARA [4] | X | | | | X | |
| Safety assessment [5] | X | X | X | | X | |
| Vital signs (HR, temp, BP) [6] | X | X | X | | X | |
| ECG [7] | | | | | | |
| Complete Blood Count, Differential, Platelets [8] | | | | X | X | |
| Serum Chemistry [9] | | | | X | X | |
| PT/PTT [10] | | | | | | |
| Urinalysis [11] | X | | | | X | |
| Marizomib infusion with hydration [12] | X | X | X | | | |
| Temozolomide [13] | X (QD * 5) | | | | | |
| Pregnancy test [14] | | | | | X | |
| Tumor measurement [15] | | | | | X | X |
| Tumor proteasome activity [16] | | | | | | |
| Tumor and blood gene signature profiling [17] | | | | | | |
| Survival and subsequent therapy | | | | | | X |

*Unless otherwise indicated, each assessment or procedure is once during the indicated week or Cycle day (+/−3 days)

1. For patients initially entering the study for Adjuvant Treatment, after informed consent is obtained, screening demographics, medical history, concomitant medications, tumor pathology assessments and consent to acquire and test archival tumor tissue samples should be obtained within 28 days prior to the start of treatment; screening radiographic/tumor assessments should be obtained within 14 days prior to study treatment; and baseline procedures and tests should be performed within 7 days prior to study treatment. For patients who completed the Concomitant Treatment portion of the study, baseline procedures should be performed.
2. Height measured at baseline only. Physical examination is a complete physical as per institutional guidelines (genitourinary examination not required unless there are related signs or symptoms) at baseline, but thereafter as directed by signs and symptoms (targeted physical examination).
3. Functional assessment using the Karnofsky Performance Status (KPS) is to be completed at baseline, at the beginning of each cycle, and at the end of treatment visit.
4. Neurological examination, including the evaluation of coordination to be performed at baseline, at the beginning of each cycle, and at the end of treatment visit using the scale for the assessment and rating of ataxia (SARA). Tests to be performed within 48 hours of scheduled dosing, except prior to Week 1, which can be done within 7 days prior to dosing.
5. Refer to standard methods for adverse event and serious adverse event reporting procedures and when reporting adverse events for hallucinations.
6. Vital Signs: (blood pressure, heart rate, and temperature) during the Adjuvant treatment portion of the study in each Cycle on Days 1, 8, and 15, immediately before the marizomib infusion and approximately 10 (±2) minutes, 30 (±5) minutes and 1 hour (±5 minutes) following the marizomib infusion. For both portions of the study vital signs are also collected as part of the physical examination.
7. ECG: Eligibility ECGs must be performed within 7 days prior to Day 1 of Cycle 1. Additional ECGs should be obtained if clinically indicated. If an ECG was obtained at baseline for Concomitant Treatment, it does not need to be repeated.
8. Hemoglobin (Hgb), hematocrit (Hct), red blood cell (RBC) count, white blood cell (WBC) count with differential, and platelets. Hematology tests to be performed within 7 days prior to Week 1 dosing, on Days 22 (or within 48 hrs of that day), and at the end of treatment visit. A decrease in absolute neutrophil count ($<1.0\times10^9$/L) or platelet count ($<50\times10^9$/L) will result in temozolomide dose reduction by one level. In the case of a temozolomide dose reduction, a complete blood count will be obtained weekly until the absolute neutrophil count is $>1.5\times10^9$/L and the platelet count is $>100\times10^9$/L. Temozolomide will be discontinued if dose reduction to <100 mg/m$^2$ is required. The next Cycle of temozolomide should not be started until absolute neutrophil count exceeds $1.5\times10^9$/L or platelet count exceeds $<100\times10^9$/L.
9. Sodium, potassium, chloride, bicarbonate, calcium, magnesium, glucose, BUN, serum creatinine, uric acid, ALT, AST, alkaline phosphatase, total protein, albumin, and total bilirubin. Chemistry will be performed within to be performed within 7 days prior Week 1 dosing, on Day 1 of each cycle, and at the end of treatment visit. Minimum criterion to continue weekly marizomib infusion on Day 1 of each week: creatinine ≤1.5×ULN.

10. [Prothrombin time (PT) or International Normalized Ratio (INR)] and [partial thromboplastin time (PTT) or activated PTT] will be performed within 7 days prior Week 1 dosing, and may be performed more often if clinically indicated.

11. Urinalysis: protein, blood, glucose, pH; microscopic (RBC, WBC, casts) if abnormal urinalysis. Urinalysis performed within 72 hours of scheduled dosing, except prior to Cycle 1, which can be done within 7 days prior to dosing.

12. IV marizomib infusion over 10 minutes. The volume of infusate will vary per patient depending on dose and BSA. Patients will receive 250 mL normal saline over approximately 30 minutes prior to the marizomib infusion. At the discretion of the Investigator, pre-hydration rate can be increased or additional normal saline can be given after the marizomib infusion is complete. Patients are to be encouraged to maintain good oral hydration during the study (e.g., 2 liters per day, as considered appropriate by the Investigator).

13. Temozolomide (TMZ) administered daily (150 mg/m$^2$) for the first 5 days of each Cycle during the Adjuvant treatment if all of the following conditions are met: absolute neutrophil count is >1.5×10$^9$/L, platelet count >100×10$^9$/L, and NCI-CTCAE, Version 4.03 nonhematological toxicity is ≤Grade 1 (except for alopecia, nausea, and vomiting). At the start of Cycle 2, temozolomide dose can be escalated to 200 mg/m$^2$ if the CTC nonhematologic toxicity for Cycle 1 is Grade ≤2 (except for alopecia, nausea, and vomiting), absolute neutrophil count ≥1.5×10$^9$/L, platelet count ≥100× 10$^9$/L. The dose remains at 200 mg/m$^2$ per day for the first 5 days of each subsequent Cycle except if toxicity occurs. If the dose was not escalated in Cycle 2, escalation should not be done in subsequent cycles. Temozolomide should be dose reduced or discontinued during Adjuvant treatment according to the hematological and nonhematological toxicity criteria (see note 9 above).

14. Pregnancy test (serum or urine) to be performed at Baseline, End-of-Treatment visit, and more frequently if clinically indicated.

15. For patients entering the Adjuvant Treatment without prior marizomib during Concomitant Treatment, baseline tumor assessments are to be made within 14 days prior to Cycle 1 Day 1. For patients entering the Adjuvant Treatment after completing Concomitant Treatment with marizomib+temozolomide+radiotherapy, baseline tumor assessment will be made at week 10 (−1 week) of Concomitant Treatment. Response should be assessed per RANO criteria during the rest period of Cycle 2 and during the rest period of every 2 cycles thereafter (±7 days). If a patient is determined to have an overall disease response of CR or PR, then disease assessments should be repeated at least 4 weeks (±up to 7 days) later to confirm the response. If tumor assessments have not been performed in the 4 weeks prior to the End-of Treatment Visit, then tumor assessments are to be done at the End-of-Treatment Visit if progression has not already been documented. Study MRI assessments to continue off treatment until disease progression or initiation of new therapy for G4 MG.

16. For patients with flash-frozen, GBM tumor tissue, assessment of pre-treatment proteasome activity levels will be performed if not done as part of the Concomitant Treatment.

17. For patients with archived formalin fixed paraffin embedded slides of GBM tumor, genomic analysis and transcriptional profiling will be conducted if not done as part of the Concomitant Treatment. A blood sample may also be collected in these patients so comparisons can be made between germ line and tumor mutations.

18. The EOT visit should occur 7 to 28 days (+7) after the last study treatment. If the EOT visit occurs less than 28 days after the last study treatment, the patient should be contacted to assess for ongoing or new adverse events at 28 days. Patients with drug-related adverse events of Grade ≥2 observed at EOT assessment should be followed-up at least monthly until the adverse event has resolved to Grade 1, the event is believed to be chronic or patient receives other anti-cancer therapy.

19. Post Treatment Follow-up visits may be made in person or other means of communication. Purpose of the follow-up, which should occur every 3 months (±14 days), is to determine survival and the start of first new anti-GBM treatment and its outcome. Publicly available data sources may be used for ascertaining survival status. If the patient did not have progressive disease at the time of the End-of-Treatment Visit, results of MM scans done as part of standard of care will be collected. Study MRI scans will continue in the post treatment follow-up period until disease progression or initiation of new GBM therapy.

Results

Patient Demographics and Baseline Characteristics

TABLE 15

| Demographics and Baseline Characteristics | |
|---|---|
| Age (mean ± SD years) | 54.8 ± 9.5 |
| Gender | |
| Male | 12 (60%) |
| Female | 8 (40%) |
| Race (Patients reporting more than one race are included in all relevant race categories) | |
| White | 17 (85%) |
| Asian | 3 (15%) |
| Baseline KPS (percentages are based on the number of patients with a non-missing baseline value) | |
| 100 | 5 (25%) |
| 90 | 12 (60%) |
| 80 | 0 |
| 70 | 1 (5%) |
| Missing | 2 (10%) |
| Time from Initial Diagnosis to First Dose of Study Drug (mean ± SD months) | 1.8 ± 1.4 |
| Prior Treatment regimens | |
| Surgery | 20 (100.0%) |
| Radiation and Temozolomide | 9 (45.0%) |
| Time Since Last Radiation Therapy to First Dose of Study Drug (mean ± SD months) | 0.4 ± 0.7 |
| Patients receiving a corticosteroid at baseline (e.g., dexamethasone) | 8 (40%) |

TABLE 16

Study Drug Exposure

| | |
|---|---|
| Number of marizomib Cycles [mean ± SD cycles, (min, max)] | 3.3 ± 2.5 (1, 8) |
| Number of Temozolomide Cycles [mean ± SD cycles, (min, max)] | 3.1 ± 2.4 (1, 8) |
| Number of Patients with ≥1 marizomib Dose Reduction* | 1 (5.0%) |
| Reasons** | |
| Adverse Event | 1 (5.0%) |
| Number of Patients with ≥1 Temozolomide Dose Reduction* | 1 (5.0%) |
| Reasons** | |
| Adverse Event | 1 (5.0%) |
| Number of Patients with Marizomib Discontinued | 1 (5.0%) |
| Reasons: | |
| Adverse Event | 1 (5.0%) |
| Number of Patients with Temozolomide Discontinued | 0 |

*A patient is counted as having a dose reduction when reduction reason is marked as "DLT," "Adverse Event," or "Other"
**Patients who had >1 dose reductions with multiple dose reduction reasons will be counted in each relevant category Safety

TABLE 17

Most Common Treatment Emergent Adverse Events in Decreasing Order

| Preferred Term | Total (N = 20) |
|---|---|
| Patients with at Least One TEAE | 20 (100.0%) |
| Fatigue | 15 (75.0%) |
| Nausea | 11 (55.0%) |
| Vomiting | 7 (35.0%) |
| Confusional state | 6 (30.0%) |
| Constipation | 6 (30.0%) |
| Hallucination | 6 (30.0%) |
| Diarrhoea | 5 (25.0%) |
| Headache | 5 (25.0%) |
| Decreased appetite | 4 (20.0%) |
| Dizziness | 4 (20.0%) |
| Memory impairment | 4 (20.0%) |
| Pain | 4 (20.0%) |
| Convulsion | 3 (15.0%) |
| Cough | 3 (15.0%) |
| Muscular weakness | 3 (15.0%) |
| Platelet count decreased | 3 (15.0%) |
| Rash maculo-papular | 3 (15.0%) |

At each level of summarization (preferred term), patients reporting more than one TEAE are counted only once

TABLE 18

Most Common Treatment-Related Treatment Emergent Adverse Events in Decreasing Order of Frequency

| AE Preferred Term | MRZ Related | TMZ Related | Related to Both |
|---|---|---|---|
| Fatigue | 13 (65.0%) | 11 (55.0%) | 10 (50.0%) |
| Nausea | 9 (45.0%) | 9 (45.0%) | 7 (35.0%) |
| Vomiting | 5 (25.0%) | 7 (35.0%) | 5 (25.0%) |
| Hallucination | 5 (25.0%) | 0 (0.0%) | 0 (0.0%) |
| Decreased appetite | 4 (20.0%) | 4 (20.0%) | 4 (20.0%) |
| Dizziness | 4 (20.0%) | 2 (10.0%) | 2 (10.0%) |
| Platelet count decreased | 2 (10.0%) | 3 (15.0%) | 2 (10.0%) |
| Constipation | 1 (5.0%) | 3 (15.0%) | 1 (5.0%) |
| Diarrhoea | 2 (10.0%) | 2 (10.0%) | 1 (5.0%) |
| Rash maculo-papular | 1 (5.0%) | 3 (15.0%) | 1 (5.0%) |
| Confusional state | 3 (15.0%) | 0 (0.0%) | 0 (0.0%) |
| Headache | 3 (15.0%) | 0 (0.0%) | 0 (0.0%) |
| Muscular weakness | 3 (15.0%) | 0 (0.0%) | 0 (0.0%) |

At each level of summarization (preferred term), patients reporting more than one treatment-related AE are counted only once

TABLE 19

Grade ≥3 Treatment Emergent Adverse Events in Decreasing Order of Frequency

| AE Preferred Term | All Patients | MRZ Related | TMZ Related | Related to Both |
|---|---|---|---|---|
| Fatigue | 3 (15.0%) | 3 (15.0%) | 1 (5.0%) | 1 (5.0%) |
| Abdominal pain | 1 (5.0%) | 0 (0.0%) | 0 (0.0%) | 0 (0.0%) |
| Dehydration | 1 (5.0%) | 1 (5.0%) | 0 (0.0%) | 0 (0.0%) |
| Hallucination | 1 (5.0%) | 1 (5.0%) | 0 (0.0%) | 0 (0.0%) |
| Headache | 1 (5.0%) | 0 (0.0%) | 0 (0.0%) | 0 (0.0%) |
| Insomnia | 1 (5.0%) | 0 (0.0%) | 0 (0.0%) | 0 (0.0%) |
| Musculoskeletal pain | 1 (5.0%) | 0 (0.0%) | 0 (0.0%) | 0 (0.0%) |
| Ovarian cyst | 1 (5.0%) | 0 (0.0%) | 0 (0.0%) | 0 (0.0%) |
| Pelvic infection | 1 (5.0%) | 0 (0.0%) | 0 (0.0%) | 0 (0.0%) |
| Platelet count decreased | 1 (5.0%) | 1 (5.0%) | 1 (5.0%) | 1 (5.0%) |
| Vomiting | 1 (5.0%) | 1 (5.0%) | 0 (0.0%) | 0 (0.0%) |

TABLE 20

Listing of Serious Adverse Events

| Patient ID | AE Preferred Term | Grade | DLT | MRZ Related/ Action Taken with MRZ | TMZ Related/ Action Taken with TMZ | Outcome |
|---|---|---|---|---|---|---|
| 104-C302 | Nephrolithiasis | Grade 3 | No | Not Suspected/ None | Not Suspected/ None | Recovered/Resolved |
| 301-A202 | Confusional state | Grade 2 | No | Suspected/ None | Not Suspected/ None | Unknown |
| | Dehydration | Grade 3 | No | Not Suspected/ None | Not Suspected/ None | Unknown |
| | Fatigue | Grade 3 | No | Suspected/ None | Not Suspected/ None | Unknown |
| | Hallucination | Grade 3 | No | Suspected/ None | Not Suspected/ None | Unknown |
| | Nausea | Grade 2 | No | Suspected/ None | Not Suspected/ None | Recovered/Resolved |

TABLE 20-continued

Listing of Serious Adverse Events

| Patient ID | AE Preferred Term | Grade | DLT | MRZ Related/ Action Taken with MRZ | TMZ Related/ Action Taken with TMZ | Outcome |
|---|---|---|---|---|---|---|
| | Vomiting | Grade 3 | No | Suspected/ None | Not Suspected/ None | Recovered/Resolved |
| 301-C202 | Convulsion | Grade 1 | No | Not Suspected/ None | Not Suspected/ None | Recovered/Resolved |
| | Ovarian cyst | Grade 3 | No | Not Suspected/ Dose Delayed | Not Suspected/ Dose Delayed | Recovering/Resolving |
| | Pelvic infection | Grade 3 | No | Not Suspected/ None | Not Suspected/ None | Recovered/Resolved |

The combination of marizomib, temozolomide and RT (MRZ+TMZ+RT) is generally well-tolerated in patients with newly diagnosed glioma. The most common MRZ-related adverse events included fatigue, nausea, vomiting, decreased appetite, dizziness, and hallucinations. The most common MRZ-related adverse event greater than or equal to grade 3 is fatigue. Three patients exhibited fatigue at a level greater than or equal to 3. One patient experienced the following MRZ-related serious adverse events (SAEs): confusion, fatigue, hallucinations, nausea, and vomiting. These adverse events did not meet the dose-limiting toxicity criteria. One subject experienced dose-limiting toxicity, experiencing dose-limiting fatigue.

Efficacy

Figure 10A:
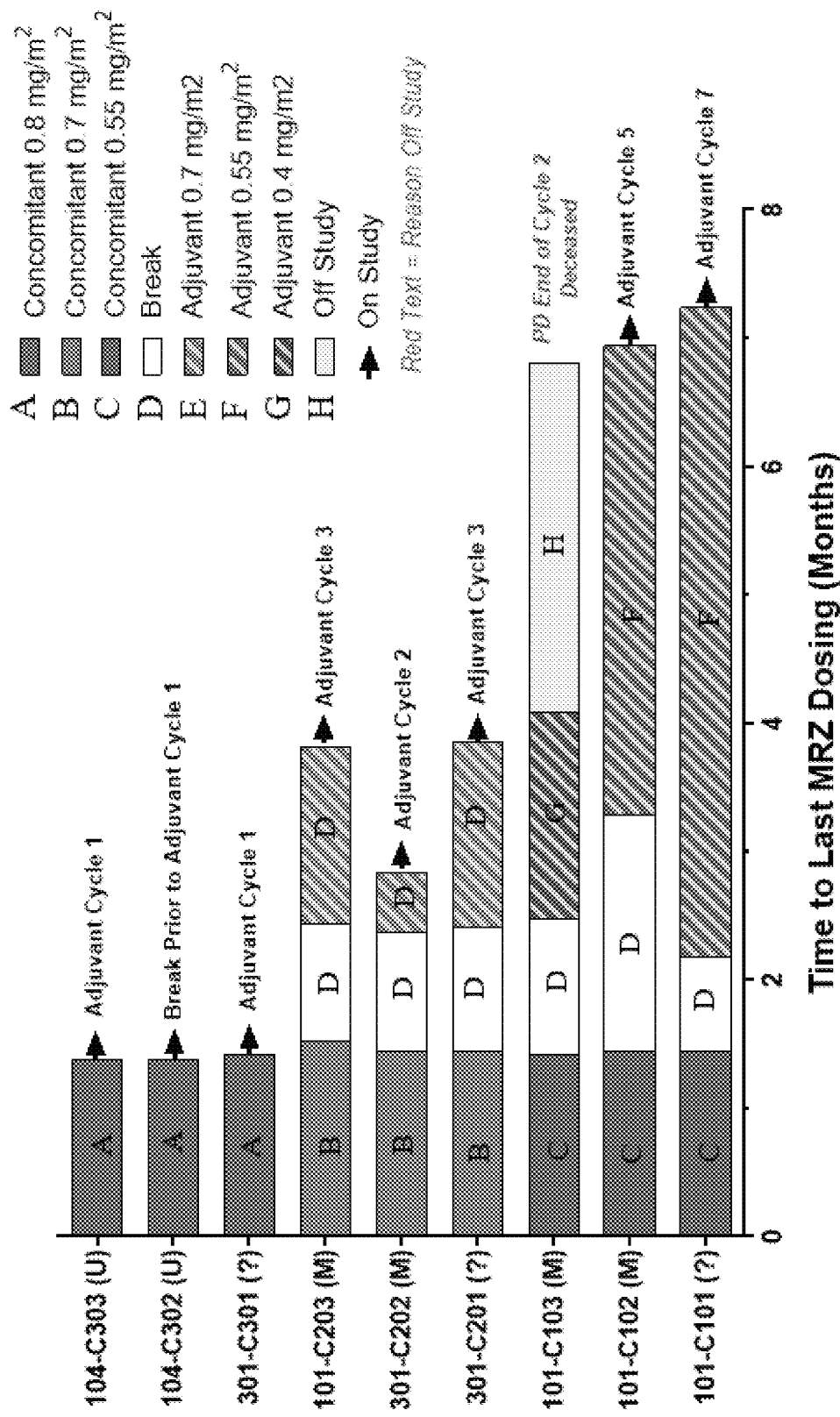
FIG. 10A shows the results of patients administered with concomitant therapy as set forth in Example 2.
Figure 10B:
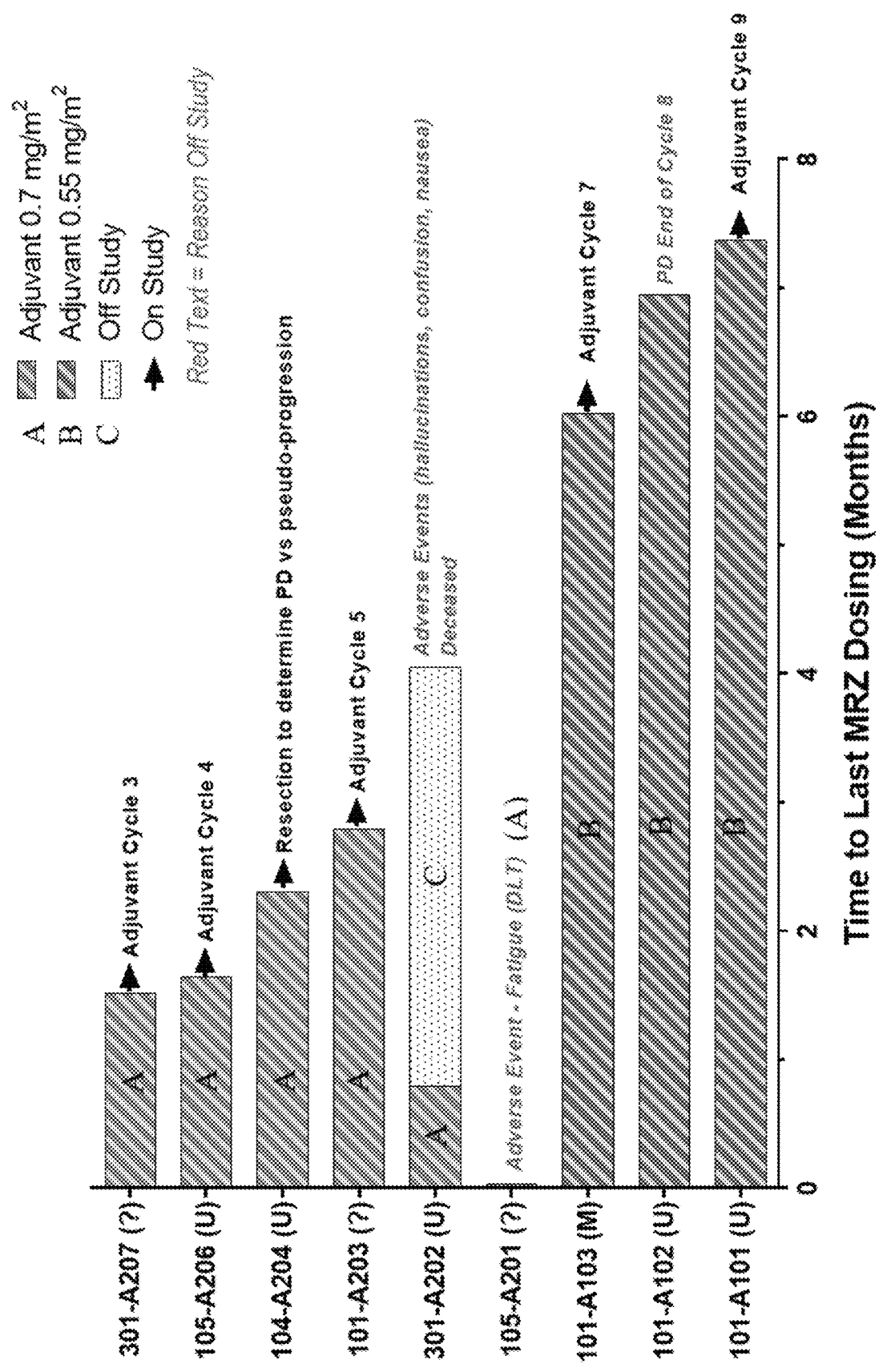
FIG. 10B shows the results of patients administered with adjuvant therapy as set forth in Example 2.

FIG. 10A shows the results of patients administered with concomitant therapy from the first dose of marizomib to progressive disease or last dose of marizomib. FIG. 10B shows the results of patients administered with adjuvant therapy from the first dose of marizomib to progressive disease or last dose of marizomib.

Example 3—Phase 1, Open-Label, Dose Escalation Study of Marizomib and Bevacizumab in WHO Grade IV Malignant Glioma This Example gives a phase 1 dose escalation combination study followed by a Phase 2 marizomib monotherapy study.

Study Objectives and Design

The primary objective was to determine the maximum tolerated dose and recommended phase II dose of marizomib+bevacizumab. The secondary objective was to evaluate the safety and activity of marizomib+bevacizumab.

An exploratory objective was to evaluate the baseline proteasome activity, marizomib and bevacizumab PK, marizomib neurological coordination (SARA), and quality of life assessment (FACT-Cog/FACT-Br)

Methods

The clinical trial was a Phase 1, dose-escalation (3+3 design) followed by dose-expansion at recommended Phase 2 Dose (RP2D). Three dose escalation cohorts were used—marizomib 0.55 (6 pts), 0.7 (3 pts), and 0.8 mg/m² (3 pts); dose-expansion 0.8 mg/m² (24 pts).

Marizomib was infused intravenous (IV; 10 min) on Days 1, 8, & 15; bevacizumab was infused IV at 10 mg/kg on Days 1 and 15. The drugs were infused on 28-Day Cycles. Tumor response is assessed every other cycle by RANO criteria. Blood marizomib pharmacokinetic parameters were assessed on Day 8, serum bevacizumab pharmacokinetic parameters were assessed on days 1 and 15; blood proteasome inhibition was assessed on days 1 and 15 every cycle. Table 21 gives the treatment parameters of the present study.

TABLE 21

Treatment Parameters of Grade IV MG Study

| Cohort (N) | IV marizomib (mg/m²) - 10 min infusion Days 1, 8, 15 q 28 days | BEV IV (mg/kg) q 14 days |
|---|---|---|
| 1 (6) | 0.55 | 10 |
| 2 (3) | 0.7 | 10 |
| 3 (3) | 0.8 | 10 |
| 4 (24) | Expansion of RP2D | 10 |

| Phase 2 | IV marizomib (0.8 mg/m²) - 10 min infusion days 1, 8, 15, q 28 days | |
|---|---|---|
| 5 | 0.8 | None |

The key eligibility criteria included patients over 18 years of age, with histological evidence of grade IV malignant glioma in first or second relapse with clear progressive disease. Participants must have completed standard radiation therapy and temozolomide. Additional criteria included no prior proteasome inhibitor (including marizomib) or anti-angiogenic therapies, and a Karnofsky Performance Score greater than or equal to 70. Criteria also included that the patient be at least four weeks from surgical resection and 12 weeks from the end of radiotherapy. Table 22 gives the demographics of the study participants.

TABLE 22

Breakdown of Patients by Phase of Study

| | Phase 1 | Phase 2 |
|---|---|---|
| # of Subjects Enrolled (per Study Phase) | 36 | 30 |
| # of Active Subjects | 1 | 4 |
| # of Inactive Subjects | 35 | 26 |

TABLE 23

Distribution of Patients Across Sites

| Site | # of Subjects Enrolled | Phase 1 Active/Inactive | Phase 2 Active/Inactive |
|---|---|---|---|
| 101 | 19 | 0/15 | 0/4 |
| 102 | 21 | 0/9 | 4/8 |
| 103 | 7 | 0/3 | 0/4 |

TABLE 23-continued

Distribution of Patients Across Sites

| Site | # of Subjects Enrolled | Phase 1 Active/Inactive | Phase 2 Active/Inactive |
|---|---|---|---|
| 104 | 7 | NA | 0/7 |
| 301 | 12 | 1/8 | 0/3 |
| Total | 66 | 1/35 | 4/26 |

TABLE 24

Demographics of Study Participants

| | MRZ + BEV (N = 36) | MRZ Monotherapy (N = 30) |
|---|---|---|
| Age (mean ± SD years) | 55.3 ± 10.1 | 55.8 ± 13.2 |
| Gender | | |
| Male | 23 (63.9%) | 17 (56.7%) |
| Female | 13 (36.1%) | 13 (43.3%) |
| Race[1] | | |
| White | 30 (83.3%) | 26 (86.7%) |
| Black or African American | 3 (8.3%) | 0 |
| Asian | 3 (8.3%) | 0 |
| Subject Declined to Provide | 0 | 3 (10.0%) |
| Missing | 0 | 1 (3.4%) |
| Baseline KPS[2] | | |
| 100 | 3 (8.6%) | 1 (3.4%) |
| 90 | 13 (37.1%) | 15 (51.7%) |
| 80 | 16 (45.7%) | 9 (31.0%) |
| 70 | 3 (8.6%) | 4 (13.8%) |
| Missing | 0 | 1 (3.4%) |
| Time from Initial Diagnosis to First Dose of Study Drug (mean ± SD months) | 12.6 ± 7.6 | 11.1 ± 7.4 |
| Tumor Recurrence | | |
| First Recurrence | 20 (55.6%) | 14 (46.7%) |
| Second Recurrence | 7 (19.4%) | 13 (43.3%) |
| >2 Recurrences | 3 (8.3%) | 0 |
| Missing Data | 6 (16.7%) | 3 (10.0%) |
| Time Since Last Progressive Disease to First Dose of Study Drug (mean ± SD months) | 0.8 ± 1.04 | 0.5 ± 0.7 |
| Prior Treatment Regimens | | |
| Surgery | 36 (100.0%) | 25 (83.3%) |
| Radiation and Temozolomide | 36 (100.0%) | 27 (90.0%) |
| Lomustine | 4 (11.1%) | 3 (10.0%) |
| Investigational Drug | 1 (2.8%) | 0 |
| Optune Device | 0 | 2 (6.7%) |
| Time Since Last Radiation Therapy to First Dose of Study Drug (mean ± SD months) | 9.0 ± 6.9 | 9.9 ± 11.1 |
| Patients Receiving a Corticosteroid at Baseline (e.g., dexamethasone) | 22 (61.1%) | 21 (72.4%) |

TABLE 25

Further Demographics of Study Participants

| Prior Therapies | |
|---|---|
| Surgery, Radiation/Temozolomide | 100% (36/36) |
| Immunotherapy | 14% (5/36) |
| Other Investigational Drug or Device | 8% (3/36) |
| Median months from last RT (range) | 7.8 (2.5-29.5) |
| Corticosteroid use at baseline | 31% (11/36) |
| Median months from last progression to C1D1 (range) | 0.8 (0.1-3.8) |
| Parameter | |
| MGMT Promoter Methylation Status (6 pts unknown) | |
| Unmethylated | 20/30 |
| Methylated | 10/30 |
| EGFRvIII Positive Status (9 pts unknown) | 4/27 |
| EGFR Amplified (9 pts unknown) | 11/27 |
| EGFR Mutated (9 pts unknown) | 8/27 |

Results

Safety

Thirty-six patients enrolled with a median age 55 years (27-76), 64% were male, Karnofsky Score >70. Duration of dosing was 0.25-15 months to date; treatment is ongoing in 3 pts. Marizomib and bevacizumab was well tolerated.

Study treatment-related Grade ≥3 adverse events: fatigue, headache, hypertension, hallucination, confusional state, ataxia, optic nerve disorder, insomnia, delusion, hyponatremia; one Grade 4 serious adverse event (appendicitis perforated, not related to study treatment), one Grade 5 serious adverse event (embolism, intracranial hemorrhage, bevacizumab-related). One patient (cohort 1) had dose limiting toxicity (fatigue); no other dose limiting toxicities occurred across the dose range.

The efficacy evaluable population (N=33) included 31 patients efficacy evaluable by RANO criteria, and one patient Grade 5 serious adverse event (no post-treatment tumor assessment). The intent-to-treat population was 36.

One patient experienced a complete response (CR), and thirteen patients experienced partial responses (PR) (including 3 with CR for target lesion). Thirteen patients experienced stable disease (SD) (including 2 patients with unconfirmed PR), 6 patients experienced progressive disease (PD), and 3 patients were not evaluable (NE, no post-treatment tumor assessment). Marizomib and bevacizumab pharmacokinetic parameters were consistent with published parameters and not affected by co-administration. Proteasome inhibition was maximal on chymotrypsin-like (CT-L) domains in cohorts 1 and 2. Dose-dependent inhibition of trypsin-like (T-L) and caspase-like (C-L) activity in cohorts 1 vs 2 suggested dose-dependent pharmacodynamics.

TABLE 26

Most Common Treatment-Related Adverse Events

| Preferred Term | MRZ 0.8 mg/m² + BEV Cohorts 3 & 4 (N = 27) | MRZ 0.8 mg/m² Monotherapy (N = 30) |
|---|---|---|
| Patients with at Least One TEAE | 27 (100.0%) | 29 (96.7%) [1] |
| Fatigue | 21 (77.8%) | 19 (63.3%) |
| Nausea | 17 (63.0%) | 11 (36.7%) |
| Headache | 12 (44.4%) | 12 (40.0%) |
| Vomiting | 16 (59.3%) | 9 (30.0%) |
| Hypertension | 11 (40.7%) | 4 (13.3%) |
| Hallucination | 12 (44.4%) | 12 (40.0%) |
| Dysphonia | 10 (37.0%) | 1 (3.3%) |
| Confusional state | 9 (33.3%) | 7 (23.3%) |
| Diarrhoea | 8 (29.6%) | 7 (23.3%) |
| Dizziness | 8 (29.6%) | 5 (16.7%) |
| Epistaxis | 8 (29.6%) | 2 (6.7%) |
| Fall | 7 (25.9%) | 4 (13.3%) |
| Constipation | 7 (25.9%) | 9 (30.0%) |
| Anaemia | 6 (22.2%) | 6 (20.0%) |

TABLE 26-continued

Most Common Treatment-Related Adverse Events

| Preferred Term | MRZ 0.8 mg/m² + BEV Cohorts 3 & 4 (N = 27) | MRZ 0.8 mg/m² Monotherapy (N = 30) |
|---|---|---|
| Ataxia | 7 (25.9%) | 6 (20.0%) |
| Hyperglycaemia | 6 (22.2%) | 8 (27.6%) |
| Infusion site pain | 4 (14.8%) | 3 (10.0%) |
| Hypokalemia | 5 (18.5%) | 8 (27.6%) |
| Insomnia | 3 (11.1%) | 14 (46.7%) |
| Platelet count decreased | 5 (18.5%) | 7 (23.3%) |
| Dysarthria | 6 (22.2) | 5 (16.7%) |

TABLE 27

Most Common Treatment-Related Adverse Events by Cause

| Preferred Term | MRZ 0.8 mg/m² + BEV Cohorts 3 & 4 (N = 27) | | | MRZ 0.8 mg/m² Monotherapy (N = 30) [1] |
|---|---|---|---|---|
| | MRZ Related | BEV Related | Related to Both | MRZ Related |
| Fatigue | 19 (70.4%) | 18 (66.7%) | 18 (66.7%) | 18 (60.0%) |
| Headache | 12 (44.4%) | 6 (22.2%) | 6 (22.2%) | 11 (36.7%) |
| Nausea | 17 (63.0%) | 2 (7.4%) | 2 (7.4%) | 9 (30.0%) |
| Vomiting | 15 (55.6%) | 4 (14.8%) | 4 (14.8%) | 7 (23.3) |
| Hypertension | 1 (3.7%) | 11 (40.7%) | 1 (3.7%) | 1 93.3%) |
| Hallucination | 12 (44.4%) | 0 (0.0%) | 0 (0.0%) | 11 (36.7%) |
| Dysphonia | 1 (3.7%) | 10 (37.0%) | 1 (3.7%) | 0 |
| Diarrhoea | 8 (29.6%) | 1 (3.7%) | 1 (3.7%) | 7 (23.3) |
| Dizziness | 8 (29.6%) | 1 (3.7%) | 1 (3.7%) | 3 (10.0%) |
| Infusion site pain | 4 (14.8%) | 1 (3.7%) | 1 (3.7%) | 2 (6.7%) |
| Confusional state | 7 (25.9%) | 1 (3.7%) | 1 (3.7%) | 6 (20.0%) |
| Epistaxis | 0 (0.0%) | 7 (25.9%) | 0 (0.0%) | 1 (3.3%) |
| Ataxia | 7 (25.9%) | 0 (0.0%) | 0 (0.0%) | 5 (16.7%) |
| Anaemia | 5 (18.5%) | 0 (0.0%) | 0 (0.0%) | 5 (16.7% |
| Constipation | 5 (18.5%) | 1 (3.7%) | 1 (3.7%) | 6 (20.0%) |
| Platelet count decreased | 2 (7.4%) | 3 (11.1%) | 1 (3.7%) | 0 |
| Muscular weakness | 3 (11.1%) | 1 (3.7%) | 1 (3.7%) | 0 |
| Stomatitis | 3 (11.1%) | 2 (7.4%) | 2 (7.4%) | 0 |
| Upper-airway cough syndrome | 0 (0.0%) | 5 (18.5%) | 0 (0.0%) | 0 |
| Fall | 3 (11.1%) | 0 (0.0%) | 0 (0.0%) | 1 (3.3%) |

TABLE 28

Treatment Related Grade ≥3 AEs by Patient

| MRZ Dose | 0.55 mg/m² Cohort 1 (N = 6) | | 0.7 mg/m² Cohort 2 (N = 3) | | 0.8 mg/m² Cohorts 3 & 4 (N = 27) | | TOTAL |
|---|---|---|---|---|---|---|---|
| Preferred Term | BEV | MRZ | BEV | MRZ | BEV | MRZ | (N = 36) |
| Ataxia | 0 | 0 | 0 | 0 | 0 | 1 | 1 |
| Confusional State | 0 | 1 | 0 | 0 | 0 | 0 | 1 |
| Delusion | 0 | 0 | 0 | 0 | 0 | 1 | 1 |
| Fatigue | 1 | 1 | 0 | 0 | 1 | 1 | 2 |
| Hallucination | 0 | 1 | 0 | 0 | 0 | 1 | 2 |
| Headache | 1 | 0 | 0 | 0 | 1 | 3 | 4 |
| Insomnia | 0 | 0 | 0 | 0 | 0 | 1 | 1 |
| Embolism | 0 | 0 | 0 | 0 | 1 | 0 | 1 |
| Hypertension | 0 | 0 | 1 | 0 | 5 | 0 | 6 |
| Intracranial Hemorrhage | 0 | 0 | 0 | 0 | 1 | 0 | 1 |
| Embolism | 0 | 0 | 0 | 0 | 1 | 0 | 1 |
| Optic Nerve Disorder | 0 | 0 | 0 | 0 | 1 | 0 | 1 |
| Proteinuria | 0 | 0 | 1 | 0 | 0 | 0 | 1 |
| Fall | 0 | 0 | 0 | 0 | 0 | 1 | 1 |
| Dyspnea | 0 | 0 | 0 | 0 | 1 | 1 | 1 |
| Hyponatremia | 0 | 0 | 0 | 0 | 0 | 1 | 1 |

Table 29 gives the study treatment-related adverse events and all adverse events greater than or equal to grade 3, as of 12 Sep. 2016.

TABLE 29

Treatment-Related AEs and All AEs ≥3

| Study Treatment-Related Adverse Events and All Grade 3 or Above Adverse Events Preferred Term | # Patients (%) with AE | Relationship to Study Treatment | | | | # Patients Grade ≥3 |
|---|---|---|---|---|---|---|
| | | Neither | BEV | MRZ | Both | |
| Fatigue | 24 (67) | 2 | 0 | 1 | 21 | 3 |
| Nausea | 21 (58) | 0 | 0 | 19 | 2 | 0 |
| Headache | 20 (56) | 2 | 1 | 5 | 12 | 5 |
| Vomiting | 17 (47) | 1 | 0 | 12 | 4 | 0 |
| Hypertension | 16 (42) | 1 | 13 | 0 | 2 | 6 |
| Hallucination | 11 (31) | 0 | 0 | 11 | 0 | 2 |
| Diarrhoea | 10 (28) | 0 | 0 | 9 | 1 | 0 |
| Dysphonia | 10 (28) | 0 | 10 | 0 | 0 | 0 |
| Dizziness | 9 (25) | 0 | 0 | 8 | 1 | 0 |
| Anaemia | 8 (22) | 2 | 0 | 6 | 0 | 0 |
| Confusional State | 8 (22) | 1 | 0 | 6 | 1 | 1 |
| Epistaxis | 8 (22) | 1 | 7 | 0 | 0 | 0 |
| Hyperglycemia | 8 (22) | 8 | 0 | 0 | 0 | 2 |
| Falls | 8 (22) | 5 | 0 | 3 | 0 | 0 |
| Hypokalemia | 7 (19) | 7 | 0 | 0 | 0 | 1 |
| Constipation | 7 (19) | 2 | 0 | 4 | 1 | 0 |
| Ataxia | 7 (19) | 1 | 0 | 6 | 0 | 1 |
| Convulsion | 7 (19) | 7 | 0 | 0 | 0 | 0 |
| Dysarthria | 7 (19) | 6 | 0 | 1 | 0 | 1 |
| Muscular Weakness | 6 (17) | 4 | 0 | 2 | 0 | 2 |
| Infusion Site Pain | 6 (17) | 0 | 0 | 6 | 0 | 0 |
| Anxiety | 6 (17) | 6 | 0 | 0 | 0 | 0 |
| Vision Blurred | 6 (17) | 3 | 0 | 3 | 0 | 0 |
| Hemiparesis | 5 (14) | 5 | 0 | 0 | 0 | 3 |
| Insomnia | 4 (11) | 2 | 1 | 1 | 0 | 1 |
| Dysphagia | 3 (8) | 3 | 0 | 0 | 0 | 1 |
| Hypotension | 3 (8) | 3 | 0 | 0 | 0 | 1 |
| Lymphocyte Count Decreased | 3 (8) | 3 | 0 | 0 | 0 | 3 |
| Dyspnoea | 3 (8) | 2 | 0 | 0 | 1 | 1 |
| Pyramidal Tract Syndrome | 3 (8) | 3 | 0 | 0 | 0 | 1 |
| Haemorrhage Intracranial | 2 (6) | 0 | 2 | 0 | 0 | 1 (Grade 5) |
| Aphasia | 2 (6) | 2 | 0 | 0 | 0 | 1 |
| Asthenia | 2 (6) | 2 | 0 | 0 | 0 | 1 |
| Embolism | 2 (6) | 0 | 2 | 0 | 0 | 1 |
| Hyponatremia | 2 (6) | 1 | 0 | 1 | 0 | 1 |
| Fracture of Femur | 1 (3) | 1 | 0 | 0 | 0 | 1 |
| Tumor Metastasis | 1 (3) | 1 | 0 | 0 | 0 | 1 |
| Optic Nerve Disorder | 1 (3) | 0 | 1 | 0 | 0 | 1 |
| Depressed Level of Consciousness | 1 (3) | 1 | 0 | 0 | 0 | 1 |
| Delusion | 1 (3) | 0 | 0 | 1 | 0 | 1 |
| Appendicitis Perforated | 1 (3) | 1 | 0 | 0 | 0 | 1 (Grade 4) |
| Ear Infection | 1 (3) | 1 | 0 | 0 | 0 | 1 |

As shown above, the combination of marizomib and bevacizumab is generally well-tolerated in patients with recurrent glioma. The most common marizomib-related adverse events include fatigue, headache, nausea, vomiting, and hallucinations. The most common marizomib-related adverse events ≥3 were headache (3) and confusional state (3). Four patients experienced marizomib-related serious adverse events (hallucinations/confusion; confusion/fatigue/muscle weakness; confusion; and cough/dyspnea). Three grade-4 adverse events were observed: blindness (bevacizumab-related); appendicitis perforated (not related); depressed level of consciousness (not related). Three grade-5 adverse events were observed: intracranial hemorrhage (BEV-related); and disease progression (in two patients; not related). One patient experienced dose-limiting toxicity: in cohort 1, because of fatigue (MRZ-related; not a serious adverse event).

Efficacy

Figure 11:
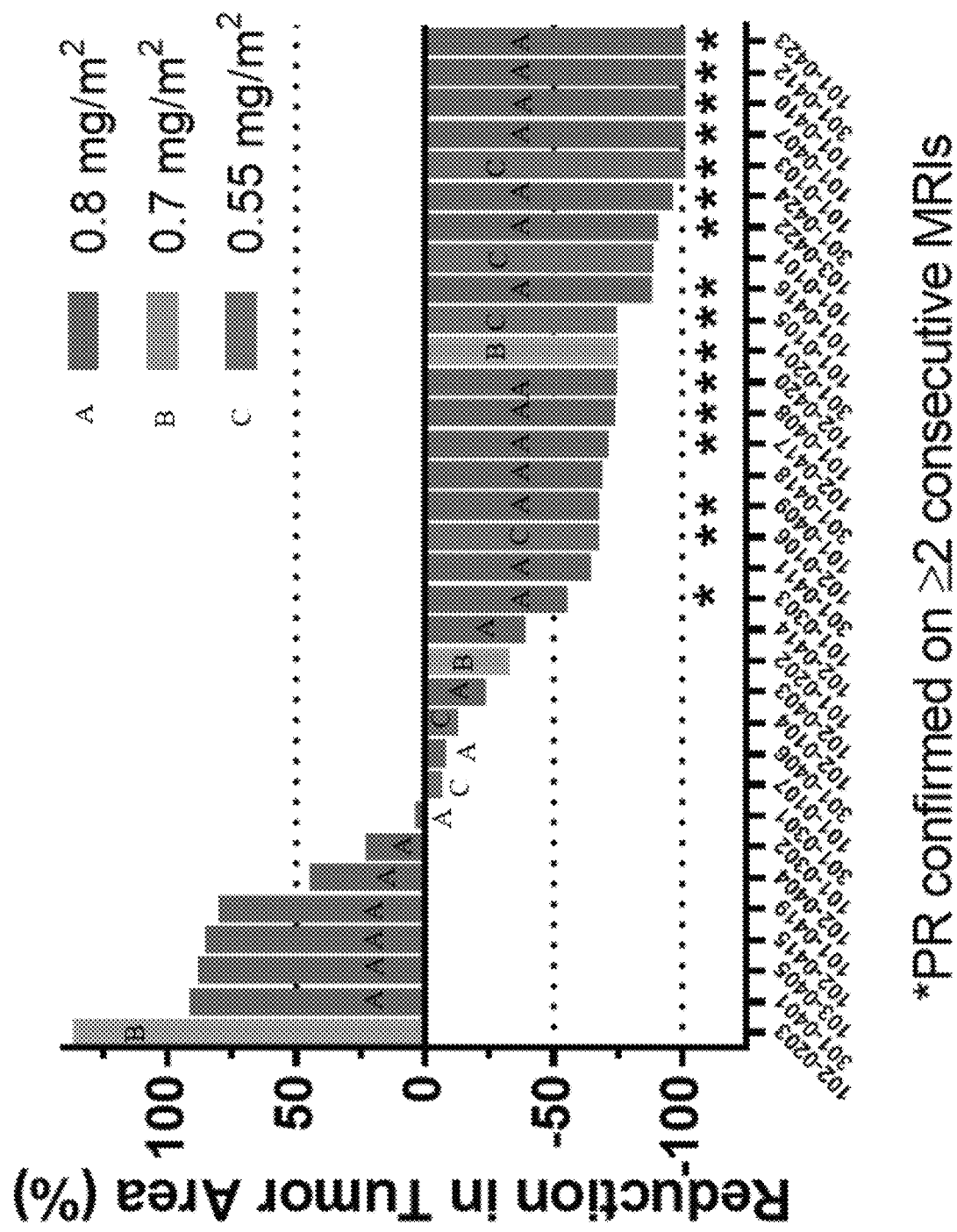
FIG. 11 shows a plot of the response of patients by RANO gliomas set forth in Example 3.
Figure 12:
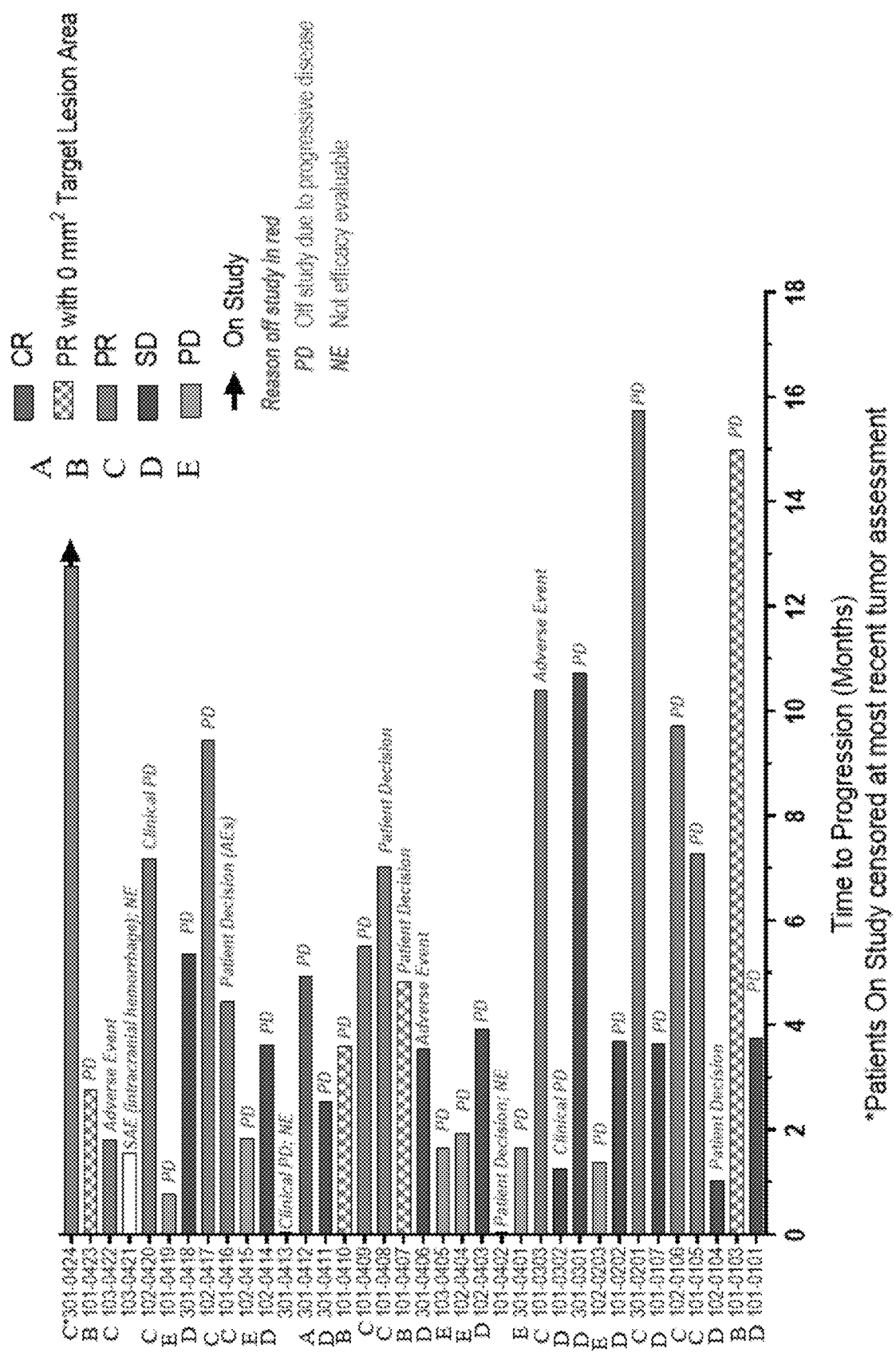
FIG. 12 shows a plot of the time to progression for subjects as set forth in Example 3.

FIG. 11 shows a plot of the best responses by RANO criteria for the 33 patients. FIG. 11 demonstrates that 25 of the 33 efficacy evaluable patients achieved a clinical benefit (RANO ≥Stable Disease) from marizomib and bevacizumab treatment. FIG. 12 shows the time to progression in the patients in the present clinical trial. Table 30 likewise shows the response rate by RANO. Table 31 shows the response rate by MGMT Promoter methylation status.

TABLE 30

Response Rate by RANO

| Best Response by RANO | Number of responses | % Efficacy Evaluable (N = 33) | % Intent to Treat (N = 36) |
|---|---|---|---|
| CR (1) + CR target/PR overall (4) + PR (11) | 16 | 48% | 44% |
| SD (including 2 unconfirmed PR) | 11 | 33% | 31% |
| PD | 6 | 18% | 17% |
| NE | 3 | NA | 8% |

TABLE 31

Response Rate by MGMT Promoter Methylation Status

| Best Response (N) | Efficacy Evaluable (N = 33) | | | ITT (N = 36) | | |
|---|---|---|---|---|---|---|
| | Unmethylated * N = 19 | Methylated N = 8 | Unknown N = 6 | Unmethylated * N = 20 | Methylated N = 10 | Unknown N = 6 |
| CR/PR (14) | 7 | 5 | 2 | 7 | 5 | 2 |
| SD (13) | 9 | 1 | 3 | 9 | 1 | 3 |
| PD (6) | 3 | 2 | 1 | 3 | 2 | 1 |
| NE (3) | — | — | — | 1 | 2 | 0 |

* Unmethylated: <8% promoter methylation by pyro-sequencing

The overall response rate was 42% (RANO ≥partial response) for the Efficacy Evaluable (EE) and 39% in the Intent To Treat (ITT) population. Five of the fourteen partial responses were complete responses for target tumor area (0 mm$^2$) on greater than or equal to 2 consecutive MRIs.

Examples of Target Lesion Complete Response

A 59-year old female patient (Patient A) had a Karnofsky performance score of 90 prior to treatment with marizomib and bevacizumab. Patient A had a brain tumor resection in October 2014. Between December 2014 and January 2015 Patient A was treated with radiotherapy and temozolomide. Between February 2015 and April 2015, Patient A received three cycles of temozolomide. In early April 2015, progressive disease (PD) was confirmed.

Patient A started marizomib treatment (0.55 mg/m$^2$) plus bevacizumab in late May 2015. After 2 cycles, the patient had a dose reduction to 0.4 mg/m$^2$ C3D1.

Figure 13:
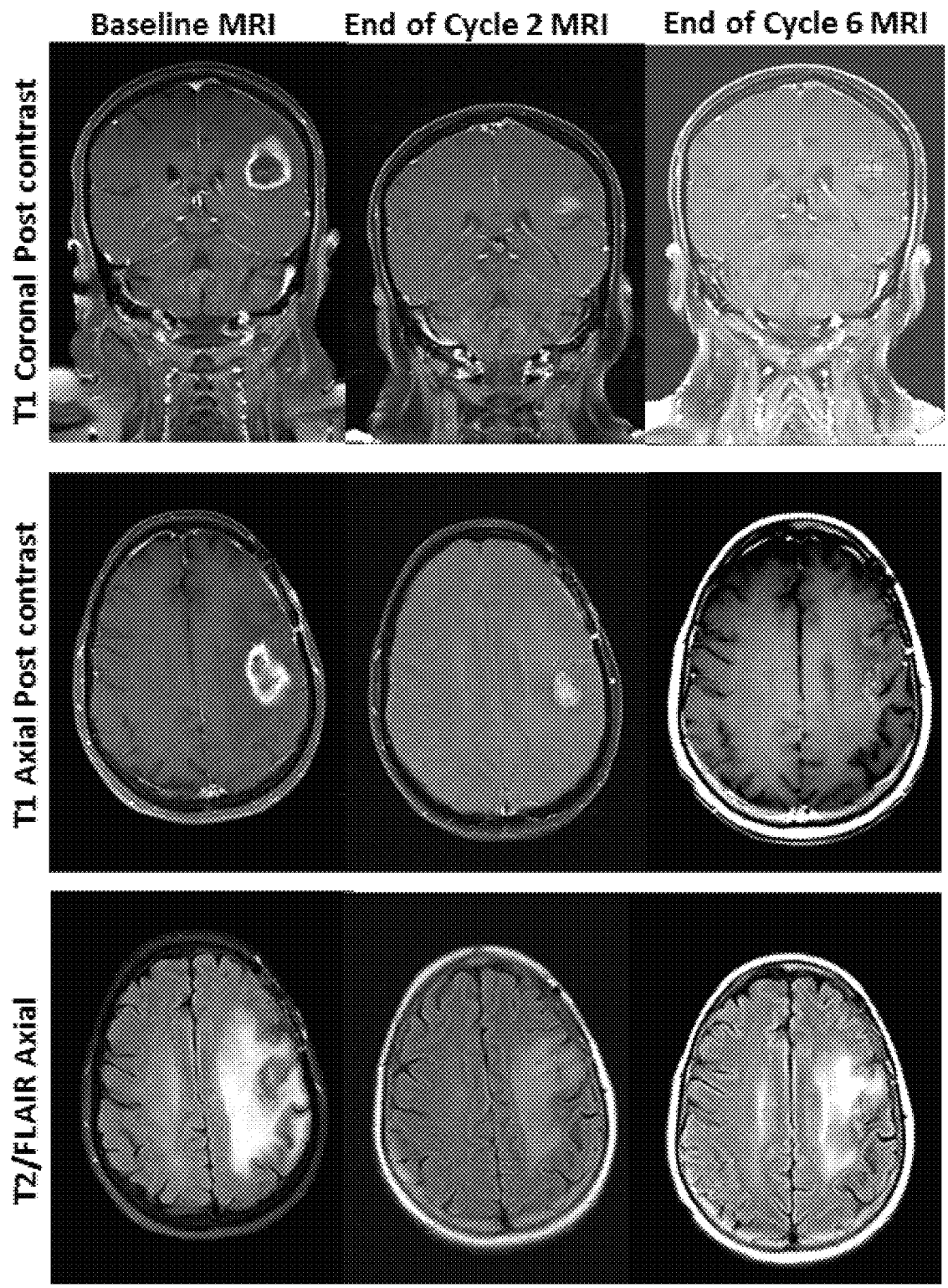
FIG. 13 shows nine MRI images of an example of target lesion complete response in Patient A gliomas set forth in Example 3.

FIG. 13 shows nine MRI images of Patient A, who achieved a complete response after treatment with marizomib and bevacizumab. The first column shows baseline MRI images, the middle column shows images after cycle 2, and the third column shows images after the end of cycle 6. The top row shows the T1 coronal post contrast, the middle row shows the T1 axial post contrast, and the bottom row shows the T2/FLAIR axial images.

Figure 14:
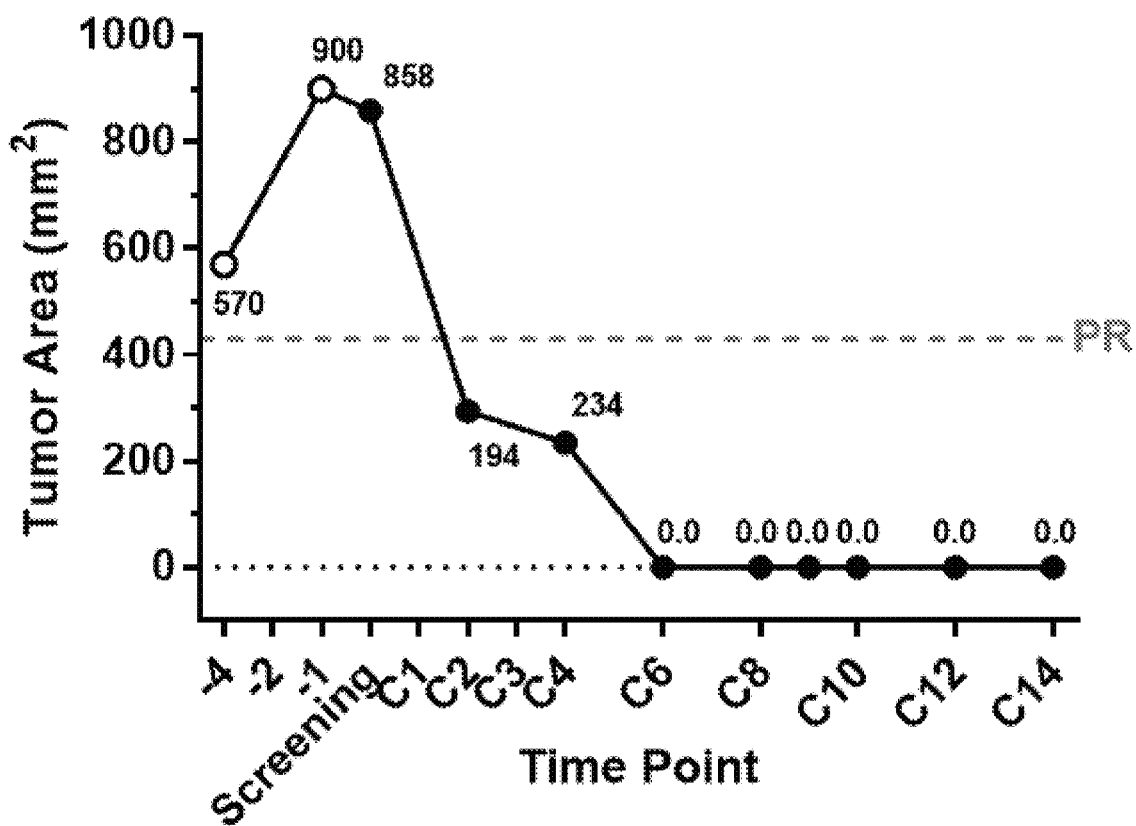
FIG. 14 shows a plot of the tumor area as a function of time in Patient A gliomas set forth in Example 3.

FIG. 14 shows a plot of Patient A's tumor size as a function of time and the number of cycles Patient A received. As shown in FIG. 14, the tumor area was reduced to 0 mm$^2$ by the sixth cycle of treatment.

A 54-year old male patient (Patient B) had a Karnofsky performance score of 90 prior to treatment with marizomib and bevacizumab. Patient B had a brain tumor resection in October 2014. Between November 2014 and January 2015, Patient B was treated with radiotherapy and temozolomide. Between February 2015 and June 2015, Patient B received five cycles of temozolomide. In late June 2015, Progressive Disease (PD) was confirmed.

Patient B started marizomib treatment (0.55 mg/m$^2$) plus bevacizumab in late July 2015. Patient B was removed from the study in March 2016 due to PD.

Figure 15:
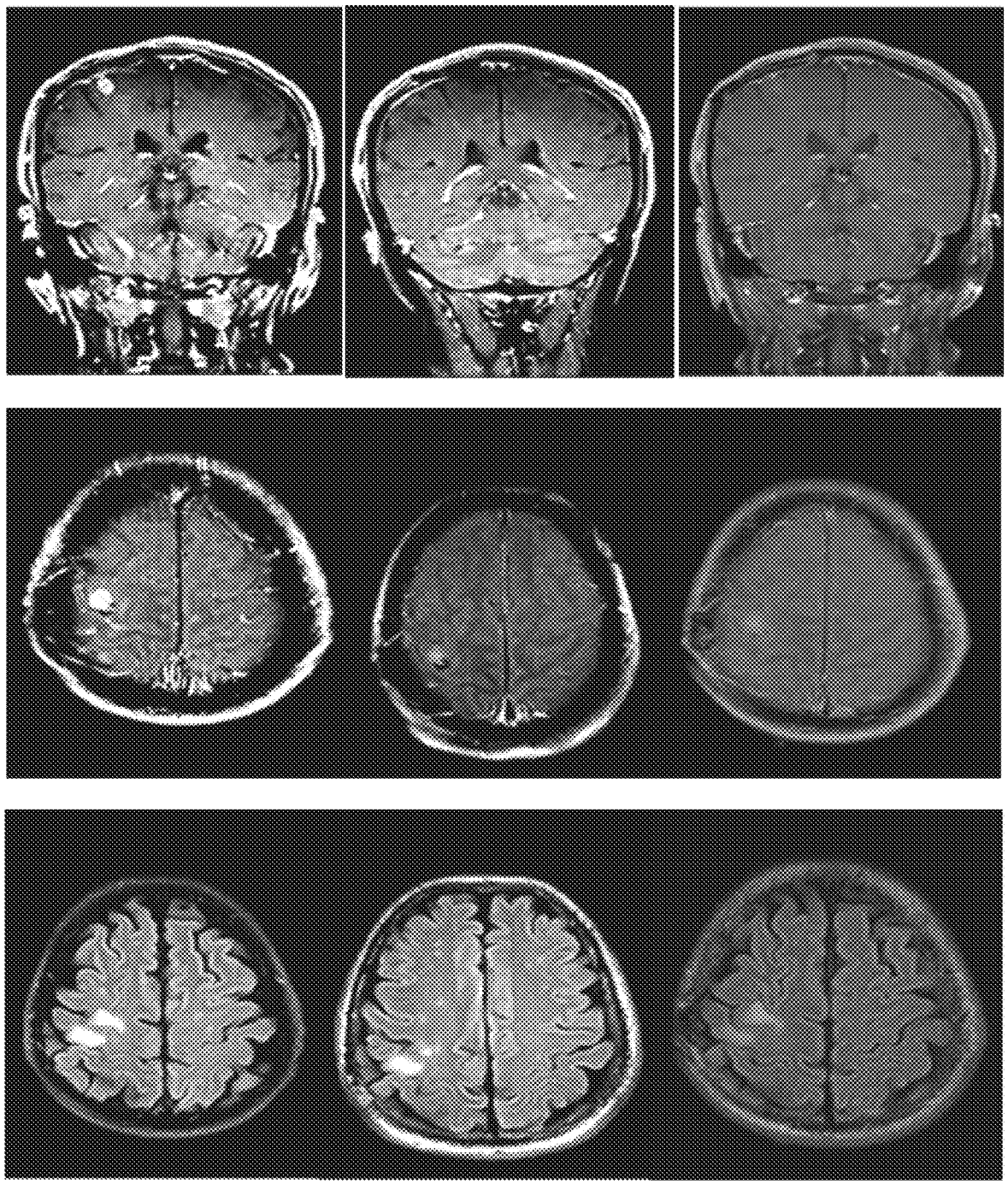
FIG. 15 shows MRI images of Patient B as set forth in Example 3.

FIG. 15 shows MRI images of Patient B. The first column shows baseline MRI images, the middle column shows images after cycle 2, and the third column shows images after the end of cycle 4. The top row shows the T1 coronal post contrast, the middle row shows the T1 axial post contrast, and the bottom row shows the T2/FLAIR axial images.

Figure 16:
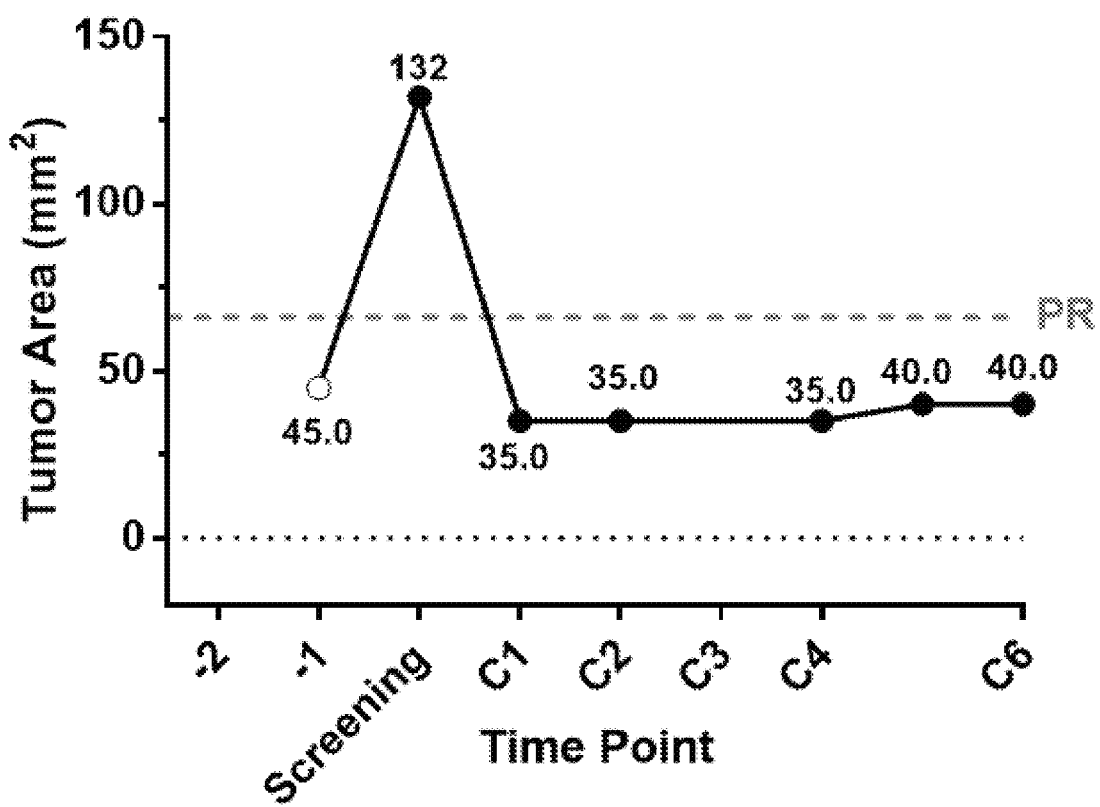
FIG. 16 shows a plot of Patient B's tumor size as a function of time and the number of cycles Patient B received as set forth in Example 3.

FIG. 16 shows a plot of Patient B's tumor size as a function of time and the number of cycles Patient B received. As shown in FIG. 16, the tumor area was reduced to 0 mm$^2$ by the fourth cycle of treatment.

A 61-year old male patient (Patient C) had a Karnofsky performance score of 80 prior to treatment with marizomib and bevacizumab. Patient C had a brain tumor resection in March 2015. Between April 2015 and May 2015 Patient C was treated with radiotherapy and temozolomide. Between June 2015 and July 2015, Patient C received two cycles of temozolomide. In August 2015, progressive disease (PD) was confirmed.

Patient C started marizomib treatment (0.55 mg/m$^2$) plus bevacizumab in August 2015.

Figure 17:
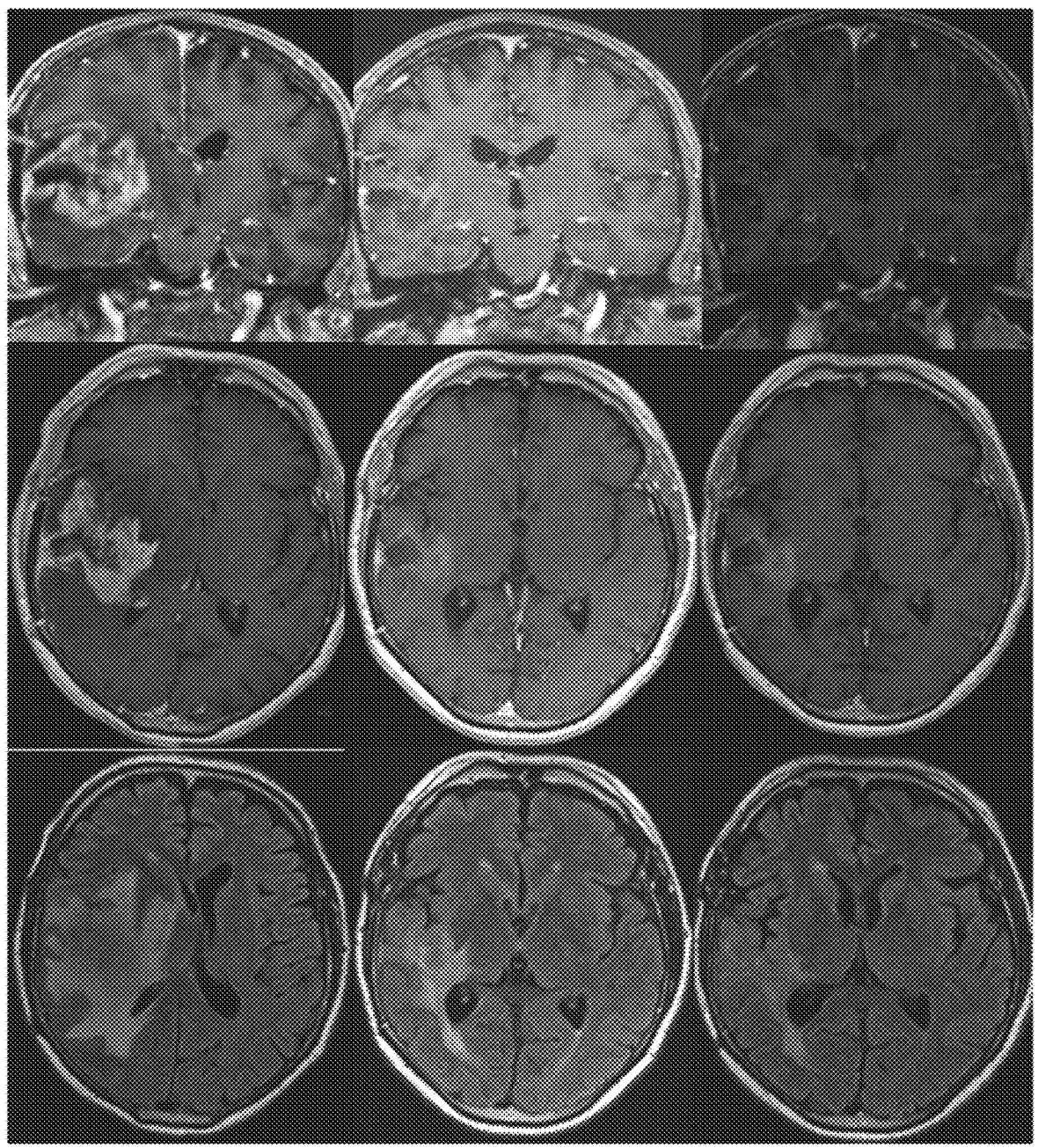
FIG. 17 shows MRI images of Patient C as set forth in Example 3.

FIG. 17 shows MRI images of Patient C. The first column shows baseline MM images, the middle column shows images after cycle 2, and the third column shows images after the end of cycle 4. The top row shows the T1 coronal post contrast, the middle row shows the T1 axial post contrast, and the bottom row shows the T2/FLAIR axial images.

Figure 18:
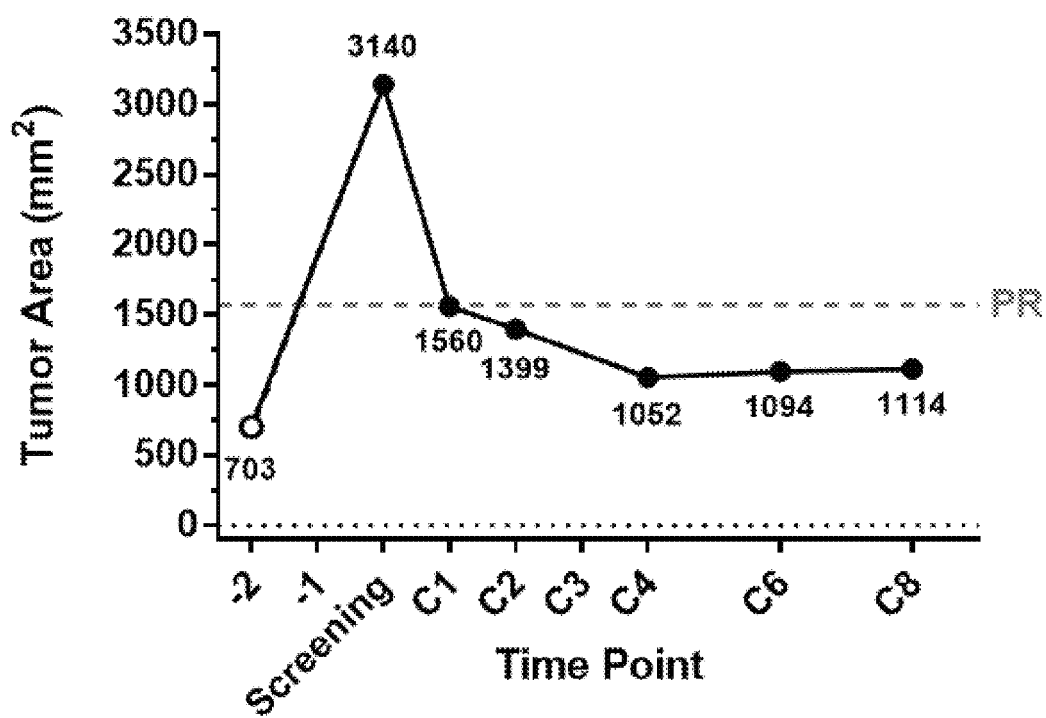
FIG. 18 shows a plot of Patient C's tumor size as a function of time and the number of cycles Patient C received as set forth in Example 3.

FIG. 18 shows a plot of Patient C's tumor size as a function of time and the number of cycles Patient C received. As shown in FIG. 18, the tumor area was reduced to about a third of its peak volume after four cycles of treatment.

A 53-year old male patient (Patient D) had a Karnofsky performance score of 90 prior to treatment with marizomib and bevacizumab. Patient D had a brain tumor resection in April 2015. Between April 2015 and June 2015 Patient D was treated with radiotherapy and temozolomide. Between July 2015 and August 2015, Patient D received three cycles of temozolomide. In September 2015, progressive disease (PD) was confirmed.

Patient D started marizomib treatment (0.7 mg/m$^2$) plus bevacizumab in late September 2015.

Figure 19:
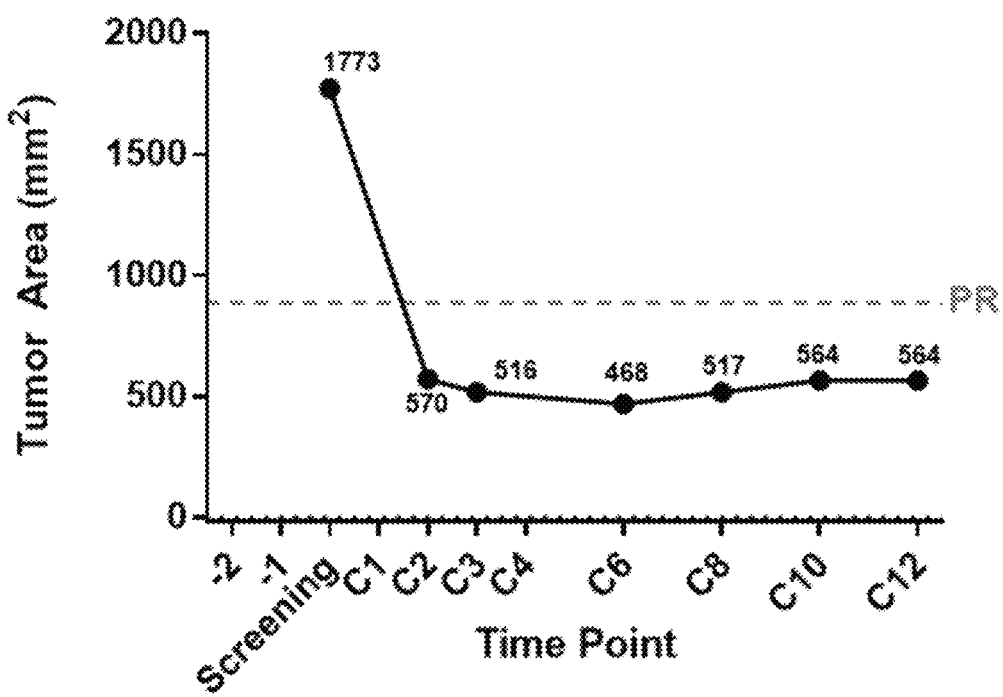
FIG. 19 shows a plot of Patient D's tumor size as a function of time and the number of cycles Patient D received as set forth in Example 3.

FIG. 19 shows a plot of Patient D's tumor size as a function of time and the number of cycles Patient D received. As shown in FIG. 19, the tumor area was reduced to about a third of its peak volume after two cycles of treatment.

A 564-year old male patient (Patient E) had a Karnofsky performance score of 90 prior to treatment with marizomib and bevacizumab. Patient E had a brain tumor resection in October 2014. Between November 2014 and December 2014 Patient E was treated with radiotherapy and temozolomide. Between February 2015 and September 2015, Patient E received temozolomide, and from February 2015 to October 2015 Patient E also received Novocure TTF treatment. In October 2015, PD was confirmed.

Patient E started marizomib treatment (0.8 mg/m$^2$) plus bevacizumab in early February 2016.

Figure 20:
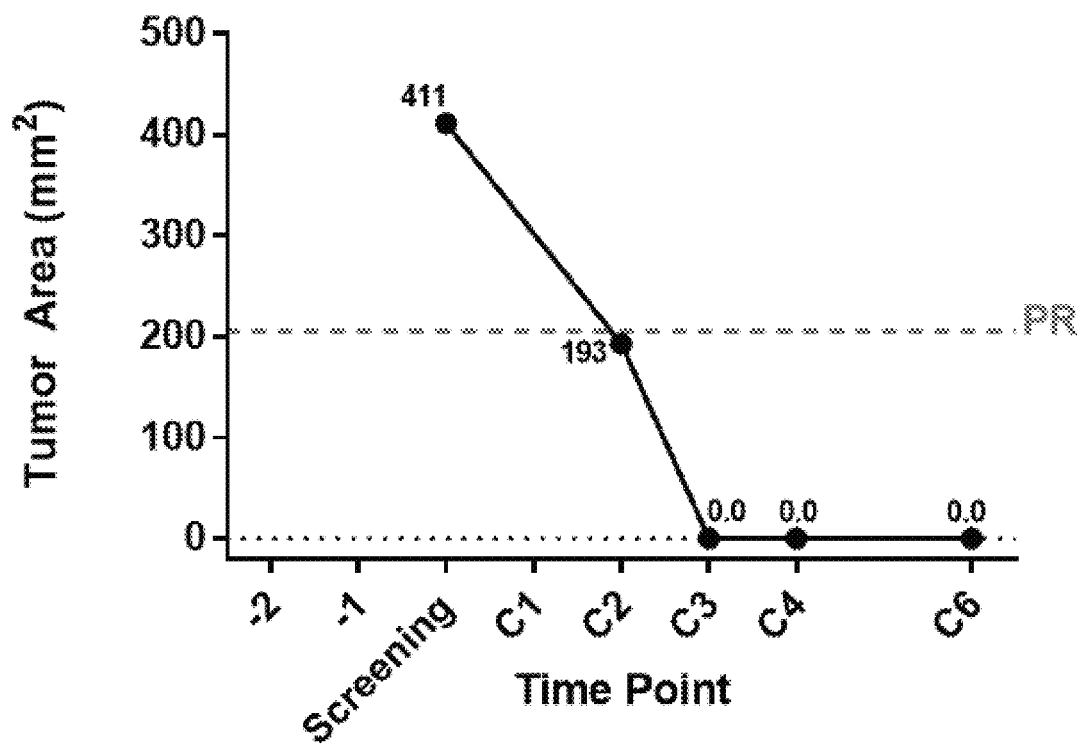
FIG. 20 shows a plot of Patient E's tumor size as a function of time and the number of cycles Patient D received as set forth in Example 3.

FIG. 20 shows a plot of Patient E's tumor size as a function of time and the number of cycles Patient E received. As shown in FIG. 20, the tumor area was reduced to about 0 mm$^2$ after three cycles of treatment.

Figure 21A:
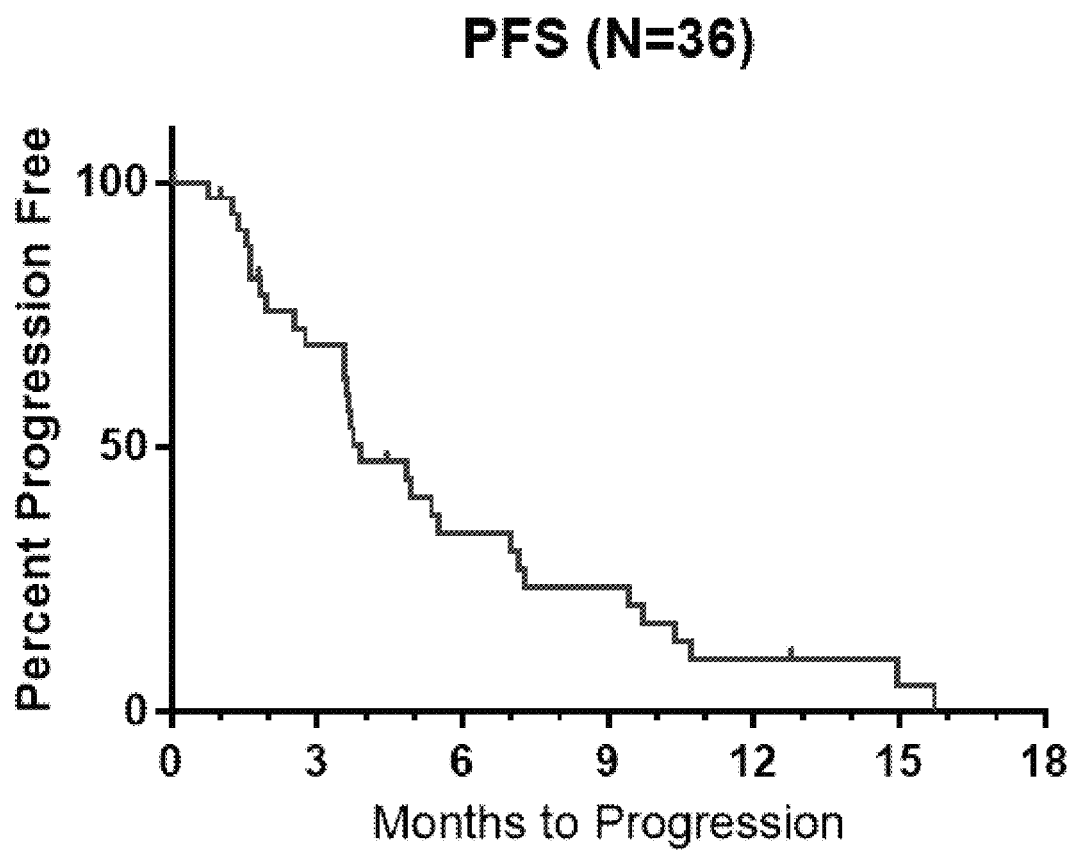
FIG. 21A shows a plot of the PFS percent as a function of time in all patients treated with marizomib for glioma as set forth in Example 3.
Figure 21B:
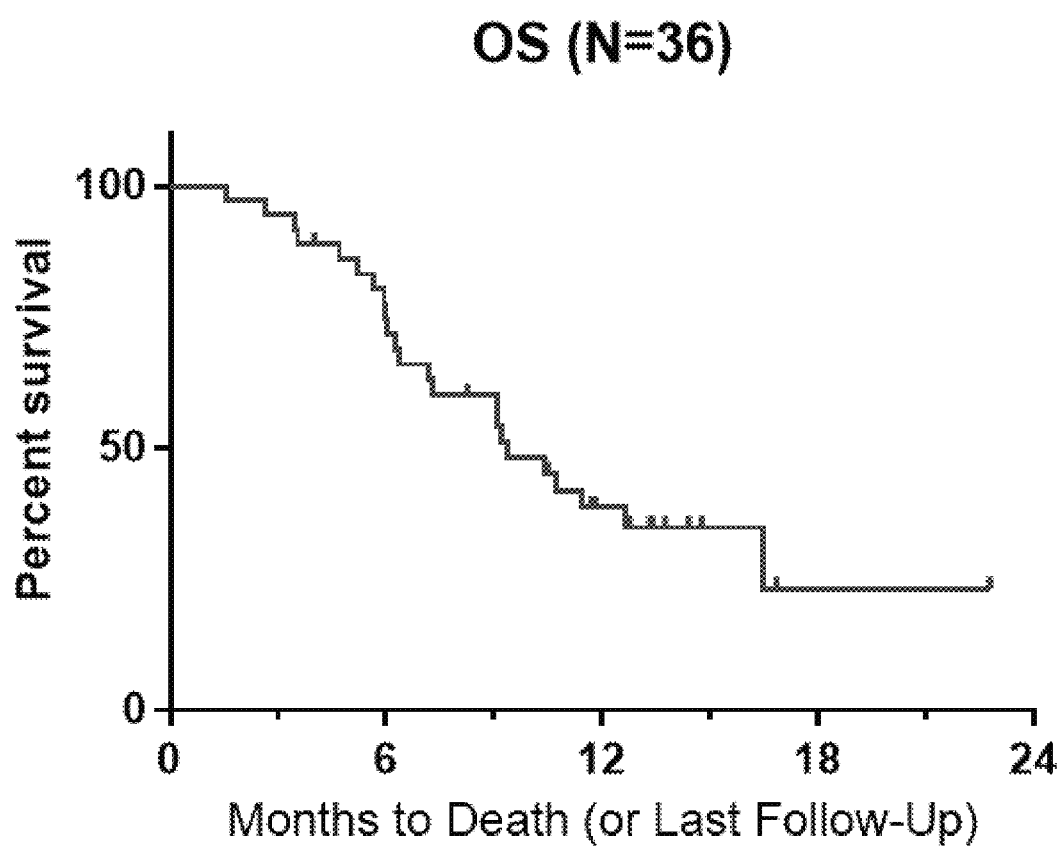
FIG. 21B shows a plot of the OS percent as a function of time in all patients treated with marizomib for glioma as set forth in Example 3.

Progression Free Survival (PFS): Overall and by MGMT Promoter Methylation Status FIG. 21A shows a plot of the progression free survival (PFS) percent as a function of time for all patients. FIG. 21B shows a plot of the overall survival (OS) percent as a function of time for all patients.

Figure 22A:
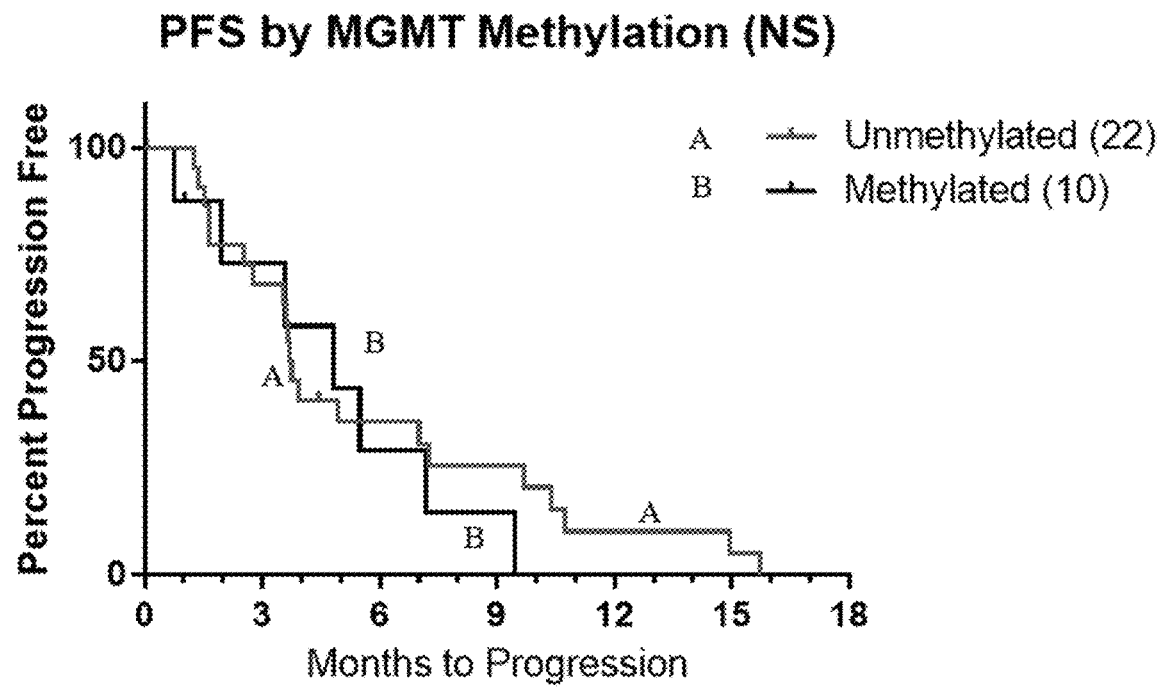
FIG. 22A shows a plot of the PFS percent by MGMT Promoter methylation status as a function of time after treatment with MRZ and BEV.
Figure 22B:
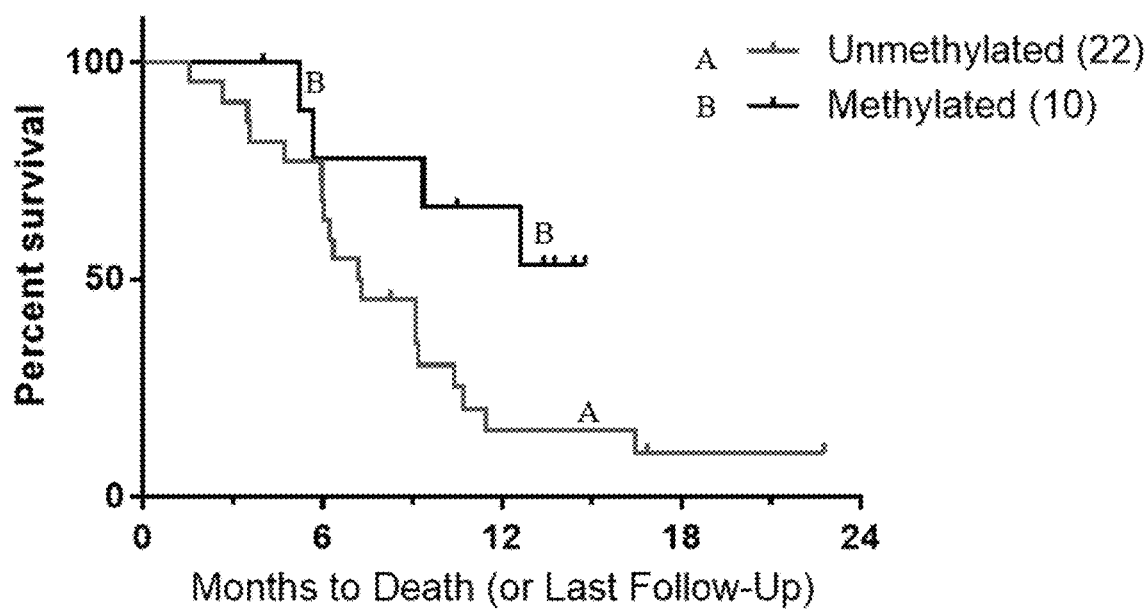
FIG. 22B shows a plot of the OS percent by MGMT Promoter methylation status as a function of time after treatment with MRZ and BEV.

FIG. 22A shows a plot of the PFS percent as a function of time for patients by O 6-methylguanine-DNA methyltransferase (MGMT) promoter methylation status (methylated or unmethylated). FIG. 22B shows a plot of overall survival (OS) percent as a function of time for patients by O 6-methylguanine-DNA methyltransferase (MGMT) promoter methylation status (methylated or unmethylated).

Figure 23A:
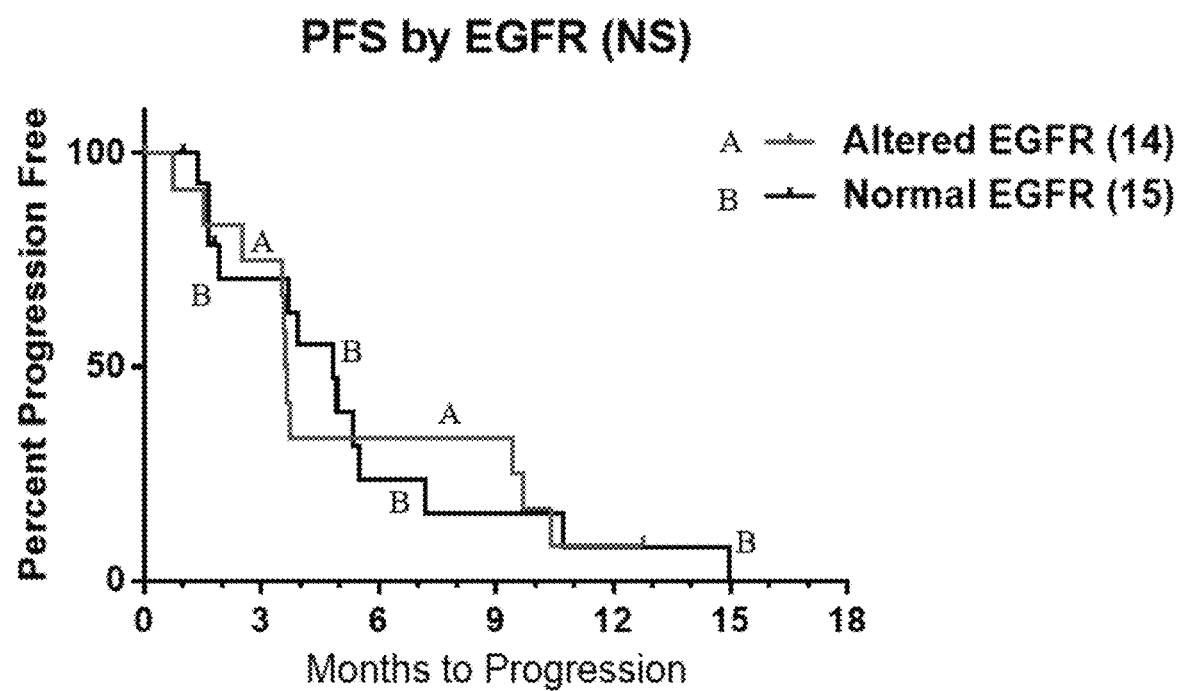
FIG. 23A shows progression free survival (PFS) as a function of time for patients by EGFR status.
Figure 23B:
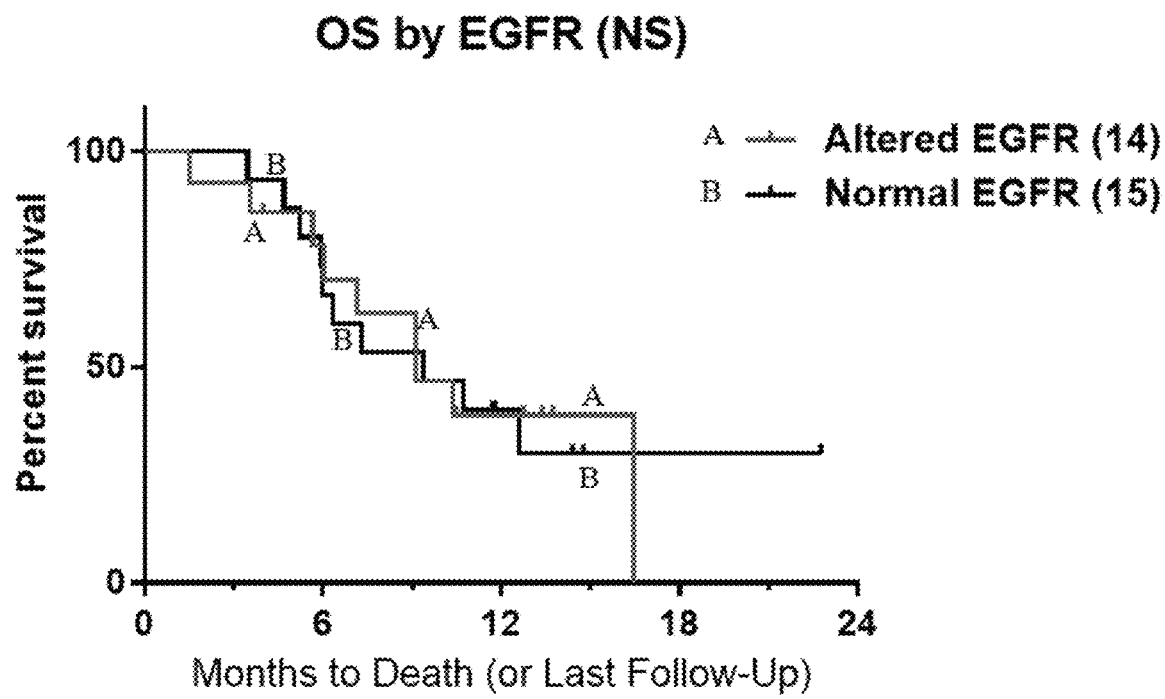
FIG. 23B shows overall survival (OS) as a function of time for patients by EGFR status.

FIG. 23A shows progression free survival (PFS) as a function of time for patients by EGFR status. FIG. 23B shows overall survival (OS) as a function of time for patients by EGFR status.

Without wishing to be bound by theory, the percentage of patients treated with marizomib and bevacizumab who have not progressed at six months was higher than patients treated with bevacizumab only. The percentage of patients with six months PFS treated with marizomib and bevacizumab was about twice that among all patients, and about four times that in patients with unmethylated MGMT promoter, in comparison with patients treated with bevacizumab only. Without wishing to be bound by theory, unmethylated MGMT promoter is a biomarker of poor prognosis in malignant glioma. Patients with unmethylated MGMT promoter can be more likely to suffer recurrent disease, and for recurrence to occur more quickly than in patients with methylated MGMT promoter. For instance, patients with unmethylated MGMT promoter who are treated with the standard of care (temozolomide and radiotherapy) can be more likely to relapse.

TABLE 32

MRZ + BEV RANO Response Rate by MGMT Promoter Methylation Status

| Best Response (N) | Efficacy Evaluable (N = 33) | | | Intent to Treat (N = 36) | | |
|---|---|---|---|---|---|---|
| | Unmethylated (N = 21) | Methylated (N = 8) | Unknown (N = 6) | Unmethylated (N = 22) | Methylated (N = 10) | Unknown (N = 4) |
| CR or PR (16) | 9 | 5 | 2 | 9 | 5 | 2 |
| SD (11) | 9 | 1 | 1 | 9 | 1 | 1 |
| PD (6) | 3 | 2 | 1 | 3 | 2 | 1 |
| NE (3) | — | — | — | 1 | 2 | 0 |

TABLE 33

MRZ + BEV PFS by MGMT Promoter Methylation Status

| | PFS | | | | | |
|---|---|---|---|---|---|---|
| | No. Censored | Median (Months) | 6 Months % | 9 Months % | 12 Months % | 18 Months % |
| Unmethylated (22) | 1 | 3.7 | 36 | 26 | 10 | 0 |
| Methylated (10) | 3 | 4.8 | 29 | 15 | 0 | 0 |

TABLE 34

MRZ + BEV OS by MGMT Promoter Methylation Status

| | OS | | | | | |
|---|---|---|---|---|---|---|
| | No. Censored | Median (Months) | 6 Months % | 9 Months % | 12 Months % | 18 Months % |
| Unmethylated (22) | 3 | 7.2 | 68 | 45 | 15 | 10 |
| Methylated (10) | 6 | Undefined | 78 | 78 | 47 | 53 |

As shown in the tables above, patients with unmethylated MGMT promoter had similar rates of overall survival and progression free survival as patients with methylated MGMT promoter.

Marizomib Monotherapy

Figure 24:
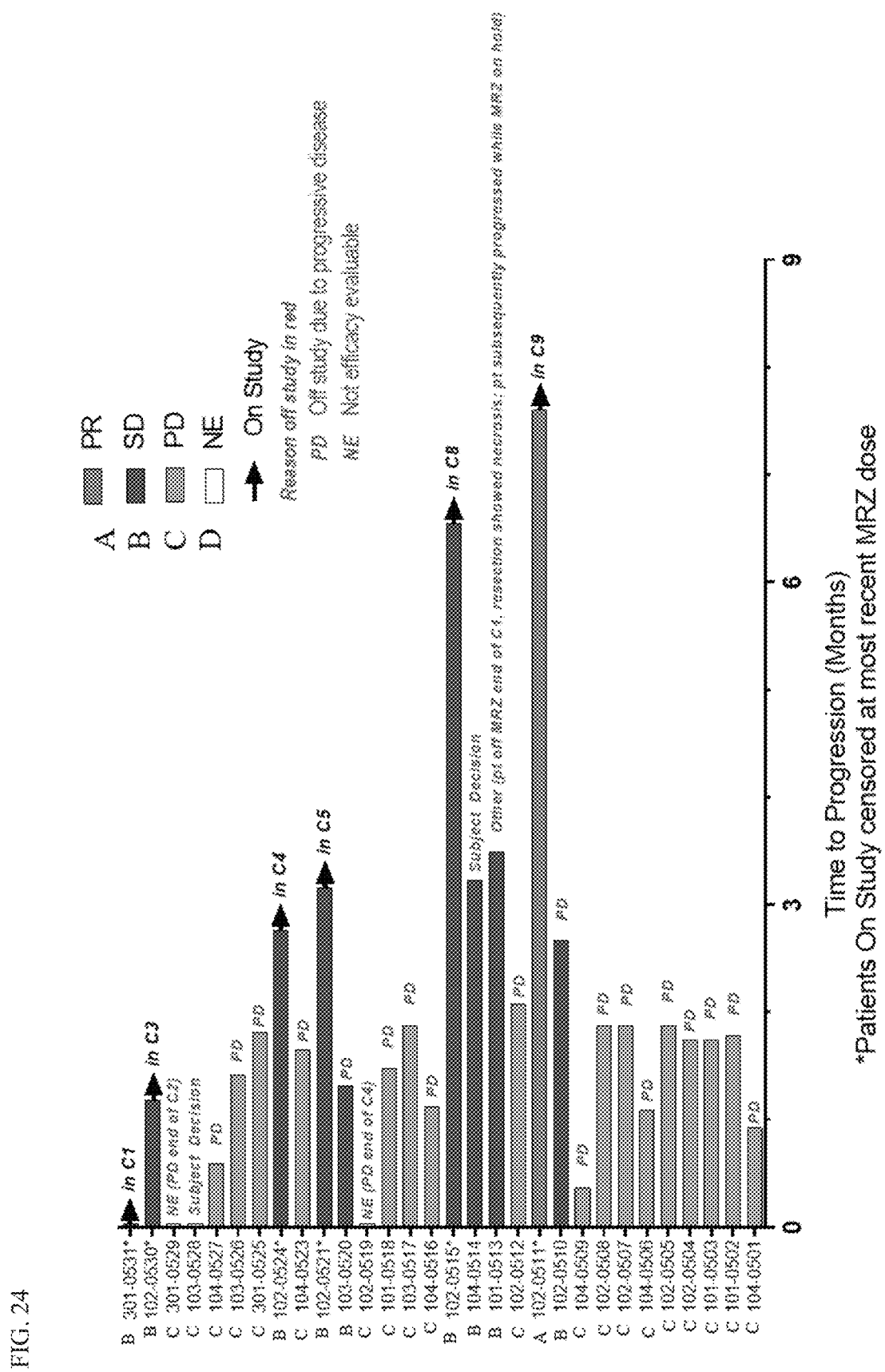
FIG. 24 shows a time to progression for patients undergoing monotherapy with marizomib as set forth in Example 3.
Figure 24:
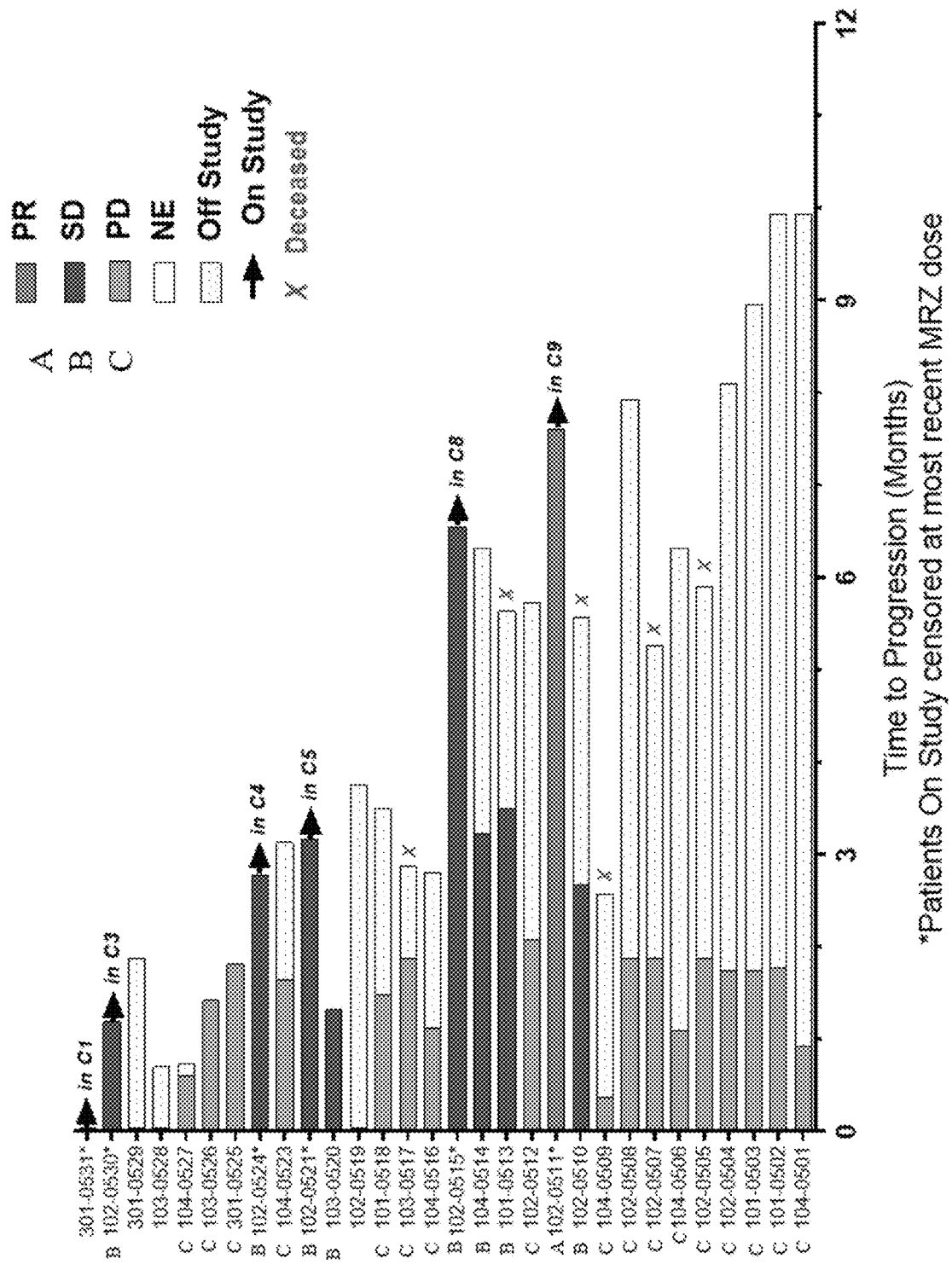

FIG. 24 shows a time to progression for patients undergoing monotherapy with marizomib.

TABLE 35

Response of Patients Treated with Marizomib Monotherapy

| | ITT (N = 30) | | |
|---|---|---|---|
| Best Response (N) | Unmethylated* N = 18 | Methylated N = 7 | Unknown N = 5** |
| CR (0) | 0 | 0 | 0 |
| PR (1) | 1 | 0 | 0 |
| SD (8) | 4 | 3 | 1 |
| PD (19) | 12 | 4 | 3 |
| NE (2) | 1 | 0 | 1 |

Figure 25A:
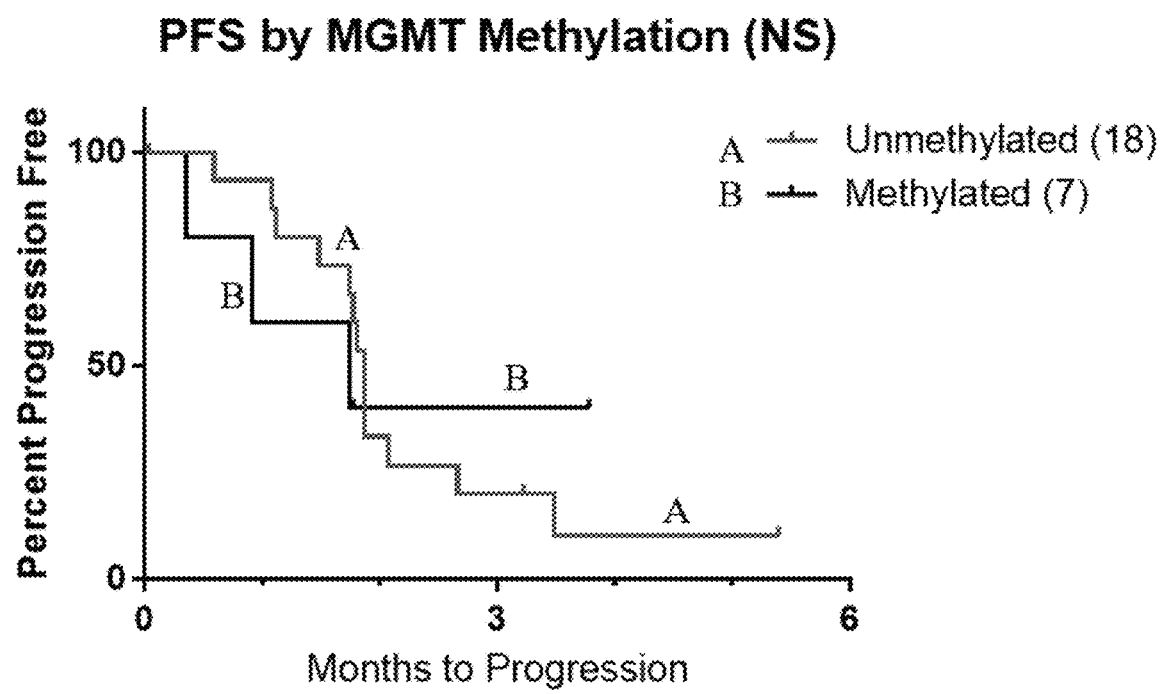
FIG. 25A shows a plot of progression-free survival for patients treated with marizomib monotherapy by methylation status.
Figure 25B:
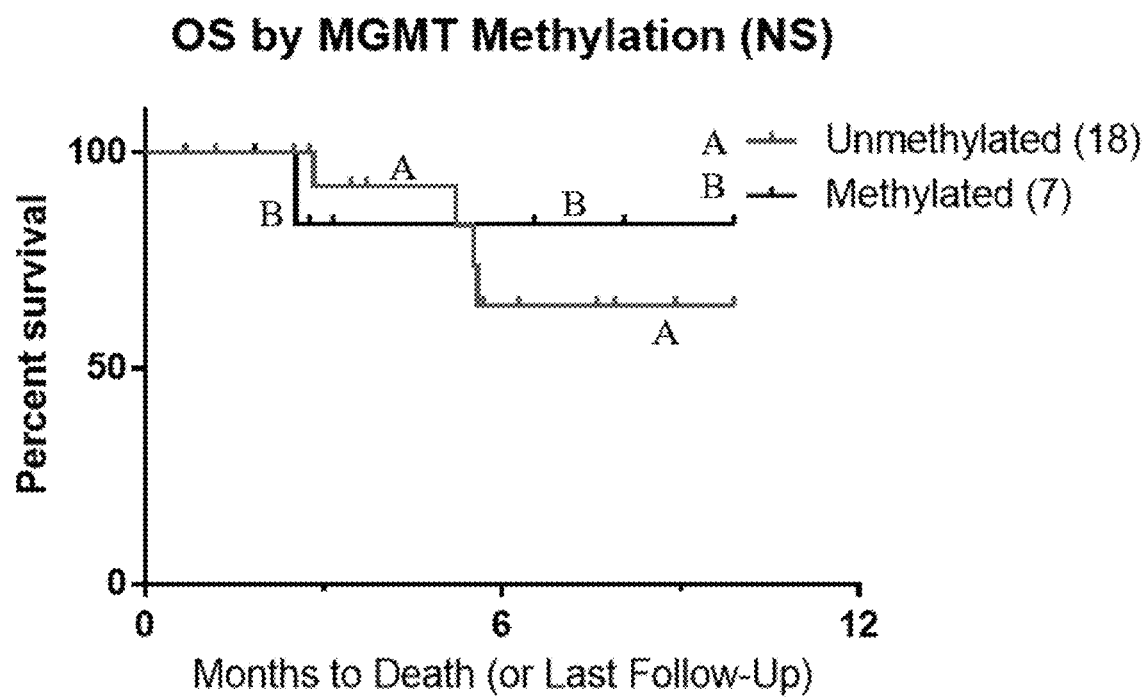
FIG. 25B shows a plot of overall survival for patients treated with marizomib monotherapy by methylation status.

FIG. 25A shows a plot of progression-free survival for patients treated with marizomib monotherapy by methylation status. FIG. 25B shows a plot of overall survival for patients treated with marizomib monotherapy by methylation status.

TABLE 36

Progression-Free Survival and Overall Survival of Patients treated with Marizomib Monotherapy

| | PFS | | | | OS | | | |
|---|---|---|---|---|---|---|---|---|
| | # Censored | Median (months) | 3 mo % | 6 mo % | # Censored | Median (months) | 6 mo % | 9 mo % |
| Unmethylated (18) | 5 | 1.9 | 20 | NA | 14 | Undefined | 65 | 65 |
| Methylated (7) | 4 | 1.7 | 40 | NA | 6 | Undefined | 83 | 83 |

TABLE 37

Progression Free Survival (PFS): Overall and by EGFR Status

| Pt ID | MGMT Promoter | EGFR* | IDH1 | TP53 |
|---|---|---|---|---|
| 0511 | Unmethylated | Normal | WT | Pathogenic Mutation |
| 0513 | Unmethylated | Unknown | Unknown | Unknown |
| 0514 | Unmethylated | Normal | WT | WT |
| 0515 | Methylated | Normal | WT | WT |
| 0521 | Methylated | Normal | R132H | Pathogenic Mutation |
| 0524 | Methylated | Normal | R132H | Pathogenic Mutation |

*Normal EGFR status = Not amplified or mutated, EGFRVIII negative

As set forth above, methylation of the MGMT promoter was determined for 27 of 30 patients. Eighteen of 27 had unmethylated MGMT promoter (67%). Additionally, 9/25 patients had altered EGFR (36%). Of these, 8 had amplified EGFR, 7 had mutated EGFR (6 of 7 also amplified) and 2 were EGFRVIII positive (both were also EGFR amplified). Four of 25 patients had the IDH1 mutation R132H (16%), and 7/25 patients had pathogenic TP53 mutations (28%). Without wishing to be bound by theory, the IDH1 mutation is commonly associated with a lower grade tumor which can subsequently progress to a grade IV malignant glioma (e.g., glioblastoma, GBM). Without wishing to be bound by theory, TP53 is a tumor suppressor. Pathogenic mutations in TP53 can suppress its activity, and in some embodiments lead to a more aggressive tumor type. glioblastoma, GBM). Without wishing to be bound by theory, TP53 is a tumor suppressor. Pathogenic mutations in TP53 can suppress its activity, and in some embodiments lead to a more aggressive tumor type.

TABLE 38

MRZ Monotherapy: 4 Patients ≥ Static Disease and >4 Cycles

| Pt ID | Screening SPD* | Diagnosis | Recurrence | Best Response | SPD | Current Cycle |
|---|---|---|---|---|---|---|
| 0511 | 703.47 | 05/15 | 2nd | PR | 231.3 | 10 |
| 0515 | 199.6 | 06/15 | 1st | SD | 259.5 | 9 |
| 0521 | 836.44 | 02/16 | 1st | SD | 832.82 | 5 |
| 0524 | 122.55 | 07/15 (07/14 astrocytoma) | 1st | SD | NA | 5 |

As set forth in Table 38, four patients were found to respond to marizomib monotherapy.

In summary, most patients demonstrated rapid progression when treated with marizomib alone. Six patients were on the study for ≥4 cycles (Table 37). All were of normal EGFR status. Three of the six patients had pathogenic TP53 mutations. Comparable tumor responses and PFS/OS results in unmethylated compared with methylated MGMT promoter status was observed.

Bevacizumab Monotherapy

Table 39 shows a comparison of the present study with a clinical trial evaluating single-agent bevacizumab in recurrent glioma for comparison.

TABLE 39

Single Agent Bevacizumab Comparator Data in Recurrent Glioma

| | 6 Months PFS | |
|---|---|---|
| Study | All | uMGMT Promoter |
| Present Study | 34% | 34% |
| BELOB Trial (BEV monotherapy) (Taal et al., 2014) | 16% | 8% |

Comparison Marizomib Monotherapy and Marizomib-Bevacizumab Combination

TABLE 40

MRZ + BEV Improved PFS & OS at 6, 9 and 12 Months Compared with Historical BEV Monotherapy Studies

| Study | Treatment | 6 mo Progression Free Survival | | | 9 mo Progression Free Survival | | | 12 Mo. Progression Free Survival | | |
|---|---|---|---|---|---|---|---|---|---|---|
| | | All Pts | Unmethylated | Methylated | All Pts | Unmethylated | Methylated | All Pts | Unmethylated | Methylated |
| Current Study | MRZ + BEV | 34% | 36% | 29% | 24% | 26% | 15% | 10% | 10% | 0% |
| Taal (BELOB) | BEV Monotherapy | 16% | 8% | 33% | 8% | 0% | 22% | 2% | 0% | 4% |
| Field (CABARET) | | 18% | NR | NR | 6% | NR | NR | 2% | NR | NR |
| Heiland (Freiburg, Germany) | | 12% | 10% | 38% | 0% | 0 % | 22% | 0% | 0% | 10% |
| Wick (EORTC 26101 P2) | | 14% | 10% | 25% | 9% | 10% | 9% | 8% | 10% | 9% |

| Study | Treatment | 6 mo Overall Survival | | | 9 mo Overall Survival | | | 12 Mo. Overall Survival | | |
|---|---|---|---|---|---|---|---|---|---|---|
| | | All Pts | Unmethylated | Methylated | All Pts | Unmethylated | Methylated | All Pts | Unmethylated | Methylated |
| Current Study | MRZ + BEV | 75% | 68% | 78% | 55% | 45% | 78% | 39% | 15% | 67% |
| Taal (BELOB) | BEV Monotherapy | 62% | 50% | 83% | 45% | 12% | 67% | 26% | 8% | 56% |
| Field (CABARET) | | 61% | NR | NR | 39% | NR | NR | 24% | NR | NR % |
| Heiland (Freiburg, Germany) | | 18% | 25% | 58% | 30% | 12% | 40% | 10% | 12% | 24% |

TABLE 41

Comparison of Marizomib Monotherapy with Marizomib-Bevacizumab Combination Therapy

| | | PFS | | OS | |
|---|---|---|---|---|---|
| | | MRZ + BEV | MRZ Mono | MRZ + BEV | MRZ Mono |
| All Patients | # (# Censored) | 36 (6) | 30 (10) | 36 (13) | 30 (24) |
| | Median | 3.9 | 1.8 | 9.4 | NA |
| | 6 mo % | 34% | NA | 75% | 64% |
| | 9 mo % | 24% | NA | 60% | 64% |
| | 12 mo % | 10% | Na | 39% | NA |
| | 18 mo % | 0% | NA | 23% | NA |
| Unmethylated MGMT Promoter | # (# Censored) | 22 (1) | 18 (5) | 22 (3) | 18 (14) |
| | Median | 3.7 | 1.9 | 7.2 | NA |
| | 6 mo % | 36% | NA | 68% | 65% |
| | 9 mo % | 26% | NA | 45% | 65% |
| | 12 mo % | 10% | NA | 15% | NA |
| | 18 mo % | 0% | NA | 10% | NA |
| Methylated | # (# Censored) | 10 (3) | 7 (4) | 10 (6) | 7 (6) |
| | Median | 4.8 | 1.7 | NA | NA |
| MGMT Promoter | 6 mo % | 29% | NA | 78% | 83% |
| | 9 mo % | 15% | NA | 78% | 83% |
| | 12 mo % | 0% | NA | 67% | NA |
| | 18 mo % | 0% | NA | 53% | NA |

As shown above, the combination of treatment with marizomib and bevacizumab led to greater overall survival and progression free survival than treatment with bevacizumab or marizomib alone.

Summary of All Patients Sorted by PFS

In the Table below, patients with bolded numbers have methylated MGMT promoters. Patients with italicized numbers are unknown or unequivocal.

TABLE 42

Summary of Patients sorted by PFS

| Pt ID* | 1p19q Deletion | EGFR Amplification | EGFR Mutation | EGFRvIII Fusion | IDH1 Mutation | CDK4 Amplification | TP53 Mutation | PFS (mo) | OS (mo) |
|---|---|---|---|---|---|---|---|---|---|
| 101-0402 | No | Yes | No | No | No | No | No | 0.03 | 10.5 |
| 301-0413 | No | Yes | No | Yes | No | No | No | 0.03 | 4.0 |
| 101-0419 | No | No | A289D | No | No | No | No | 0.8 | 7.7 |

TABLE 42-continued

Summary of Patients sorted by PFS

| Pt ID* | 1p19q Deletion | EGFR Amplification | EGFR Mutation | EGFRvIII Fusion | IDH1 Mutation | CDK4 Amplification | TP53 Mutation | PFS (mo) | OS (mo) |
|---|---|---|---|---|---|---|---|---|---|
| *103-0422* | No | No | No | No | No | No | No | 0.9 | 9.0 |
| 102-0104 | No | No | No | No | No | Yes | No | 1.0 | 9.4 |
| 101-0302 | | | | | | | | 1.2 | 2.7 |
| 102-0203 | No | No | No | No | No | No | No | 1.4 | 4.7 |
| 103-0421 | No | Yes | G598V | | | No | No | 1.5 | 1.5 |
| 301-0401 | No | No | No | No | No | No | No | 1.6 | 3.5 |
| 103-0405 | 1p | No | No | No | No | No | No | 1.6 | 6.0 |
| *102-0415* | | | | | | | | 1.8 | 7.8 |
| 102-0404 | No | No | No | No | No | No | S127Y | 1.9 | 5.2 |
| 301-0411 | 19q | Yes | No | Yes | No | No | No | 2.5 | 6.0 |
| 101-0423 | | | | | | | | 2.8 | 5.5 |
| 301-0406 | No | No | P596L | No | No | No | C135R | 3.6 | 3.6 |
| 101-0410 | No | Yes | A289V | No | E62fs | No | No | 3.6 | 5.7 |
| 102-0414 | No | Yes | G598V | | No | No | | 3.6 | 6.4 |
| 101-0107 | No | Yes | S768I | Yes | No | No | No | 3.6 | 7.2 |
| 101-0202 | No | No | No | | No | No | No | 3.7 | 6.3 |
| 101-0101 | No | Yes | No | No | No | Yes | No | 3.8 | 9.1 |
| 102-0403 | No | No | No | No | No | No | No | 3.9 | 7.3 |
| 101-0416 | | | | | | | | 4.4 | 5.4 |
| 101-0407 | No | No | No | No | No | Yes | H179Y | 4.8 | 9.2 |
| 301-0412 | 19q | No | No | No | No | No | N235S | 4.9 | 6.0 |
| *301-0418* | No | No | No | No | No | No | | 5.4 | 8.8 |
| 101-0409 | No | No | No | No | No | No | No | 5.5 | 8.7 |
| *301-0424* (on study) | No | Yes | R324L | No | No | Yes | No | 7.2 | 9.4 |
| 102-0417 | No | Yes | No | No | No | No | No | 7.6 | 9.0 |
| 102-0420 | 1p | | | No | | | | 7.2 | 7.2 |
| 101-0408 | | | | | | | | 7.0 | 9.2 |
| 101-0105 | | | | | | | | 7.3 | 11.4 |
| 102-0106 | 1p | Yes | No | Yes | No | No | No | 9.7 | 16.4 |
| 101-0303 | No | No | A767_P772 duplication | No | No | Yes | No | 10.4 | 10.4 |
| 301-0301 | 1p & 19q | No | No | | No | No | P151S | 10.7 | 10.7 |
| 301-0201 | | | | | | | | 13.5 | 15.0 |
| 101-0103 | 19q | No | No | No | No | No | No | 15.0 | 17.5 |

Pharmacokinetic and Pharmacodynamic Parameters.

Table 43 shows a summary of the pharmacokinetic and pharmacodynamic parameters for marizomib and bevacizumab.

TABLE 43

Pharmacokinetic and Pharmacodynamic Summary

| Parameter (Units) | 0.55 mg/m² | 0.7 mg/m² | 0.8 mg/m² |
|---|---|---|---|
| Marizomib PK determined on C1D8 | | | |
| $T_{1/2}$ (min) | 8.2 ± 0.8 (4) | 16.0 ± 8.08 (3) | 7.27 ± 0.423 (3) |
| $T_{max}$ (min) | 15.5 ± 1.4 (6) | 21.3 ± 1.3)0 (3) | 8.0 ± 0 (3) |
| $C_{max}$ (ng/mL) | 23.1 ± 11.3 (6) | 64.9 ± 1.73 (3) | 26.5 ± 7.92 (3) |
| $AUC_{last}$ (min*ng/mL) | 265 ± 101 (6) | 193 ± 85 (2) | 392 ± 115 (3) |
| Vd (L) | 54.4 ± 10.6 (4) | 48.3 ± 16.1 (3) | 55.0 ± 19.7 (3) |
| $CL_{obs}$ (L/hr) | 297 ± 73.0 (4) | 272 ± 166 (3) | 304 ± 85.0 (3) |
| BEV PK determined on C1D1 & C1D15 | | | |
| $C_{max}$ D1 (µg/mL) | 275 ± 37.5 (6) | 193 ± 8 (2) | 267 ± 13.3 (3) |
| $C_{min}$ D15 (µg/mL) | 89.7 ± 6.2 (6) | 81.1 ± 17.4 (2) | 85.0 ± 9.87 (3) |
| $C_{max}$ D15 (µg/mL) | 351 ± 46.6 (5) | 402 ± 123 (3) | 380 ± 56.5 (2) |
| Proteasome subunit inhibition in PWB post-Marizomib infusion (peak effect) | | | |
| % CT-L inhibition | 100 ± 0 (5) | 100 ± 0 (3) | 100 ± 0 (3) |
| % T-L inhibition | 52.0 ± 8.0 (5) | 77.3 ± 10.5 (3) | 69.3 ± 7.2 (3) |
| % C-L inhibition | 21.0 ± 7.8 (5) | 50.4 ± 9.1 (3) | 51.9 ± 8.3 (3) |

Figure 26:
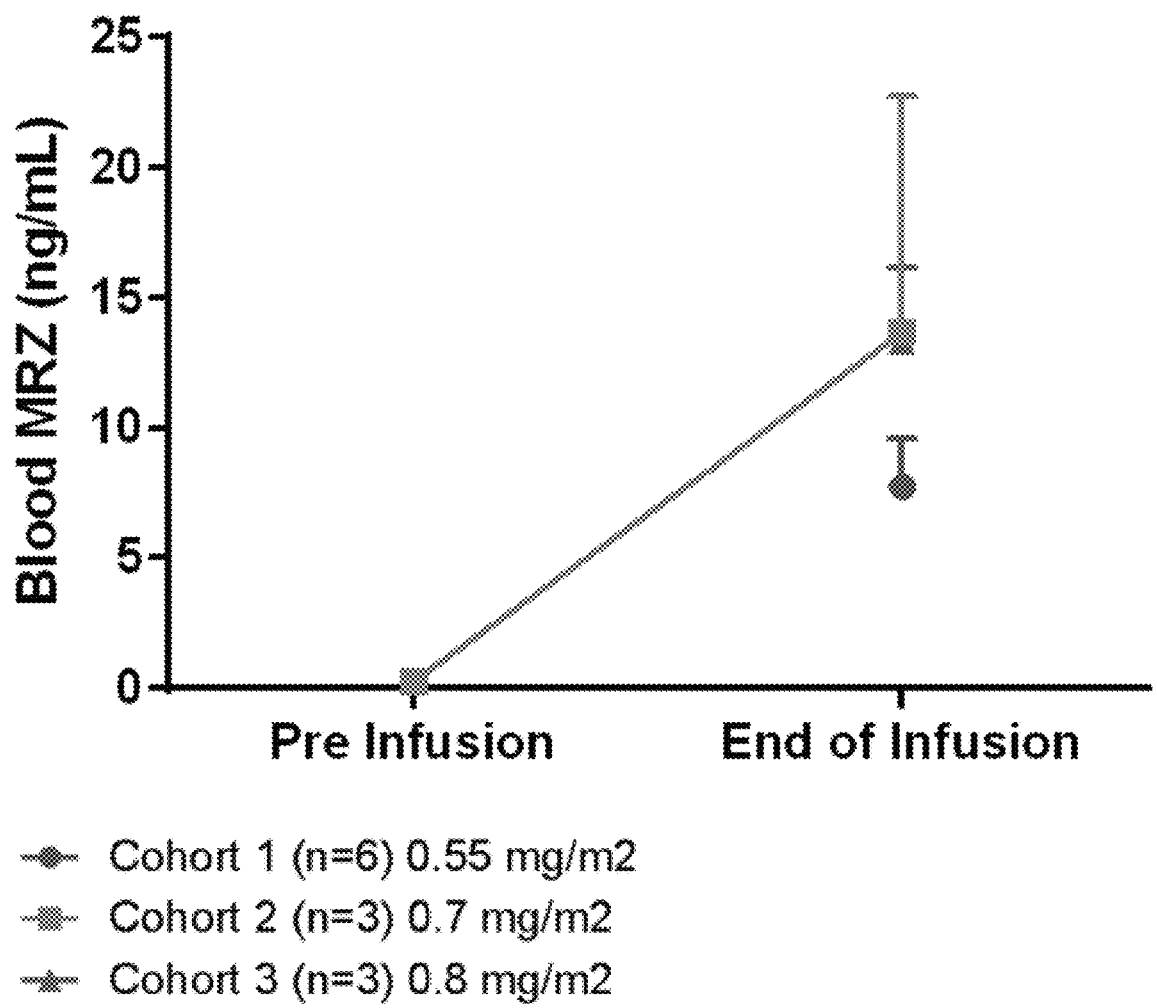
FIG. 26 shows the concentration of marizomib in the blood of a patient C1D1 pre- and post-infusion.
Figure 27:
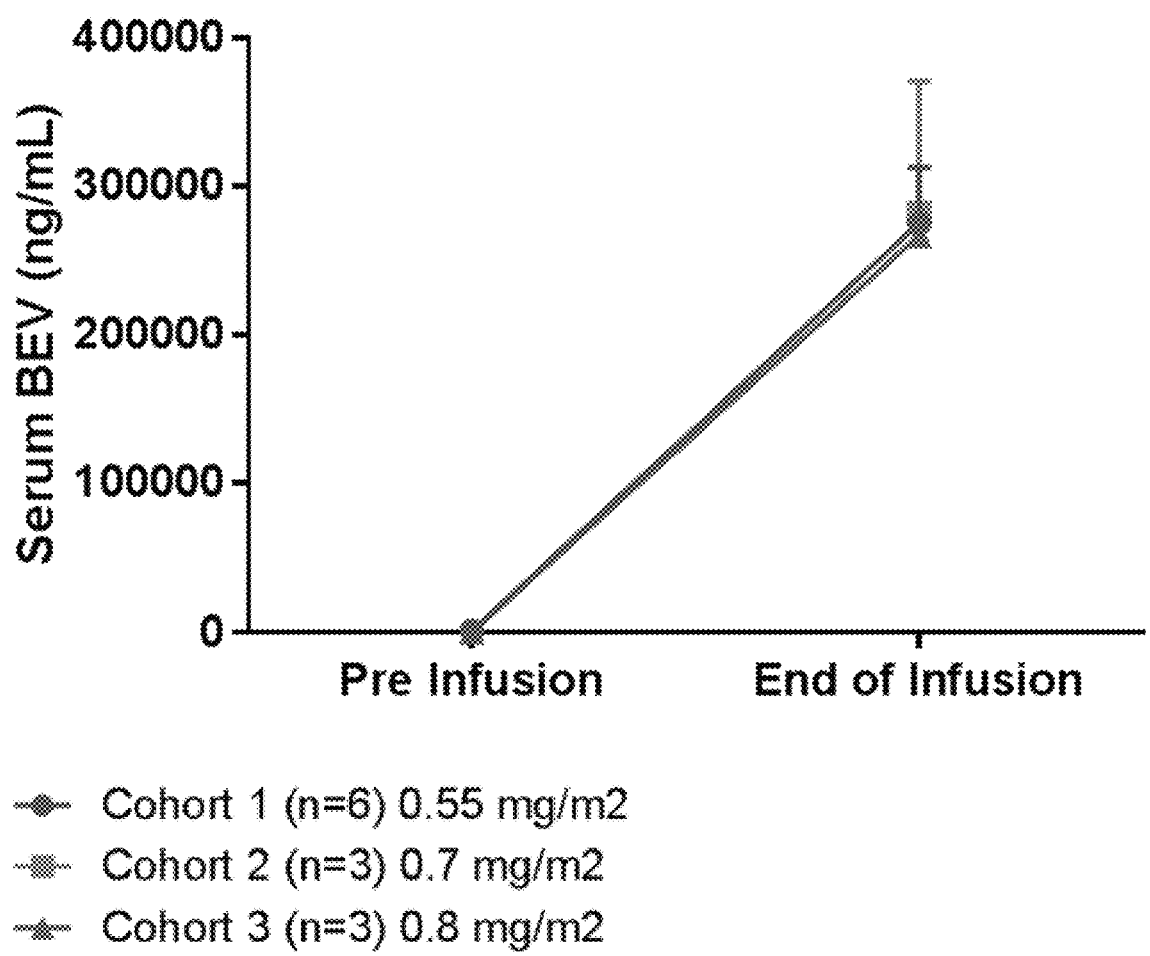
FIG. 27 shows the concentration of bevacizumab in the serum of a patient C1D1 pre- and post-infusion.
Figure 28:
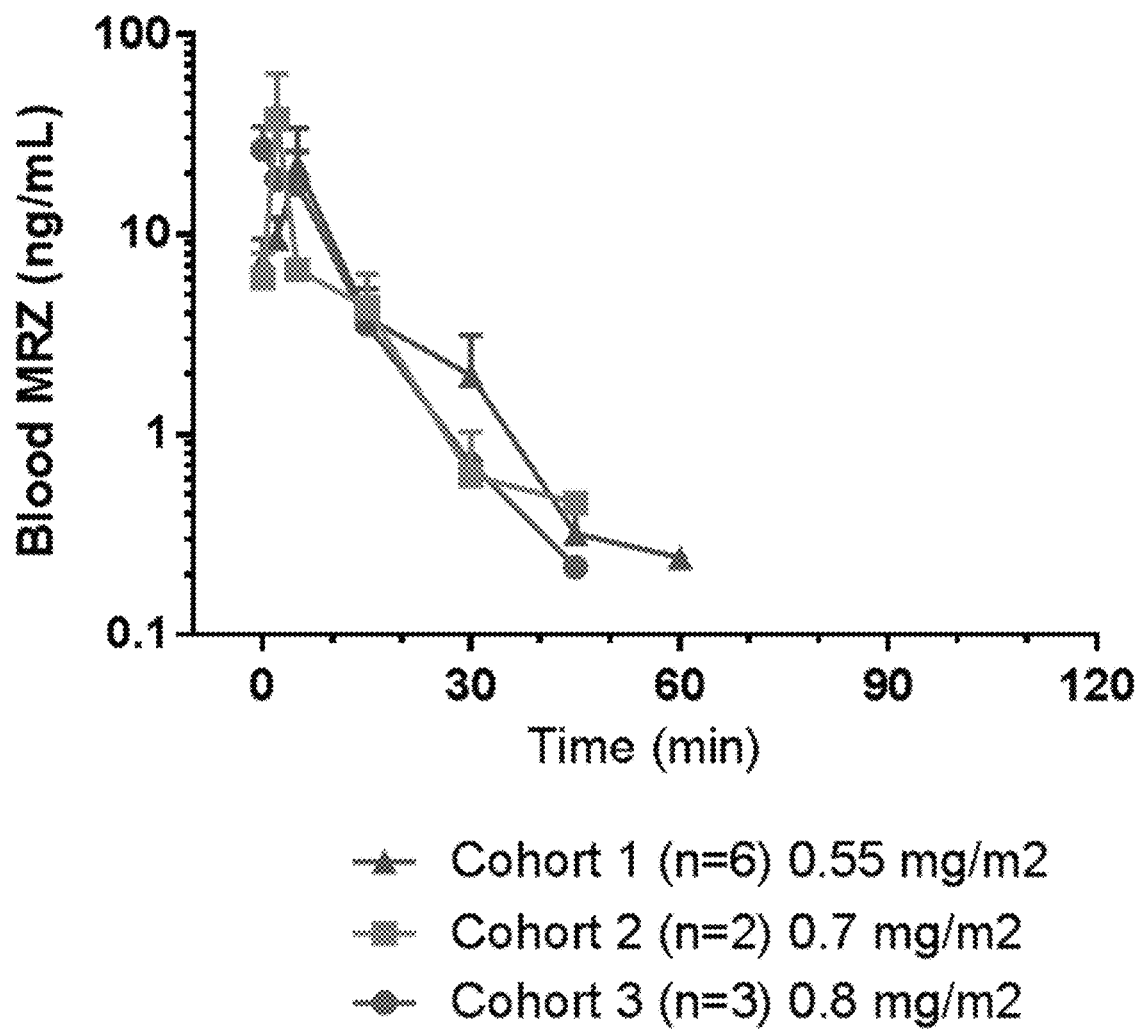
FIG. 28 shows the concentration of marizomib in the blood as a function of time on C1D8.
Figure 29:
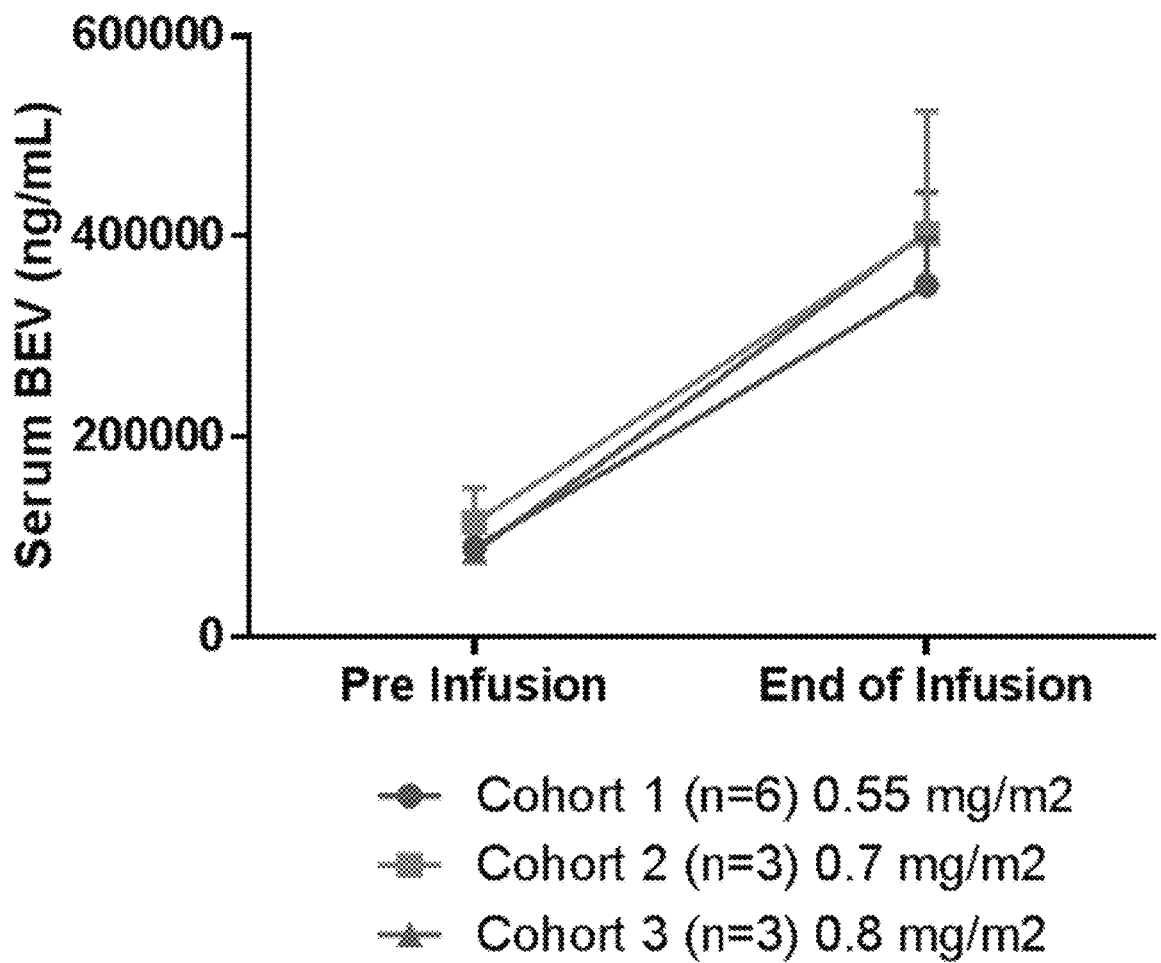
FIG. 29 shows concentration of bevacizumab in serum pre- and post-infusion for different cohorts on C1D15.

FIG. 26 shows the concentration of marizomib in the blood of patients on C1D1 pre- and post-infusion. FIG. 27 shows the concentration of bevacizumab in the serum of patients C1D1 pre- and post-infusion. FIG. 28 shows the concentration of marizomib in the blood as a function of time on C1D8. FIG. 29 shows concentration of bevacizumab in serum pre- and post-infusion for different cohorts on C1D15.

As set forth in FIGS. 26-29, the mean $C_{max}$ of bevacizumab across all dose cohorts was 275 µg/mL on Day 1; the mean $C_{min}$ of bevacizumab on Day 15 was 95 µg/mL; and the mean $C_{max}$ of bevacizumab on Day 1 was 379 µg/mL. The results agree with published literature precedent for $C_{max}$ of bevacizumab of 284 µg/mL at Day 0 for a 10 mg/kg dose (Gordon et al., 2001).

Example 4—Phase 1, Multicenter, Open-Label, Dose-Escalation, Combination Study of Marizomib and Bevacizumab in Bevacizumab-Naive Subjects with WHO Grade IV Malignant Glioma Followed by Phase 2 Trials of Single Agent Marizomib and Combination Marizomib and Bevacizumab Example 4 represents updates to the procedure and protocol set forth in Example 3.

Protocol Synopsis

Title

A Phase 1, Multicenter, Open-label, Dose-escalation, Combination Study of Marizomib and Bevacizumab in Bevacizumab-Naïve Subjects with WHO Grade IV Malignant Glioma Followed by Phase 2 Trials of Single Agent Marizomib and Combination Marizomib and Bevacizumab Indication WHO Grade IV Malignant Glioma (G4 MG) in bevacizumab-naïve subjects Background and Study Rationale The study population includes subjects with G4 MG (including glioblastoma and gliosarcoma) who are in first or second relapse and who have not previously received any bevacizumab (BEV) or other anti-angiogenic agents, including sorafenib, sunitinib, axitinib, pazopanib, everolimus, or cilengitide, or marizomib (MRZ) or any other proteasome inhibitor, including bortezomib (BTZ), carfilzomib (CFZ), or ixazomib (IXZ).

One of the few treatment options currently approved for recurrent G4 MG is BEV with a 6-month progression-free survival (PFS) rate of ~43% and median overall survival (OS) of ~9 months ( ). Additional treatment options are needed for these subjects. The Phase 1 (Part 1) portion of this study suggested activity of the combination of BEV and MRZ. The Phase 2 (Part 2) portion of the study explored the single agent activity of MRZ. The Part 3 portion of the study explores the activity of the combination of MRZ and BEV, using an intrapatient dose-escalation dosing regimen, in a Phase 2 setting.

Published literature indicates that targeting the proteasome in glioma cells has shown significant anti-tumor activity ( ). In vitro studies of multiple glioma cell lines were highly sensitive to MRZ. MRZ has relatively little effect on neural stem/progenitor cells suggesting minimal neurotoxicity while severely affecting both malignant glioma stem cells and glioma cell lines. MRZ potently and robustly inhibited migration and invasion of human glioblastoma (GBM) cell lines in two different assays. Treatment with MRZ decreased matrix invasion by either of two GBM lines by approximately 90%, a highly significant effect. Preclinical data demonstrate that MRZ crosses the blood brain barrier ( ). In addition, preclinical studies have demonstrated proteasome inhibition with BTZ stimulates VEGF levels suggesting that there may be a synergy combining proteasome inhibitors with VEGF inhibitors ( ).

The preliminary clinical data with respect to tolerability and early evidence of promising activity of MRZ with or without dexamethasone has been shown in results from ongoing Phase 1 clinical studies in subjects with advanced solid tumors, refractory non-Hodgkin's lymphoma, and relapsed/refractory multiple myeloma.

Based on these pre-clinical and clinical data, the addition of MRZ to BEV could be a promising combination regimen in recurrent GBM.

Part 1 (Phase 1) established 0.8 mg/m2 MRZ plus BEV (fixed dose, 10 mg/kg) to be the recommended Phase 2 dose (RP2D), however the MTD as per protocol definition was not reached. Part 2 was conducted to determine the contribution towards efficacy of MRZ to the combination by determining the single agent activity of MRZ in a Phase 2 setting.

Analysis of ongoing safety and efficacy data of patients in the Part 1 (Phase 1) portion of the study suggest that doses that cause central nervous system (CNS) adverse events (AEs) appear to be more active than those that do not. The Part 3 (Phase 2) portion of the study (added with Amendment 3) is to determine point estimates for objective response rate (ORR), PFS, and OS for patients who receive the combination of MRZ and BEV with MRZ titrated to toxicity on an individual patient basis (intrapatient dose escalation).

Objectives
Part 1 Phase 1
Primary Objective
To determine the maximum tolerated dose (MTD) or Maximum Administered Dose (MAD) and recommended Phase 2 dose (RP2D) of the combination of marizomib (MRZ)+bevacizumab (BEV) with MRZ as a once weekly dose for 3 weeks of a 28-day cycle and with a fixed dose and schedule of BEV (10 mg/kg administered on Days 1 and 15) in subjects with progressive or recurrent G4 MG, who have not previously been treated with either an anti-angiogenic agent including but not limited to, BEV or a proteasome inhibitor including, but not limited to, MRZ.
Secondary Objectives
To evaluate the safety of the combination of MRZ+BEV in the subject population.
To evaluate activity of the combination of MRZ+BEV in the subject population including:
Radiographic Overall Response Rate (ORR) (RANO 2010 criteria)
Progression-free Survival (PFS)
Overall Survival (OS)
To evaluate the pharmacokinetics (PK) of MRZ and BEV when administered in combination in the subject population.
To assess the blood proteasome inhibition pharmacodynamic (PD) activity of the combination of MRZ+BEV in the subject population.
Exploratory Objectives
To evaluate baseline tumor proteasome activity, gene signature and transcriptional profiling using pre-study, archived tissue samples.
To evaluate neurological coordination assessment using the Scale for the Assessment and Rating for Ataxia (SARA).
To evaluate Quality of Life Assessments using Functional Assessment of Cancer Therapy (FACT) questionnaires:
FACT-Cognitive Function (FACT-Cog)
FACT-Brain (FACT-Br)
Part 2 Phase 2
Primary Objective
To assess the activity of a once weekly dose for 3 weeks of a 28-day cycle of MRZ in subjects with progressive or recurrent G4 MG, who have not previously been treated with either an anti-angiogenic agent or a proteasome inhibitor.
Secondary Objectives
To evaluate the safety of single agent MRZ in the subject population.
Exploratory Objectives
To evaluate baseline tumor proteasome activity, gene signature and transcriptional profiling using pre-study, archived tissue samples.
To evaluate neurological coordination assessment using the Scale for the Assessment and Rating for Ataxia (SARA).
To evaluate Quality of Life Assessments using Functional Assessment of Cancer Therapy (FACT) questionnaires:
FACT-Cognitive Function (FACT-Cog)
FACT-Brain (FACT-Br)
Part 3 Phase 2
Primary Objective
To assess the activity of the combination of once weekly MRZ dosing for 3 weeks (allowing for intra-patient dose escalation) and every other week dosing of BEV at 10 mg/kg in 28-day cycle in subjects with progressive or recurrent G4 MG, who have not previously been treated with either an anti-angiogenic agent or a proteasome inhibitor.
Secondary Objectives
To evaluate the safety of combination of MRZ with intrapatient dose escalation and BEV at a fixed dose in the subject population.
Exploratory Objectives
To evaluate baseline tumor proteasome activity, gene signature and transcriptional profiling using pre-study, archived tissue samples.
To evaluate neurological coordination assessment using the Scale for the Assessment and Rating for Ataxia (SARA).
To evaluate Quality of Life Assessments using Functional Assessment of Cancer Therapy (FACT) questionnaires:
FACT-Cognitive Function (FACT-Cog)
FACT-Brain (FACT-Br)
Study Design
Part 1 of this protocol is a Phase 1, open-label, 3+3, dose-escalation study in subjects with WHO Grade IV Malignant Glioma (G4 MG) who are in first or second relapse and who have not previously received any BEV or other anti-angiogenic agent, including sorafenib, sunitinib, axitinib, pazopanib, everolimus, or cilengitide or MRZ or any other proteasome inhibitor, including BTZ, CFZ, or IXZ. Three to 6 evaluable subjects per cohort will be enrolled: approximately 24 subjects to determine the MTD or MAD (Part 1 Dose-escalation) and an addition of at least 12 more subjects to confirm the MTD/MAD and determine the RP2D (Part 2 Expansion Cohort) and assess preliminary activity to a total of up to 36 subjects. Subjects may not be enrolled in more than 1 cohort.

The Phase 1 portion will be followed by Part 2, a Phase 2 portion of the trial of single agent MRZ administered as a 10-minute infusion at a dose of 0.8 mg/m2 (the RP2D from Phase 1) every week for 3 weeks in 28-day cycles. This portion of the trial will be conducted as a 2-stage sequential design of up to 30 response-evaluable patients.

The Part 2 Phase 2 portion of the trial will be followed by Part 3, a Phase 2 study of combination MRZ using intrapatient dose escalation and BEV at a fixed dose. MRZ will be administered as a 10-minute infusion every week for 3 weeks in 28-day cycles at a starting dose of 0.8 mg/m2 (the RP2D from Part 1 Phase 1). After the first cycle without a dose-limiting adverse event (DLAE), the dose of MRZ will be increased to 1.0 mg/m2 and after 1 more cycle without a DLAE the dose of MRZ will be increased to 1.2 mg/m2. BEV will be administered every 2 weeks (Days 1 and 15 of each 28-day cycle) at a fixed dose of 10 mg/kg. DLAEs are MRZ-related AEs 1) related to disturbances in the cerebellum (i.e., ataxia, dizziness, dysarthria, fall, gait disturbances) plus hallucinations of any grade or 2) Grade ≥2 other AEs. This portion of the trial will be conducted in approximately 40 eligible patients of which, based on the AEs seen in Part 1 of the study, about 24 patients are expected to be eligible for intra-patient dose escalation.
Study Treatments
MRZ is an investigational product that will be provided by the Sponsor. BEV is available commercially and will be provided by the Investigator via prescription to subjects who are enrolled into the Phase 1 portion of this study.
Study Treatment
Part 1 Phase 1
All subjects will receive intravenous (IV) MRZ infusion followed by IV BEV infusion as follows:
IV MRZ will be administered as a 10-minute (or longer) IV infusion on Days 1, 8, and 15 of every 28-day cycle. IV hydration will be given both before and after the infusion.
IV BEV will be administered as an IV infusion (90 minutes 1st dose, 60 minutes 2nd dose and 30 minutes afterward assuming tolerability) at a dose of 10 mg/kg on Days 1 and 15 of every 28-day cycle. BEV will be administered approximately 10 minutes after the end of the MRZ infusion when co-administered on the same day.

Part 2 Phase 2

All subjects will receive IV MRZ infusion.

MRZ will be administered as a 10-minute, IV infusion on Days 1, 8, and 15 of every 28-day cycle. IV hydration will be given before the infusion.

Part 3 Phase 2

All subjects will receive IV MRZ infusion and IV BEV infusion.

MRZ will be administered as a 10-minute, IV infusion on Days 1, 8, and 15 of every 28-day cycle using intra-patient dose escalation. Starting dose will be 0.8 mg/m2 (RP2D dose). Assuming the starting dose was tolerated and no DLAE was observed, the dose will be increased to 1.0 mg/m2 after 1 cycle. Assuming the increased dose was tolerated again and no DLAE was observed, the dose of MRZ will be increased to 1.2 mg/m2 after 1 cycle. Dose reductions will be applied as necessary and according to the toxicities noted.

If the starting dose is not tolerated (after appropriate medical treatment of adverse events, if applicable, the dose will be decreased to 0.7 mg/m2. A further reduction to 0.55 mg/m2 is allowed, if necessary.

BEV will be administered as an IV infusion (90 minutes 1st dose, 60 minutes 2nd dose and 30 minutes afterward assuming tolerability) at a fixed dose of 10 mg/kg on Days 1 and 15 of every 28-day cycle. BEV will be administered approximately 10 minutes after the end of the MRZ infusion when co-administered on the same day. Dose reductions of BEV will not be made, but dose delay or discontinuation will be made depending upon the observed adverse events.

Dose-Limiting Toxicity Part 1 Phase 1 (only)

For the Phase 1 portion of the trial, dose-limiting toxicity (DLT) is defined as the occurrence of any of the following adverse events (AEs) related to study treatment observed during Cycle 1, using National Cancer Institute Common Terminology Criteria for Adverse Events version 4.03 (NCI-CTCAE v 4.03) to determine severity:

Grade 3 thrombocytopenia or Grade 2 thrombocytopenia with bleeding.

Grade 4 neutropenia or anemia lasting for more than 4 days.

Febrile neutropenia.

Any ≥Grade 2 neurological event lasting more than 4 days.

Grade 3 or 4 non-hematological toxicity (excluding alopecia) lasting for more than 4 days despite adequate supportive therapy or preventing the next scheduled dose from being administered within 4 days of scheduled day; for ≥Grade 3 fatigue to be considered a DLT, it must be present for more than 7 days.

Subjects without DLT in Cycle 1 who do not receive 3 MRZ doses or 2 BEV doses within 5 weeks from first dose will not be evaluable for DLT and will be replaced.

Part 1 Phase 1 Dose Escalation Subjects who have completed Screening procedures and meet all eligibility criteria may be enrolled into the study.

A 3+3 design will be used to define the MTD/MAD for MRZ+BEV combination treatment in 28 day cycles, with MRZ administered on Days 1, 8, and 15 and BEV on Days 1 and 15.

MRZ dosing will begin at 0.55 mg/m2 once weekly (Cohort 1). Additional dose cohorts are planned as shown below (Table 44):

TABLE 44

Dose Cohorts for MRZ + BEV Combination

| Cohort | IV MRZ<br>Days 1, 8, and 15 | IV BEV<br>Days 1 and 15 |
|---|---|---|
| −2 | 0.3 mg/m$^2$ | 10 mg/kg |
| −1 | 0.4 mg/m$^2$ | 10 mg/kg |
| 1 | 0.55 mg/m$^2$ | 10 mg/kg |
| 2 | 0.7 mg/m$^2$ | 10 mg/kg |
| 3 | 0.8 mg/m$^2$ | 10 mg/kg |
| 4 | Additional cohorts with extended infusion duration if required | 10 mg/kg |

Initially 3 subjects will be enrolled into a cohort, commencing with Cohort 1 and the doses shown in Table 44 above. Dose escalation will proceed as follows:

If none of the first 3 evaluable subjects in a dose cohort experience a DLT during Cycle 1, then enrollment into the next dose cohort can be initiated.

If ≥2 of the first 3 evaluable subjects in a dose cohort experience a DLT during Cycle 1, then the MTD has been exceeded and dose escalation will not proceed.

If 1 of the first 3 evaluable subjects in a dose cohort experiences a DLT during Cycle 1, then an additional 3 subjects will be enrolled into the same cohort.

If 1/6 evaluable subjects in the expanded 6-subject cohort experiences a DLT during Cycle 1, then the next higher dose cohort can be tested and enrollment of the next 3 subjects at the next higher dose level can be initiated.

If ≥2/6 evaluable subjects in the expanded 6-subject cohort experience a DLT during Cycle 1, then the MTD has been exceeded and no further dose escalation will occur.

The MTD is defined as the dose level below the cohort where DLT is observed in at least 2 subjects in the same cohort during Cycle 1. Intermediate dosing levels may be explored if indicated. Additional cohorts starting below the MTD for the 10-minute infusion may be enrolled to explore extended infusion lengths. The dose of 0.8 mg/m2 will not be exceeded and will be the MAD. The RP2D is the MTD/MAD unless further safety information suggests a lower dose for future trials.

Once the MTD or Maximum Administered Dose (MAD) has been identified, a cohort of at least 12 additional, evaluable subjects will be treated at the MTD/MAD to further confirm the safety and to assess preliminary activity for the combination treatment. This cohort may be used to determine the RP2D.

Part 2 Phase 2 Dose Escalation Dose escalation of MRZ was not allowed in this portion of the study.

Part 3 Phase 2 Intrapatient Dose Escalation MRZ dosing will start at 0.8 mg/m2 given on Days 1, 8, and 15 in 28 day cycles as a 10 minute IV infusion. If the patient tolerates the MRZ dose during the first cycle without DLAE, the dose of MRZ will be increased to 1.0 mg/m2 and after 1 more cycle without a DLAE, the dose of MRZ will be increased to 1.2 mg/m2. DLAEs are MRZ-related AEs 1) related to disturbances in the cerebellum (i.e., ataxia, dizziness, dysarthria, fall, gait disturbances) plus hallucinations of any grade or 2) Grade ≥2 other AEs.

If the starting dose is not tolerated after appropriate medical treatment of AEs in the first cycle, then the dose will be decreased to 0.7 mg/m2 with no further dose increases allowed.

BEV will be administered as an IV infusion (90 minutes 1st dose, 60 minutes 2nd dose and 30 minutes afterward assuming tolerability) at a dose of 10 mg/kg on Days 1 and 15 of every 28-day cycle. BEV will be administered approximately 10 minutes after the end of the MRZ infusion when co-administered on the same day. The dose of BEV will not increase. No dose adjustments will be made to BEV dosing, although doses may be delayed or discontinued.

No. Subjects Part 1 Phase 1: 36 subjects were enrolled in the study at multiple centers.

Part 2 Phase 2: Up to 30 response-evaluable subjects will be enrolled in the study at multiple centers.

Part 3 Phase 2: Up to 40 eligible subjects will be enrolled in the study at multiple centers.

Study Population

The study population includes subjects with G4 MG (including glioblastoma and gliosarcoma) who are in first or second relapse and who have not previously received any BEV or other anti-angiogenic agent, including sorafenib, sunitinib, axitinib, pazopanib, everolimus, or cilengitide or MRZ or any other proteasome inhibitor, including BTZ, CFZ, or IXZ. The eligibility criteria are the same for both Phase 1 and Phase 2 portions of the trial except where noted.

Inclusion Criteria

Subjects must meet the following criteria to be eligible for study participation:

Understand and voluntarily sign and date an informed consent document prior to any study related assessments/procedures are conducted.

Males and females of age ≥18 years at the time of signing of the informed consent document.

All subjects must have histologic evidence of G4 MG (including glioblastoma and gliosarcoma) and radiographic evidence of recurrence or disease progression (defined as either a greater than 25% increase in the largest bidimensional product of enhancement, a new enhancing lesion, or significant increase in T2 FLAIR). Subjects must have at least 1 measurable lesion by RANO criteria (≥10 mm in 2 perpendicular diameters).

Subjects must have previously completed standard radiation therapy and been exposed to temozolomide. Patients must be in first or second relapse.

Subjects with archival tumor tissue suitable for proteasome activity and genetic testing must give permission to access and test the tissue; subjects without archival tumor tissue are eligible.

No prior treatment with MRZ or any other proteasome inhibitors, including BTZ, CFZ, or IXZ or BEV or any other anti-angiogenic agents, including sorafenib, sunitinib, axitinib, pazopanib, everolimus, or cilengitide.

No investigational agent within 4 weeks prior to first dose of study drug.

At least 4 weeks from surgical resection and at least 12 weeks from end of radiotherapy prior to enrollment in this study, unless relapse is confirmed by tumor biopsy or new lesion outside of radiation field, or if there are two MRIs confirming progressive disease that are ~8 weeks apart.

Subjects with a history of seizures must be on a stable dose of anti-epileptic drugs (AEDs) and without seizures for 14 days prior to enrollment in patients enrolled prior to Amendment 2. Subjects enrolled after Amendment 2 is approved with a history of seizures must be on a stable dose of anti-epileptic drugs (AEDs) for 7 days prior to enrollment.

All AEs resulting from prior chemotherapy, surgery, or radiotherapy, must have resolved to NCI-CTCAE (v. 4.03) Grade ☐1 (except for laboratory parameters outlined below).

Laboratory results within 7 days prior to MRZ administration (transfusions and/or growth factor support may not be used to meet this criteria):

Platelet count ≥100×109/L.

Hemoglobin ≥9 g/dL.

Absolute neutrophil count (ANC) ≥1.5×109/L/

Serum bilirubin ≤1.5×upper limit of normal (ULN) or ≤3×ULN if Gilbert's disease is documented.

Aspartate transaminase (AST) ≤2.5 ULN.

Alanine transaminase (ALT) ≤2.5 ULN.

Serum creatinine ≤1.5×ULN.

Urine protein: creatinine ratio ≤1.0 at screening.

Karnofsky Performance Status (KPS) score ≥70%.

For women of child-bearing potential and for men with partners of child-bearing potential, subject must agree to take contraceptive measures for duration of treatments and for 3 months after the last dose of MRZ and 6 months after the last dose of BEV, whichever is longer.

Willing and able to adhere to the study visit schedule and other protocol requirements.

Exclusion Criteria:

Subjects with any of the following will be excluded from participation in the study:

Co-medication that may interfere with study results, e.g., immuno-suppressive agents other than corticosteroids. (Steroid therapy for control of cerebral edema is allowed at the discretion of the Investigator. Subjects should be on a stable dose of steroids for at least 1 week prior to first dose of MRZ.)

Evidence of CNS hemorrhage on baseline MRI or CT scan (except for post-surgical, asymptomatic Grade 1 hemorrhage that has been stable for at least 3 months for subjects enrolled prior to Amendment 2 and for at least 4 weeks in subjects enrolled after Amendment 2 is approved).

History of thrombotic or hemorrhagic stroke or myocardial infarction within 6 months.

Chemotherapy administered within 4 weeks (except 6 weeks for nitrosoureas, 12 weeks for an implanted nitrosoureas wafer, and 1 week from metronomic chemotherapy, like daily temozolomide and etoposide) prior to Day 1 of study treatment, unless the subject has recovered from all expected toxicities from the chemotherapy.

Pregnancy or breast feeding.

Uncontrolled intercurrent illness including, but not limited to, ongoing or active infection requiring IV antibiotics & psychiatric illness/social situations that would limit compliance with study requirements, or disorders associated with significant immunocompromised state.

Known previous/current malignancy requiring treatment within ≤3 years except for cervical carcinoma in situ, squamous or basal cell skin carcinoma, and superficial bladder carcinoma.

Any comorbid condition that confounds the ability to interpret data from the study as judged by the Investigator or Medical Monitor.

BEV-Specific Concerns (Note: These exclusion criteria also apply to the Part 2 Phase 2 portion of the study even though BEV is not administered so that the patient populations among Part 1, Part 2, and Part 3 are similar):

Any prior history of hypertensive crisis or hypertensive encephalopathy.

Systolic blood pressure (BP)>150 mmHg or diastolic BP>100 mmHg.

Unstable angina.

New York Heart Association Grade ≥II congestive heart failure.

History of myocardial infarction within 6 months.

Subjects with mean QTcF interval >500 ms.

Clinically significant peripheral vascular disease

Evidence of bleeding diathesis, coagulopathy as documented by an elevated (≥1.5×ULN) prothrombin time (PT), partial thromboplastin time (PTT), or bleeding time. The use of full-dose oral or parenteral anticoagulants is permitted as long as the PT or aPTT is within therapeutic limits (according to the medical standard of the enrolling institution) and the subject has been on a stable dose of anticoagulants for at least 2 weeks prior to the first study treatment.

Major surgical procedure, open biopsy, or significant traumatic injury within 28 days prior to Day 1 or anticipation of need for major surgical procedure during course of the study.

Minor surgical procedures, fine needle aspirations or core biopsies within 7 days prior to Day 1.

History of abdominal fistula, GI perforation, or intra-abdominal abscess within 6 months prior to Day 1.

Serious, non-healing wound, ulcer, or bone fracture requiring surgical intervention Length of Study Participation Subjects may continue on study treatment until disease progression, unacceptable toxicity, withdrawal of consent, or termination of the study. For subjects who discontinue study drug for reasons other than disease progression, whenever possible, tumor assessment will continue as per protocol until disease progression. After disease progression, subjects will be followed for survival and the start of first new anti-GBM therapy and its outcome.

Investigational Product/Background Therapy/Route/Regimen

Part 1 Phase 1

MRZ will be administered IV over 10 minutes. Other infusion lengths may be explored. Volume of administration will vary based on assigned dose (Table 44) and subject body surface area (BSA). To mitigate the possibility of renal dysfunction, subjects will receive normal saline administered at 350 mL/hour for 1 hour before and for 2 hours after the MRZ infusion. The MRZ infusion will be started after approximately 350 mL of saline have been given over 1 hour. After the MRZ infusion has been completed, approximately 700 mL of saline will be given over 2 hours, for a total volume of saline infusion equal to approximately 1 L. Post infusion hydration may be reduced at the discretion of the Investigator. The lyophilized drug product contains 2 mg API and 60 mg sucrose bulk excipient. Cartons contain one vial of lyophile together with a Diluent vial containing 55% propylene glycol, 5% ethanol, and 40% citrate buffer pH 5 (20 mL fill; 10 mL intended for use).

BEV will be administered as an IV infusion (90 minutes 1st dose, 60 minutes 2nd dose and 30 minutes afterward assuming tolerability) as described in the current package insert. BEV will be administered approximately 10 minutes after the end of the MRZ infusion when co-administered on the same day.

Part 2 Phase 2

MRZ will be administered IV over 10 minutes at a dose of 0.8 mg/m2. To mitigate the possibility of renal dysfunction, subjects will receive normal saline administered at 250 mL for 30 minutes before the MRZ infusion. The lyophilized drug product is the same as used in the Phase 1 portion.

Part 3 Phase 2

MRZ will be administered IV over 10 minutes at a starting dose of 0.8 mg/m2. Based on the patient's tolerability, the dose of MRZ may be increased after Cycles 1 and 2. The lyophilized drug product is the same as used in the other portions of the study. For this part of the protocol, hydration prior to the MRZ dose is not required.

BEV will be administered as an IV infusion (90 minutes 1st dose, 60 minutes 2nd dose and 30 minutes afterward assuming tolerability) as described in the current package insert. BEV will be administered approximately 10 minutes after the end of the MRZ infusion when co-administered on the same day.

Procedures

Study visits and procedures will be performed as outlined in Table 45. The study will consist of Screening, Baseline, Treatment, and Follow-up periods.

Screening

The screening period may not exceed a 28-day window (with an extra 3 day window for unavoidable delays) prior to start of study treatment (Cycle 1 Day 1). Assessments will include medical history, cancer history including previous treatments, and tumor assessments. Tumor assessment must have a baseline MM scan with contrast within 14 (+3) days prior to first treatment with investigational product.

Baseline

Physical examination including Karnofsky Performance Status (KPS), neurological evaluation, neurological coordination assessment using the Scale for the Assessment and Rating of Ataxia (SARA), quality of life assessment using the FACT-Cog and FACT-Br, vital signs measurement, electrocardiogram (ECG), and laboratory tests are to be conducted within 7 days prior to Cycle 1 Day 1.

Treatment

Subjects may continue on study treatment until disease progression, unacceptable toxicity, withdrawal of consent, or termination of the study. Assessment will include Mill scans at the end of every even numbered cycle (±7 days) using RANO 2010 criteria for assessment. Responses (complete response [CR] and partial response [PR]) should be confirmed by repeat scans performed 4 weeks (±2 days) later.

Functional status using the KPS, neurological coordination assessment using the SARA, and quality of life assessment using the FACT-Cog and FACT-Br will be assessed regularly.

Subjects who discontinue study drug for reasons other than disease progression whenever possible will continue tumor assessment as per protocol schedule until progression.

End-of-Treatment Visit

Subject will be followed for safety for 28 (+7) days after discontinuation of trial therapy (Part 1 Phase 1 and Part 3 Phase 2: both MRZ and BEV; Part 2 Phase 2: MRZ).

Post Study Follow-up

All subjects will be followed in the long-term survival follow-up period for as long as they are alive. Long-term follow up will occur every 3 months (±7 days) after the End-of-Treatment visit. Telephone contact will be sufficient to document survival status. During the follow-up period, the following information will be collected: survival, and first subsequent anti-malignant glioma regimens (regimen, start and end date, and treatment outcome).

Overview of Assessments Activity (Efficacy) Assessments

Tumor response, including progressive disease, will be assessed with MRI every 2 cycles (at the end of each even-numbered cycle of therapy) according to the RANO 2010 criteria, including:

Radiographic Response Rate
Progression-free Survival (PFS)
Overall Survival (OS)
Pharmacokinetic Assessments: MRZ (Part 1 Phase 1 only)

Blood samples will be taken for peak and trough measurements, pre-dose and immediately prior to (end of infusion) EOI, on Cycle 1 Day 1. On Cycle 1 Day 15 full PK sampling will be done: pre-dose, immediately prior to EOI and then 2, 5, 15, 30, 45, 60, 90 and 120 minutes post infusion. The following PK parameters will be estimated by non-compartmental analysis:

Maximum observed blood drug concentration (Cmax)
Time of maximum blood concentration (tmax)
Elimination half-life (t½)
Area under the blood concentration-time curve (AUC0-t, AUC0-inf)
Clearance (CL)
Volume of distribution (Vd)
Pharmacokinetic Assessments: BEV (Part 1 Phase 1 only)

Pre-dose and immediately prior to EOI serum samples will be taken on Cycle 1 Days 1 and 15 to assess BEV peak and trough levels in plasma.

Blood Pharmacodynamic Assessments (Part 1 Phase 1 only)

Change in proteasome activities in packed whole blood (PWB) lysates and peripheral blood mononuclear cell (PBMC) lysates, comparing pre-drug and post drug levels on Days 1, 8, and 15 of Cycle 1; Days 1 and 15 of each Cycle thereafter; and at the End-of Treatment Visit.

Tumor Biomarker Assessments (Exploratory) Assessment of pre-treatment proteasome activity, genomic analysis and transcriptional profiling in flash-frozen and/or formalin fixed paraffin embedded, archived subject tumor sample tissue (at the discretion of the Sponsor), and if archived tumor tissue is available.

Statistical Analyses Overview

Part 1 Phase 1

A 3+3 design will be utilized to determine the MTD/MAD for MRZ+BEV combination treatment in 28-day cycles. (Subjects who do not have a DLT will be replaced if they discontinue treatment with MRZ or BEV in Cycle 1 for any other reasons.) After MTD/MAD has been determined in the dose-escalation part of the study, at least 12 additional subjects will be treated at the MTD/MAD to confirm the safety and assess the preliminary activity for the combination of MRZ+BEV.

For all analyses by dose cohorts, the MTD/MAD confirmation cohort subjects will be combined with the corresponding dose cohort in the MTD/MAD determination phase as one single dose cohort.

Part 2 Phase 2

A 2-stage sequential design will be utilized in Phase 2. Fifteen response-evaluable patients will be in the first stage. If at least 1 response is observed, then the trial will be expanded, and an additional 15 response-evaluable patients will be treated. If at least 5 responses are observed in the 30 response-evaluable patients, then MRZ will be considered active as a single agent.

Part 3 Phase 2

Forty eligible patients will be treated. Assuming there are 30 deaths observed (i.e., 25% of the subjects are censored), the resulting 95% confidence interval (CI) is 7.2-14.8 months, with a width equal to 7.6 months for an estimated median survival of 10 months.

Activity (All Parts)

Tumor response, including PD activity, progression-free survival (PFS), and overall survival (OS) will be assessed. Tumor response will be assessed by the Investigators using RANO 2010 criteria. The overall confirmed response rate will be presented. The response rate, PFS, and OS will also be tabulated by dose cohorts in Part 1 Phase 1 and for all response-evaluable patients in Part 2 Phase 2 and Part 3 Phase 2. Endpoints of response based on tumor assessments will be calculated for subjects who received at least 3 doses of MRZ and had at least 1 post-dose tumor evaluation.

Safety (All Parts)

All subjects will be evaluated for safety analysis if they receive at least one dose of MRZ or BEV in Phase 1 or MRZ in Phase 2. The safety data will be presented in individual listings and summary tables, including frequency tables for adverse events and frequency and shift tables for laboratory variables. The safety population will be all subjects who received at least one dose of either study drug in Phase 1 or MRZ in Phase 2.

Pharmacokinetics (PK) (Part 1 Phase 1 only)

Non-compartmental analyses will be performed. The following PK parameters will be calculated using standard non-compartmental analysis: maximum observed blood drug concentration (Cmax), time of maximum blood concentration (Tmax), elimination half-life (T½), area under the blood concentration-time curve (AUC0-inf), clearance (CL), and volume of distribution. Blood concentrations and computed PK parameters for MRZ will be listed and summarized by cohort (mean, geometric mean, standard deviation, coefficient of variation, minimum, maximum and number of observations). Subject population for PK will be all subjects who received at least one dose of either study drug and had at least one post-infusion sample analyzed.

Pharmacodynamics (Part 1 Phase 1 only)

Change in proteasome activities in WPB lysates and PBMC lysates, comparing pre-drug and post drug levels.

TABLE 45

Schedule of Assessments and Procedures, All Cycles

| | Screen [1] | Baseline [1] | Cycle 1 | | | Cycle 2+ | | | End of Treatment [22] | Post Study Follow-up [23] |
|---|---|---|---|---|---|---|---|---|---|---|
| | | | Study Day | | | | | | | |
| | −28 to −1 | −7 to −1 | 8 | 15 | 1 | | 8 | 15 | | |
| | | | | | Window | | | | | |
| | Up to | Up to Day −8 | 1 | ±1 | ±1 | ±1 | ±1 | ±1 | +7 | ±7 |
| Informed consent | X | | | | | | | | | |
| Medical | X | | | | | | | | | |
| Concomitant medications [1] | X | X | X | X | X | X | X | X | X | X |
| Physical examination, height [2] | | X | | | | | | | | |
| Targeted physical, weight, BSA [2] | | X | X | | X | | | | X | |
| Karnofsky Performance Status (KPS) [3] | | X | X | | X | | | | X | |

TABLE 45-continued

Schedule of Assessments and Procedures, All Cycles

| | Screen [1] | Baseline [1] | Cycle 1 | | | Cycle 2+ | | | End of Treatment [22] | Post Study Follow-up [23] |
|---|---|---|---|---|---|---|---|---|---|---|
| | | | \multicolumn{6}{c}{Study Day} | | |
| | −28 to −1 | −7 to −1 | 8 | 15 | 1 | | 8 | 15 | | |
| | | | | | \multicolumn{3}{c}{Window} | | | |
| | Up to | Up to Day −8 | 1 | ±1 | ±1 | ±1 | ±1 | ±1 | +7 | ±7 |
| Neurological examination and assessment, SARA [4] | | X | X | | | X | | | X | |
| Quality of life assessments (FACT-Cog, FACT-Br) [5] | | X | | | | At the beginning of each even numbered cycle | | | X | |
| Toxicity evaluation [6] | | | X | X | X | X | X | X | | |
| Vital signs (HR, temp, BP) [7] | | X | X | X | X | X | X | X | X | |
| ECG [8] | | X | X | | X | | | | X | |
| Complete Blood Count, Differential Platelets[9] | | X | | X | X | X | | X | X | |
| Serum Chemistry [10] | | X | | X | X | X | | X | X | |
| PT/PTT [11] | | X | X | | | X | | | X | |
| Urinalysis[12] | | X | X | | | X | | | X | |
| Marizomib infusion [13] | | | X | X | X | X | X | X | | |
| Bevacizumab infusion [14] | | | X | | X | X | | X | | |
| Blood PK sampling (MRZ) [15] | | | X | | X | | | | | |
| Blood PK sampling (BEV) [16] | | | X | | X | | | | | |
| Pregnancy test [17] | | X | | | | | | | X | |
| Blood Proteasome assay [18] | | | X | X | X | X | | X | X | |
| Tumor measurement [19] | X (−14 to −1) (3-day) | | | | | At the end of each even numbered cycle | | | X | |
| Tumor proteasome activity [20] | X | | | | | | | | | |
| Tumor gene signature profiling [21] | X | | | | | | | | | |

1. Within 7 days of starting treatment except consent, demographics, medical history, concomitant medications, complete physical examination, radiographic/tumor assessments, and consent to acquire and test archival tumor tissue samples, which can be obtained within 28 days prior to the start of treatment.
2. Height measured at baseline only. Physical Examination is a complete physical as per institutional guidelines (genitourinary examination not required unless there are related signs or symptoms) at baseline, but thereafter as directed by signs and symptoms (targeted physical examination).
3. Functional assessment using the Karnofsky Performance Status (KPS) is to be completed at baseline, at the beginning of each cycle, and at the end of treatment. See
4. Neurological examination, including the evaluation of coordination to be performed at baseline, at the beginning of each cycle, and at the end of treatment using the Scale for the assessment and rating of ataxia (SARA). See
5. Quality of life assessments using the FACT-Cog and FACT-Br are to be completed at baseline, at the beginning of each even numbered cycle (i.e., C2D1, C4D1, etc.), and at the end of treatment. FACT forms are not validated in all languages. In cases where the patient is not fluent in a language covered by the FACT forms, these assessments will not be made.
6. Toxicity evaluation is an assessment of reported and observed adverse events, in the Phase 1 portion of the study, following the MRZ and BEV administrations compared to pre-dose findings. Toxicity evaluation is an assessment of reported and observed adverse events, in the Phase 2 portions (Parts 2 and 3) of the study, following the MRZ administration compared to pre-dose findings.
7. Vital Signs: (blood pressure, heart rate, and temperature) during the Phase 1 portion of the study in Cycle 1, Days 1 and 15: immediately before the MRZ infusion and immediately before the BEV infusion and approximately 10 (±2) minutes, 30 (±5) minutes and 1 hour (±5 minutes) following the BEV infusion. Cycle 2+, Days 1 and 15: prior to the MRZ infusion and prior to the BEV infusion and 30 (±5) minutes following each BEV infusion. In all cycles, Day 8, immediately before the MRZ infusion and 30 (±5) minutes following each MRZ infusion. During the Phase 2 portions (Parts 2 and 3) of the study, in Cycle 1, Days 1, 8, and 15: immediately before the MRZ infusion and approximately 10 (±2) minutes, 30 (±5) minutes and 1 hour (±5 minutes) following the MRZ infusion. Cycle 2+, Days 1, 8, and 15: prior to the MRZ infusion and 30 (±5) minutes following each MRZ infusion. For all portions of the study vital signs are also collected as part of the physical examination.
8. ECG: Eligibility ECGs must be performed within 7 days prior to Day 1. ECGs will be collected Cycle 1 only (Days 1 and 15), within 60 minutes prior to the MRZ infusion and within 5 (±1) minutes following the MRZ infusion. An End-of-Treatment ECG is to be collected. Additional ECGs should be obtained if clinically indicated.
9. Hemoglobin (Hgb), hematocrit (Hct), red blood cell (RBC) count, white blood cell (WBC) count with differential, and platelets. Hematology tests can be performed within 72 hours of scheduled dosing except prior to Cycle 1, which can be done within 7 days prior to dosing. Should a subject experience a Grade 4 hematologic toxicity, the appropriate test will be monitored in accordance with institutional guidelines (at minimum: weekly) until Grade ≤2. The following tests should meet minimum stipulations prior to entry into Cycle 2+: Hgb ≥8 g/dL; platelets ≥75×10$^9$/L.
10. Sodium, potassium, chloride, bicarbonate, calcium, magnesium, glucose, BUN, serum creatinine, uric acid, ALT, AST, alkaline phosphatase, total protein, albumin, and total bilirubin. Chemistry will be performed within 72 hours of scheduled dosing except prior to Cycle 1, which can be done within 7 days prior to dosing. Minimum re-treatment criterion prior to the beginning of each new cycle: creatinine ≤1.5×ULN.
11. Prothrombin time (PT) or International Normalized Ratio (INR) and partial thromboplastin time (PTT) may be performed more often if clinically indicated. Coagulation tests will be performed within 72 hours of scheduled dosing except prior to Cycle 1, which can be done within 7 days prior to dosing.
12. Urinalysis: protein, blood, glucose, pH; microscopic (RBC, WBC, casts) if abnormal urinalysis. Urinalysis performed within 72 hours of scheduled dosing, except prior to Cycle 1, which can be done within 7 days prior to dosing.
13. Subjects are to be encouraged to maintain good oral hydration during the study (e.g., 2 liters per day, as considered appropriate by the Investigator). Part 1 MRZ infusion: injected over 10 minutes (or longer depending upon cohort). The volume of infusate will vary per subject depending on dose and BSA. In Part 1 Phase 1 subjects will receive normal saline started prior to and following the infusion administered at ~350 mL/hour, with the infusion to occur after ~350 mL have been given with a total volume of infusion to equal one liter. In Part 2 Phase 2 subjects will receive 250 mL normal saline over 30 minutes prior to the MRZ infusion. At the discretion of the Investigator, additional normal saline can be given after the MRZ infusion is complete. Part 3 Phase 2: No pre-dose hydration is required unless re-instituted after safety review by the Medical Monitor, representatives of the Sponsor, and the participating investigators. In each patient the dose will be increased if tolerated to 1.0 mg/m$^2$ after Cycle 1 and to 1.2 mg/m$^2$ after Cycle 2. Dose escalation after dose reduction is not recommended but will be allowed only with the approval of the Sponsor's Medical Monitor.
14. BEV administered as an IV infusion. First dose should be infused over 90 minutes and if tolerated, the second infusion may be given over 60 minutes, and if tolerated, subsequent infusions may be given over 30 minutes. Infusions may be interrupted or lengthened to treat or prevent infusion-related reactions. BEV is administered approximately 10 minutes after the end of the MRZ infusion. BEV is not given during Part 2 Phase 2.
15. Blood PK Sampling (MRZ) (during Part 1 Phase 1 dose escalation only): On Cycle 1 Day 1, MRZ samples will be obtained before treatment and just prior to end of infusion. On Cycle 1 Day 15, MRZ samples will be obtained before treatment, just prior to end of infusion, and 2, 5, 15, 30, 45, 60, 90, and 120 minutes after the infusion. Every effort should be made to collect samples at the prescribed times, but deviations up to 10% of the time point are allowed. Additional samples may be collected if the subject experiences a potentially drug-related SAE. Use Sponsor-provided PK kits. Process, store and ship samples per instructions in Study Reference Manual.
16. Blood PK Sampling (BEV) (during Part 1 Phase 1 dose escalation only): For BEV Cycle 1 Day 1 and 15, BEV plasma samples will be obtained before treatment and just prior to end of infusion. Use Sponsor-provided PK kits. Every effort should be made to collect samples at the prescribed times, but deviations up to 10% of the time point are allowed. Use Sponsor-provided PK kits. Process, store and ship samples per instructions in Study Reference Manual.
17. Pregnancy test (serum or urine) to be performed at Baseline, End-of-Treatment visit, and more frequently if clinically indicated.
18. Blood proteasome assay (during Part 1 Phase 1 dose escalation only): Cycle 1 Day 1 (before treatment and 1 hour post MRZ infusion), Day 8 (before treatment and 1 hour post MRZ infusion), and Day 15 (before treatment and 1 hour post MRZ infusion). Starting Cycle 2 and thereafter, Day 1 (before treatment and 1 hour post MRZ infusion) and on Day 15 (before treatment and 1 hour post MRZ infusion). A sample will be drawn at the End of Treatment visit. On Cycle 2 Day 1 (pre MRZ infusion or on Cycle 1 Day 29 if the subject does not go on to Cycle 2 or Cycle 2 is delayed. A sample will be drawn at the time that a complete response or partial response or disease progression is determined.
19. Tumor assessment: Baseline tumor assessments are to be made within 14 days (3-day time window) prior to Cycle 1 Day 1. Response should be assessed (RANO 2010) during the rest period of Cycle 2 and during the rest period of every 2 cycles thereafter (±7 days). If a subject is determined to have an overall disease response of CR or PR, then disease assessments should be repeated approximately 4 (±2 days) weeks later to confirm the response. If tumor assessments have not been performed in the 4 weeks prior to the End-of Treatment Visit, then tumor assessments are to be done at the End-of Treatment Visit. If a patient has a standard of care tumor assessment done prior to giving Informed Consent, but within the 14 day (3-day window), that is available to the investigator, then that tumor assessment can serve as a baseline and another screening MM is not required.
20. For subjects with flash-frozen, GBM tumor tissue, assessment of pre-treatment proteasome activity levels will be performed.
21. For subjects with archived blocks of GBM tumor, genomic analysis and transcriptional profiling will be conducted. A blood sample will also be collected prior to C1D1 dosing in these subjects so comparisons can be made between germ line and tumor mutations.
22. Subjects with drug-related AEs of Grade ≥2 observed at the End-of-Treatment assessment should be followed-up at least monthly until the AE has resolved to Grade 1, the event is believed to be chronic or subject receives other anti-cancer therapy.
23. Post Study Follow-up visits may be made in person or other means of communication. Purpose of the follow up, which should occur every 3 months (±7 days), is to determine survival and the start of first new anti-GBM systemic treatment and its outcome.

1. Study Objectives
1.1. Primary Objective
Part 1 Phase 1

The primary objective of the study is To determine the maximum tolerated dose (MTD) or maximum administered dose (MAD) and recommended Phase 2 dose (RP2D) of the combination of marizomib (MRZ)+bevacizumab (BEV) with MRZ as a once weekly dose for 3 weeks of a 28-day cycle and a fixed dose and schedule of BEV (10 mg/kg administered on Days 1 and 15) in subjects with WHO Grade 4 malignant glioma (G4 MG), who have not previously been treated with either an anti-angiogenic agent including, but not limited to, BEV or a proteasome inhibitor including, but not limited to, MRZ.

Part 2 Phase 2
To assess the activity of a once weekly dose for 3 weeks of a 28-day cycle of MRZ in subjects with progressive or recurrent G4 MG, who have not previously been treated with either an anti-angiogenic agent or a proteasome inhibitor.
Part 3 Phase 2
To assess the activity of the combination of once weekly MRZ dosing for 3 weeks (allowing for intra-patient dose escalation) and every other week dosing of BEV at 10 mg/kg in 28-day cycle in subjects with progressive or recurrent G4 MG, who have not previously been treated with either an anti-angiogenic agent or a proteasome inhibitor.
1.2. Secondary Objectives
Part 1 Phase 1
The secondary objectives of the study are:
To evaluate the safety of the combination of MRZ+BEV in the subject population.
To evaluate activity of the combination of MRZ+BEV in the subject population:
Radiographic Response Rate
Progression-free Survival (PFS)
Overall Survival (OS)
To evaluate the pharmacokinetics (PK) of MRZ and BEV when administered in combination in the subject population.
To assess the whole blood proteasome pharmacodynamic (PD) activity of the combination of MRZ+BEV in the subject population.
Part 2 Phase 2
To evaluate the safety of single agent MRZ in the subject population.
Part 3 Phase 2
To evaluate the safety of combination of MRZ and BEV with intrapatient dose escalation and BEV at a fixed dose in the subject population.
1.3. Exploratory Objectives
Part 1 Phase 1, Part 2 Phase 2, and Part 3 Phase 2
The exploratory objectives of the study are
To evaluate baseline tumor proteasome activity, gene signature, and transcriptional profiling and correlation with activity using pre-study, archived tissue samples.
To evaluate neurological coordination assessment using the Scale for the Assessment and Rating for Ataxia (SARA).
To evaluate Quality of Life Assessments using the Functional Assessment of Cancer Therapy (FACT) questionnaires:
FACT-Cognitive Function (FACT-Cog)
FACT-Brain (FACT-Br)
2. Study Endpoints
2.1. Primary Endpoint(s)
Part 1 Phase 1
Maximum tolerated dose (MTD) or Maximum Administered Dose (MAD)
Recommended Phase 2 Dose (RP2D)
Part 2 Phase 2
Best response
Part 3 Phase 2
Overall survival (OS)
2.2. Secondary Endpoint(s)
Part 1 Phase 1 and Part 2 Phase 2 Safety
Type, incidence and severity of adverse events (AEs)
Type, incidence and severity of serious adverse events (SAEs)
Type, incidence and severity of dose-limiting toxicities (DLTs)
Activity
Radiographic overall response rate (ORR)
Progression-free survival (PFS)
Overall survival (OS)
Part 3 Phase 2
Safety
Type, incidence and severity of adverse events (AEs)
Type, incidence and severity of serious adverse events (SAEs)
Type, incidence and severity of dose-limiting adverse events (DLAEs)
Activity
Radiographic overall response rate (ORR)
Progression-free survival (PFS)
Pharmacokinetics for MRZ (Part 1 Phase 1 only)
Maximum observed blood drug concentration ($C_{max}$)
Time of maximum blood concentration ($t_{max}$)
Elimination half-life ($t_{1/2}$)
Area under the blood concentration-time curve ($AUC_{0-t}$, $AUC_{0-inf}$)
Clearance (CL)
Volume of distribution (Vd)
Pharmacokinetics for BEV (Part 1 Phase 1 only)
Peak and trough levels in plasma
Pharmacodynamic Assessment (Part 1 Phase 1 only)
Change in proteasome activities in packed whole blood (PWB)
2.3. Exploratory Endpoint(s)
Part 1 Phase 1, Part 2 Phase 2 and Part 3 Phase 2
To evaluate baseline tumor proteasome activity, gene signature and transcriptional profiling using pre-study, archived tissue samples.
To evaluate neurological coordination assessment using the Scale for the Assessment and Rating for Ataxia (SARA).
To evaluate Quality of Life Assessments using Functional Assessment of Cancer Therapy (FACT) questionnaires:
FACT-Cognitive Function (FACT-Cog)
FACT-Brain (FACT-Br)
3. Overall Study Design
3.1. Study Design
This is a Phase 1, multicenter, open-label, 3+3, dose-escalation study in subjects with G4 MG who are in first or second relapse and who have not previously received any BEV or other anti-angiogenic agent, including: sorafenib, sunitinib, axitinib, pazopanib, everolimus, or cilengitide or MRZ or any other proteasome inhibitor, including bortezomib (BTZ), carfilzomib (CFZ), or ixazomib (IXZ). Three to 6 evaluable subjects per cohort will be enrolled: up to 24 subjects to determine the MTD/MAD (Part 1 dose-escalation) and an additional 12 or more subjects to confirm the MTD/MAD (Part 2 MTD/MAD expansion) to a total of up to 36 subjects and assess preliminary activity. Subjects may not be enrolled in more than 1 cohort and there will be no intra-subject dose escalation.

The Phase 1 portion will be followed by a Phase 2 portion of the trial of single agent MRZ administered as a 10-minute infusion at a dose of 0.8 mg/m² (the MAD) every week for 3 weeks in 28-day cycles. This portion of the trial will be conducted as a 2-stage sequential design of up to 30 response-evaluable patients.

The Part 2 Phase 2 portion of the trial will be followed by Part 3 Phase 2 of combination MRZ and BEV. MRZ will be administered as a 10-minute infusion every week for 3 weeks in 28-day cycles at a starting dose of 0.8 mg/m² (the RP2D from Phase 1). After 1 cycle without a DLAE, the dose will be incremented to 1.0 mg/m² and then, if the dose is tolerated, to 1.2 mg/m² in Cycle 2 and thereafter. BEV will be administered every 2 weeks (Days 1 and 15 of each 28-day cycle) at a fixed dose of 10 mg/kg. This portion of the trial will be conducted with 40 eligible patients.

3.2. Study Design Rationale

Part 1 Phase 1

Figure 30:
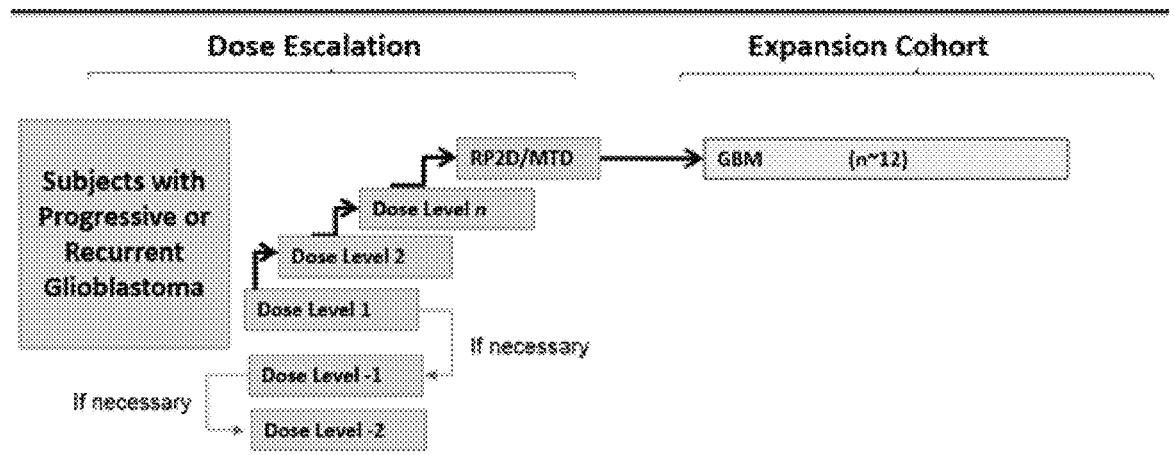
FIG. 30 shows the overall study design of a Phase 1 clinical trial set forth in Examples 3 and 4.

The study is a classical 3+3 design that is often used in Phase 1 cancer studies. Standard evaluations for safety and activity are employed. The schema is provided in FIG. 30.

Part 2 Phase 2

The study is a modified 2-stage design (Green and Dahlberg 1992). Standard evaluations for safety and activity are employed. Fifteen response-evaluable patients will be entered in the first stage. If no objective responses are observed, the trial will be terminated. If 1 or more responses are observed, then the second stage will be implemented with an additional 15 response-evaluable patients treated. If at least 5 responses are observed, MRZ will be considered active as a single agent.

Part 3 Phase 2

The study is designed to determine the OS in patients treated with intrapatient dose escalation of MRZ with a constant dose of BEV.

3.3. Study Duration

Subjects may continue on study treatment until disease progression, unacceptable toxicity, withdrawal of consent, or termination of the study. Once discontinued from the study treatment, subjects will enter a long-term follow-up period (Post Study Follow-Up) for documentation of survival and the start of first new anti-GBM therapy and its outcome. Post Study Follow-up will occur every 3 months (±7 days) after the 28-day post-treatment discontinuation visit (End-of-Treatment visit).

3.4. End of Trial

The End of Trial is defined as the date of receipt of the last data point from the last remaining subject that is required for primary, secondary and/or exploratory analysis.

Procedures

Study visits and procedures will be performed as outlined in Table 45.

The study will consist of Screening, Baseline, Treatment, and Follow-up periods. Except where otherwise stated, the procedures apply to both Phase 1 and Phase 2 portions of the study.

Screening

Screening procedures may not be done prior to the signing and dating of the Informed Consent Form (ICF). However, the results of tumor assessments done as part of standard of care that are within the 14-day (3-day window) screening period do not have to be repeated if they were done at the participating site. However, if results are not available, then tumor assessments are to be conducted within 14 days prior to Cycle 1 Day 1. The screening period for assessments that include medical history (including demographics and cancer history), prior medications and procedures may not exceed a 28 days (with a 3-day window for scheduling conflicts) window prior to start of study treatment (Cycle 1 Day 1) for assessments that include medical history including demographics and cancer history, prior medications and procedures.

Baseline

Physical examination including height, weight, and vital signs, Karnofsky Performance Status (KPS) scale, ECGs, laboratory tests including hematology, coagulation, chemistry, urinalysis; and, as appropriate, pregnancy tests are to be done within 7 days (with a 2-day window for scheduling conflicts) prior to Cycle 1 Day 1. Neurological coordination assessment using the Scale for the Assessment and Rating of Ataxia (SARA) and quality of life assessment using the FACT-Cog and FACT-Br.

Treatment

Safety tests and procedures will be performed according to the Schedule of Assessments and Procedures (Table 45). PK and PD samples will be obtained prior to the start of treatment and then after dosing at selected time points for Part 1 Phase 1. Assessments will include MRI scans at the end of every even numbered cycle (±7 days) using RANO 2010 criteria for assessment. Patients in the Part 1 Phase 2 and Part 3 Phase 2 portions of the study may continue treatment with MRZ for 1 or 2 cycles after an MM indicates progression if according to the investigator's judgement this is in the best interest of the patient and/or if the investigator interprets that the MM indicates possible pseudoprogression, and there is no significant clinical deterioration of the patient.

Functional status using the KPS will be conducted in both Phases. Neurological coordination assessment using the SARA and quality of life assessment using the FACT-Cog and FACT-Br will be assessed regularly.

Subjects may continue on study treatment until disease progression, unacceptable toxicity, withdrawal of consent, or termination of the study.

End-of-Treatment Visit

An End-of-Treatment Visit should occur when a subject discontinues study treatment 28 (+7) days after the last dose of MRZ or BEV, whichever is later in the Part 1 Phase 1 and Part 3 Phase 2 portions and after the last dose of MRZ in the Part 2 Phase 2 portion of the study. Tests are primarily to ensure there are no late occurring AEs and that AEs have resolved or have stabilized. Additional follow-up visits may be conducted to follow ongoing AEs that are resolving. If a subject cannot or will not make this visit, attempts to gather information on the status of AEs should be made by telephone or other means.

Post Study Follow-up

All subjects will be followed for survival during the follow-up period for as long as they are alive. Post Study follow-up will occur every 3 months (±7 days) after the End-of-Treatment Visit. During long-term follow-up, the following information will be collected: survival, first subsequent anti-GBM systemic regimens, and treatment outcomes.

Activity Assessments

Tumor response, including progressive disease, will be assessed with MRI at the end of every 2 cycles of therapy according to the RANO criteria, including:

Radiographic Overall Response Rate

Progression-free Survival (PFS)

Overall Survival (OS)

Confirmation of response at 4 weeks (±2 days) after the response is to be performed.

If the Investigator believes that an MM indicating tumor progression by RANO criteria may reflect pseudoprogression, and there is no significant clinical deterioration of the patient, the patient may be continued for 1 or 2 additional cycles (at the discretion of the Investigator based on the patient's clinical condition) before another MRI assessment is conducted. If a patient is taken off study for progressive disease by imaging and subsequent biopsy or surgical resection shows no evidence of disease, the patient will be counted as a responder. In this case, the patient may return to the trial for additional treatment with MRZ, using a post-procedure MRI as the new baseline.

Pharmacokinetic (PK) Assessments: MRZ (Part 1 Phase 1 only)

Blood should be drawn from the contralateral arm to the infusion site and using an indwelling catheter to avoid multiple needle sticks is recommended. Sample collection time should be recorded on the tube label and Case Report Form (CRF) as day: hour: minute. Nominal time of blood collection are given as "time points"; it is critical that an accurately collected actual time of the sample is written on the CRF and on the blood tubes (date entered as dd:mm:yyyy; time entered using a 24-hour clock, hh:mm). For MRZ samples will be obtained before treatment and just prior to end of infusion on Cycle 1 Day 1. On Cycle 1 Day 15, MRZ blood samples will be obtained before treatment, just prior to end of infusion, and 2, 5, 15, 30, 45, 60, 90, and 120 minutes after the infusion. Every effort should be made to collect samples at the prescribed times, but deviations up to 10% of the time point are allowed. Additional samples may be collected if the subject experiences a potentially drug-related SAE. After blood collection, neutralizing solution must be added. Use Sponsor-provided PK kits. Process, store and ship samples per instructions in Study Reference Manual.

PK parameters that will be determined include:
Maximum observed blood drug concentration ($C_{max}$)
Time of maximum blood concentration ($t_{max}$)
Elimination half-life ($t_{1/2}$)
Area under the blood concentration-time curve ($AUC_{0-t}$, $AUC_{0-inf}$)
Clearance (CL)
Volume of distribution (Vd)

PK Assessments: BEV (Part 1 Phase 1 only)
For BEV pre-dose and immediately prior to EOI, plasma samples will be taken on Days 1 and 15 to assess BEV peak and trough levels. Process, store and ship samples per instructions in Study Reference Manual. PK assessment of BEV is not done in Phase 2.

Pharmacodynamic (PD) Assessments (Part 1 Phase 1 only)
Change in proteasome activities (whole blood lysates and PBMC lysates), comparing pre-drug and post drug levels The laboratory correlates include assessment of the percentage inhibition of proteasome function (evaluated by measurement of CT-L, T-L and C-L activity in blood isolates such as whole blood and PBMC lysates.
Process, store and ship samples per instructions in Study Reference Manual.

Tumor Proteasome Activity
For subjects with flash frozen GBM tumor tissue, proteasome activity will be determined by qualified assay. Instructions on shipping these samples will be provided in the Study Reference Manual.

Gene Profiling
Prior to Amendment 2, gene signature profiling was to be performed using the Decision Dx-GBM test from Castle Bioscience to determine the molecular signature for a GBM tumor. This assay was not conducted on any patient samples, and no future testing by this method is planned. After Amendment 2 is approved, for subjects with archived blocks of GBM tumor, a proteasome based gene expression analysis will be performed. This analysis will focus on quantitation of the β1, β2, and β5 catalytic subunits of the proteasome to determine whether gene expression correlates to enzymatic activity measured in frozen tumor tissue. If a relationship is observed between enzymatic activity and gene expression, this may enable a correlation between MRZ clinical response and proteasome subunit expression in archival tissue. These studies aim to determine whether a predictive biomarker for MRZ-responsive patients can be identified. If we are unable to observe a correlation between enzymatic activity and catalytic subunit gene expression levels, we may undertake a wider genetic profiling study to determine whether a gene signature predictive of MRZ response can be identified. Instructions on shipping these samples will be provided in the Study Reference Manual.

Karnofsky Performance Status
The Karnofsky Performance Status (KPS) allows patients to be classified as to their functional impairment. This can be used to measure changes in a patient's ability to function. The Karnofsky Performance Status scores range from 0 to 100. A higher score signifies the patient is better able to carry out daily activities.

Scale for the Assessment and Rating of Ataxia
The Scale for the Assessment and Rating of Ataxia (SARA) is a clinical scale that is based on a semiquantitative assessment of cerebellar ataxia on an impairment level. It has eight items with total scores ranging from 0 (no ataxia) to 40 (most severe ataxia). Scores for the eight items range as follows: no ataxia, 1: gait (0-8 points), 2: stance (0-6 points), 3: sitting (0-4 points), 4: speech disturbance (0-6 points), 5: finger chase (0-4 points), 6: nose-finger test (0-4 points), 7: fast alternating hand movement (0-4 points), 8: heel-shin slide (0-4 points), and 40: severe ataxia. For motor activities of the four extremities (items 5-8), assessments are performed bilaterally, and the mean values are used to obtain the total score.

Quality of Life Assessments
FACT-Cog
The Functional Assessment of Cancer Therapy-Cognitive Function (FACT-Cog) is a 37-item validated subjective neuropsychological instrument designed to evaluate cancer subjects' perceived cognitive deterioration on their quality of life. A 6.9 to 10.6 points reduction of the FACT-Cog score corresponds to the smallest clinically-relevant perceived cognitive deterioration. These estimates are important as they can facilitate the interpretation of subjects'-reported cognitive changes and sample size estimation.

FACT-Br
The Functional Assessment of Cancer Therapy-Brain (FACT-Br) is a commonly used instrument measuring general quality of life (QOL) that reflects symptoms or problems associated with brain malignancies across 5 scales. The measure yields information about total QOL, as well as information about the dimensions of physical well-being, social/family well-being, emotional well-being, functional well-being, and disease specific concerns. The FACT-Br is written at the 4th grade reading level, and subjects can fill it out in 5-10 minutes. The self-report can be completed by the subject with little or no assistance in subjects who are not neurologically incapacitated. Subjects rate all 5 items using a 5-point Likert scale ranging from 0 (not at all) to 4 (very much). Overall, higher ratings suggest higher QOL. Items are totaled to produce the following subscales, along with an overall QOL score: physical well-being (7 items); social/family well-being (7 items); emotional well-being (6 items); functional well-being (7 items); and concerns relevant to subjects with brain tumors (23 items).

Study Population
The study population includes subjects with G4 MG (including glioblastoma and gliosarcoma) who are in first or second relapse and who have not previously received any BEV or other anti-angiogenic agent, including sorafenib, sunitinib, axitinib, pazopanib, everolimus, or cilengitide or MRZ or any other proteasome inhibitor, including BTZ, CFZ, or IXZ.

3.5. Number of Subjects and Sites
Thirty-six subjects were enrolled in the study at multiple sites in Part 1 Phase 1 and 30 response-evaluable patients will be enrolled in Part 2 Phase 2. Forty response evaluable patients in Part 3 Phase 2 will be enrolled as per this Amendment 3.

3.6. Inclusion Criteria

Subjects must satisfy the following criteria to be enrolled in the study. These criteria apply to both the Phase 1 portion including the expansion cohort and both the Part 2 and Part 3 Phase 2 portions.

1. Understand and voluntarily sign and date an informed consent document prior to any study related assessments/procedures are conducted.
2. Males and Females ≥18 years of age at the time of signing the informed consent document.
3. All subjects must have histologic evidence of G4 MG (including glioblastoma and gliosarcoma) and radiographic evidence of recurrence or disease progression (defined as either a greater than 25% increase in the largest bidimensional product of enhancement, a new enhancing lesion, or significant increase in T2 FLAIR). Subjects must have at least 1 measurable lesion by RANO criteria (≥10 mm in 2 perpendicular diameters).
4. Subjects must have previously completed standard radiation therapy and been exposed to temozolomide. Patients must be in first or second relapse.
5. Subjects with archival tumor tissue suitable for proteasome activity and genetic testing must give permission to access and test the tissue; subjects without archival tumor tissue are eligible.
6. No prior treatment with MRZ or any other proteasome inhibitors, including BTZ, CFZ, and IXZ or BEV or any other anti-angiogenic agents, including sorafenib, sunitinib, axitinib, pazopanib, everolimus or cilengitide.
7. No investigational agent within 4 weeks prior to first dose of study drug.
8. At least 4 weeks from surgical resection and 12 weeks from end of radiotherapy prior to enrollment in this study, unless relapse is confirmed by tumor biopsy, or new lesion outside of radiation field, or if there are two MRIs confirming progressive disease that are 8 weeks apart.
9. Subjects with a history of seizures must be on a stable dose of anti-epileptic drugs (AEDs) and without seizures for 14 days prior to enrollment in patients enrolled prior to Amendment 2. Subjects enrolled after Amendment 2 is approved with a history of seizures must be on a stable dose of anti-epileptic drugs (AEDs) for 7 days prior to enrollment.
10. All AEs resulting from prior chemotherapy, surgery, or radiotherapy, must have resolved to US National Cancer Institute Common Terminology Criteria for Adverse Events Version 4.03 (NCI-CTCAE v. 4.03) Grade (except for laboratory parameters outlined below).
11. Laboratory results within 7 days prior to MRZ administration (transfusions and/or growth factor support may not be used to meet this criteria):
    Platelet count ≥100×10$^9$/L.
    Hemoglobin ≥9 g/dL.
    Absolute neutrophil count (ANC)≥1.5×10$^9$/L.
    Serum bilirubin ≤1.5×upper limit of normal (ULN) or ≤3×ULN if Gilbert's disease is documented.
    Aspartate transaminase (AST)≤2.5 ULN.
    Alanine transaminase (ALT)≤2.5 ULN.
    Serum creatinine ≤1.5×ULN.
    Urine protein: creatinine ratio ≤1.0
12. Karnofsky Performance Status (KPS) score 70%.
13. For women of child-bearing potential and for men with partners of child-bearing potential, subject must agree to take contraceptive measures for duration of treatment and for 3 months after the last dose of MRZ or 6 months after the last dose of BEV, whichever is longer.
14. Willing and able to adhere to the study visit schedule and other protocol requirements.

3.7. Exclusion Criteria

The presence of any of the following will exclude a subject from enrollment. Co-medication that may interfere with study results, e.g., immuno-suppressive agents other than corticosteroids. (Steroid therapy for control of cerebral edema is allowed at the discretion of the Investigator. Subjects should be on a stable dose of steroids for at least 1 week prior to first dose of MRZ.)

1. Evidence of CNS hemorrhage on baseline MRI or CT scan (except for post-surgical, asymptomatic Grade 1 hemorrhage that has been stable for at least 3 months for subjects enrolled prior to Amendment 2 and for at least 4 weeks in subjects enrolled after Amendment 2 is approved).
2. History of thrombotic or hemorrhagic stroke or myocardial infarction within 6 months.
3. Chemotherapy administered within 4 weeks (except 6 weeks for nitrosoureas, 12 weeks for nitrosourea wafer, and 1 week from metronomic chemotherapy, like daily temozolomide and etoposide) prior to Day 1 of study treatment, unless the subject has recovered from all expected toxicities from the chemotherapy.
4. Pregnancy or breast feeding.
5. Uncontrolled intercurrent illness including, but not limited to, ongoing or active infection requiring IV antibiotics & psychiatric illness/social situations that would limit compliance with study requirements, or disorders associated with significant immunocompromised state.
6. Known previous/current malignancy requiring treatment within ≤3 years except for cervical carcinoma in situ, basal cell carcinoma, and superficial bladder carcinoma.
7. Any comorbid condition that confounds the ability to interpret data from the study as judged by the Investigator or Medical Monitor.

BEV-Specific Concerns (all Parts) (Note: These Exclusion Criteria Apply to the Part 2 Phase 2 Portion of the Study Even Though BEV is not Administered so that the Patient Populations Among Part 1, Part 2, and Part 3 are similar):

8. Any prior history of hypertensive crisis or hypertensive encephalopathy.
9. Systolic blood pressure (BP)>150 mmHg or diastolic BP>100 mmHg.
10. Unstable angina.
11. New York Heart Association Grade ≥II congestive heart failure.
12. History of myocardial infarction within 6 months.
13. Subjects with mean QTcF interval >500 ms.
14. Clinically significant peripheral vascular disease.
15. Evidence of bleeding diathesis or coagulopathy as documented by an elevated (≥1.5×ULN) prothrombin time (PT), partial thromboplastin time (PTT), or bleeding time. The use of full-dose oral or parenteral anticoagulants is permitted as long as the PT or aPTT is within therapeutic limits (according to the medical standard of the enrolling institution) and the subject has been on a stable dose of anticoagulants for at least 2 weeks prior to the first study treatment.

16. Major surgical procedure, open biopsy, or significant traumatic injury within 28 days prior to Day 1 or anticipation of need for major surgical procedure during course of the study.
17. Minor surgical procedures, fine needle aspirations or core biopsies within 7 days prior to Day 1.
18. History of abdominal fistula, GI perforation, or intra-abdominal abscess within 6 months prior to Day 1.
19. Serious, non-healing wound, ulcer, or bone fracture requiring surgical intervention.

Description of Study Treatments 3.8. Treatment Administration and Schedule 7.2.1. Marizomib Drug Product The lyophilized drug product contains 2 mg API and 60 mg sucrose bulk excipient. Cartons contain one vial of lyophile together with a Diluent vial containing 55% propylene glycol, 5% ethanol, and 40% citrate buffer pH 5 (20 mL fill; 10 mL intended for use). The lyophile drug product reconstituted with 10 mL diluent results in a dosing solution comprised of 55% propylene glycol, 40% citrate buffer and 5% ethanol, with 6 mg/mL sucrose as a pharmaceutical excipient. The drug is delivered at 0.2 mg/mL at a final dosing solution of pH ~6. A dose of 0.7 mg/m2 will result in approximately 7 mL of infusate.

3.8.1. Administration of MRZ in Part 1 Phase 1

MRZ will be administered IV over 10 minutes or longer depending upon cohort (refer to Directions for Use regarding directions for administration time). Volume of administration will vary based on assigned dose (see Table 46) and subject body surface area (BSA). To mitigate the possibility of renal dysfunction, subjects will receive normal saline administered at 350 mL/hour for 1 hour before and for 2 hours after the MRZ infusion. The MRZ infusion will be started after approximately 350 mL of saline have been given over 1 hour. After the MRZ infusion has been completed, approximately 700 mL of saline will be given over 2 hours, for a total volume of saline infusion equal to approximately 1 L.

Subjects should maintain good oral hydration during the study (e.g., 2 L/day). The volume and duration of hydration may be reduced at the discretion of the Investigator, especially for subjects with low body weight or with conditions sensitive to fluid overload.

Subjects must not drive a vehicle or operate heavy machinery while on this study.

The lyophilized drug product contains 2 mg API and 60 mg sucrose bulk excipient. Cartons contain one vial of lyophile together with a Diluent vial containing 55% propylene glycol, 5% ethanol, and 40% citrate buffer pH 5 (20 mL fill; 10 mL intended for use). The lyophilized drug product reconstituted with 10 mL diluent results in a dosing solution comprised of 55% propylene glycol, 40% citrate buffer and 5% ethanol, with 6 mg/mL sucrose as a pharmaceutical excipient. The drug is delivered at 0.2 mg/mL at a final dosing solution of pH ~6. A dose of 0.7 mg/m$^2$ will result in approximately 7 mL of infusate.

3.8.2. Administration of BEV in Part 1 Phase 1 and Part 3 Phase 2

BEV will be administered as an IV infusion (90 minutes 1$^{st}$ dose, and if tolerated 60 minutes 2$^{nd}$ dose and 30 minutes on subsequent doses if tolerated) as described in the current package insert. MRZ will be administered prior to BEV when co-administered on the same day.

3.8.3. Administration of MRZ in Part 2 Phase 2

MRZ (0.8 mg/m$^2$) will be administered IV over 10 minutes (refer to Directions for Use). To mitigate the possibility of renal dysfunction, subjects will receive normal saline administered at 250 mL over ~30 minutes before the MRZ infusion. The lyophilized drug product is the same as used in Phase 1.

Subjects should maintain good oral hydration during the study (e.g., 2 L/day). The volume and duration of hydration may be reduced at the discretion of the Investigator, especially for subjects with low body weight or with conditions sensitive to fluid overload.

Subjects must not drive a vehicle or operate heavy machinery while on this study.

3.8.4. Administration of MRZ in Part 3 Phase 2

MRZ will be administered IV over 10 minutes (refer to Directions for Use). The lyophilized drug product is the same as used in Part 1 Phase 1 and Part 2 Phase 2.

Starting dose in each patient will be 0.8 mg/m$^2$. Intrapatient dose escalation will be used. Patients who tolerate the dose in Cycle 1 will have the dose increased by 0.2 mg/m$^2$ to 1.0 mg/m$^2$ for Cycle 2 (an increase of 25%) and if the Cycle 2 dose is tolerated, to 1.2 mg/m$^2$ (an increase of 20%) for Cycle 3 and subsequent cycles.

Because renal damage has not been a safety issue with the shortened hydration schedule used in Part 2 Phase 2, intravenous hydration prior to MRZ dosing will not be used. Subjects should be encouraged to maintain good oral hydration during the study (e.g., 2 L/day). Should renal function become a safety issue, predose hydration will be reinstated if thought necessary by the medical monitor and study team and the participating investigators.

Subjects must not drive a vehicle or operate heavy machinery while on this study.

3.8.5. Dose Schedules

Part 1 Phase 1

All subjects will receive MRZ+BEV as follows:

IV Marizomib (MRZ)

MRZ will be administered as a 10-minute IV infusion on Days 1, 8, and 15 of every 28-day cycle. Infusion durations may be lengthened to ameliorate toxicity for individual subjects or for cohorts with agreement between the Investigators and the Sponsor. For dosing details, see Table 46.

Minimum re-treatment criterion prior to the beginning of each new cycle:

creatinine ≤1.5×ULN, Hgb ≥8 g/dL, platelets ≥75×10$^9$/L.

IV BEV

BEV will be administered as an IV infusion (90 minutes 1st dose, 60 minutes 2nd dose and 30 minutes afterward) at a dose of 10 mg/kg on Days 1 and 15. BEV will be administered approximately 10 minutes after the end of the MRZ infusion when co-administered on the same day.

In the case of dosing delay, BEV should always be given on the day that MRZ is administered. If BEV is discontinued for AEs, the subject may continue on MRZ alone. If MRZ is discontinued, then the subject will be discontinued from the trial. If MRZ is delayed, BEV should also be delayed. Both drugs will be discontinued once disease progression is documented.

MRZ dosing will begin at 0.55 mg/m$^2$ once weekly (Cohort 1). Additional dose cohorts are planned as shown in Table 46.

TABLE 46

Dose Cohorts for MRZ + BEV Combination

| Cohort | IV MRZ Day 1, 8, and 15 of Each 28-Day Cycle | IV BEV Day 1 and 15 of Each 28-Day Cycle |
| --- | --- | --- |
| −2 | 0.3 mg/m² | 10 mg/kg |
| −1 | 0.4 mg/m² | 10 mg/kg |
| 1 | 0.55 mg/m² | 10 mg/kg |
| 2 | 0.7 mg/m² | 10 mg/kg |
| 3 | 0.8 mg/m² | 10 mg/kg |
| 4 | Additional cohorts with extended infusion duration if required | 10 mg/kg |

Part 1 Phase 1 Expansion Cohort and Part 2 Phase 2
IV Marizomib (MRZ)

MRZ (0.8 mg/m²) will be administered as a 10-minute IV infusion on Days 1, 8, and 15 of every 28-day cycle. Infusion durations may be lengthened to ameliorate toxicity for individual subjects with agreement between the Investigator and the Sponsor.

Detailed instructions for MRZ dose modifications and actions are provided in Table 47.

TABLE 47

Marizomib Dose Modification Guidelines for Part 1 Phase 1 Expansion and Part 2 Phase 2

| Toxicity | MRZ Dose Modification & Action |
| --- | --- |
| Grade 2 Central Nervous System Disorders | Consider holding MRZ until toxicity resolves. When toxicity resolves, consider reinitiating with reduced dose of MRZ (to be determined in discussion with the Medical Monitor, but at least a decrease of 0.1 mg/m²). |
| Grade 3 Nervous System Disorder AEs | Hold MRZ until toxicity resolves. When toxicity resolves, reinitiate with reduced dose of MRZ (to be determined in discussion with the Medical Monitor, but at least a decrease of 0.1 mg/m² at start of next cycle). |
| Other Grade 3 MRZ-related AEs | Hold MRZ until toxicity resolves. When toxicity resolves, reinitiate with reduced dose of MRZ (to be determined in discussion with the Medical Monitor, but at least a decrease of 0.1 mg/m² at start of next cycle). |
| Grade 4 Hematologic MRZ-related AEs | Hold MRZ until toxicity resolves. When toxicity resolves, reinitiate with reduced dose of MRZ (to be determined in discussion with the Medical Monitor, but at least a decrease of 0.1 mg/m² at start of next cycle). |
| Nonhematological Grade 4 MRZ-related AEs | Permanently discontinue all study treatment. |

This table was added with Amendment 2 and applies to patients entered under Amendment 2 whether in the Phase 1 Dose Expansion or Phase 2 portions of the study.

In addition to the guidelines in Table 47 if a subject has a drug-related event that requires a 14-day delay in therapy, then MRZ dose reduction is appropriate. If recovery from toxicities is prolonged beyond 14 days, then the dose of MRZ will be decreased by 0.1 mg/m² when dosing resumes. After MRZ dose interruption, reassessment of safety laboratory tests is required prior to resuming MRZ treatment. Prior to initiation of subsequent cycles, results for the following tests must meet study entry criteria: liver functions tests (LFTs), serum creatinine, and complete blood count.

The minimum permitted dose level for MRZ is 0.5 mg/m². If toxicity recurs at the minimum permitted dose of MRZ, all study treatment should be discontinued. Dose re-escalation is not permitted for MRZ.

Part 3 Phase 2
IV Marizomib

MRZ will be administered as a 10-minute IV infusion on Days 1, 8, and 15 of every 28-day cycle.

Starting dose for each patient will be 0.8 mg/m².

Doses will be rounded to the nearest tenth of a mg.

Assuming the patient tolerates the dose in Cycle 1, the dose will be increased to 1.0 mg/m² for Cycle 2, and if that dose is tolerated to 1.2 mg/m² in Cycle 3 and beyond.

DLAEs are MRZ-related AEs 1) related to disturbances in the cerebellum (i.e., ataxia, dizziness, dysarthria, fall, gait disturbances) plus hallucinations of any grade or 2) Grade ≥2 other AEs.

Doses will be dose delayed and/or dose reduced or discontinued for DLAEs related to MRZ as described in Table 48.

TABLE 48

Marizomib Dose Modification Guidelines in Part 3 Phase 2

| Toxicity | MRZ Dose Modification & Action |
| --- | --- |
| Grade 2 Central Nervous System Adverse Events | Monitor the toxicity. Medically treat the toxicity if treatment is available. If treatment is successful, maintain the dose. If the patient cannot tolerate the toxicity consider dose delay and/or dose reduction. Discuss the case with the Medical Monitor. |
| Grade 3 Central Nervous System Adverse Events | Medically treat the toxicity if treatment is available. If treatment is successful, maintain the dose. If treatment is unsuccessful, hold MRZ until toxicity resolves to Grade 1 or less. When toxicity resolves, consider reinitiating with reduced dose of MRZ to be determined in discussion with the Medical Monitor, but at least a decrease of 0.1 mg/m² at start of next dose. |
| Other Grade 3 MRZ-related Adverse Events | Medically treat the toxicity if treatment is available. If treatment is successful, maintain the dose. If treatment is not successful, hold MRZ until toxicity resolves to Grade 1 or less. When toxicity resolves, reinitiate with reduced dose of MRZ to be determined in discussion with the Medical Monitor, but at least a decrease of 0.1 mg/m² at start of next dose. |
| Grade 4 Hematologic MRZ-related Adverse Events | Medically treat the toxicity if treatment is available. Hold MRZ until toxicity resolves to Grade 1 or less. When toxicity resolves, consider reinitiating with reduced dose of MRZ to be determined in discussion with the Medical Monitor, but at least a decrease of 0.1 mg/m² at start of next dose). |
| Nonhematological Grade 4 MRZ-related Adverse Events | Permanently discontinue all study treatment. |

In addition to the guidelines in Table 48, if a subject has a MRZ-related event that requires a 14-day delay in therapy (calculated from the scheduled date of the next dose), then MRZ dose reduction is appropriate. If recovery from MRZ-related AEs is prolonged beyond 14 days, then the dose of MRZ will be decreased by 0.1 mg/m² when dosing resumes unless an alternative plan is approved by the Sponsor's Medical Monitor.

Dose re-escalation is not permitted for MRZ unless approved by the Sponsor's Medical Monitor.

All dose increases require approval of the Sponsor's Medical Monitor.

IV BEV

BEV will be administered as an IV infusion (90 minutes 1st dose, 60 minutes 2nd dose and 30 minutes afterward) at a dose of 10 mg/kg on Days 1 and 15. BEV will be administered approximately 10 minutes after the end of the MRZ infusion when co-administered on the same day.

In the case of dosing delay, BEV should always be given on the day that MRZ is administered. If BEV is discontinued for AEs, the subject may continue on MRZ alone. If MRZ is discontinued, then the subject will be discontinued from the trial. If MRZ is delayed, BEV should also be delayed. Both drugs will be discontinued once disease progression is documented.

There are no recommended dose reductions. According to the Warnings and Precautions and Dose Modification sections of the Avastin® United States Prescribing Information, the following actions are recommended:

Perforation or Fistula: Discontinue BEV if perforation or fistula occurs.

Wound Healing: Discontinue BEV for wound dehiscence and wound healing complications requiring medical intervention Hemorrhage: Discontinue BEV in patients with serious hemorrhage Arterial Thromboembolic Events (ATE) (e.g., myocardial infarction, cerebral infarction): Discontinue BEV for severe ATE.

Venous Thromboembolic Events (VTE): Discontinue BEV for life-threatening (Grade 4) VTE, including pulmonary embolism Hypertension: Monitor blood pressure and treat hypertension. Temporarily suspend BEV if not medically controlled. Discontinue BEV for hypertensive crisis or hypertensive encephalopathy.

Posterior Reversible Encephalopathy Syndrome (PRES): Discontinue BEV.

Proteinuria: Monitor proteinuria by dipstick urine analysis for the development or worsening of proteinuria with serial urinalyses during BEV therapy. Patients with a 2+ or greater urine dipstick reading should undergo further assessment with a 24-hour urine collection. Suspend BEV administration for ≥2 grams of proteinuria/24 hours and resume when proteinuria is <2 gm/24 hours. Discontinue BEV in patients with nephrotic syndrome.

Infusion Reactions: Stop BEV for severe infusion reactions and administer appropriate medical therapy.

3.8.6. Dose-Limiting Toxicity

Part 1 Phase 1

Dose-limiting toxicity (DLT) is defined as the occurrence of any of the following AEs related to one of the drugs or the combination observed during Cycle 1, using NCI-CTCAE (v 4.03):

≥Grade 3 thrombocytopenia or Grade 2 thrombocytopenia with bleeding.

Grade 4 neutropenia or anemia lasting for more than 4 days.

Febrile neutropenia.

Any ≥Grade 2 neurological event lasting more than 4 days.

Grade 3 or 4 non-hematologic toxicity (excluding alopecia), lasting for more than 4 days despite adequate supportive therapy or preventing the next scheduled dose from being administered within 4 days of scheduled day; for ≥Grade 3 fatigue to be considered a DLT, it must be present for more than 7 days.

Subjects without DLT in Cycle 1 who do not receive 3 MRZ doses or 2 BEV doses within 5 weeks from first dose will not be evaluable for DLT and will be replaced.

Part 2 Phase 2

If at any time after 3 subjects are enrolled, the incidence of AEs that fit the definition of DLT from Phase 1 occurs in >33% of the subjects, then enrollment will be paused. Available data will be reviewed and a decision regarding continuing to enroll subjects at the 0.8 mg/m$^2$ over 10 minutes dose in Phase 2 is agreed between the Sponsor and Investigators. Adjustment downward on dose or lengthening infusion duration will be considered and the Phase 2 portion restarted at the selected dose and infusion time.

Part 3 Phase 2

The term DLT is not applicable to this portion of the study. DLAEs, defined as MRZ-related AEs 1) related to disturbances in the cerebellum (i.e., ataxia, dizziness, dysarthria, fall, gait disturbances) plus hallucinations of any grade or 2) Grade ≥2 other AEs will be used to determine if MRZ doses should be delayed, reduced, or discontinued.

3.8.7. Dose Escalation Process and MTD/MAD Determination

Part 1 Phase 1 (only)

Initially 3 subjects will be enrolled into a cohort, commencing with Cohort 1 and the doses shown in Table 46. Dose escalation will proceed as follows:

If none of the first 3 evaluable subjects in a dose cohort experience a DLT during Cycle 1, then enrollment into the next dose cohort can be initiated.

If ≥2 of the first 3 evaluable subjects in a dose cohort experience a DLT during Cycle 1, then the MTD has been exceeded and dose escalation will not proceed.

If 1 of the first 3 evaluable subjects in a dose cohort experiences a DLT during Cycle 1, then an additional 3 subjects will be enrolled into the same cohort.

If 1/6 evaluable subjects in the expanded 6-subject cohort experiences a DLT during Cycle 1, then the next higher dose cohort can be tested and enrollment of the next 3 subjects at the next higher dose level can be initiated.

If ≥2/6 evaluable subjects in the expanded 6-subject cohort experience a DLT during Cycle 1, then the MTD has been exceeded and no further dose escalation will occur.

The MTD is defined as the dose level below the cohort where DLT is observed in at least 2 subjects in the same cohort during Cycle 1. Intermediate dosing levels may be explored if indicated. The dose of 0.8 mg/m$^2$ will not be exceeded and will be the MAD.

During the dose escalation phase of the protocol, if 2 DLTs are noted in the first 2 subjects of a cohort prior to the third subject being enrolled, the third subject will not be enrolled in that cohort. If there is 1 DLT in the first 3 subjects and the cohort is expanded and another DLT is noted prior to enrolling all 6 subjects in the cohort, further enrollment in that cohort will be halted. If during the dose expansion phase there are ≥3 DLTs in the first 6 or fewer subjects then the MTD will be reassessed by the Investigators and Sponsor.

Once the MTD/MAD has been identified, a cohort of at least 12 additional, evaluable subjects for a total of 36 subjects will be treated at the MTD/MAD to further confirm the safety and to assess preliminary activity for the combination treatment. This cohort may be used to determine the RP2D.

3.9. Method of Treatment Assignment

Part 1 Phase 1

Treatments consist of IV doses of MRZ and BEV. Subjects will enter the study sequentially and be assigned to a cohort (dose level) based on the evaluation of subjects who were previously treated according to the dose escalation scheme. Once the RP2D is determined, subjects will be treated at the RP2D in the expansion cohort unless the Investigators and Sponsor agree to a lower dose for safety reasons.

Part 2 Phase 2

Treatments consist of IV doses of MRZ. Subjects will enter the study sequentially.

Part 3 Phase 2

Treatment consists of IV doses of MRZ and BEV. Subjects will enter the study sequentially.

Concomitant Medications and Procedures 3.10. Permitted Concomitant Medications and Procedures Concomitant medications to treat comorbid conditions and adverse events are permitted. Enzyme-inducing anti-epileptic drugs (EIAEDs) are allowed. Steroids are allowed and dosing is at the discretion of the Investigator. Consideration should be given to treating hallucinations with anti-psychotic drugs such as olanzapine or quetiapine and fatigue with stimulating agents such as methylphenidate.

In studies to date, MRZ has caused clinically significant nausea and vomiting requiring the use of antiemetics as therapy and also as prophylaxis. Therefore, both the therapeutic and prophylactic use of antiemetics is allowed in this study at the discretion of the Investigator.

3.11. Prohibited Concomitant Medications and Procedures

Medications to treat the underlying malignancy are not permitted and their use constitutes progressive disease and subjects must discontinue study treatment. Investigational agents of any kind are not permitted.

3.12. Required Concomitant Medications and Procedures

There are no required concomitant medications or procedures.

Statistical Analyses 3.13. Overview

Part 1 Phase 1

A 3+3 design will be utilized to determine the MTD/MAD for combination treatment of MRZ+BEV in each 28-day cycle. Subjects who do not have a DLT in the first cycle of a dose cohort will be replaced if they discontinue treatment with MRZ or BEV in Cycle 1 for any other reason. Subjects who miss a dose of MRZ or BEV or cannot receive all doses within 5 weeks from first dose during Cycle 1 and do not have a DLT will not be evaluable for DLT and will be replaced. After MTD/MAD has been determined in the dose-escalation part of the study, at least 12 additional subjects will be treated at the MTD/MAD in an expansion cohort to confirm the safety and assess the preliminary activity for the combination of MRZ+BEV administered up to a total of 36 subjects.

For all analyses by dose cohorts, the MTD/MAD confirmation cohort subjects will be combined with the corresponding dose cohort in the MTD/MAD determination phase as one single dose cohort.

Part 2 Phase 2

Patients enrolled in the Phase 2 portion of the protocol will receive 0.8 mg/m$^2$ MRZ IV on Days 1, 8, and 15 of 28-day cycles. A minimum of 15 response-evaluable patients will be enrolled in Stage 1, and up to 15 additional response-evaluable patients will be enrolled in Stage 2, for a maximum of 30 response-evaluable patients. After the first 15 response-evaluable patients in the first stage have received 2 or more cycles of therapy, there will be a recommendation of whether to enroll the second stage based on an assessment of both safety and efficacy. If there are no safety concerns and clinical benefit is demonstrated with evidence of disease response, defined as at least one response (partial response (PR) or better) as determined by RANO criteria, in 15 response-evaluable patients, then 15 additional response-evaluable patients will be enrolled in Phase 2. Otherwise, there will be no further enrollment into the study.

Efforts will be made to ensure the correct number of patients is accrued, and enrollment will be carefully monitored and communicated with the sites. There may be instances where, as a result of simultaneous screening activities, patients may qualify for the study at the same time, resulting in slight over-enrollment.

Part 3 Phase 2

A sample size of 40 eligible patients is based on wanting a reasonably precise estimate of median OS.

Efforts will be made to ensure the correct number of patients is accrued, and enrollment will be carefully monitored and communicated with the sites. There may be instances where, as a result of simultaneous screening activities, patients may qualify for the study at the same time, resulting in slight over-enrollment.

3.14. Study Population Definitions

All subjects who receive at least one dose of study medication (MRZ or BEV) will be considered enrolled in the study and will be in the Safety Population. All subjects who receive at least one dose of study medication and have at least 1 post dose PK sample will be in the PK Population. All subjects who receive at least 1 cycle of therapy and have at least 1 post treatment tumor assessment will be in the Activity (Efficacy) Population (Response-evaluable Population).

3.15. Sample Size

Part 1 Phase 1

Up to 36 subjects will be enrolled in the MTD/MAD determination and confirmation (expansion cohort) parts of the study.

Part 2 Phase 2

Fifteen response-evaluable patients will be enrolled in the first stage of a 2-stage design. If there is at least 1 PR or better and there are no safety concerns in the first 15 response-evaluable patients, then the second stage of 15 response-evaluable patients will be opened. If ≥5 patients respond by the end of the second accrual stage (n=30), the conclusion can be drawn that MRZ is promising, unless other considerations indicate otherwise.

The assumption for Phase 2 for sample size (for 30 patients) is a null hypothesis (Ho) that the true response rate is ≤5% versus the alternative hypothesis (Ha) that the true response rate is at least 20%. The significance level (i.e., the probability of rejecting Ho when it is true) is 0.05. The power (i.e., the probability of rejecting Ho when the alternative is true) is 80%.

Part 3 Phase 2

A sample size of 40 patients is based on wanting a reasonably precise estimate of OS. Assuming 10 patients will be alive at the time of statistical analysis, there will be 30 deaths observed (i.e., 25% of the subjects are censored). The resulting 95% confidence interval (CI) is 7.2-14.8 months, with a width equal to 7.6 months, around an estimated median survival of 10 months.

3.16. Activity (Efficacy) Analysis

Tumor response including PD, progression-free survival (PFS), and overall survival (OS) will be assessed by the Investigators using RANO 2010 criteria. The overall confirmed response rate will be examined. The overall response rate, PFS, and OS will also be tabulated by dose cohorts. Results of Phase 1 and the two Phase 2 portions of the study will not be combined.

3.17. Pharmacokinetic Analysis (Part 1 Phase 1 only)

Non-compartmental analyses will be performed. The following PK parameters will be calculated: maximum observed blood drug concentration ($C_{max}$), time of maximum blood concentration ($T_{max}$), elimination half-life ($T_{1/2}$), area under the blood concentration-time curve ($AUC_{0-inf}$), clearance (CL), and volume of distribution (Vd).

Blood concentrations and computed PK parameters for MRZ will be listed and summarized by cohort (mean, geometric mean, standard deviation, coefficient of variation, minimum, maximum and number of observations).

3.18. Pharmacodynamic Analysis (Part 1 Phase 1 only)

PD analysis will include change in proteasome activities (whole blood lysates and PBMC lysates) by comparing pre-drug and post drug levels on Days 1, 8, and 15 (i.e., for each dose) of Cycle 1 and Days 1 and 15 (i.e., for the first and last doses) of each cycle thereafter.

Adverse Events 3.19. Monitoring, Recording and Reporting of Adverse Events

An adverse event (AE) is any noxious, unintended, or untoward medical occurrence that may appear or worsen in a subject during the course of a study. It may be a new intercurrent illness, a worsening concomitant illness, an injury, or any concomitant impairment of the subject's health, including laboratory test values (as specified by the criteria in Section 10.3), regardless of etiology. Any worsening (i.e., any clinically significant adverse change in the frequency or intensity of a pre-existing condition) should be considered an AE.

Overdose (accidental or intentional), abuse, withdrawal, sensitivity or toxicity to study treatment should be reported as an AE. If an overdose is associated with an AE, the overdose and AE should be reported as separate terms. Any sequelae of an accidental or intentional overdose of an investigational product should be reported as an AE on the AE CRF. If the sequelae of an overdose are an SAE, then the sequelae must be reported on an SAE report form and on the AE CRF. The overdose resulting in the SAE should be identified as the cause of the event on the SAE report form and CRF but should not be reported as an SAE itself. Medication errors, defined as an overdose with >105% of drug administered, or underdose, defined as <95% of dose administered, are to be reported as AEs. Prescribed dose reductions for AEs are not considered medication errors.

All subjects will be monitored for AEs during the study. Assessments may include monitoring of any or all of the following parameters: the subject's clinical symptoms, laboratory, pathological, radiological or surgical findings, physical examination findings, or findings from other tests and/or procedures.

All SAEs will be recorded by the Investigator from the time the subject signs informed consent until 28 days after the last dose of study treatment and those SAEs made known to the Investigator at any time thereafter that are suspected of being related to study treatment. AEs are recorded from the start of the first infusion of study treatment. AEs occurring before the first infusion of IP are considered medical history and should be recorded on the medical history CRF. AEs and serious adverse events (SAEs) will be recorded on the AE page of the CRF and in the subject's source documents. Evaluation of Adverse Events A qualified Investigator will evaluate all adverse events as to:

3.19.1. Seriousness

A serious adverse event (SAE) is any AE occurring at any dose that:

Results in death;

Is life-threatening (i.e., in the opinion of the Investigator, the subject is at immediate risk of death from the AE);

Requires inpatient hospitalization or prolongation of existing hospitalization (hospitalization is defined as an inpatient admission, regardless of length of stay);

Results in persistent or significant disability/incapacity (a substantial disruption of the subject's ability to conduct normal life functions);

Is a congenital anomaly/birth defect;

Constitutes an important medical event.

Important medical events are defined as those occurrences that may not be immediately life threatening or result in death, hospitalization, or disability, but may jeopardize the subject or require medical or surgical intervention to prevent one of the other outcomes listed above. Medical and scientific judgment should be exercised in deciding whether such an AE should be considered serious.

Events not considered to be SAEs are hospitalizations for:

A standard procedure for protocol therapy administration. However, hospitalization or prolonged hospitalization for a complication of therapy administration will be reported as an SAE.

Routine treatment or monitoring of the studied indication not associated with any deterioration in condition.

The administration of blood or platelet transfusion as routine treatment of studied indication. However, hospitalization or prolonged hospitalization for a complication of such transfusion remains a reportable SAE.

A procedure for protocol/disease-related investigations (e.g., surgery, scans, endoscopy, sampling for laboratory tests, bone marrow sampling). However, hospitalization or prolonged hospitalization for a complication of such procedures remains a reportable SAE.

Hospitalization or prolongation of hospitalization for technical, practical, or social reasons, in absence of an AE.

A procedure that is planned (i.e., planned prior to starting of treatment on study); must be documented in the source document and the CRF. Hospitalization or prolonged hospitalization for a complication remains a reportable SAE.

An elective treatment of or an elective procedure for a pre-existing condition unrelated to the studied indication.

Emergency outpatient treatment or observation that does not result in admission, unless fulfilling other seriousness criteria above.

Severity/Intensity

For both AEs and SAEs, the Investigator must assess the severity/intensity of the event.

The severity/intensity of AEs will be graded based upon the subject's symptoms according to the current active minor version of the Common Terminology Criteria for Adverse Events.

The term "severe" is often used to describe the intensity of a specific event (as in mild, moderate or severe myocardial infarction); the event itself, however, may be of relatively minor medical significance (such as severe headache). This criterion is not the same as "serious" which is based on subject/event outcome or action criteria associated with events that pose a threat to a subject's life or functioning.

Seriousness, not severity, serves as a guide for defining regulatory obligations.

3.19.2. Causality

The Investigator must determine the relationship between the administration of study treatment and the occurrence of an AE/SAE as Not Suspected or Suspected as defined below: Not suspected: Means a causal relationship of the adverse event to study treatment administration is unlikely or remote, or other medications, therapeutic interventions, or underlying conditions provide a sufficient explanation for the observed event. Suspected: Means there is a reasonable possibility that the administration of study treatment caused the adverse event. 'Reasonable possibility' means there is evidence to suggest a causal relationship between the study treatment and the adverse event.

Causality should be assessed and provided for every AE/SAE based on currently available information. Causality is to be reassessed and provided as additional information becomes available. For regulatory purposes, it is the Sponsor that is responsible for making the final causality assessment.

3.19.3. Duration

For both AEs and SAEs, the Investigator will provide a record of the start and stop dates of the event. For AEs that become SAEs, the start date of the SAE will be when the seriousness criteria are met. The original AE will have a stop date the same as the start date of the SAE. The SAE will have a stop date of when the seriousness criteria are no longer met. If the AE continues after the seriousness criteria are no longer met, then a new AE will be recorded with a start date the same as the SAE stop date and a stop date when the AE is completely resolved. In all cases, the AE must have the same verbatim term throughout. Within the duration of the SAE or AE, the maximum grade should be used to categorize severity.

3.19.4. Action Taken

The Investigator will report the action taken with each study drug as a result of an AE or SAE, as applicable (e.g., discontinuation, interruption, or reduction of study treatment, as appropriate) and report if concomitant and/or additional treatments were given for the event.

3.19.5. Outcome

The Investigator will report the outcome of the event for both AEs and SAEs.

All SAEs that have not resolved upon discontinuation of the subject's participation in the study must be followed until recovered, recovered with sequelae, returned to baseline, stabilized, or died (due to the SAE or due to another cause).

3.20. Abnormal Laboratory Values

An abnormal laboratory value is to be considered an AE if the abnormality:

results in discontinuation from the study;
requires treatment, modification/interruption of IP dose, or any other therapeutic intervention; or
is judged to be of significant clinical importance.

Regardless of severity grade, only laboratory abnormalities that fulfill a seriousness criterion need to be documented as a serious adverse event.

If a laboratory abnormality is one component of a diagnosis or syndrome, then only the diagnosis or syndrome should be recorded on the AE page of the CRF. If the abnormality was not a part of a diagnosis or syndrome, then the laboratory abnormality should be recorded as the AE. If possible, the laboratory abnormality should be recorded as a medical term and not simply as an abnormal laboratory result (e.g., record thrombocytopenia rather than decreased platelets).

Discontinuations

The following events are considered sufficient reasons for discontinuing a subject from the investigational product and/or from the study:

Protocol Violation
Non-Compliance
Adverse Event
Subject Developed a DLT
Subject Decision
Withdrew Consent
Investigator Decision
Disease Progression
Pregnancy
Death
Other Example 5—Phase 1, Multicenter, Open-Label, Dose-Escalation Study of Marizomib (MRZ) and Bevacizumab (BEV) in WHO Grade IV Malignant Glioma (G4 MG)

Abstract

Background: MRZ is an irreversible, brain-penetrant, pan-proteasome inhibitor (PI) that inhibits glioma cell proliferation and invasion in vitro, prolongs survival in in vivo MG tumor models (Di et al., Neuro-Oncol 2016; 18:840). Intravenous (IV) MRZ has been administered to ~300 patients (pts) with solid tumors and hematologic cancers. In this ongoing trial, the safety, pharmacodynamics, and efficacy of MRZ and BEV is evaluated in G4 MG pts in first or second relapse who are BEV-naïve and have had no prior anti-angiogenic or PI therapy.

Methods: Phase 1, dose-escalation (3+3 design) followed by dose-expansion at recommended Phase 2 Dose (RP2D); three dose escalation cohorts—MRZ 0.55 (6 pts), 0.7 (3 pts), and 0.8 mg/m2 (3 pts); dose-expansion 0.8 mg/m2 (24 pts). MRZ infused IV (10 min) on Days 1, 8, & 15; BEV IV 10 mg/kg on Days 1 & 15; 28-Day Cycles. Tumor response is assessed every other Cycle by RANO criteria; blood MRZ PK assessed Day 8, serum BEV PK assessed Days 1 and 15; blood proteasome inhibition assessed Days 1 & 15 every Cycle.

Results: All data reported as of 17 May 2016. 36 pts enrolled with median age 55 yrs (27-76), 64% male, Karnofsky Score >70. Duration of dosing 0.5-11.6 months to date; treatment ongoing in 16 pts. MRZ+BEV was well tolerated. Study treatment-related Grade ≥3 AEs: fatigue, headache, hypertension, hallucination, confusional state, ataxia; one Grade 4 SAE (appendicitis perforated, not related to study treatment), one Grade 5 SAE (intracranial hemorrhage, BEV-related). One pt (cohort 1) had DLT (fatigue); no other DLTs occurred across the dose range. Efficacy Evaluable population (N=31) includes 30 pts efficacy evaluable by RANO criteria, and one pt Grade 5 SAE (no post-treatment tumor assessment). N=36 for the intent-to-treat population. Fourteen partial responses (PR) (including 5 with complete response (CR) for target lesion, and 2 unconfirmed PRs), 11 stable disease (SD), 5 progressive disease (PD), 5 not evaluable (NE, no post-treatment tumor assessment). MRZ and BEV PK were consistent with published parameters and not affected by co-administration. Proteasome inhibition maximal on CT-L in cohorts 1 and 2; dose-dependent inhibition of T-L and C-L activity in cohorts 1 vs 2 suggests dose-dependent pharmacodynamics.

Conclusions: The MRZ+BEV combination was well tolerated and demonstrates promising early signs of efficacy in recurrent G4 MG patients.

Study Objectives and Design

Objectives

Primary: Determine the MTD and RP2D of MRZ+BEV

Secondary: Evaluate safety and activity of MRZ+BEV

Exploratory: Evaluate baseline proteasome activity, MRZ and BEV PK, MRZ neurological coordination (SARA), and quality of life assessment (FACT-Cog/FACT-Br)

| Cohort (N) | MRZ IV (mg/m$^2$) - 10 min infusion Days 1, 8, 15 q 28 days | BEV IV (mg/kg) q 14 days |
|---|---|---|
| 1 (6) | 0.55 | 10 |
| 2 (3) | 0.7 | 10 |
| 3 (3) | 0.8 | 10 |
| 4 (24) | Expansion of RP2D | 10 |

Key Eligibility Criteria

≥18 years; Histological evidence of G4 malignant glioma in first or second relapse; No prior proteasome inhibitor or anti-angiogenic therapies; KPS≥70

Results

Demographics (N=36)

| Parameter | |
|---|---|
| Median age, years (range) | 55 (27-76) |
| Male, % | 64% (23/36) |
| Karnofsky Performance Status (KPS) | |
| 100 - Normal, no complaints | 9% (3/35) |
| 90 - Able to carry on normal activity | 37% (13/35) |
| 80 - Normal activity with effort | 45% (16/35) |
| 70 - Unable to carry on normal activity, cares for self | 9% (3/35) |
| Prior therapies | |
| Surgery/Radiation/Temozolomide | 100% (36/36) |
| Immunotherapy | 11% (4/36) |
| Other Investigational Drug or Device | 8% (3/36) |
| MGMT Promoter Methylation Status (21 pts unknown) | |
| Unmethylated | 14/15 |
| Methylated | 1/15 |
| EGFRvIII Positive Status (21 pts unknown) | 2/15 |

Safety

| | Study Treatment Related AEs and All ≥Grade 3 AEs | | | | | | |
|---|---|---|---|---|---|---|---|
| | # Patients | | Relationship to Rx | | | | # Events |
| Preferred Term | (%) with AE | # Events | Neither | BEV | MRZ | Both | Grade ≥3 |
| Fatigue | 22 (61) | 49 | 2 | 0 | 1 | 46 | 2 |
| Headache | 18 (50) | 43 | 2 | 2 | 6 | 33 | 3 |
| Nausea | 17 (47) | 36 | 0 | 0 | 36 | 0 | 0 |
| Hypertension | 14 (39) | 25 | 2 | 22 | 0 | 1 | 6 |
| Vomiting | 13 (35) | 19 | 0 | 0 | 16 | 3 | 0 |
| Diarrhoea | 10 (27) | 13 | 0 | 0 | 12 | 1 | 0 |
| Dysphonia | 10 (27) | 10 | 0 | 10 | 0 | 0 | 0 |
| Hallucination | 10 (27) | 16 | 0 | 0 | 16 | 0 | 3 |
| Confusional State | 7 (19) | 10 | 1 | 0 | 8 | 1 | 1 |
| Constipation | 7 (19) | 8 | 2 | 0 | 5 | 1 | 0 |
| Dizziness | 7 (19) | 14 | 0 | 0 | 13 | 1 | 0 |
| Epistaxis | 7 (19) | 9 | 1 | 8 | 0 | 0 | 0 |
| Hyperglycemia | 7 (19) | 16 | 16 | 0 | 0 | 0 | 3 |
| Hypokalemia | 7 (19) | 10 | 8 | 0 | 1 | 1 | 0 |
| Anaemia | 6 (17) | 11 | 2 | 0 | 9 | 0 | 0 |
| Ataxia | 6 (17) | 11 | 1 | 0 | 10 | 0 | 2 |
| Convulsion | 6 (17) | 6 | 5 | 0 | 0 | 1 | 0 |
| Aphasia | 5 (14) | 5 | 5 | 0 | 0 | 0 | 1 |
| Dysarthria | 5 (14) | 6 | 5 | 0 | 1 | 0 | 1 |
| Hemiparesis | 4 (11) | 6 | 6 | 0 | 0 | 0 | 3 |
| Muscular Weakness | 4 (11) | 7 | 4 | 0 | 3 | 0 | 1 |
| Dysphagia | 3 (8) | 3 | 3 | 0 | 0 | 0 | 1 |
| Hypotension | 3 (8) | 3 | 3 | 0 | 0 | 0 | 1 |
| Insomnia | 3 (8) | 3 | 2 | 0 | 1 | 0 | 1 |
| Lymphocyte Count Decreased | 3 (8) | 5 | 5 | 0 | 0 | 0 | 3 |
| Dyspnoea | 2 (6) | 3 | 1 | 0 | 0 | 2 | 1 |
| Ear Infection | 2 (6) | 2 | 2 | 0 | 0 | 0 | 1 |
| Haemorrhage Intracranial | 2 (6) | 2 | 0 | 2 | 0 | 0 | 1 (Grade 5) |
| Pyramidal Tract Syndrome | 2 (6) | 3 | 3 | 0 | 0 | 0 | 1 |
| Appendicitis Perforated | 1 (3) | 1 | 1 | 0 | 0 | 0 | 1 (Grade 4) |
| Asthenia | 1 (3) | 2 | 2 | 0 | 0 | 0 | 1 |
| Delusion | 1 (3) | 1 | 0 | 0 | 1 | 0 | 1 |
| Embolism | 1 (3) | 1 | 0 | 1 | 0 | 0 | 1 |

Figure 46:
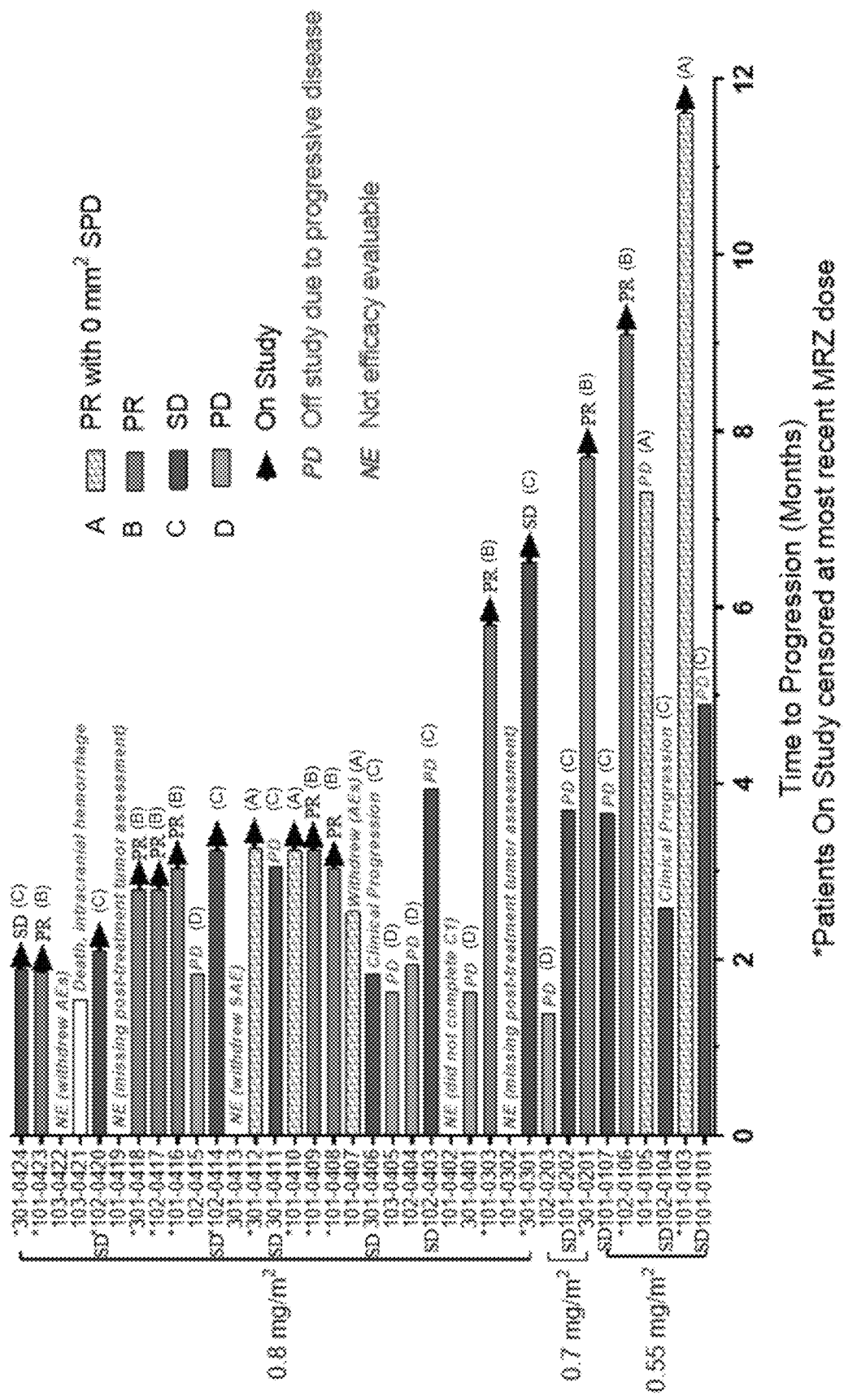
FIG. 46 shows the time to progression of patients treated with MRZ and BEV as set forth in Example 5.

Results—Clinical Activity
Best Response by RANO
FIG. 46 shows the time to progression of patients treated with MRZ and BEV. Twenty-five of the 31 Efficacy Evaluable (EE) patients achieved clinical benefit (RANO ≥SD) from MRZ+BEV treatment

| Best Response by RANO | # | % EE (N = 31) | % ITT (N = 36) |
|---|---|---|---|
| CR target/PR overall (5) + PR (7) + unconfirmed PR (2) | 14 | 45 | 39 |
| SD | 11 | 35 | 31 |
| PD | 5 | 16 | 14 |
| Not Evaluable | 5 | — | 14 |

Figure 47A:
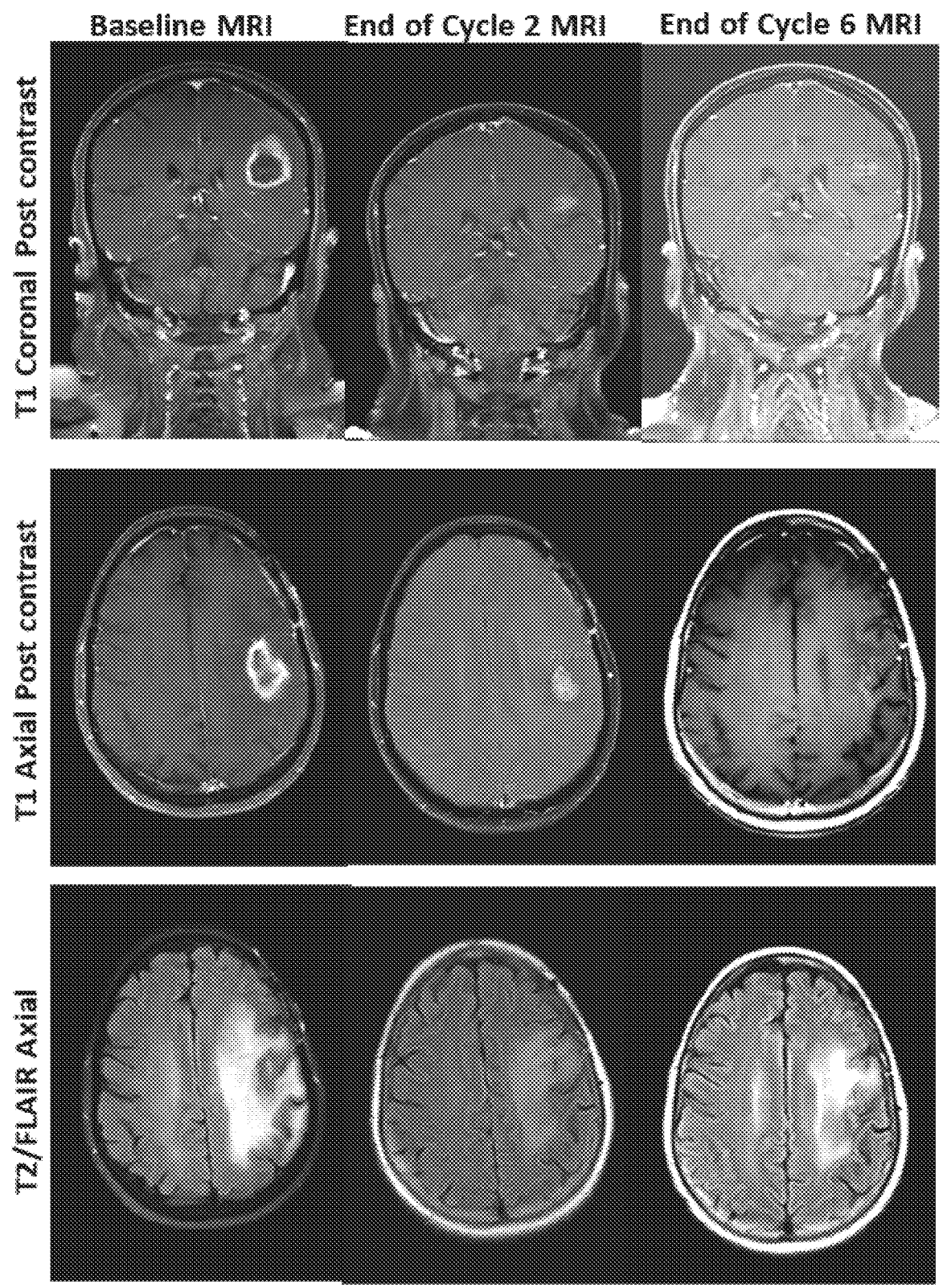
FIG. 47A shows an example of MRI showing target lesions for a patient with complete response as set forth in Example 5.
Figure 47B:
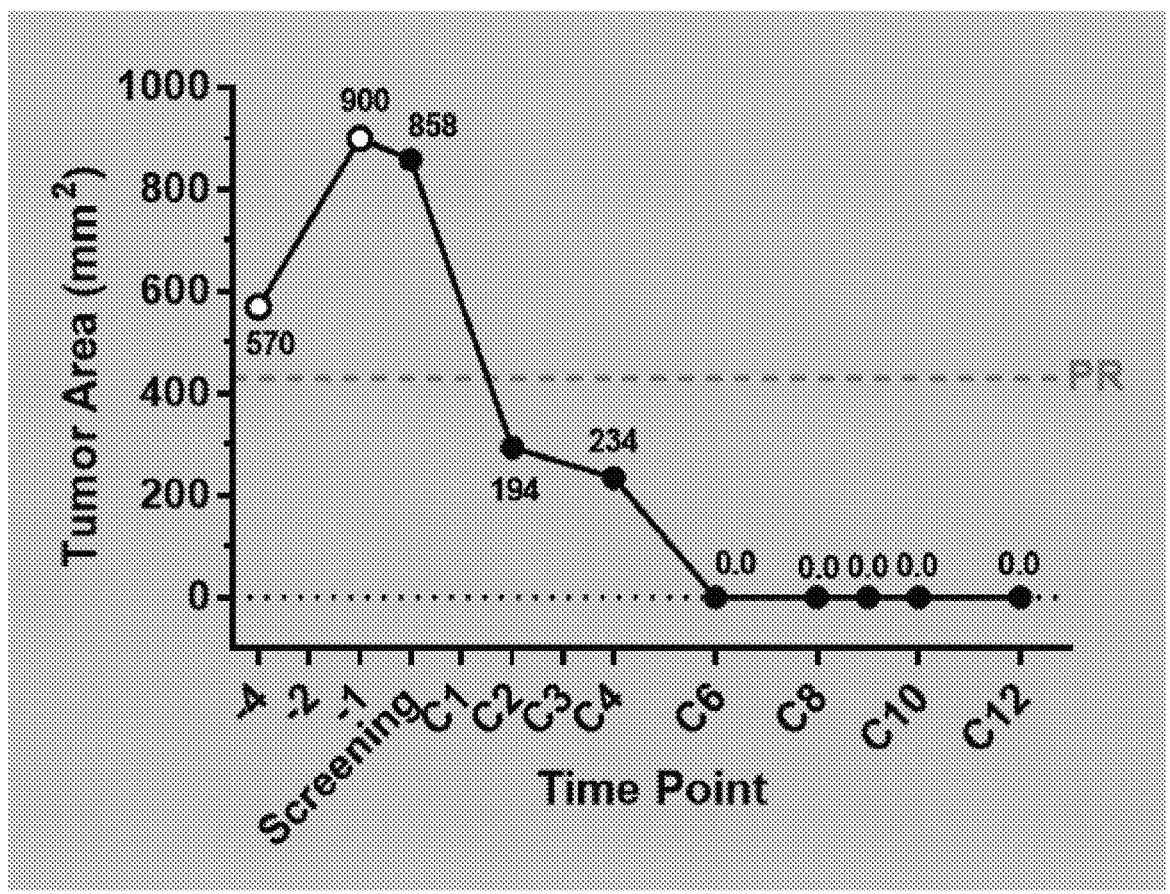
FIG. 47B shows a plot of the dose reduction for the patient set forth in Example 5.

Overall Response Rate=45% (RANO ≥PR) for efficacy evaluable & 39% in ITT population. 5 of the 14 PRs were CR for target tumor area (0 mm2) on ≥2 consecutive MRIs
Time to Progression
FIG. 46 shows the time to progression of patients treated with MRZ and BEV.
Example of Target Lesion CR (PT 101-0103)
Patient: 59 F, KPS 90; 16 Oct. 2014: Brain tumor resection; December 2014-January 2015: XRT+TMZ; February 2015-April 2015: TMZ (3 cycles); 3 Apr. 2015: Confirmed PD.
Started MRZ (0.55 mg/m$^2$)+BEV on 22 May 2015 Currently in Cycle 14; Dose reduction to 0.4 mg/m$^2$ C3D1
FIG. 47A shows an example of MRI showing target lesions for a patient with complete response. FIG. 47B shows a plot of the dose reduction for the patient.
PK/PD Summary

| Parameter (Units) | 0.55 mg/m$^2$ | 0.7 mg/m$^2$ | 0.8 mg/m$^2$ |
|---|---|---|---|
| MRZ PK determined on C1D8 | | | |
| $T_{1/2}$ (min) | 8.8 ± 0.8 (3)* | 32.0 (1) | 7.6 ± 0.9 (2) |
| $T_{max}$ (min) | 4.0 ± 0.6 (6) | 11.3 ± 9.3 (3) | 0.0 ± 0 (3) |
| $C_{max}$ (ng/mL) | 23 ± 11 (6) | 65 ± 31 (3) | 26 ± 8 (3) |
| $AUC_{last}$ (min*ng/mL) | 236 ± 108 (6) | 193 ± 85 (2) | 243 ± 77 (3) |
| $V_{ss\ obs}$ (mL/m$^2$) | 12971 ± 7600 (3) | 7377 (1) | 12379 ± 8698 (2) |
| $CL_{obs}$ (mL/min/m$^2$) | 2665 ± 1063 (3) | 162 (1) | 3822 ± 1798 (2) |
| BEV PK determined on C1D1 & C1D15 | | | |
| $C_{max}$ D1 (μg/mL) | 275 ± 37 (6) | 282 ± 89 (3) | 267 ± 133 (3) |
| $C_{min}$ D15 (μg/mL) | 90 ± 6.2 (6) | 114 ± 34 (3) | 85 ± 9.9 (3) |
| $C_{max}$ D15 (μg/mL) | 351 ± 47 (5) | 402 ± 123 (3) | 404 ± 40 (3) |
| Proteasome subunit inhibition in PWB post-MRZ infusion (peak effect) | | | |
| % CT-L inhibition | 100 ± 0 (5) | 100 ± 0 (3) | In progress |
| % T-L inhibition | 52.0 ± 8.0 (5) | 77.3 ± 10.5 (3) | |
| % C-L inhibition | 21.0 ± 7.8 (5) | 50.4 ± 9.1 (3) | |

Summary
MRZ+BEV combination demonstrates good tolerability and promising signs of efficacy in recurrent glioma patients.
Most common AEs related to study drugs include fatigue, headache, nausea, hypertension, vomiting, diarrhea, dysphonia, hallucination, and weakness.

Most common MRZ related >Grade 3 AEs were hallucination and headache.
Relatively few study treatment related SAEs.
Majority of patients ($^{24}/_{31}$) derive clinical benefit.
5 patients tumor area by MRI decreased to 0 mm2 on ≥2 MRI scans.
16 of 36 patients enrolled remain on study.
RANO response is 45% in efficacy evaluable and 36% in ITT.
MRZ & BEV PK consistent with previous trials.
MRZ monotherapy study in recurrent glioma has been initiated; a study in newly diagnosed glioma patients will be initiated shortly.

Example 6—Marizomib (MRZ) with Bevacizumab (BEV) in WHO Grade IV Malignant Glioma (G4 MG): Full Enrollment Results from the Phase 1, Multicenter, Open-Label Study MRZ is an irreversible, brain-penetrant, pan-proteasome inhibitor (PI) with anti-MG efficacy preclinically in vitro and in vivo. The safety, PK, and activity of MRZ+BEV is evaluated in BEV-naïve G4 MG pts in first or second relapse (no prior anti-angiogenic or PI therapy), in a 3+3 dose-escalation (MRZ 0.55 (6 pts), 0.7 (3 pts), and 0.8 mg/m$^2$ (3 pts)) followed by dose-expansion (0.8 mg/m$^2$, 24 pts). Treatments administered IV, 28-day cycles: MRZ (10 min) days 1, 8, & 15; BEV (10 mg/kg) days 1 & 15. Tumor response assessed every other cycle by RANO criteria; MRZ and BEV PK, and proteasome inhibition in circulating blood cells also evaluated.
Data reported as of 17 May 2016; median age 55 yrs (range 27-76 yrs), 64% male, Karnofsky score ≥70. Duration of dosing 0.5-11.6 months to date; treatment ongoing in 16 pts. Study treatment-related Grade ≥3 AEs: fatigue, headache, hypertension, hallucination, confusional state, ataxia; one Grade 4 SAE (appendicitis perforated, not related to study treatment), one Grade 5 SAE (intracranial hemorrhage, BEV-related). One pt (cohort 1) had DLT (fatigue); no other DLTs occurred. N=36 for the intent-to-treat population; 30 pts efficacy evaluable by RANO criteria, 6 pts without post-treatment tumor assessment. Overall response (≥partial response, PR) 39% ($^{14}/_{36}$, including 5 with complete target lesion response and 2 unconfirmed PRs); 11 stable disease, 5 progressive disease. PFS 6-months is 39%; median OS not yet calculable. MGMT promoter status known for 15 of 36 pts; 14 unmethylated (uMGMT promoter), 1 methylated. Seven of 14 uMGMT promoter pts achieved ≥PR; 49% PFS 6-months in uMGMT promoter subgroup. Substantial activity in uMGMT promoter subgroup suggests therapeutic advantage provided by brain-penetrant PI in comparison with BEV single agent publications. MRZ+BEV combination is well tolerated with promising early signs of efficacy in recurrent G4 MG pts.
A Phase 1 MRZ+BEV dose-escalation combination study followed by a Phase 2 MRZ monotherapy study
(a) WHO Grade IV malignant glioma in their first or second relapse with clear progressive disease
(b) Must have completed standard radiation therapy and temozolomide
(c) No prior treatment with any anti-angiogenic agent or MRZ
(d) At least 4 weeks from surgical resection and 12 weeks from end of radiotherapy.

| Cohorts | MRZ IV (mg/m²) - 10 min infusion Days 1, 8, 15 q 28 days | IV bevacizumab (mg/kg) q 14 days |
|---|---|---|
| 1 | 0.55 | 10 |
| 2 | 0.7 | 10 |
| 3 | 0.8 | 10 |
| 4 | Expansion of RP2D | 10 |

| Phase 2 | IV marizomib (0.8 mg/m²) - 10 min infusion Days 1, 8, 15 q 28 days | |
|---|---|---|
| 5 | 0.8 | None 1 |

| Parameter | |
|---|---|
| Median age, years (range) | 55 (27-76) |
| Male, % | 64% (23/36) |
| Karnofsky Performance Status (KPS) | |
| 100 - Normal, no complaints | 9% (3/35) |
| 90 - Able to carry on normal activity | 37% (13/35) |
| 80 - Normal activity with effort | 45% (16/35) |
| 70 - Unable to carry on normal activity, cares for self | 9% (3/35) |
| Prior therapies | |
| Surgery/Radiation/Temozolomide | 100% (36/36) |
| Immunotherapy | 11% (4/36) |
| Other Investigational Drug or Device | 8% (3/36) |
| MGMT Promoter Methylation Status (21 pts unknown) | |
| Unmethylated | 14/15 |
| Methylated | 1/15 |
| EGFRvIII Positive Status (21 pts unknown) | 2/15 |

MRZ & BEV combination is well tolerated in patients with recurrent glioma. Most common AEs related to study drugs include fatigue, headache, nausea, hypertension, vomiting, diarrhea, dysphonia, hallucination, and weakness. Most common MRZ related >Grade 3 AEs were hallucination and headache.

Figure 48A:
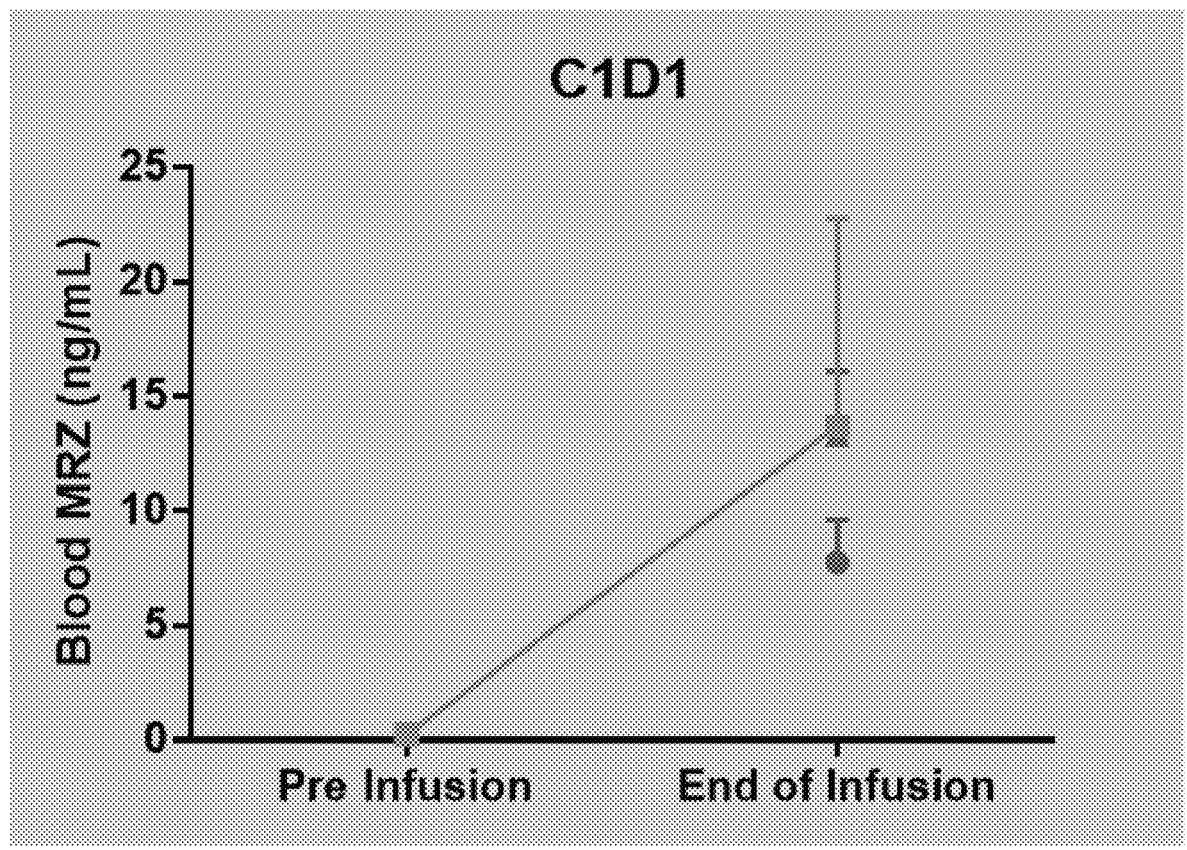
FIG. 48A shows blood concentration of MRZ after cycle 1 of MRZ and BEV on day 1.
Figure 48B:
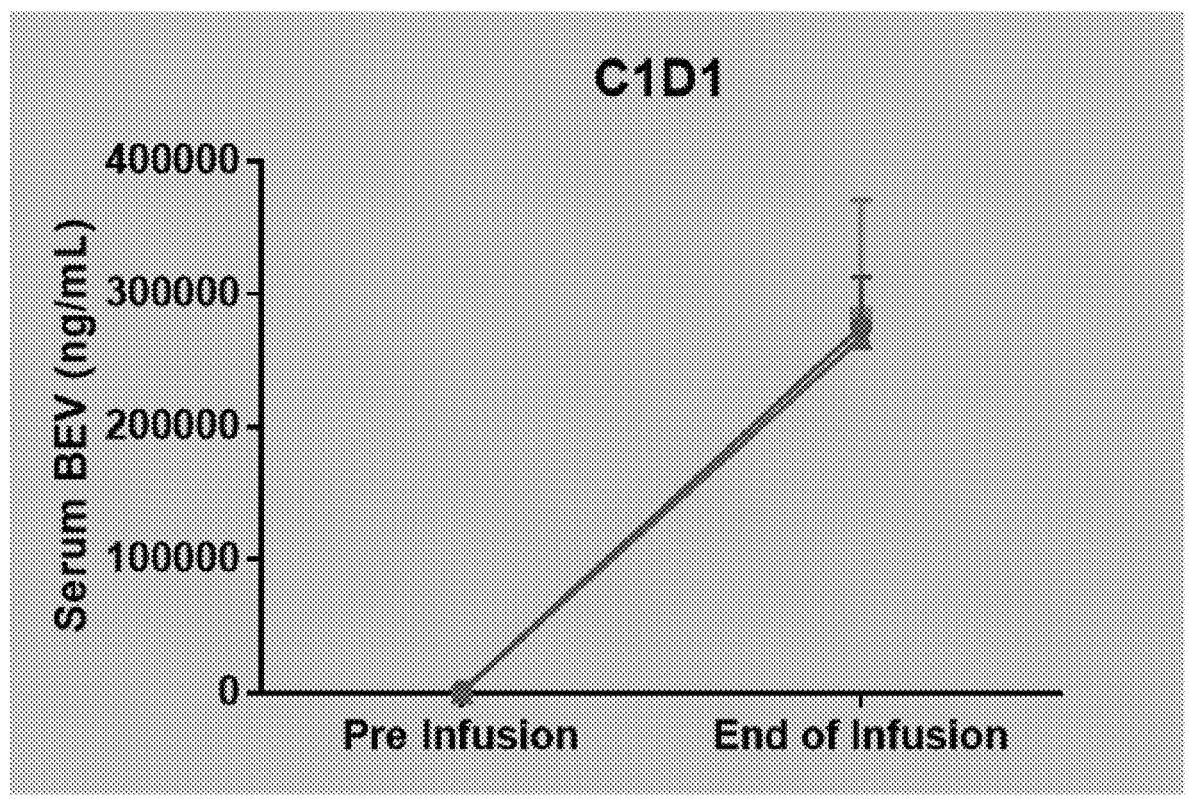
FIG. 48B shows serum concentration of BEV after cycle 1 of MRZ and BEV on day 1.
Figure 48C:
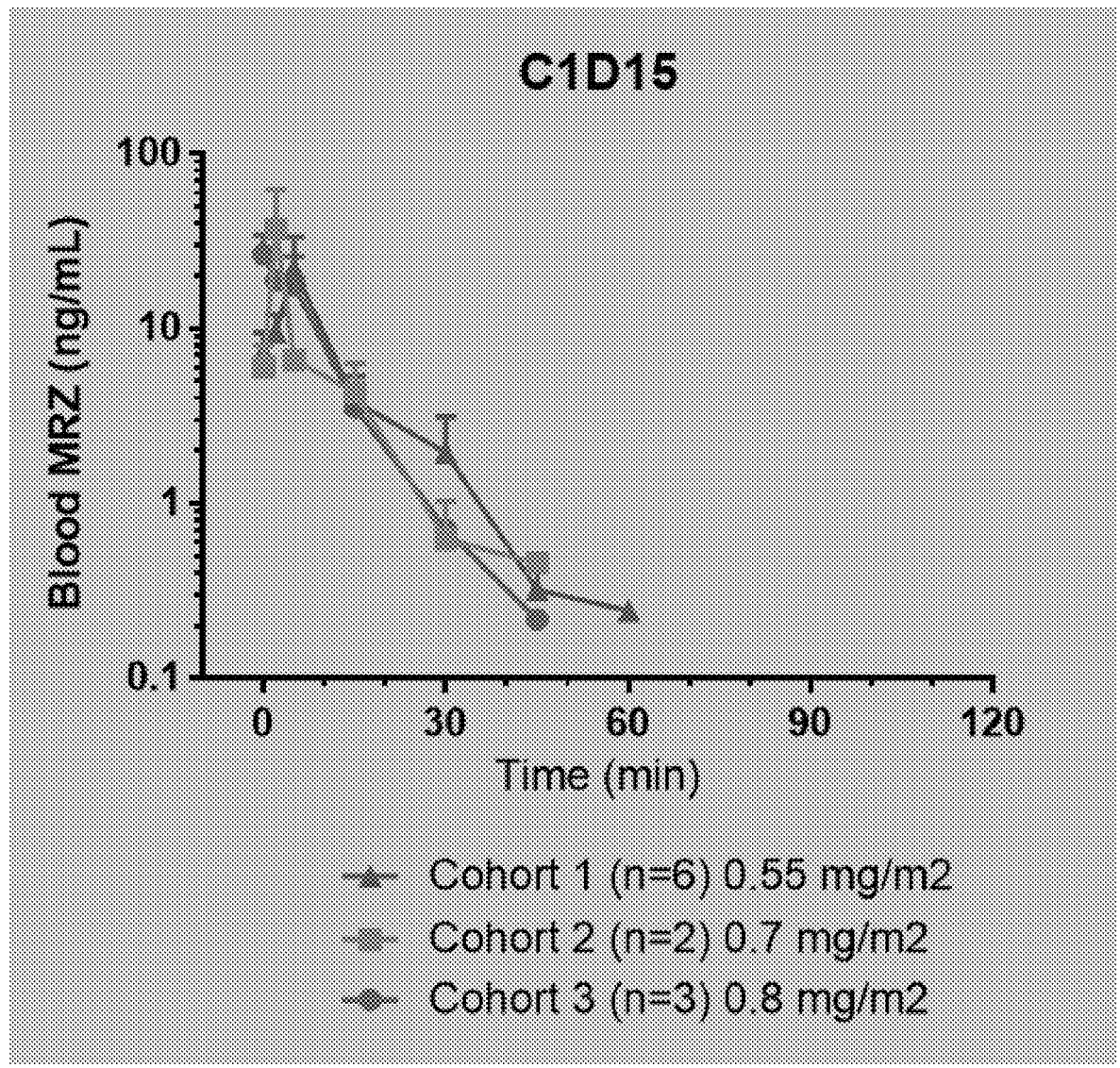
FIG. 48C shows blood concentration of MRZ after cycle 1 of MRZ and BEV on day 15.
Figure 48D:
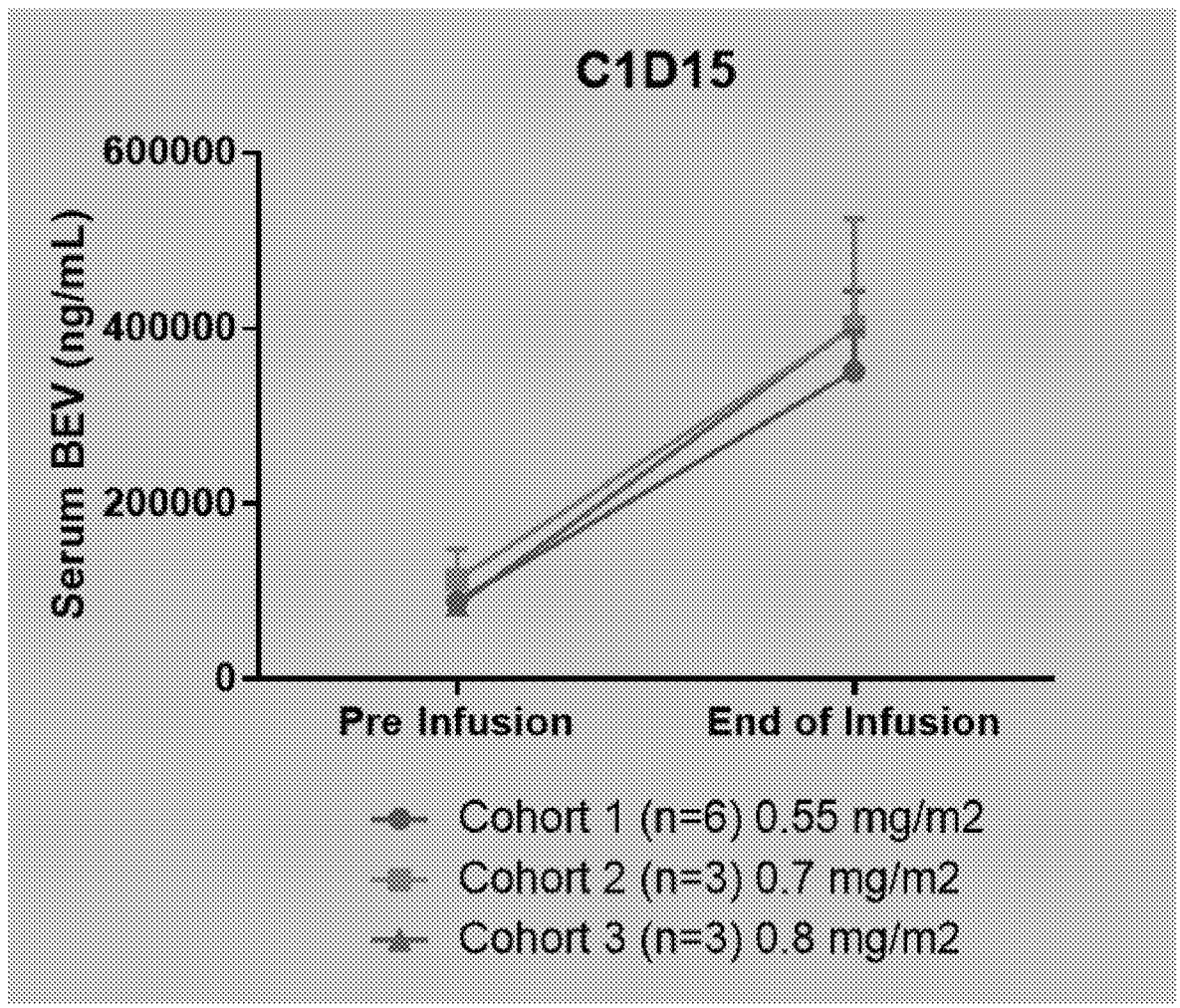
FIG. 48D shows serum concentration of BEV after cycle 1 of MRZ and BEV on day 15.

FIG. 48A shows blood concentration of MRZ after cycle 1 of MRZ and BEV on day 1. FIG. 48B shows serum concentration of BEV after cycle 1 of MRZ and BEV on day 1. FIG. 48C shows blood concentration of MRZ after cycle 1 of MRZ and BEV on day 15. FIG. 48D shows serum concentration of BEV after cycle 1 of MRZ and BEV on day 15.

Figure 49:
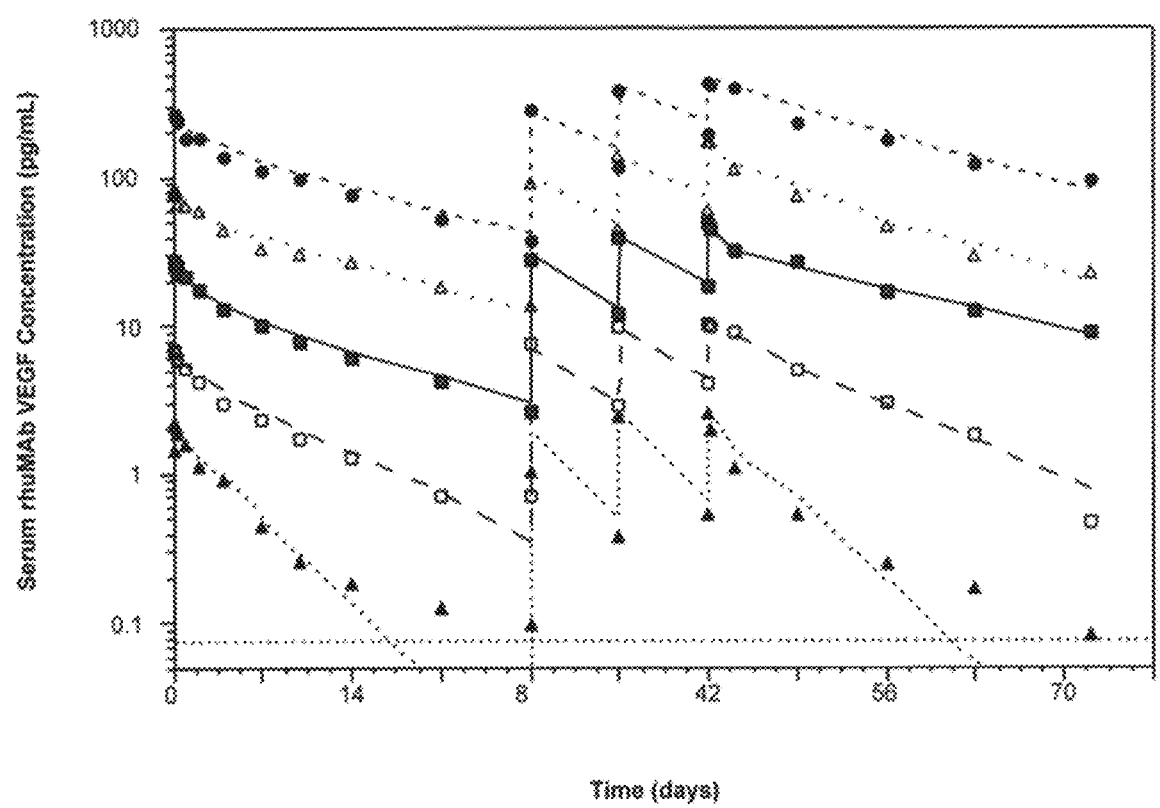
FIG. 49 shows that there is no effect of MRZ on BEV pharmacokinetics.

FIG. 49 shows that there is no effect of MRZ on BEV pharmacokinetics. BEV PK in Study 108: Mean Day 1 $C_{max}$ 275 μg/mL; Mean Day 15 $C_{min}$ 95 μg/mL; Mean Day 15 $C_{max}$ 379 μg/mL (Gordon et al., JCO 2001; 19:843).

PKPD Data Summary

| Parameter (Units) | 0.55 mg/m² | 0.7 mg/m² | 0.8 mg/m² |
|---|---|---|---|
| MRZ PK determined on C1D8 | | | |
| $T_{1/2}$ (min) | 8.8 ± 0.8 (3)* | 32.0 (1) | 7.6 ± 0.9 (2) |
| $T_{max}$ (min) | 4.0 ± 0.6 (6) | 11.3 ± 9.3 (3) | 0.0 ± 0 (3) |
| $C_{max}$ (ng/mL) | 23 ± 11 (6) | 65 ± 31 (3) | 26 ± 8 (3) |
| $AUC_{last}$ (min*ng/mL) | 236 ± 108 (6) | 193 ± 85 (2) | 243 ± 77 (3) |
| $V_{ss\ obs}$ (mL/m²) | 12971 ± 7600 (3) | 7377 (1) | 12379 ± 8698 (2) |
| $CL_{obs}$ (mL/min/m²) | 2665 ± 1063 (3) | 162 (1) | 3822 ± 1798 (2) |
| BEV PK determined on C1D1 & C1D15 | | | |
| $C_{max}$ D1 (μg/mL) | 275 ± 37 (6) | 282 ± 89 (3) | 267 ± 133 (3) |
| $C_{min}$ D15 (μg/mL) | 90 ± 6.2 (6) | 114 ± 34 (3) | 85 ± 9.9 (3) |
| $C_{max}$ D15 (μg/mL) | 351 ± 47 (5) | 402 ± 123 (3) | 404 ± 40 (3) |
| Proteasome subunit inhibition in PWB post-MRZ infusion (peak effect) | | | |
| % CT-L inhibition | 100 ± 0 (5) | 100 ± 0 (3) | In progress |
| % T-L inhibition | 52.0 ± 8.0 (5) | 77.3 ± 10.5 (3) | |
| % C-L inhibition | 21.0 ± 7.8 (5) | 50.4 ± 9.1 (3) | |

As in previous IV infusion studies, MRZ demonstrated a short T1/2, large Vd, and high CL. All MRZ doses resulted in similar exposure ($C_{max}$ and AUC). BEV PK consistent with published parameters and not affected by co-administration of MRZ. Maximal inhibition of CT-L activity in PWB in cohorts 1 and 2. Dose-dependent proteasome inhibition observed in PBMC and on T-L and C-L activity, suggesting dose-dependent pharmacodynamic response (data not shown).

Figure 50:
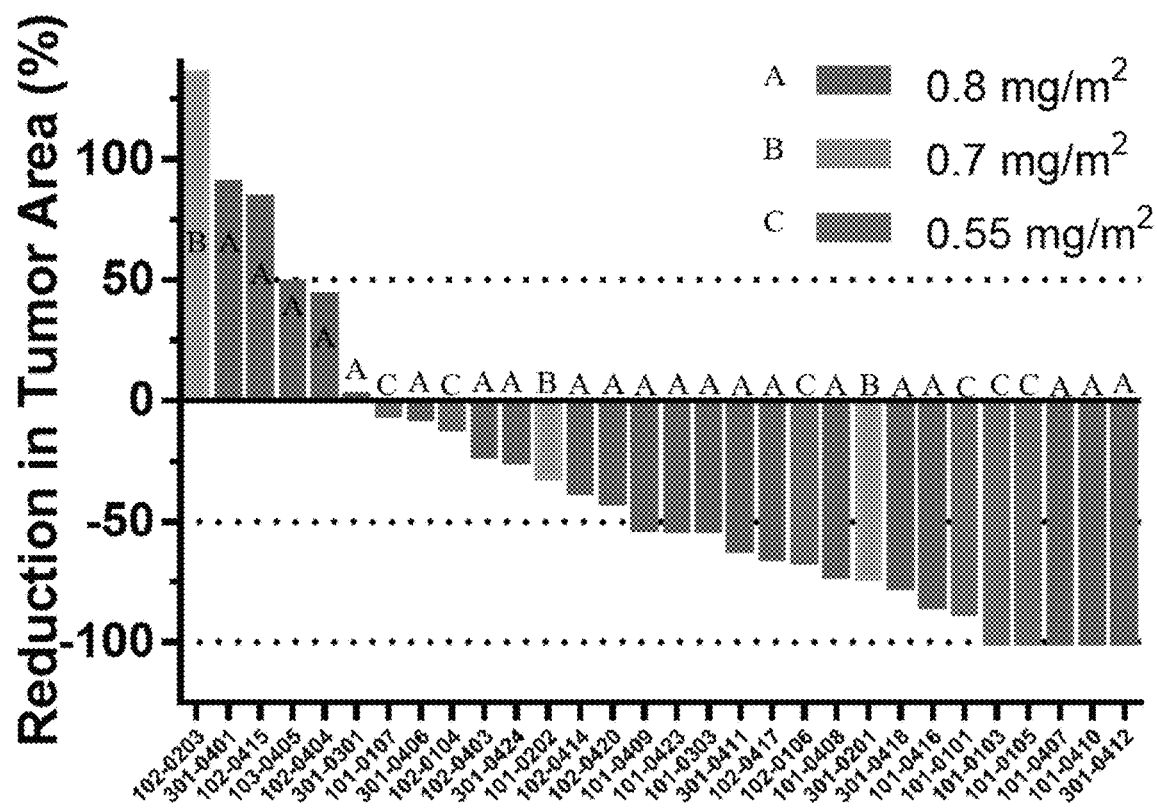
FIG. 50 shows the reduction in tumor area (%) for patients treated with MRZ and BEV.

FIG. 50 shows the reduction in tumor area (%) for patients treated with MRZ and BEV.

Figure 51A:
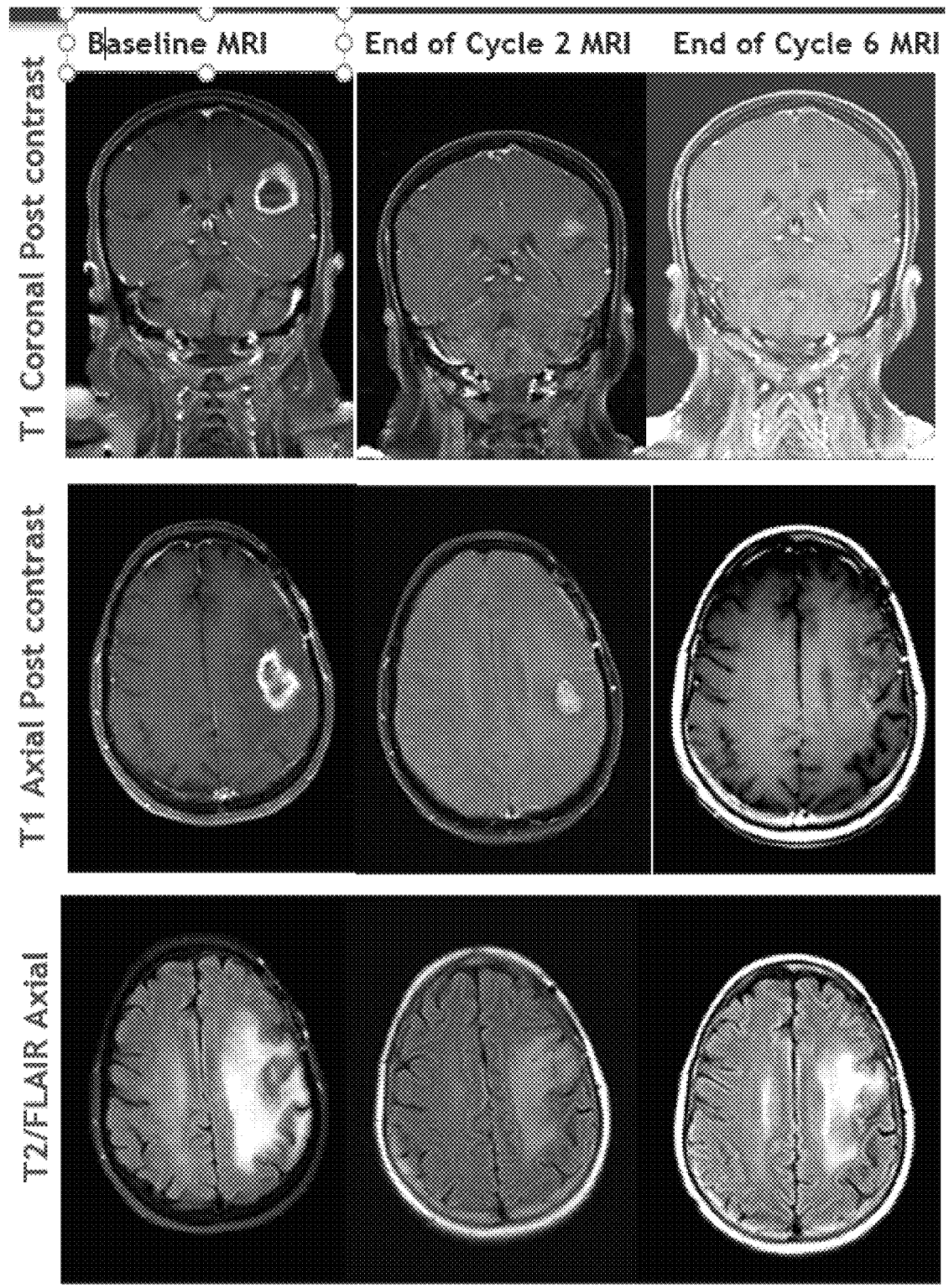
FIG. 51A shows MRI images of patient 101-0103 after treatment with MRZ and BEV
Figure 51B:
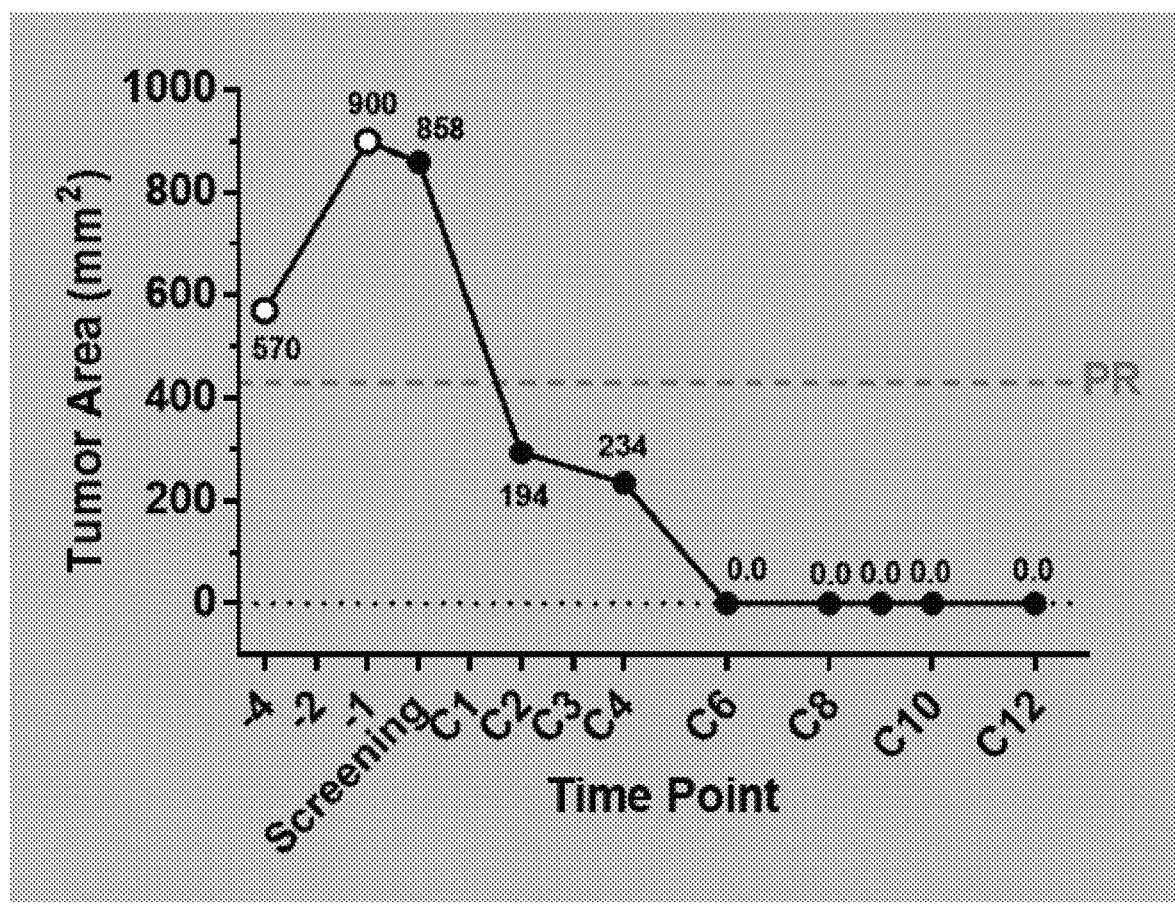
FIG. 51B shows a plot of patient 101-0103's tumor area after treatment with MRZ and BEV.

FIG. 51A shows MRI images of patient 101-0103 after treatment with MRZ and BEV. FIG. 51B shows a plot of the patient's tumor area after treatment with MRZ and BEV. Patient 101-0103: 59 F, KPS 90; 16 Oct. 2014: Brain tumor resection; December 2014-January 2015: RT+TMZ; February 2015-April 2015: TMZ (3 cycles); 3 Apr. 2015: Confirmed PD.

Started MRZ (0.55 mg/m²)+BEV on 22 May 2015; Dose reduction to 0.4 mg/m² C3D1; Currently in Cycle 14.

Figure 52A:
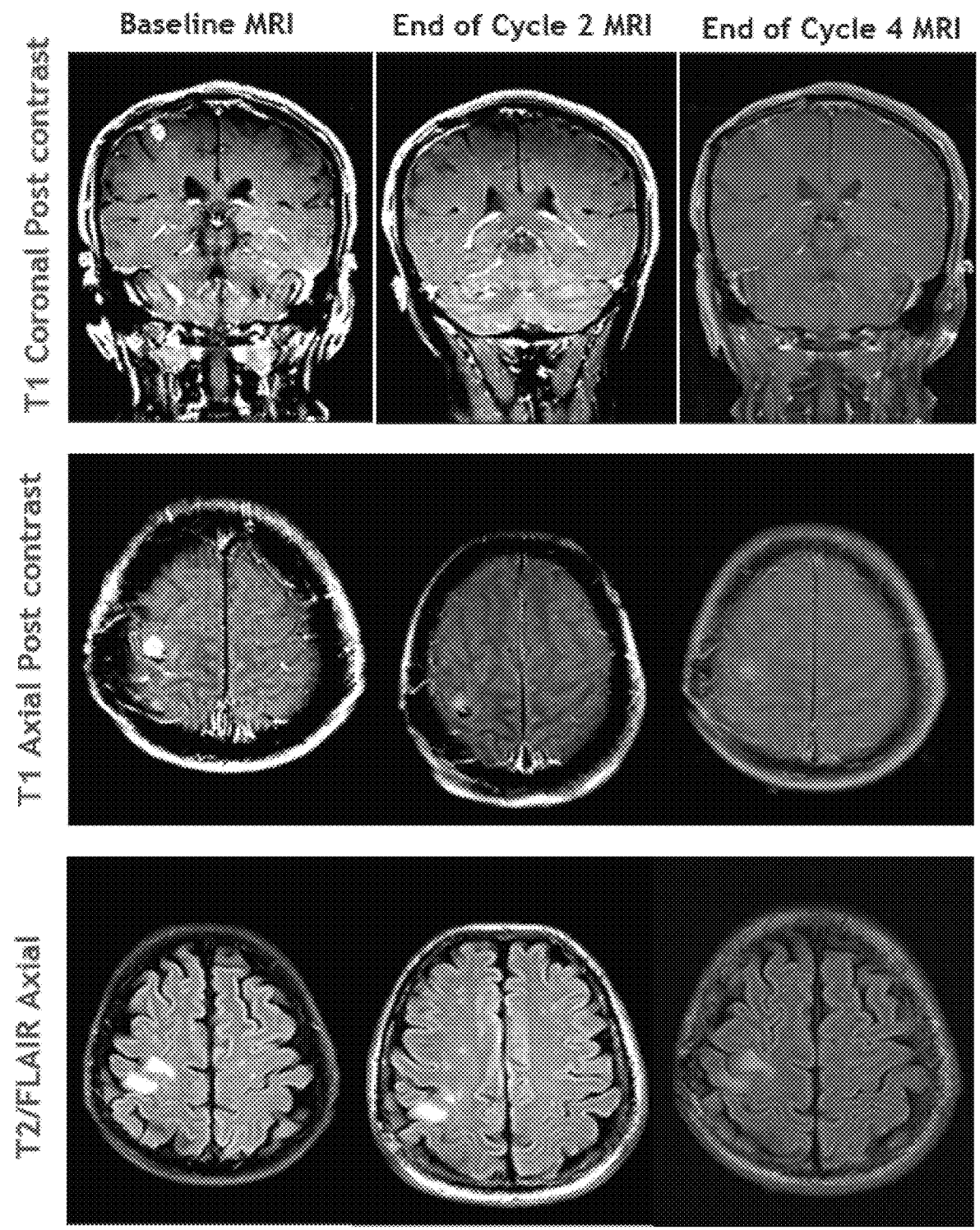
FIG. 52A shows MRI images of patient 101-0105 after treatment with MRZ and BEV.
Figure 52B:
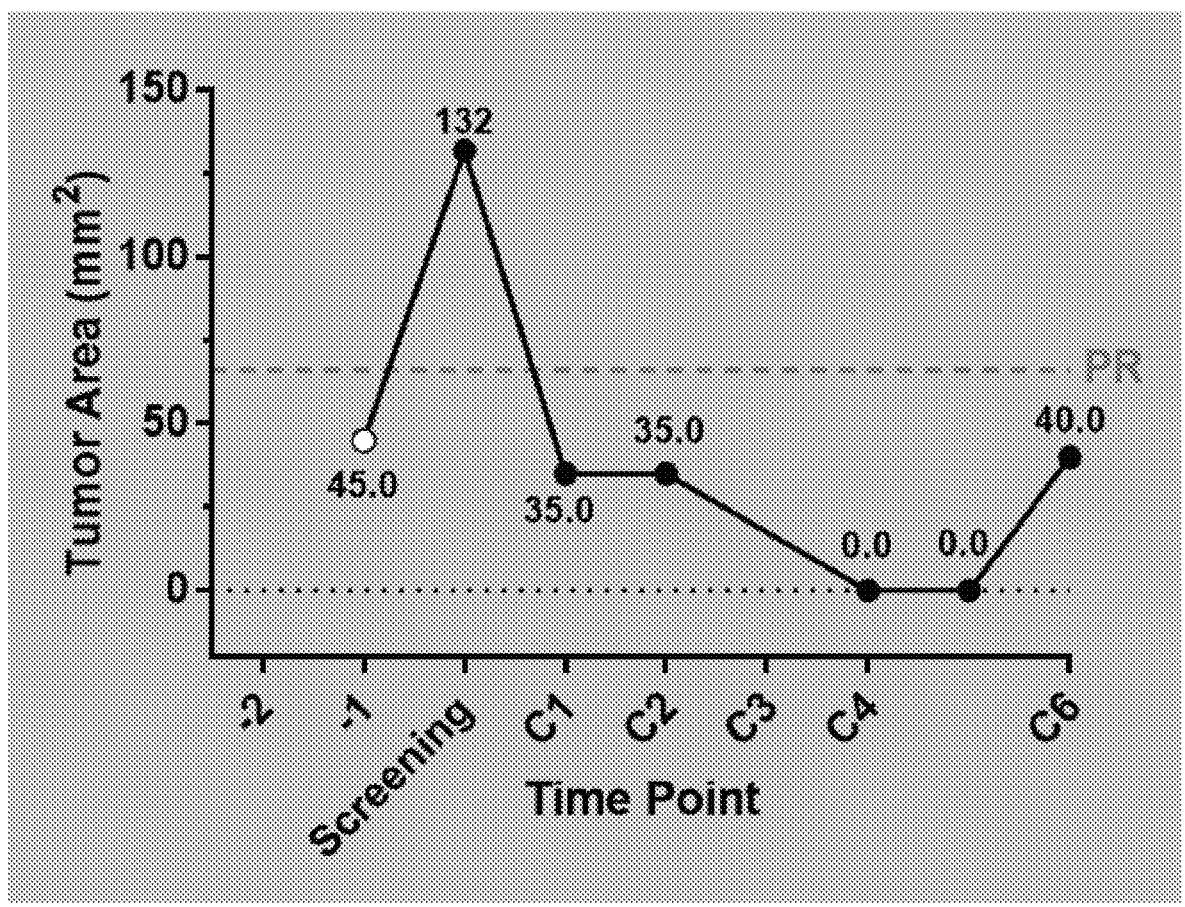
FIG. 52B shows a plot of the patient 101-0105's tumor area after treatment with MRZ and BEV.

FIG. 52A shows MRI images of patient 101-0105 after treatment with MRZ and BEV. FIG. 52B shows a plot of the patient 101-0105's tumor area after treatment with MRZ and BEV. Patient 101-0105: 54/M, KPS 90; 25 Oct. 2014: Brain tumor resection; November 2014-January 2015: RT+TMZ; February 2015-June 2015: TMZ (5 cycles); 29 Jun. 2015: Confirmed PD.

Started MRZ (0.55 mg/m2)+BEV on 31 Jul. 2015; Off study due to PD 9 Mar. 2016.

Figure 53A:
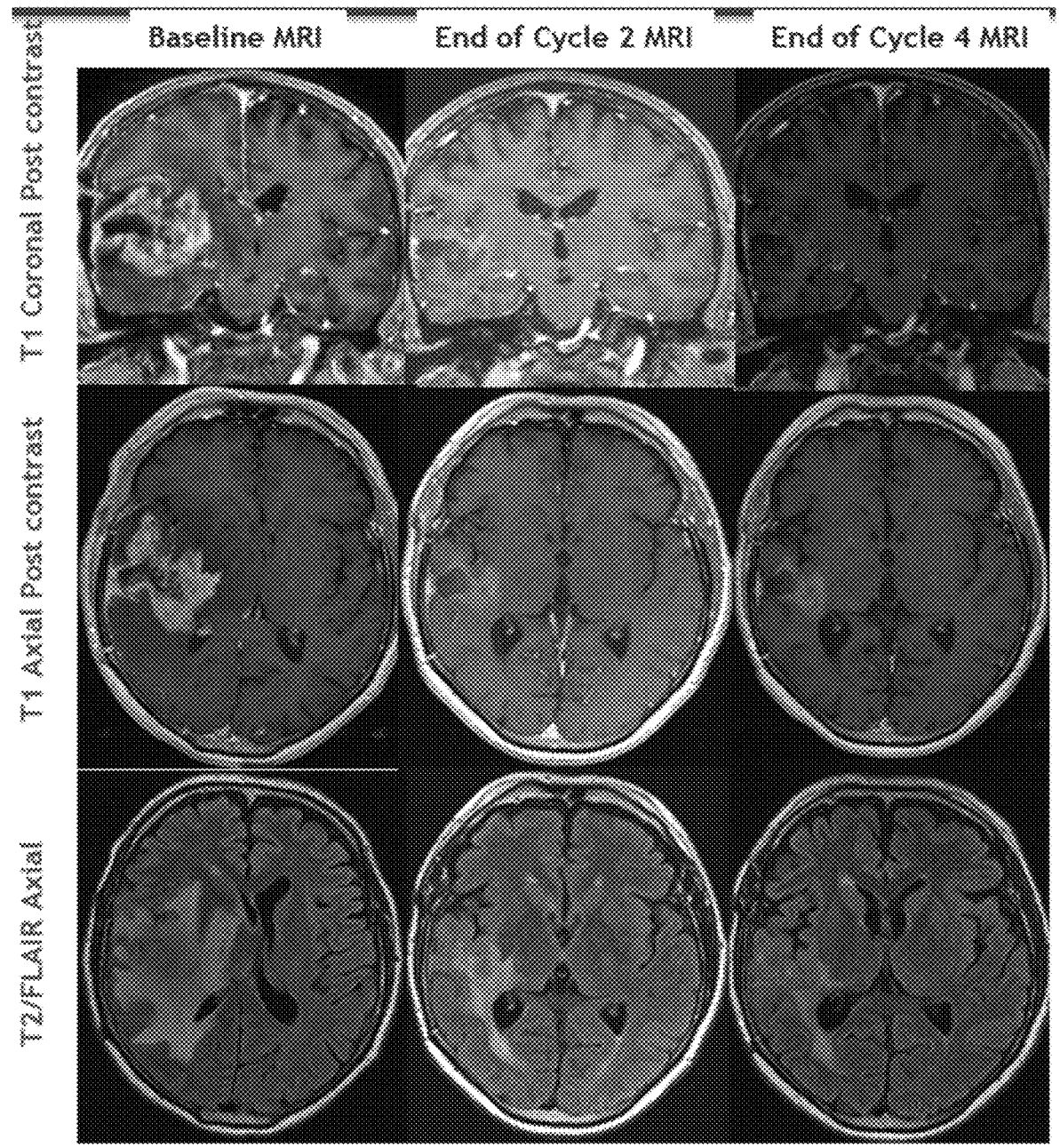
FIG. 53A shows MRI images of patient 101-0106 after treatment with MRZ and BEV.
Figure 53B:
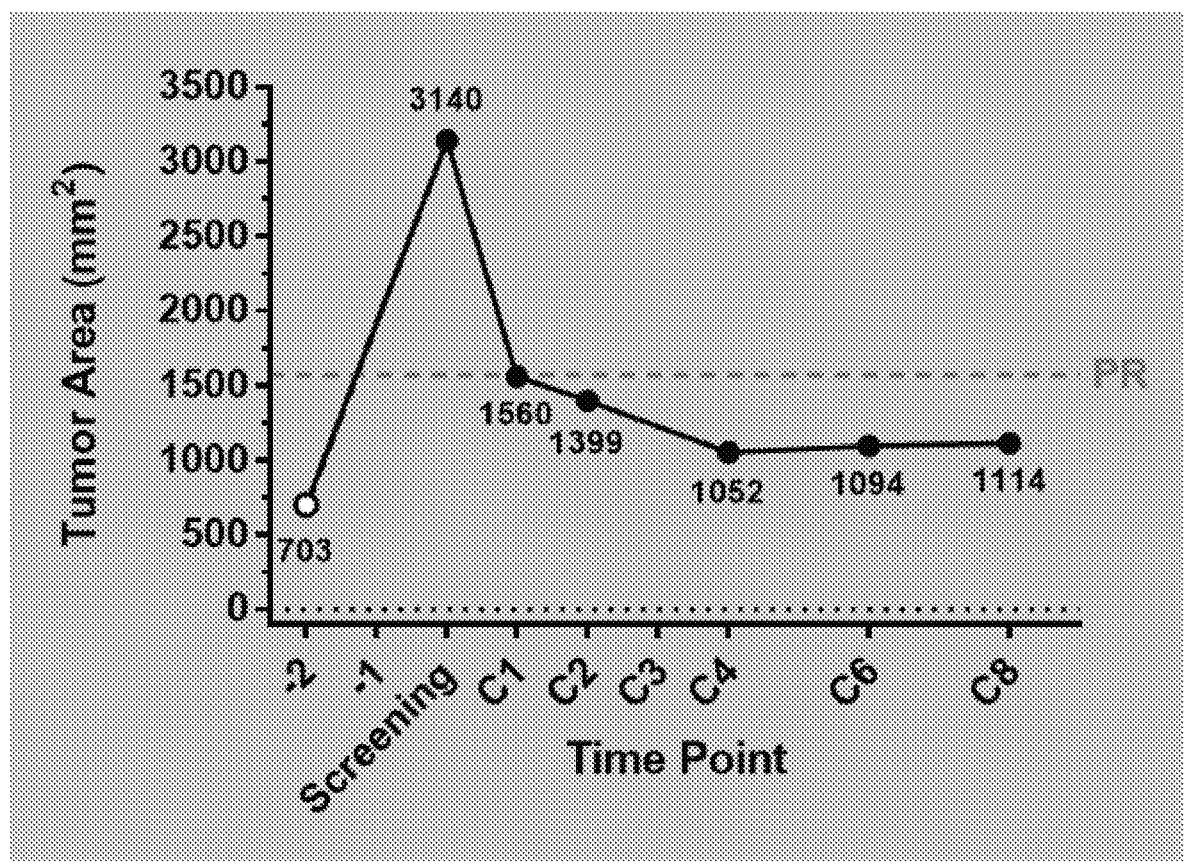
FIG. 53B shows a plot of the patient 101-0106's tumor area after treatment with MRZ and BEV.

FIG. 53A shows MRI images of patient 101-0106 after treatment with MRZ and BEV. FIG. 53B shows a plot of the patient 101-0106's tumor area after treatment with MRZ and BEV. Patient 102-0106: 61 year old male, KPS 80; March 2015: Brain tumor resection; April 2015-May 2015: RT+TMZ; June 2015-July 2015: TMZ (2 cycles); 10 Aug. 2015: Confirmed PD Started MRZ (0.55 mg/m2)+BEV on 12 Aug. 2015 Currently in Cycle 10.

Figure 54:
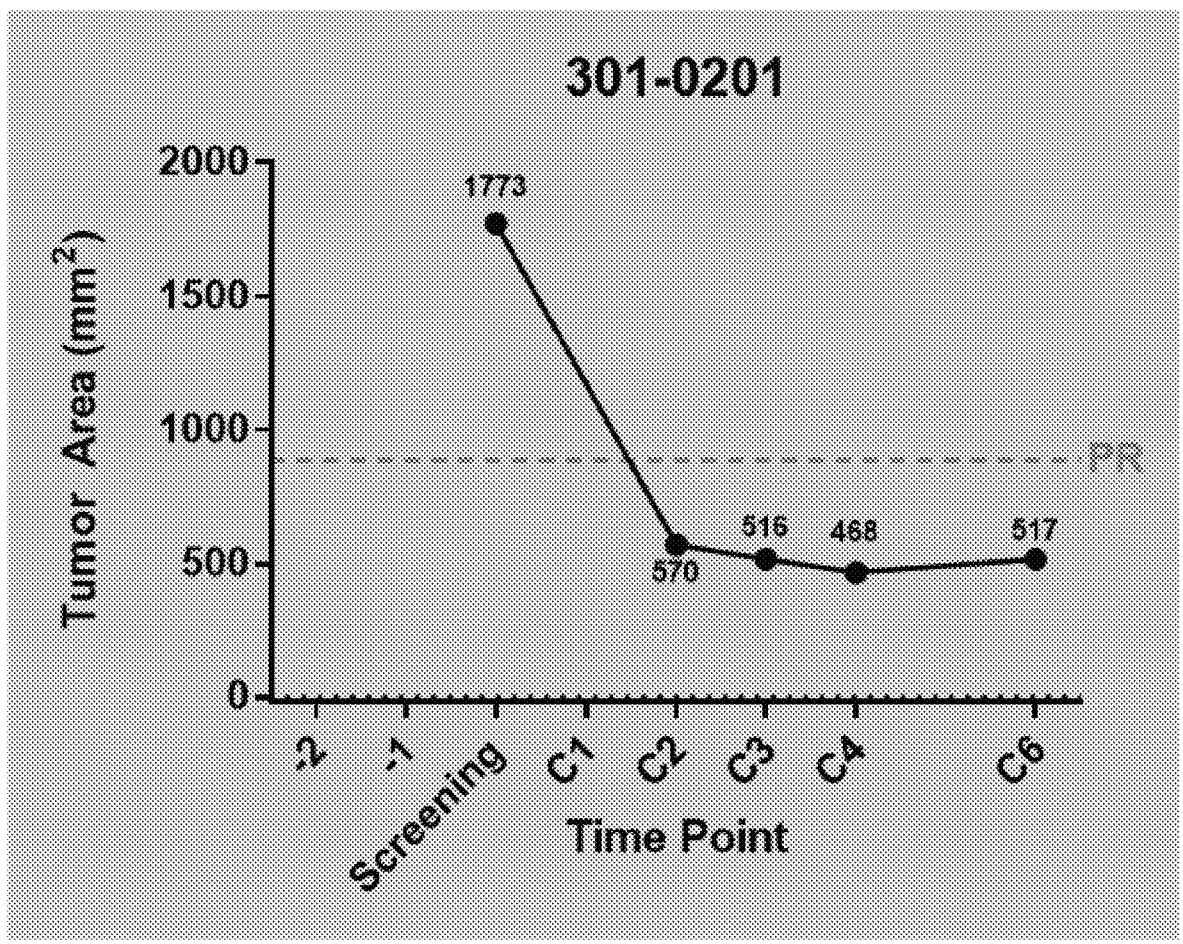
FIG. 54 shows a plot of tumor area for patient 301-0201.

FIG. 54 shows a plot of tumor area for patient 301-0201. Patient 301-0201: 53 year old male, KPS 90; April 2015: Brain tumor resection; April 2015-June 2015: RT+TMZ; July 2015-August 2015: TMZ (3 cycles); 10 Sep. 2015: Confirmed PD Started MRZ (0.7 mg/m2)+BEV on 23 Sep. 2015 Currently in Cycle 9

Figure 55:
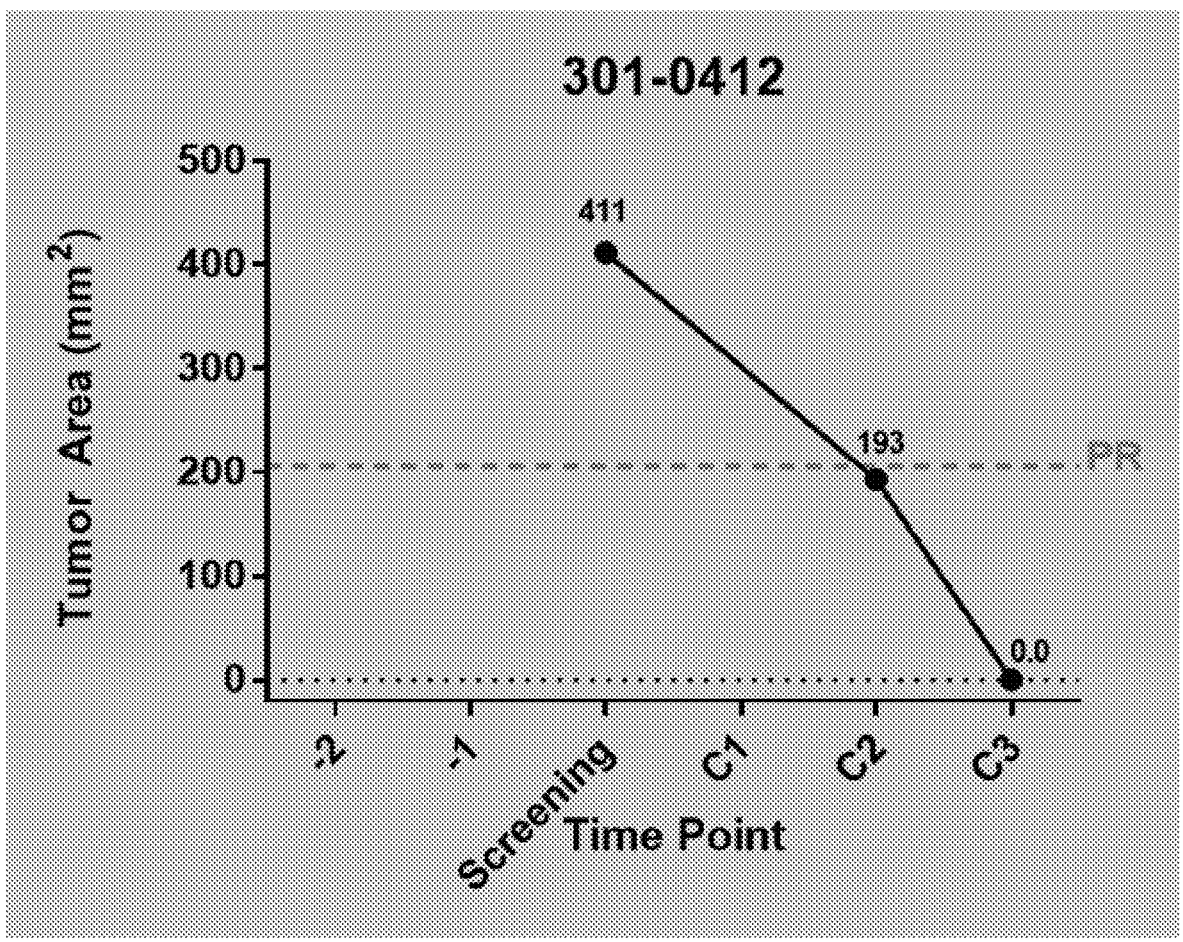
FIG. 55 shows a plot of tumor area for patient 301-0412.

FIG. 55 shows a plot of tumor area for patient 301-0412. Patient 301-0412: 64 year old male, KPS 90; October 2014: Brain tumor resection; November 2014-December 2014: RT+TMZ; February 2015-September 2015: TMZ; February 2015-October 2015:TMZ+Novocure; 15 Oct. 2015: Confirmed PD Started MRZ (0.8 mg/m2)+BEV on 2 Feb. 2016; Currently in Cycle 5
RANO Response Rate by Efficacy Evaluable & ITT

| Best Response | Patient # | Efficacy Evaluable (N = 31) | ITT (N = 36) |
|---|---|---|---|
| CR/PR (5) + PR (7) + uPR (2) | 14 | 45% | 39% |
| SD | 11 | 35% | 31% |
| PD | 5 | 16% | 14% |
| NE (6)* | 6 | NA | 14% |

Note:
*Patient 102-0421 is included in the total of non-evaluable (NE) patients population since per protocol is efficacy evaluable, but not evaluable by RANO (no MRI).

| Best Response (N) | Efficacy Evaluable (N = 31) | | | ITT (N = 36) | | |
|---|---|---|---|---|---|---|
| | Unknown N = 19 pts | *Unmethylated N = 11 pts | Methylated N = 1 pt | Unknown N = 21 pts | *Unmethylated N = 14 pts | Methylated N = 1 pt |
| CR/PR (5) + PR (7) + uPR (2) | 6 | 7 | 1 | 6 | 7 | 1 |
| SD (11) | 9 | 2 | 0 | 9 | 2 | 0 |
| PD (5) | 4 | 1 | 0 | 4 | 1 | 0 |
| NE (6)** | — | 1 | — | 2 | 4 | 0 |

*unmethylated: non-methylated or hypomethylated per site pathology report
Note:
**Patient 102-0421 is included in the total of non-evaluable (NE) patients population since per protocol is efficacy evaluable, but not evaluable by RANO (hypomethylated MGMT promoter).

Figure 56:
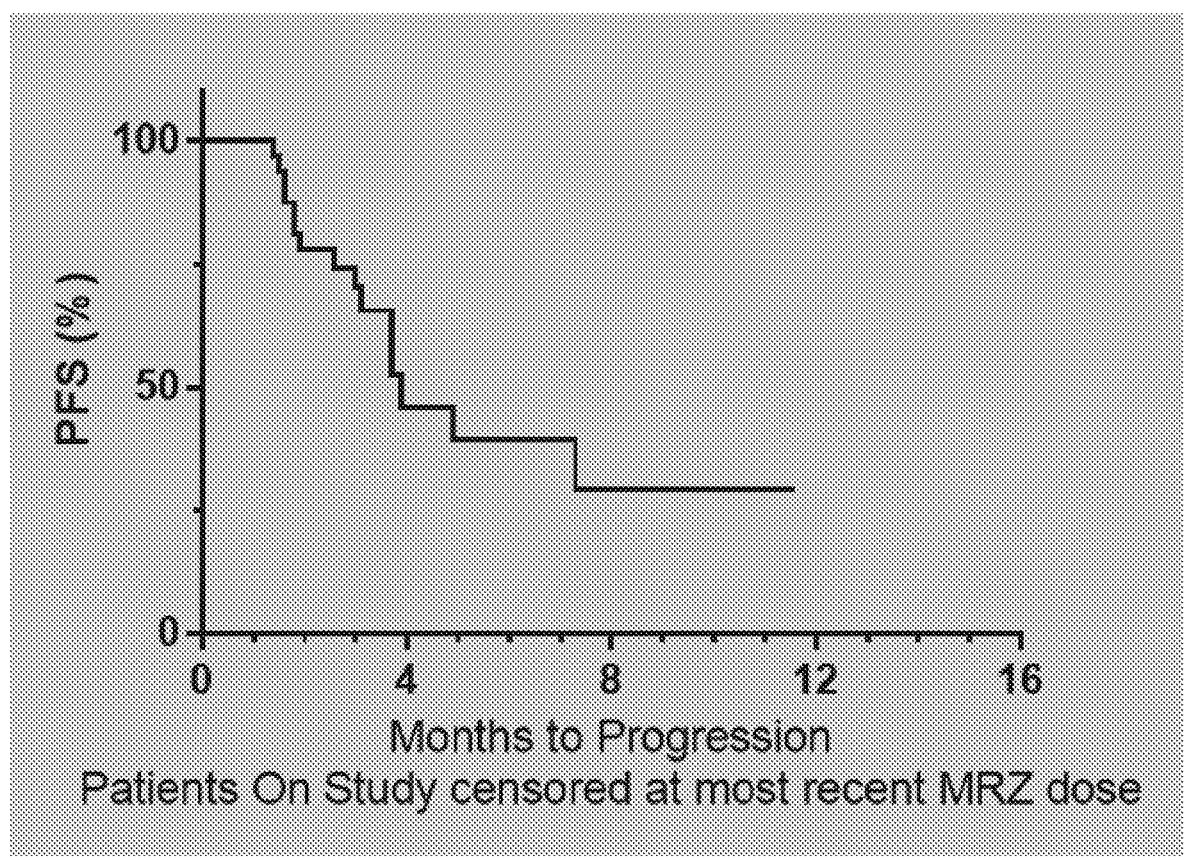
FIG. 56 shows a plot of overall progression free survival.

FIG. 56 shows a plot of overall progression free survival. Intent to Treat (N=36) 6 mo. PFS: 39%. 15 events (14 PD, 1 death); 21 censored including 5 lost to early follow-up.

Figure 57:
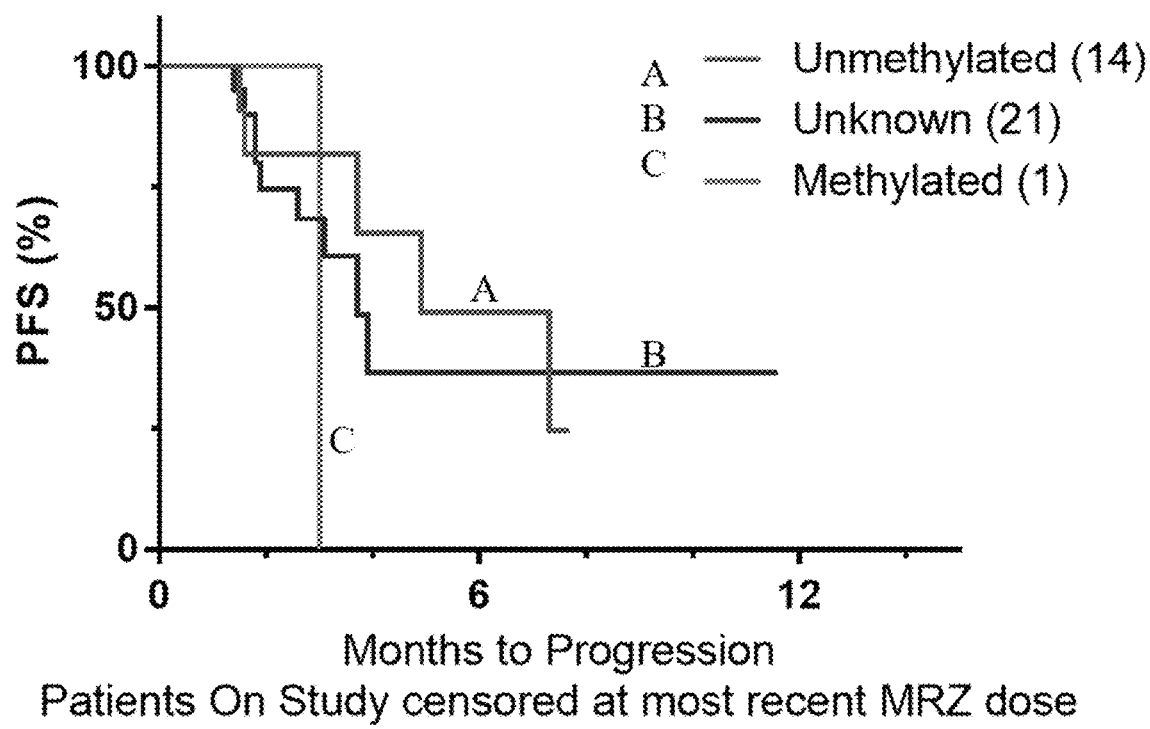
FIG. 57 shows a plot of progression free survival overall and by MGMT Promoter methylation status.

FIG. 57 shows a plot of progression free survival overall and by MGMT promoter methylation status. Intent to treat (N=36). 6 mo PFS unmethylated: 49%; 60 mo PFS Unknown: 36%.

Single Agent BEV Comparator Data in Recurrent Glioma

| | 6 mo PFS | |
|---|---|---|
| STUDY | All | uMGMT Promoter |
| MRZ-108 | 39% | 49% |
| BELOB trial BEV monotherapy arm (Taal et al., 2014) | 16% | 8% |

Efficacy

The majority of recurrent GBM patients (25/31) derive clinical benefit from the MRZ+BEV combination. 5 patients tumor area by MRI decreased to 0 mm² on ≥2 consecutive MRI scans.

As of the 17 May data cut. 16 of 36 patients enrolled remain on study. RANO response rate (including unconfirmed responses) is 45% in efficacy evaluable and 39% in ITT population. PFS 6 months: 39% in ITT population.

Safety 36 patients evaluable for safety. MRZ+BEV combo well tolerated, no DLTs at 0.8 mg/m2. Most common study treatment related AEs: fatigue, headache, nausea, hypertension, vomiting, diarrhea, dysphonia, hallucination, and weakness. MRZ overcomes compensatory hyperactivation of proteasome subunits resulting in pan-subunit inhibition.

Efficacy

Majority of recurrent GBM patients (25/31 efficacy evaluable) derive clinical benefit from the MRZ+BEV combination. 16 of 31 efficacy-evaluable pts remain on study. RANO response 45% (Efficacy Evaluable) and 39% (ITT). 5 patients tumor area by MRI decreased to 0 mm². PFS 6 months is 39% in ITT population. MRZ monotherapy stage of the study initiated with one patient dosed at 0.8 mg/m² Phase 1b Study in Newly Diagnosed G4 MG: Marizomib (MRZ)+Temozolomide (TMZ)+Radiotherapy (RT)

Figure 58:
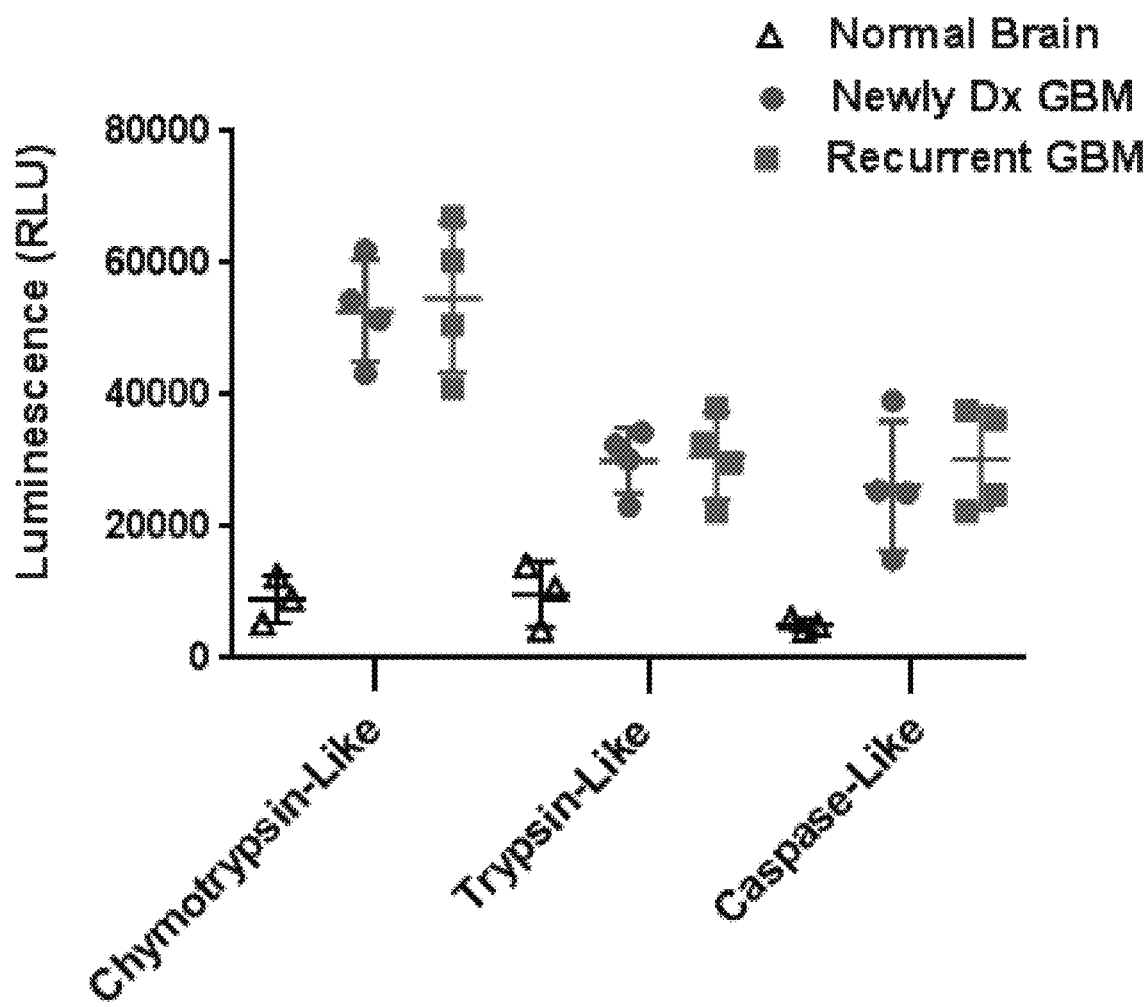
FIG. 58 shows proteasome activity may be elevated in newly diagnosed and recurrent GBM compared with a normal brain.

FIG. 58 shows proteasome activity may be elevated in newly diagnosed and recurrent GBM compared with a normal brain. The data presented in FIG. 58 are from the same four patients. MRZ Penetrates the BBB and Inhibits Proteasome Activity in Rodent Brain

| CMPD (IV) | Mouse | 20S Proteasome Activity (% Inhibition) | | | | | |
|---|---|---|---|---|---|---|---|
| | | Blood | | Tumor | | Brain | |
| | | Trough | Peak (2 hr) | Trough | Peak (2 hr) | Trough | Peak (2 hr) |
| BTZ | 1 | 18 | 81 | 64 | 83 | NE | NE |
| | 2 | 13 | 83 | 41 | 93 | NE | NE |
| MRZ | 1 | 87 | 99 | 15 | 56 | 52 | 94 |
| | 2 | 87 | 99 | 0 | 77 | 41 | 98 |

NE, No Effect

MRZ, but not BTZ, inhibits CT-L activity in brain of tumor-bearing mouse. In a quantitative whole body autoradiography study in rats, significant distribution of MRZ to brain was observed. ~30% of the plasma $C_{max}$.

Figure 59:
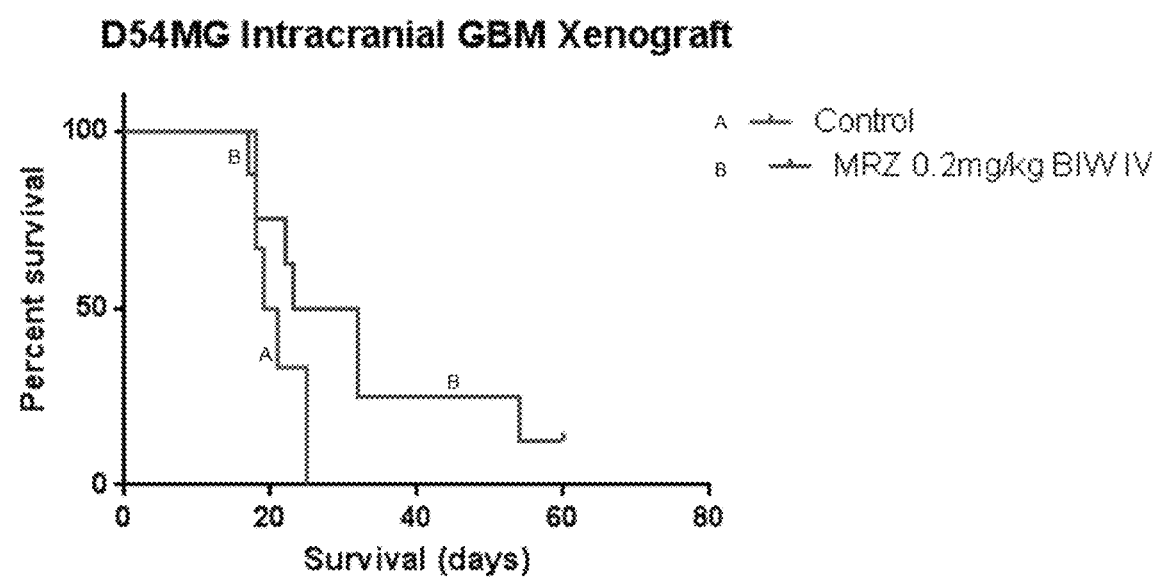
FIG. 59 shows MRZ is Active in Intracranial GBM Xenograft.

FIG. 59 shows MRZ is Active in Intracranial GBM Xenograft. 1×10⁵ D54MG cells implanted into right frontal lobes of athymic BALB/c nu/nu mice. MRZ administered IV twice weekly.

Figure 60A:
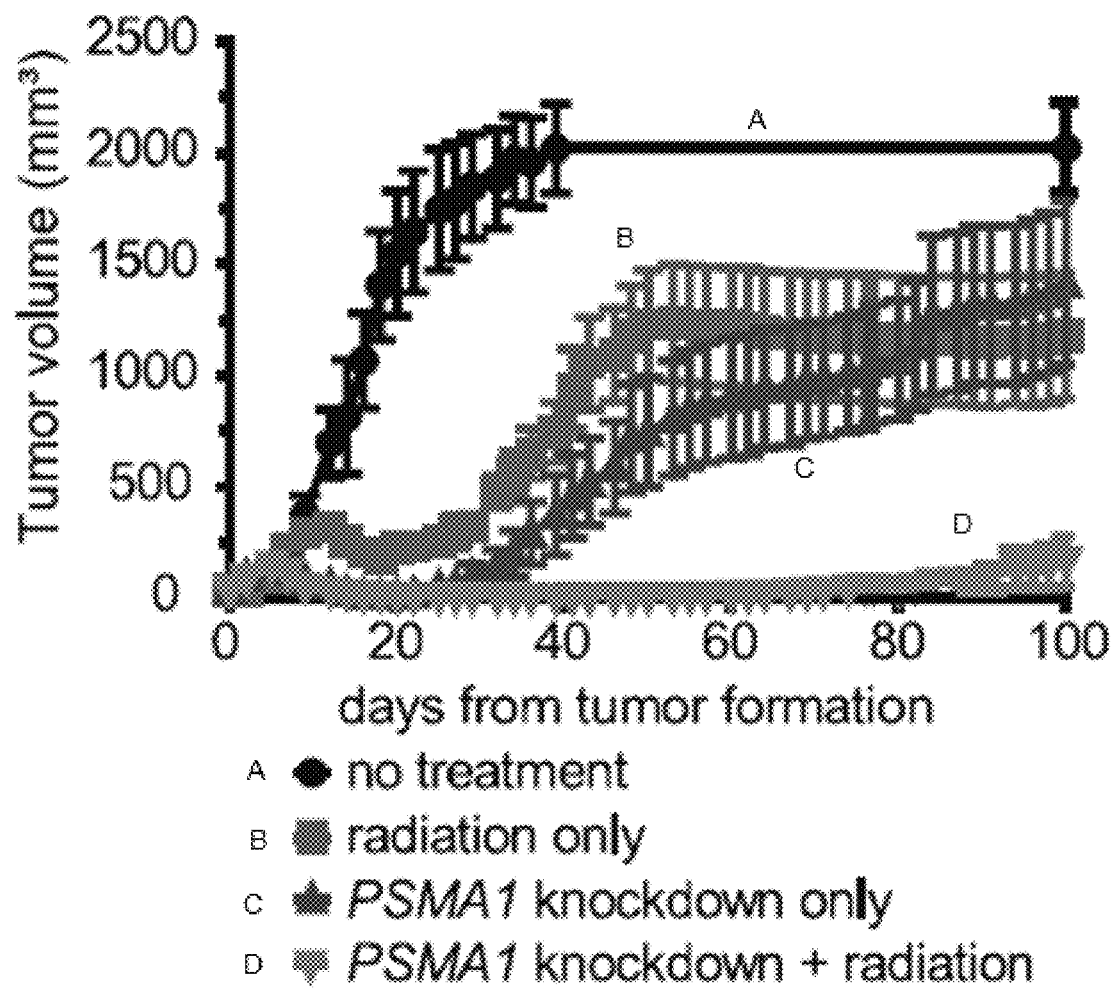
FIG. 60A shows tumor volume as a function of time.
Figure 60B:
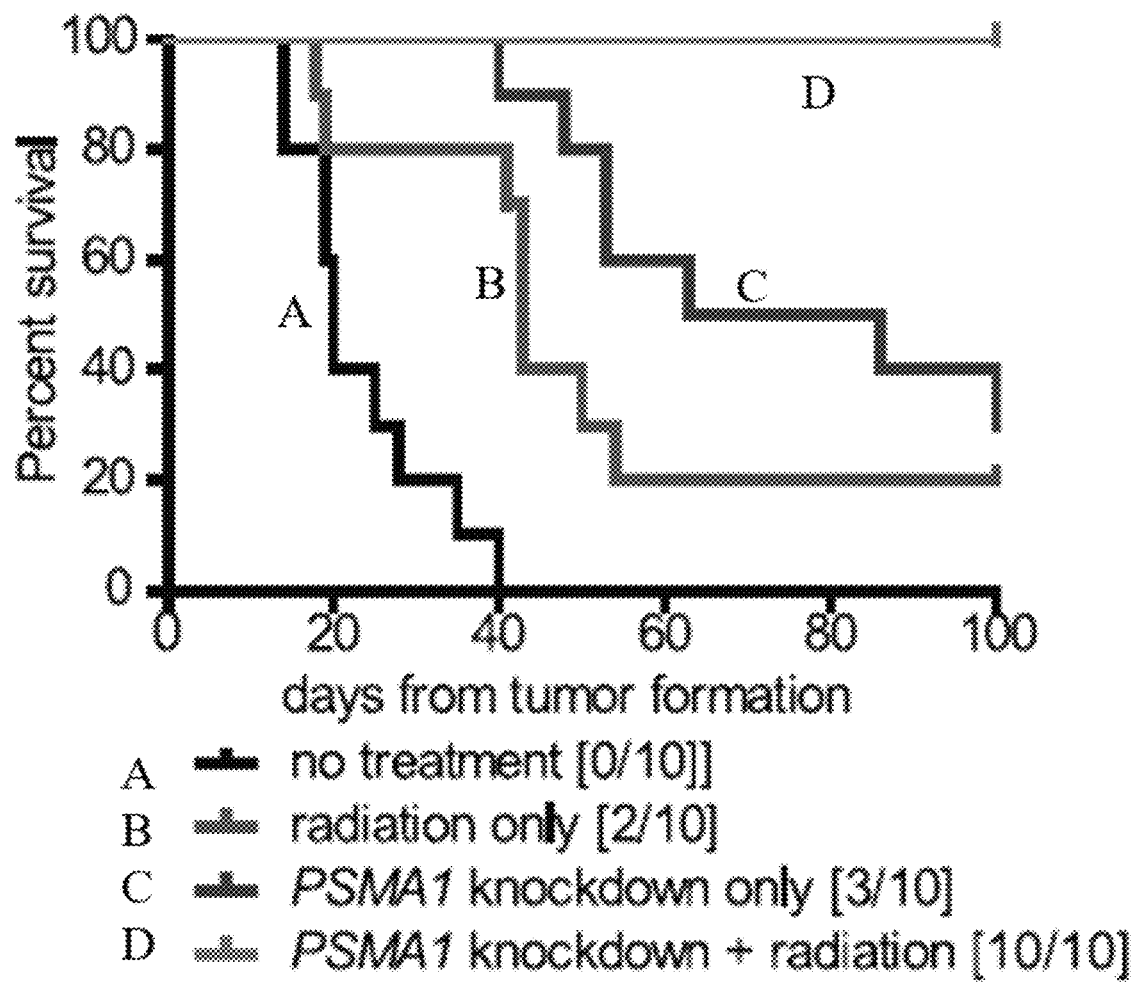
FIG. 60B shows percent survival as a function of time.

FIGS. 60A and 60B show proteasome inhibition (PI) Radiosensitizes tumor growth in vivo. FIG. 60A shows tumor volume as a function of time. FIG. 60B shows percent survival as a function of time. PI by RNAi radiosensitizes NSCLC. PI impairs radiation-induced DNA double strand break repair by 80-90%.

Figure 61A:
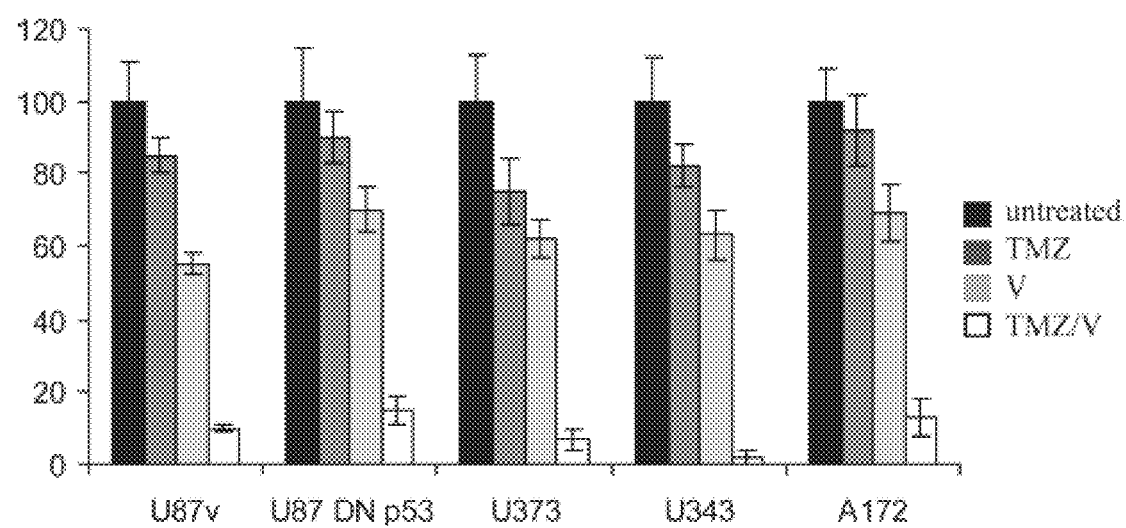
FIG. 61A shows PI synergizes with TMZ (P53 wildtype and mutant cell lines).
Figure 61B:
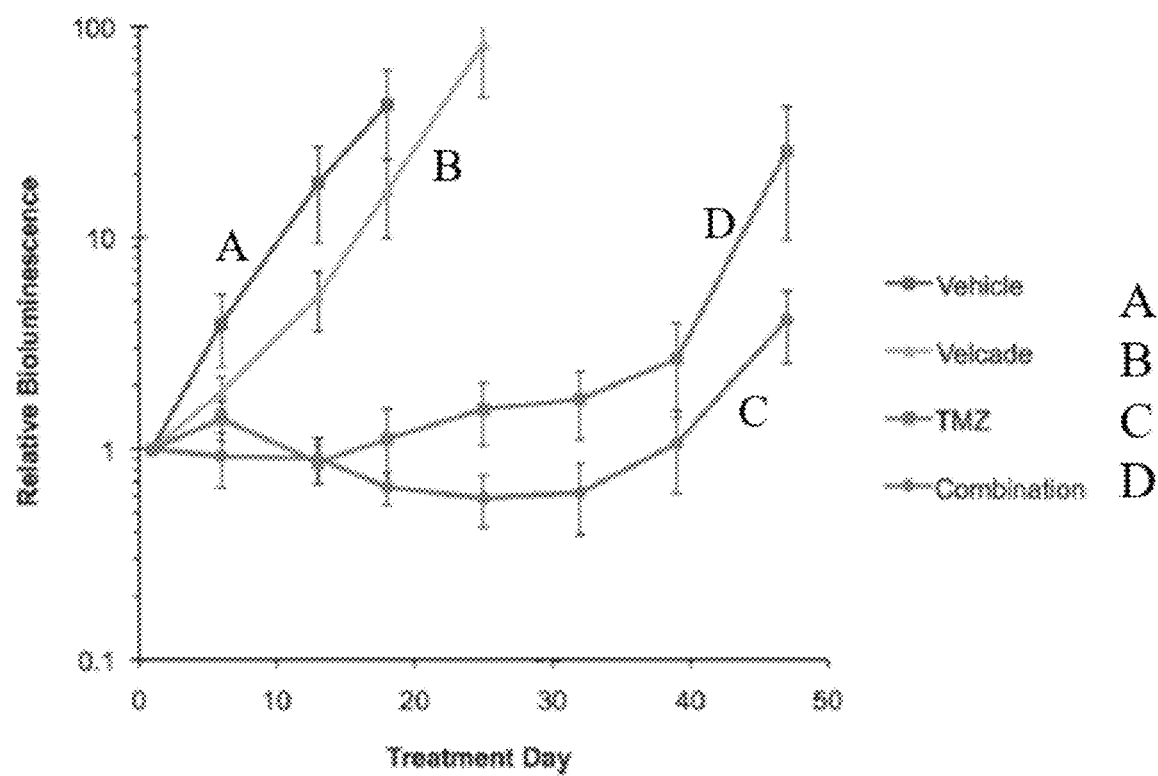
FIG. 61B shows relative bioluminescence as a function of time.
Figure 61C:
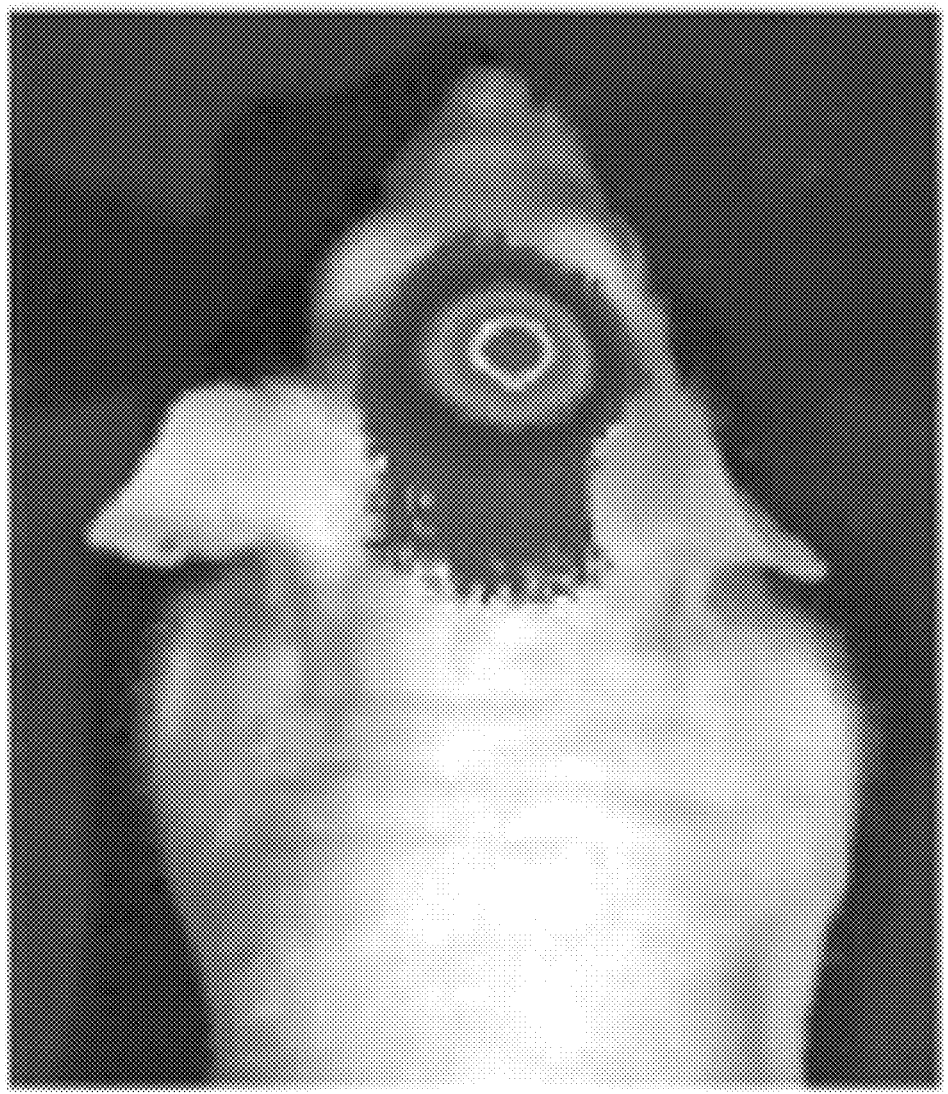
FIG. 61C shows PI sensitized to TMZ in vivo.

FIG. 61A-61C show synergistic Activity of BTZ+TMZ in GBM U87 Glioma Cells in vitro and in vivo. FIG. 61A shows PI synergizes with TMZ (P53 wildtype and mutant cell lines). FIG. 61B shows relative bioluminescence as a function of time. FIG. 61C shows PI sensitized to TMZ in vivo.

Example 7—Phase 1, Open-Label, Dose Escalation Study of Marizomib and Bevacizumab in WHO Grade IV Malignant Glioma This Example gives a phase 1 dose escalation combination study followed by a Phase 2 marizomib monotherapy study.

Study Objectives and Design

The primary objective was to determine the maximum tolerated dose and recommended phase II dose of marizomib+bevacizumab. The secondary objective was to evaluate the safety and activity of marizomib+bevacizumab.

An exploratory objective was to evaluate the baseline proteasome activity, marizomib and bevacizumab PK, marizomib neurological coordination (SARA), and quality of life assessment (FACT-Cog/FACT-Br)

Methods

The clinical trial was a Phase 1, dose-escalation (3+3 design) followed by dose-expansion at recommended Phase 2 Dose (RP2D). Three dose escalation cohorts were used—marizomib 0.55 (6 pts), 0.7 (3 pts), and 0.8 mg/m$^2$ (3 pts); dose-expansion 0.8 mg/m$^2$ (24 pts). Marizomib was infused intravenous (IV; 10 min) on Days 1, 8, & 15; bevacizumab was infused IV at 10 mg/kg on Days 1 and 15. The drugs were infused on 28-Day Cycles. Tumor response is assessed every other cycle by RANO criteria. Blood marizomib pharmacokinetic parameters were assessed on Day 8, serum bevacizumab pharmacokinetic parameters were assessed on days 1 and 15; blood proteasome inhibition was assessed on days 1 and 15 every cycle. Table 49 gives the treatment parameters of the present study.

TABLE 49

Treatment Parameters of Grade IV MG Study

| Cohort (N) | IV marizomib (mg/m$^2$) - 10 min infusion Days 1, 8, 15 q 28 days | BEV IV (mg/kg) q 14 days |
| --- | --- | --- |
| 1 (6) | 0.55 | 10 |
| 2 (3) | 0.7 | 10 |
| 3 (3) | 0.8 | 10 |
| 4 (24) | Expansion of RP2D | 10 |

| Phase 2 | IV marizomib (0.8 mg/m2) - 10 min infusion days 1, 8, 15, q 28 days | |
| --- | --- | --- |
| 5 | 0.8 | None |

The key eligibility criteria included patients over 18 years of age, with histological evidence of grade IV malignant glioma in first or second relapse with clear progressive disease. Participants must have completed standard radiation therapy and temozolomide. Additional criteria included no prior proteasome inhibitor (including marizomib) or anti-angiogenic therapies, and a Karnofsky Performance Score greater than or equal to 70. Criteria also included that the patient be at least four weeks from surgical resection and 12 weeks from the end of radiotherapy. Table 50 gives the demographics of the study participants.

TABLE 50

Demographics of Study Participants

| Parameter | |
| --- | --- |
| Median age, years (range) | 55 (27-76) |
| Male, % | 64% (23/36) |
| Karnofsky Performance Status (KPS) | |
| 100 - Normal, no complaints | 9% (3/35) |
| 90 - Able to carry on normal activity | 37% (13/35) |
| 80 - Normal activity with effort | 45% (16/35) |
| 70 - Unable to carry on normal activity, cares for self | 9% (3/35) |
| Prior therapies | |
| Surgery/Radiation/Temozolomide | 100% (36/36) |
| Immunotherapy | 14% (5/36) |
| Other Investigational Drug or Device | 8% (3/36) |
| MGMT Promoter Methylation Status (6 pts unknown) | |
| Unmethylated | 20/30 |
| Methylated | 10/30 |
| EGFRvIII Positive Status (9 pts unknown) | 4/27 |
| EGFR Amplified (9 pts unknown) | 11/27 |
| EGFR Mutated (9 pts unknown) | 8/27 |

Results

Efficacy data reported as of 26 Oct. 2016. 36 patients enrolled with a median age 55 years (27-76), 64% were male, Karnofsky Score >70. Duration of dosing was 0.25-15 months to date; treatment is ongoing in 3 pts. Marizomib and bevacizumab was well tolerated.

Study treatment-related Grade ≥3 adverse events: fatigue, headache, hypertension, hallucination, confusional state, ataxia, optic nerve disorder, insomnia, delusion, hyponatremia; one Grade 4 serious adverse event (appendicitis perforated, not related to study treatment), one Grade 5 serious adverse event (embolism, intracranial hemorrhage, bevacizumab-related). One patient (cohort 1) had dose limiting toxicity (fatigue); no other dose limiting toxicities occurred across the dose range.

The efficacy evaluable population (N=33) included 31 patients efficacy evaluable by RANO criteria, and one patient Grade 5 serious adverse event (no post-treatment tumor assessment). The intent-to-treat population was 36.

One patient experienced a complete response (CR), and thirteen patients experienced partial responses (PR) (including 3 with CR for target lesion). Thirteen patients experienced stable disease (SD) (including 2 patients with unconfirmed PR), 6 patients experienced progressive disease (PD), and 3 patients were not evaluable (NE, no post-treatment tumor assessment). Marizomib and bevacizumab pharmacokinetic parameters were consistent with published parameters and not affected by co-administration. Proteasome inhibition was maximal on chymotrypsin-like (CT-L) domains in cohorts 1 and 2. Dose-dependent inhibition of trypsin-like (T-L) and caspase-like (C-L) activity in cohorts 1 vs 2 suggested dose-dependent pharmacodynamics.

Table 51 gives the study treatment-related adverse events and all adverse events greater than or equal to grade 3, as of 12 Sep. 2016.

TABLE 51

Study Treatment-Related Adverse Events and All
Grade 3 or above Adverse Events Preferred Term

| | # Patients (%) with AE | Relationship to Study Treatment | | | | # Patients Grade ≥3 |
|---|---|---|---|---|---|---|
| | | Neither | BEV | MRZ | Both | |
| Fatigue | 24 (67) | 2 | 0 | 1 | 21 | 3 |
| Nausea | 21 (58) | 0 | 0 | 19 | 2 | 0 |
| Headache | 20 (56) | 2 | 1 | 5 | 12 | 5 |
| Vomiting | 17 (47) | 1 | 0 | 12 | 4 | 0 |
| Hypertension | 16 (42) | 1 | 13 | 0 | 2 | 6 |
| Hallucination | 11 (31) | 0 | 0 | 11 | 0 | 2 |
| Diarrhoea | 10 (28) | 0 | 0 | 9 | 1 | 0 |
| Dysphonia | 10 (28) | 0 | 10 | 0 | 0 | 0 |
| Dizziness | 9 (25) | 0 | 0 | 8 | 1 | 0 |
| Anaemia | 8 (22) | 2 | 0 | 6 | 0 | 0 |
| Confusional State | 8 (22) | 1 | 0 | 6 | 1 | 1 |
| Epistaxis | 8 (22) | 1 | 7 | 0 | 0 | 0 |
| Hyperglycemia | 8 (22) | 8 | 0 | 0 | 0 | 2 |
| Falls | 8 (22) | 5 | 0 | 3 | 0 | 0 |
| Hypokalemia | 7 (19) | 7 | 0 | 0 | 0 | 1 |
| Constipation | 7 (19) | 2 | 0 | 4 | 1 | 0 |
| Ataxia | 7 (19) | 1 | 0 | 6 | 0 | 1 |
| Convulsion | 7 (19) | 7 | 0 | 0 | 0 | 0 |
| Dysarthria | 7 (19) | 6 | 0 | 1 | 0 | 1 |
| Muscular Weakness | 6 (17) | 4 | 0 | 2 | 0 | 2 |
| Infusion Site Pain | 6 (17) | 0 | 0 | 6 | 0 | 0 |
| Anxiety | 6 (17) | 6 | 0 | 0 | 0 | 0 |
| Vision Blurred | 6 (17) | 3 | 0 | 3 | 0 | 0 |
| Hemiparesis | 5 (14) | 5 | 0 | 0 | 0 | 3 |
| Insomnia | 4 (11) | 2 | 1 | 1 | 0 | 1 |
| Dysphagia | 3 (8) | 3 | 0 | 0 | 0 | 1 |
| Hypotension | 3 (8) | 3 | 0 | 0 | 0 | 1 |
| Lymphocyte Count Decreased | 3 (8) | 3 | 0 | 0 | 0 | 3 |
| Dyspnoea | 3 (8) | 2 | 0 | 0 | 1 | 1 |
| Pyramidal Tract Syndrome | 3 (8) | 3 | 0 | 0 | 0 | 1 |
| Haemorrhage Intracranial | 2 (6) | 0 | 2 | 0 | 0 | 1 (Grade 5) |
| Aphasia | 2 (6) | 2 | 0 | 0 | 0 | 1 |
| Asthenia | 2 (6) | 2 | 0 | 0 | 0 | 1 |
| Embolism | 2 (6) | 0 | 2 | 0 | 0 | 1 |
| Hyponatremia | 2 (6) | 1 | 0 | 1 | 0 | 1 |
| Fracture of Femur | 1 (3) | 1 | 0 | 0 | 0 | 1 |
| Tumor Metastasis | 1 (3) | 1 | 0 | 0 | 0 | 1 |
| Optic Nerve Disorder | 1 (3) | 0 | 1 | 0 | 0 | 1 |
| Depressed Level of Consciousness | 1 (3) | 1 | 0 | 0 | 0 | 1 |
| Delusion | 1 (3) | 0 | 0 | 1 | 0 | 1 |
| Appendicitis Perforated | 1 (3) | 1 | 0 | 0 | 0 | 1 (Grade 4) |
| Ear Infection | 1 (3) | 1 | 0 | 0 | 0 | 1 |

Figure 62:
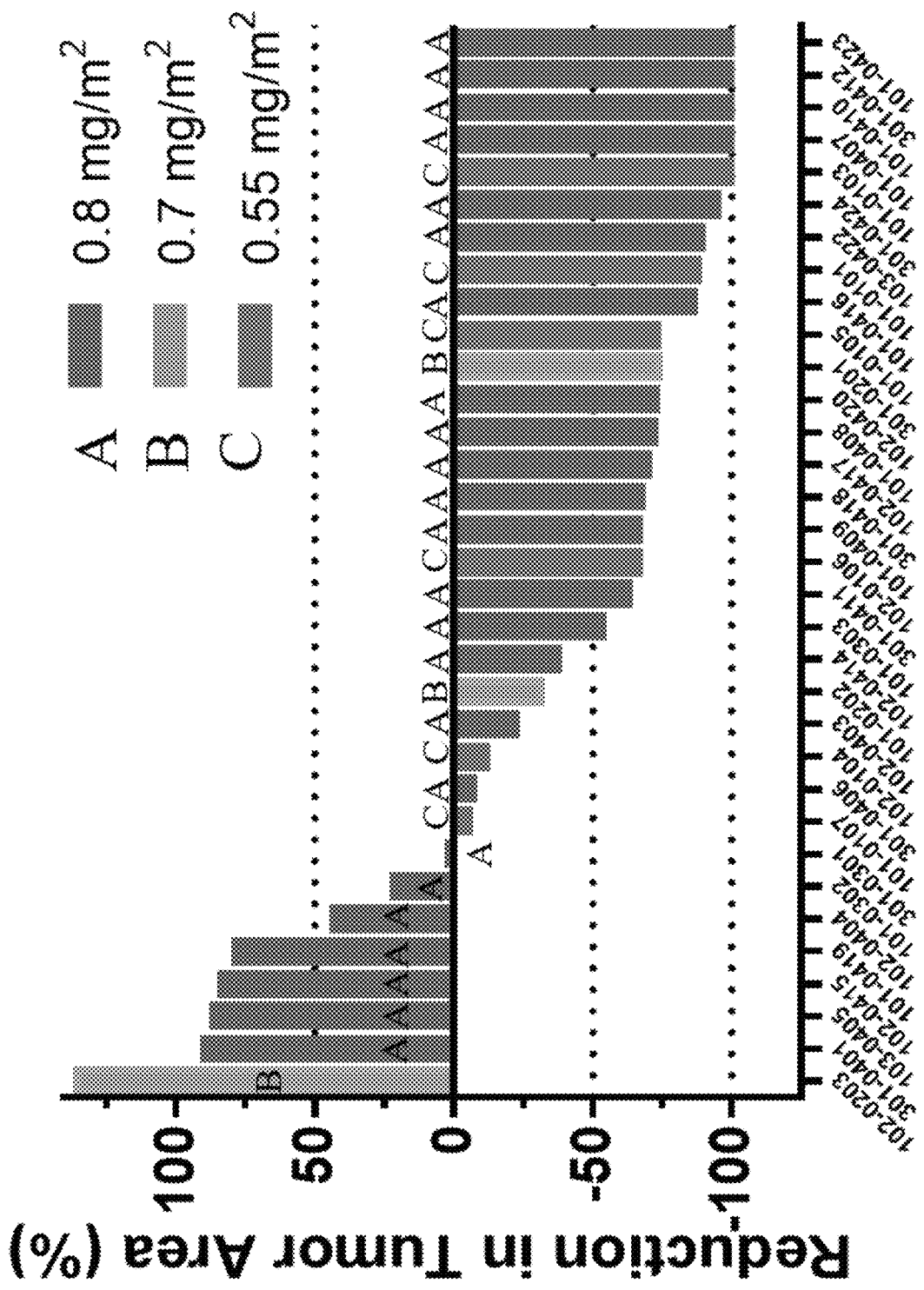
FIG. 62 shows a plot of the response by RANO for the Phase 1 trial for malignant glioma.
Figure 63:
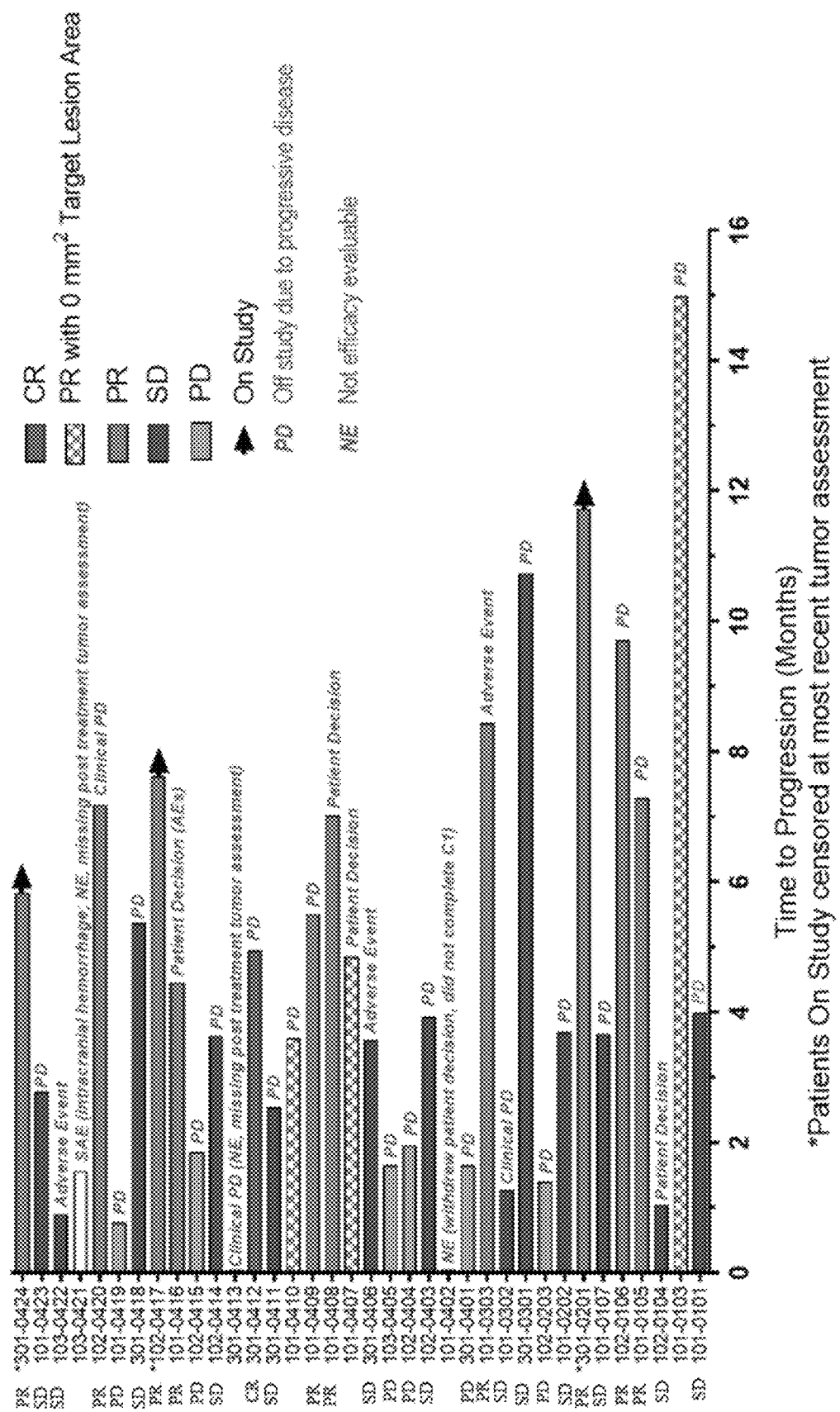
FIG. 63 shows a plot of the time to progression for the Phase 1 trial for malignant glioma.

FIG. 62 shows a plot of the best responses by RANO criteria for the 33 patients. FIG. 62 demonstrates that 25 of the 33 efficacy evaluable patients achieved a clinical benefit (RANO ≥Stable Disease) from marizomib and bevacizumab treatment. FIG. 63 shows the time to progression in the patients in the present clinical trial. Table 52 likewise shows the response rate by RANO. Table 53 shows the response rate by MGMT Promoter methylation status.

TABLE 52

Response Rate by RANO

| Best Response by RANO | # | % EE (N = 33) | % ITT (N = 36) |
|---|---|---|---|
| CR (1) + CR target/PR overall (3) + PR (10) | 14 | 42% | 39% |
| SD (including 2 unconfirmed PR) | 13 | 39% | 36% |
| PD | 6 | 18% | 17% |
| NE | 3 | NA | 8% |

TABLE 53

Response Rate by MGMT Promoter Methylation Status

| Best Response (N) | Evaluable (N = 33) Efficacy | | | ITT (N = 36) | | |
|---|---|---|---|---|---|---|
| | Unmethylated* N = 19 | Methylated N = 8 | Unknown N = 6 | Unmethylated* N = 20 | Methylated N = 10 | Unknown N = 6 |
| CR/PR (14) | 7 | 5 | 2 | 7 | 5 | 2 |
| SD (13) | 9 | 1 | 3 | 9 | 1 | 3 |
| PD (6) | 3 | 2 | 1 | 3 | 2 | 1 |
| NE (3) | — | — | — | 1 | 2 | 0 |

*Unmethylated: <8% promoter methylation by pyro-sequencing

The overall response rate was 42% (RANO ≥partial response) for the Efficacy Evaluable (EE) and 39% in the Intent To Treat (ITT) population. Five of the fourteen partial responses were complete responses for target tumor area (0 mm$^2$) on greater than or equal to 2 consecutive MRIs. Examples of Target Lesion Complete Response A 59-year old female patient (Patient A) had a Karnofsky performance score of 90 prior to treatment with marizomib and bevacizumab. Patient A had a brain tumor resection in October 2014. Between December 2014 and January 2015 Patient A was treated with radiotherapy and temozolomide. Between February 2015 and April 2015, Patient A received three cycles of temozolomide. In early April 2015, progressive disease (PD) was confirmed.

Patient A started marizomib treatment (0.55 mg/m$^2$) plus bevacizumab in late May 2015. After 2 cycles, the patient had a dose reduction to 0.4 mg/m$^2$ C3D1.

Figure 64:
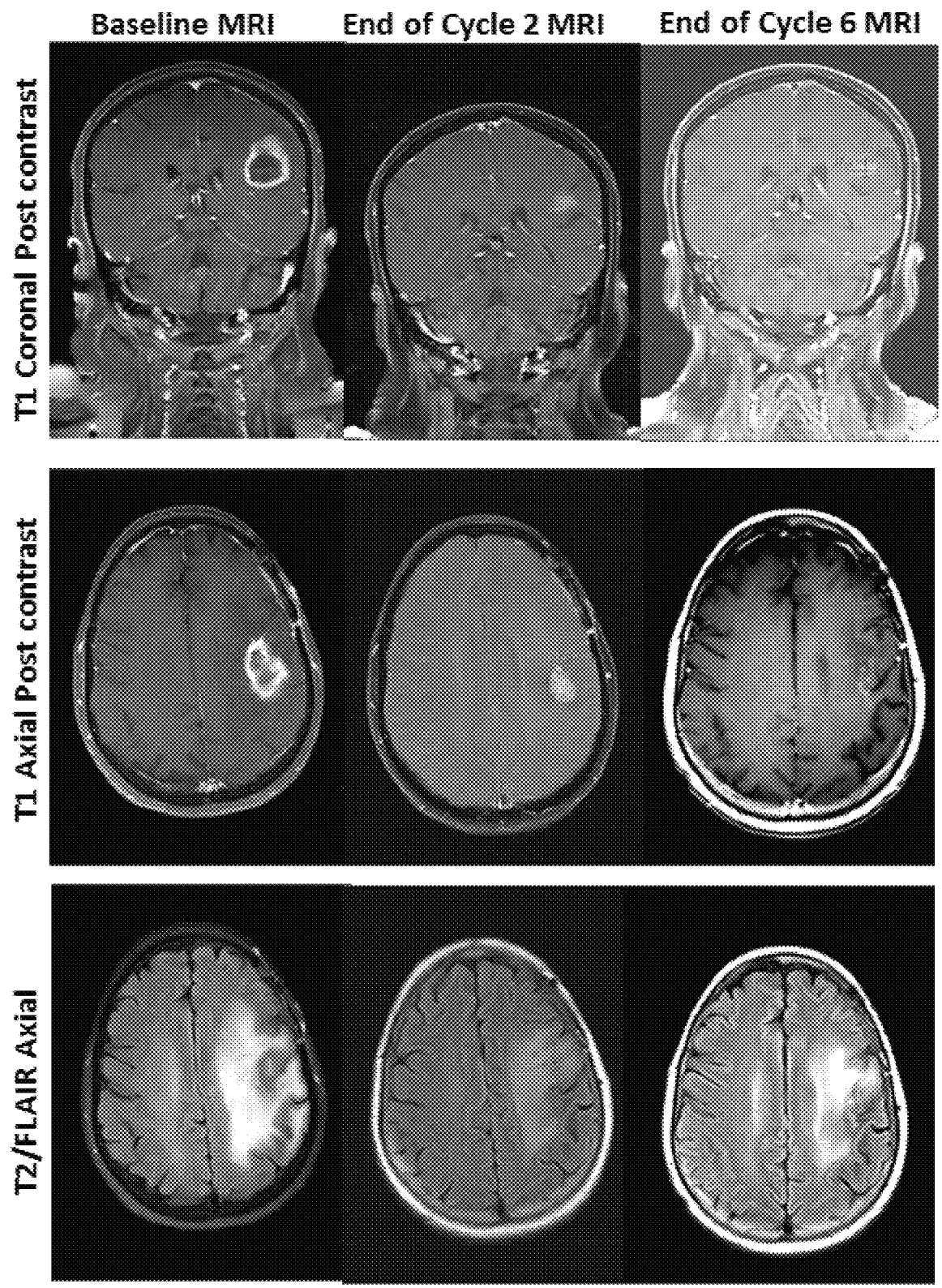
FIG. 64 shows nine MM images of an example of target lesion complete response in a patient in the Phase 1 trial for malignant glioma.

FIG. 64 shows MRI images of Patient A, who achieved a complete response after treatment with marizomib and bevacizumab. The first column shows baseline MRI images, the middle column shows images after cycle 2, and the third column shows images after the end of cycle 6. The top row shows the T1 coronal post contrast, the middle row shows the T1 axial post contrast, and the bottom row shows the T2/FLAIR axial images.

Figure 65:
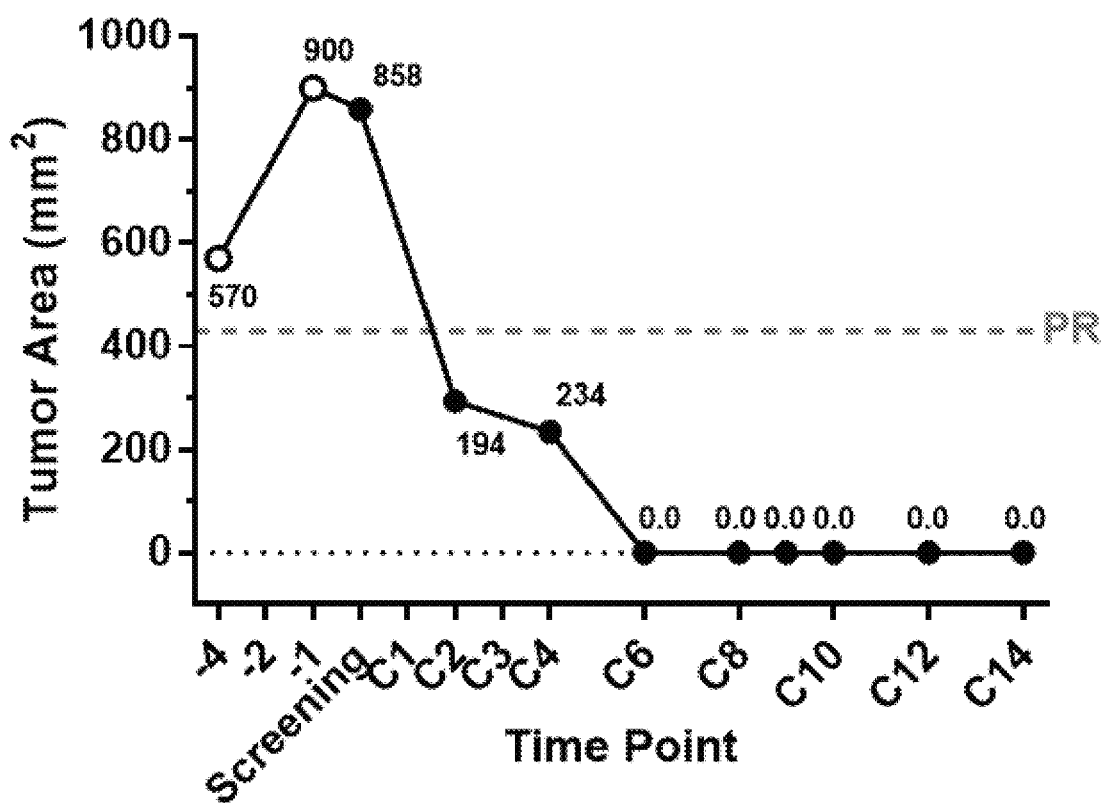
FIG. 65 shows a plot of the tumor area as a function of time in a patient in the Phase 1 trial for malignant glioma.

FIG. 65 shows a plot of Patient A's tumor size as a function of time and the number of cycles Patient A received. As shown in FIG. 65, the tumor area was reduced to 0 mm$^2$ by the sixth cycle of treatment.

A 54-year old male patient (Patient B) had a Karnofsky performance score of 90 prior to treatment with marizomib and bevacizumab. Patient B had a brain tumor resection in October 2014. Between November 2014 and January 2015, Patient B was treated with radiotherapy and temozolomide. Between February 2015 and June 2015, Patient B received five cycles of temozolomide. In late June 2015, Progressive Disease (PD) was confirmed.

Patient B started marizomib treatment (0.55 mg/m$^2$) plus bevacizumab in late July 2015. Patient B was removed from the study in March 2016 due to PD.

Figure 66:
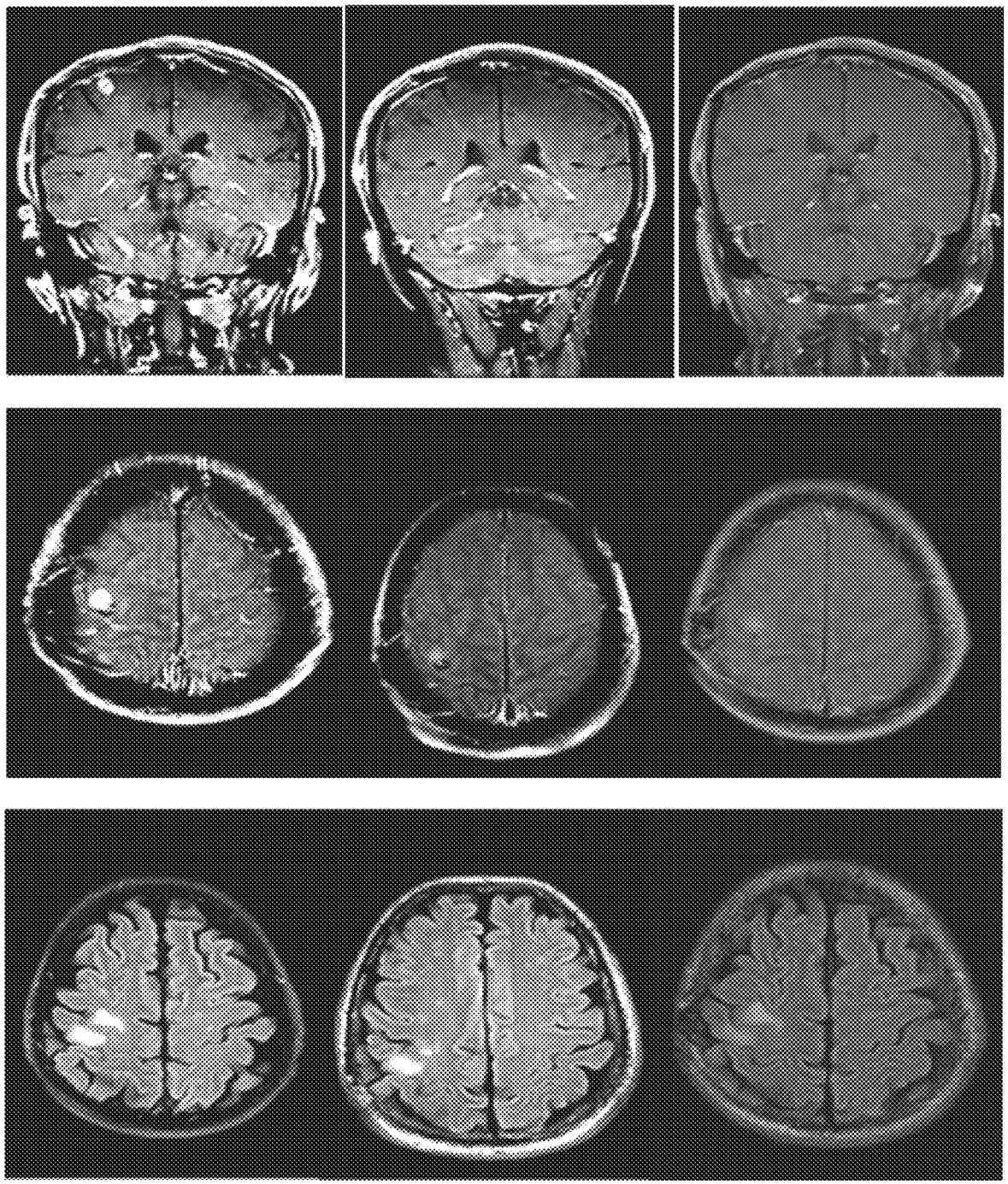
FIG. 66 shows MRI images of Patient B.

FIG. 66 shows MRI images of Patient B. The first column shows baseline MRI images, the middle column shows images after cycle 2, and the third column shows images after the end of cycle 4. The top row shows the T1 coronal post contrast, the middle row shows the T1 axial post contrast, and the bottom row shows the T2/FLAIR axial images.

Figure 67:
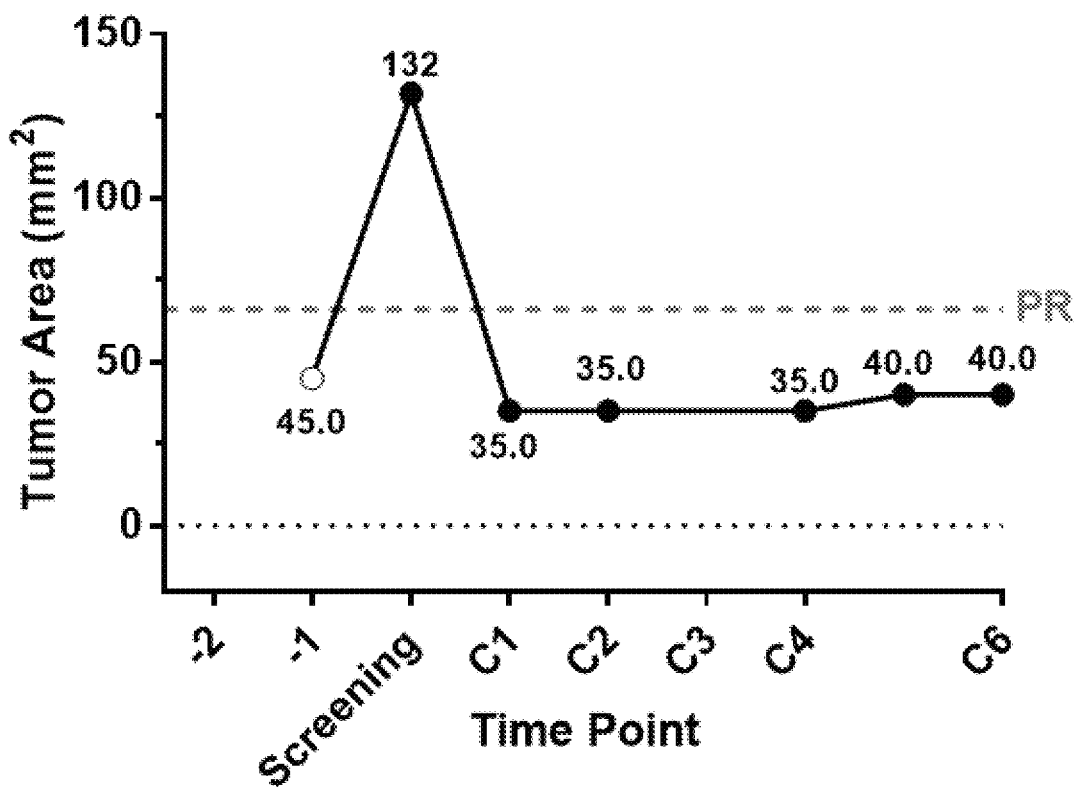
FIG. 67 shows a plot of Patient B's tumor size as a function of time and the number of cycles Patient B received.

FIG. 67 shows a plot of Patient B's tumor size as a function of time and the number of cycles Patient B received. As shown in FIG. 67, the tumor area was reduced to 0 mm$^2$ by the fourth cycle of treatment.

A 61-year old male patient (Patient C) had a Karnofsky performance score of 80 prior to treatment with marizomib and bevacizumab. Patient C had a brain tumor resection in March 2015. Between April 2015 and May 2015 Patient C was treated with radiotherapy and temozolomide. Between June 2015 and July 2015, Patient C received two cycles of temozolomide. In August 2015, progressive disease (PD) was confirmed.

Patient C started marizomib treatment (0.55 mg/m$^2$) plus bevacizumab in August 2015.

Figure 68:
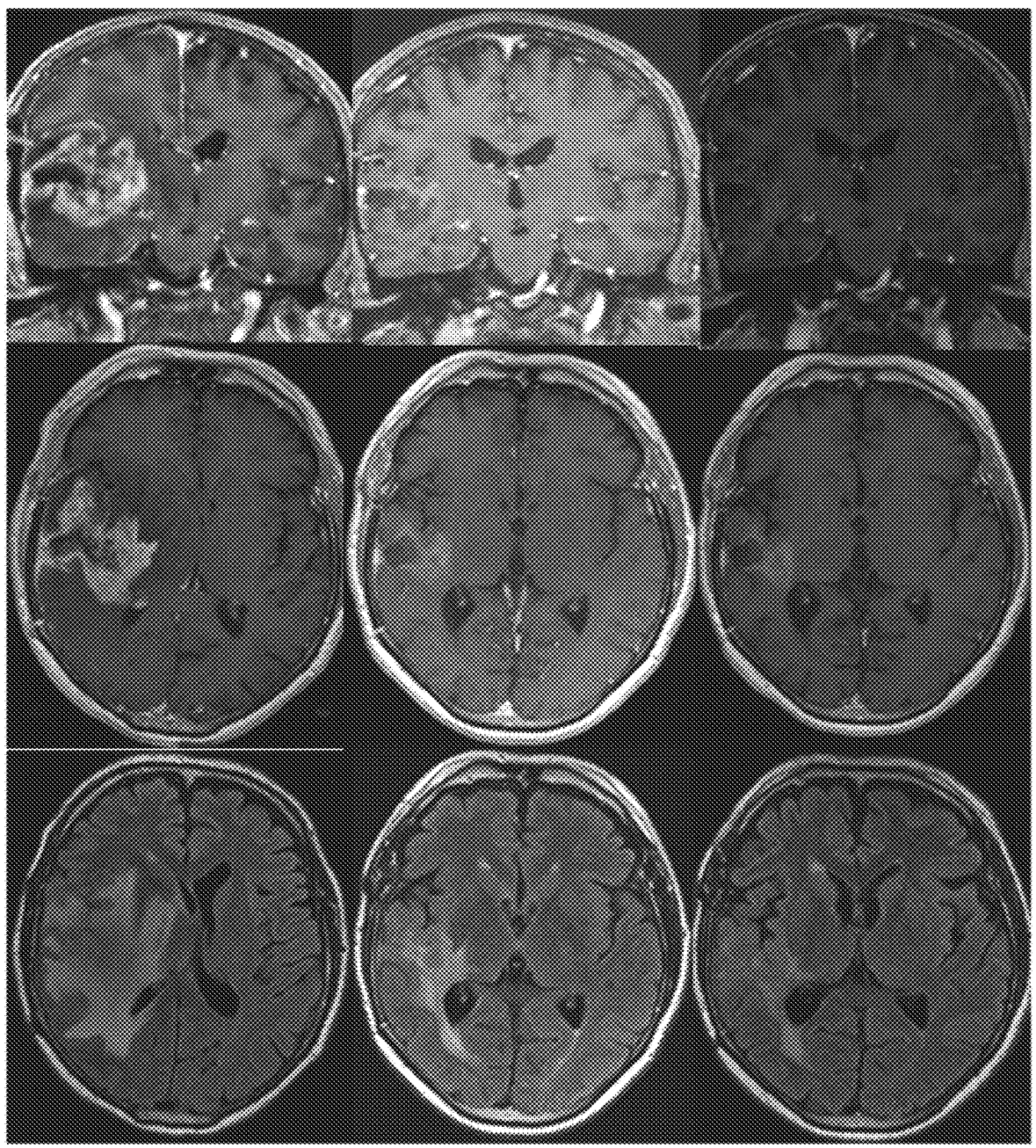
FIG. 68 shows MRI images of Patient C.

FIG. 68 shows MRI images of Patient C. The first column shows baseline MRI images, the middle column shows images after cycle 2, and the third column shows images after the end of cycle 4. The top row shows the T1 coronal post contrast, the middle row shows the T1 axial post contrast, and the bottom row shows the T2/FLAIR axial images.

Figure 69:
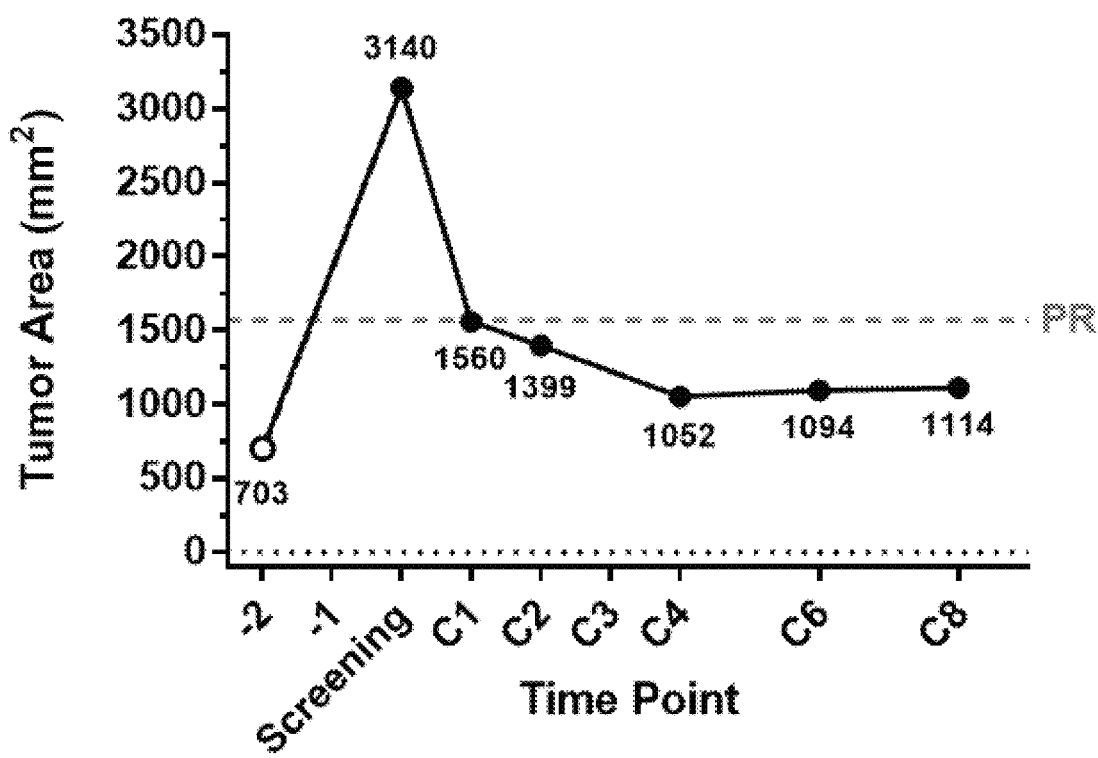
FIG. 69 shows a plot of Patient C's tumor size as a function of time and the number of cycles Patient C received.

FIG. 69 shows a plot of Patient C's tumor size as a function of time and the number of cycles Patient C received. As shown in FIG. 69, the tumor area was reduced to about a third of its peak volume after four cycles of treatment.

A 53-year old male patient (Patient D) had a Karnofsky performance score of 90 prior to treatment with marizomib and bevacizumab. Patient D had a brain tumor resection in April 2015. Between April 2015 and June 2015 Patient D was treated with radiotherapy and temozolomide. Between July 2015 and August 2015, Patient D received three cycles of temozolomide. In September 2015, progressive disease (PD) was confirmed.

Patient D started marizomib treatment (0.7 mg/m$^2$) plus bevacizumab in late September 2015.

Figure 70:
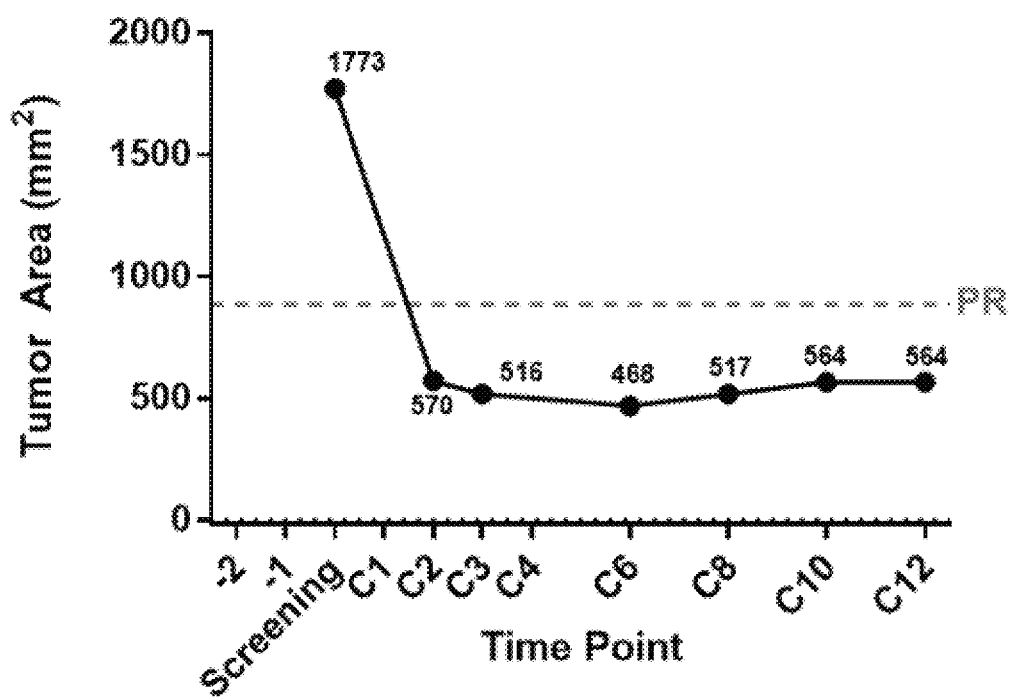
FIG. 70 shows a plot of Patient D's tumor size as a function of time and the number of cycles Patient D received.

FIG. 70 shows a plot of Patient D's tumor size as a function of time and the number of cycles Patient D received. As shown in FIG. 70, the tumor area was reduced to about a third of its peak volume after two cycles of treatment.

A 54-year old male patient (Patient E) had a Karnofsky performance score of 90 prior to treatment with marizomib and bevacizumab. Patient E had a brain tumor resection in October 2014. Between November 2014 and December 2014 Patient E was treated with radiotherapy and temozolomide. Between February 2015 and September 2015, Patient E received temozolomide, and from February 2015 to October 2015 Patient E also received Novocure TTF treatment. In October 2015, PD was confirmed.

Patient E started marizomib treatment (0.8 mg/m$^2$) plus bevacizumab in early February 2016.

Figure 71:
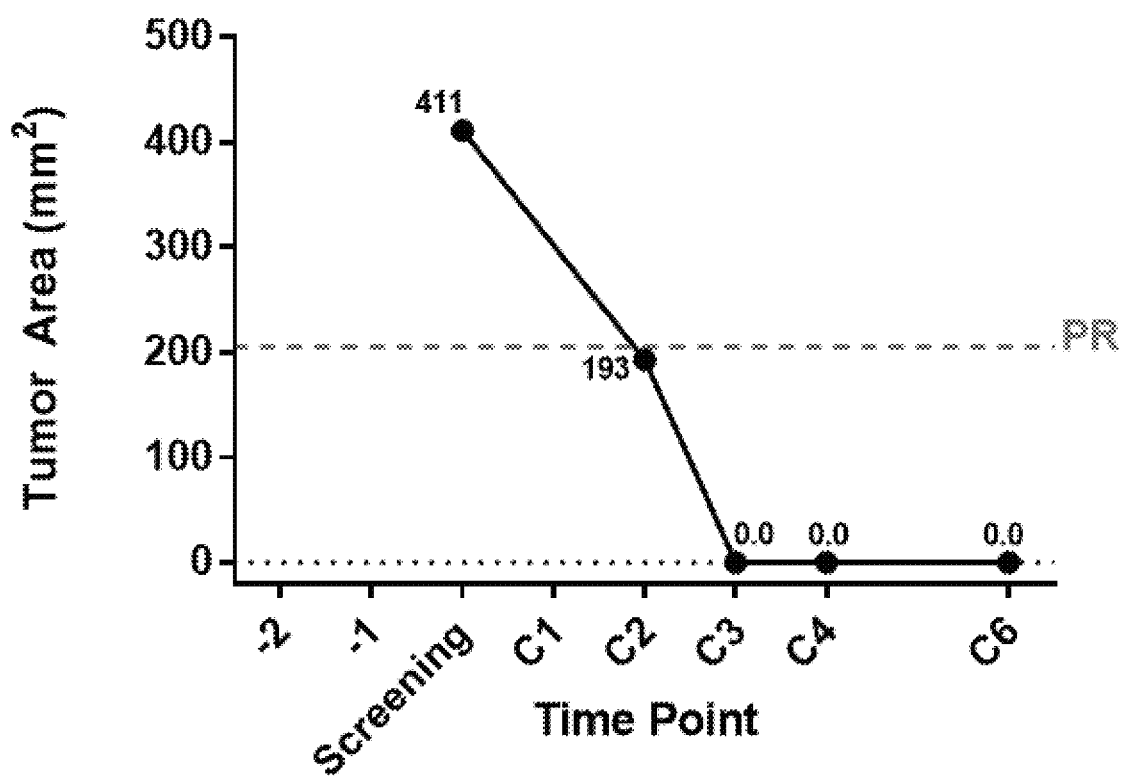
FIG. 71 shows a plot of Patient E's tumor size as a function of time and the number of cycles Patient D received.

FIG. 71 shows a plot of Patient E's tumor size as a function of time and the number of cycles Patient E received. As shown in FIG. 71, the tumor area was reduced to about 0 mm$^2$ after three cycles of treatment.

Figure 72:
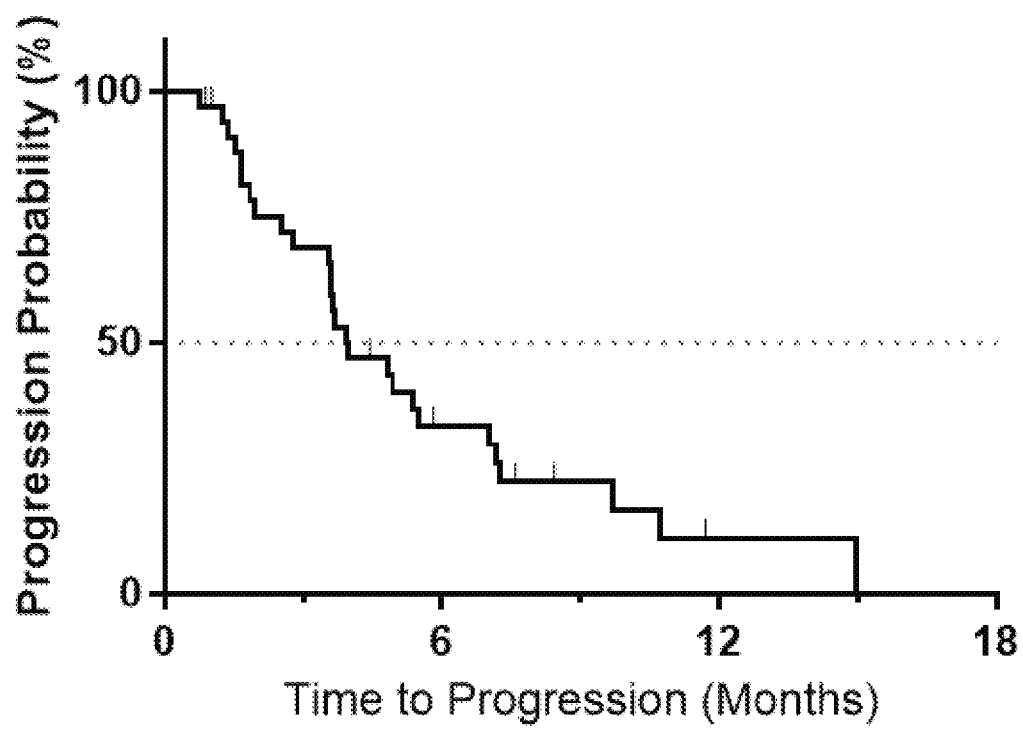
FIG. 72 shows a plot of the PFS percent as a function of time in all patients.
Figure 73:
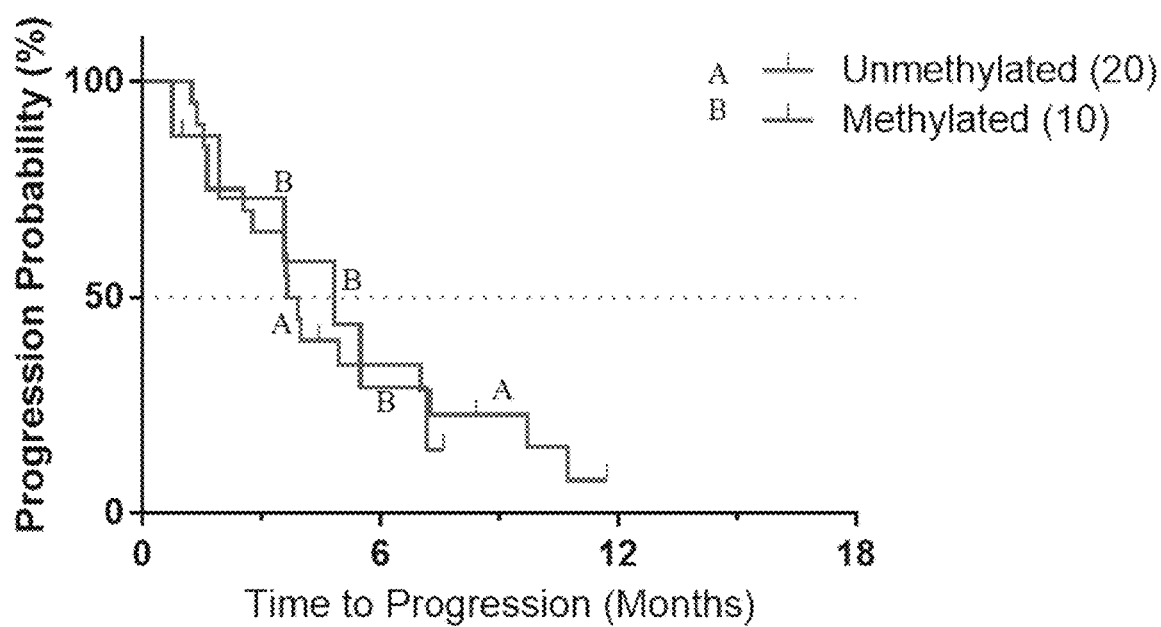
FIG. 73 shows a plot of the PFS percent by MGMT Promoter methylation status as a function of time.

Progression Free Survival (PFS): Overall and by MGMT Promoter Methylation Status FIG. 72 shows a plot of the progression free survival (PFS) percent as a function of time for all patients. FIG. 73 shows a plot of the PFS percent as a function of time for patients by O 6-methylguanine-DNA methyltransferase (MGMT) promoter methylation status (methylated or unmethylated). Without wishing to be bound by theory, the percentage of patients treated with marizomib and bevacizumab who have not progressed at six months was higher than patients treated with bevacizumab only. The percentage of patients with six months PFS treated with marizomib and bevacizumab was about twice that among all patients, and about four times that in patients with unmethylated MGMT promoter, in comparison with patients treated with bevacizumab only. Without wishing to be bound by theory, unmethylated MGMT promoter is a biomarker of poor prognosis in malignant glioma. Patients with unmethylated MGMT promoter can be more likely to suffer recurrent disease, and for recurrence to occur more quickly than in patients with methylated MGMT promoter. For instance, patients with unmethylated MGMT promoter who are treated with the standard of care (temozolomide and radiotherapy) can be more likely to relapse.

Table 54 shows a comparison of the present study with a clinical trial evaluating single-agent bevacizumab in recurrent glioma for comparison.

TABLE 54

Single Agent Bevacizumab Comparator Data in Recurrent Glioma

| Study | 6 Months PFS | |
|---|---|---|
| | All | uMGMT Promoter |
| Present Study | 34% | 34% |
| BELOB Trial (BEV monotherapy) (Taal et al., 2014) | 16% | 8% |

Pharmacokinetic and Pharmacodynamic Parameters.

Table 55 shows a summary of the pharmacokinetic and pharmacodynamic parameters for marizomib and bevacizumab.

TABLE 55

Pharmacokinetic and Pharmacodynamic Summary

| Parameter (Units) | 0.55 mg/m$^2$ | 0.7 mg/m$^2$ | 0.8 mg/m$^2$ |
|---|---|---|---|
| Marizomib PK determined on C1D8 | | | |
| $T_{1/2}$ (min) | 8.2 ± 0.8 (4) | 16.0 ± 8.08 (3) | 7.27 ± 0.423 (3) |
| $T_{max}$ (min) | 15.5 ± 1.4 (6) | 21.3 ± 1.3)0 (3) | 8.0 ± 0 (3) |
| $C_{max}$ (ng/mL) | 23.1 ± 11.3 (6) | 64.9 ± 1.73 (3) | 26.5 ± 7.92 (3) |
| $AUC_{last}$ (min*ng/mL) | 265 ± 101 (6) | 193 ± 85 (2) | 392 ± 115 (3) |
| Vd (L) | 54.4 ± 10.6 (4) | 48.3 ± 16.1 (3) | 55.0 ± 19.7 (3) |
| $CL_{obs}$ (L/hr) | 297 ± 73.0 (4) | 272 ± 166 (3) | 304 ± 85.0 (3) |
| BEV PK determined on C1D1 & C1D15 | | | |
| $C_{max}$ D1 (µg/mL) | 275 ± 37.5 (6) | 193 ± 8 (2) | 267 ± 13.3 (3) |
| $C_{min}$ D15 (µg/mL) | 89.7 ± 6.2 (6) | 81.1 ± 17.4 (2) | 85.0 ± 9.87 (3) |
| $C_{max}$ D15 (µg/mL) | 351 ± 46.6 (5) | 402 ± 123 (3) | 380 ± 56.5 (2) |
| Proteasome subunit inhibition in PWB post-Marizomib infusion (peak effect) | | | |
| % CT-L inhibition | 100 ± 0 (5) | 100 ± 0 (3) | 100 ± 0 (3) |
| % T-L inhibition | 52.0 ± 8.0 (5) | 77.3 ± 10.5 (3) | 69.3 ± 7.2 (3) |
| % C-L inhibition | 21.0 ± 7.8 (5) | 50.4 ± 9.1 (3) | 51.9 ± 8.3 (3) |

Figure 74:
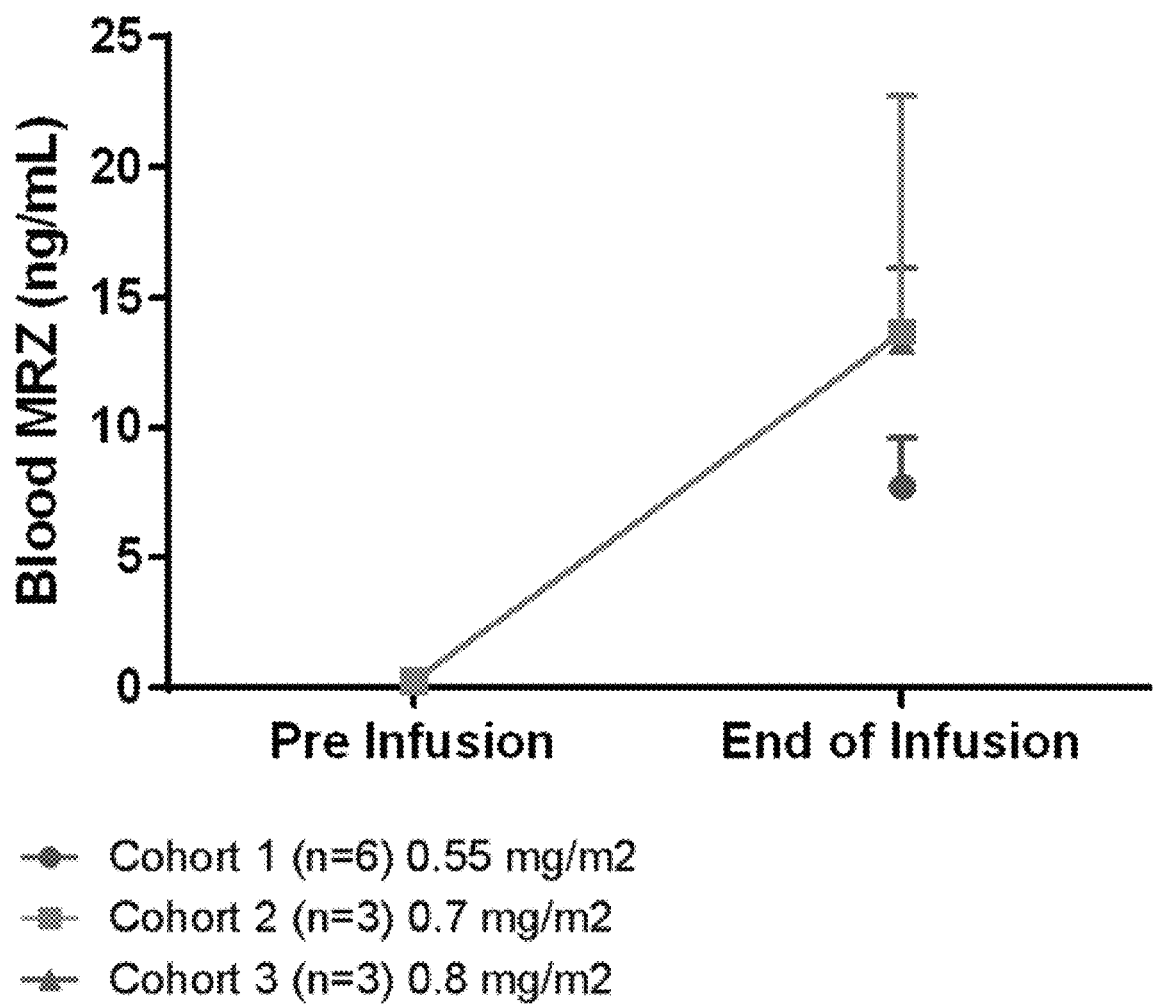
FIG. 74 shows the concentration of marizomib in the blood of a patient C1D1 pre- and post-infusion.
Figure 75:
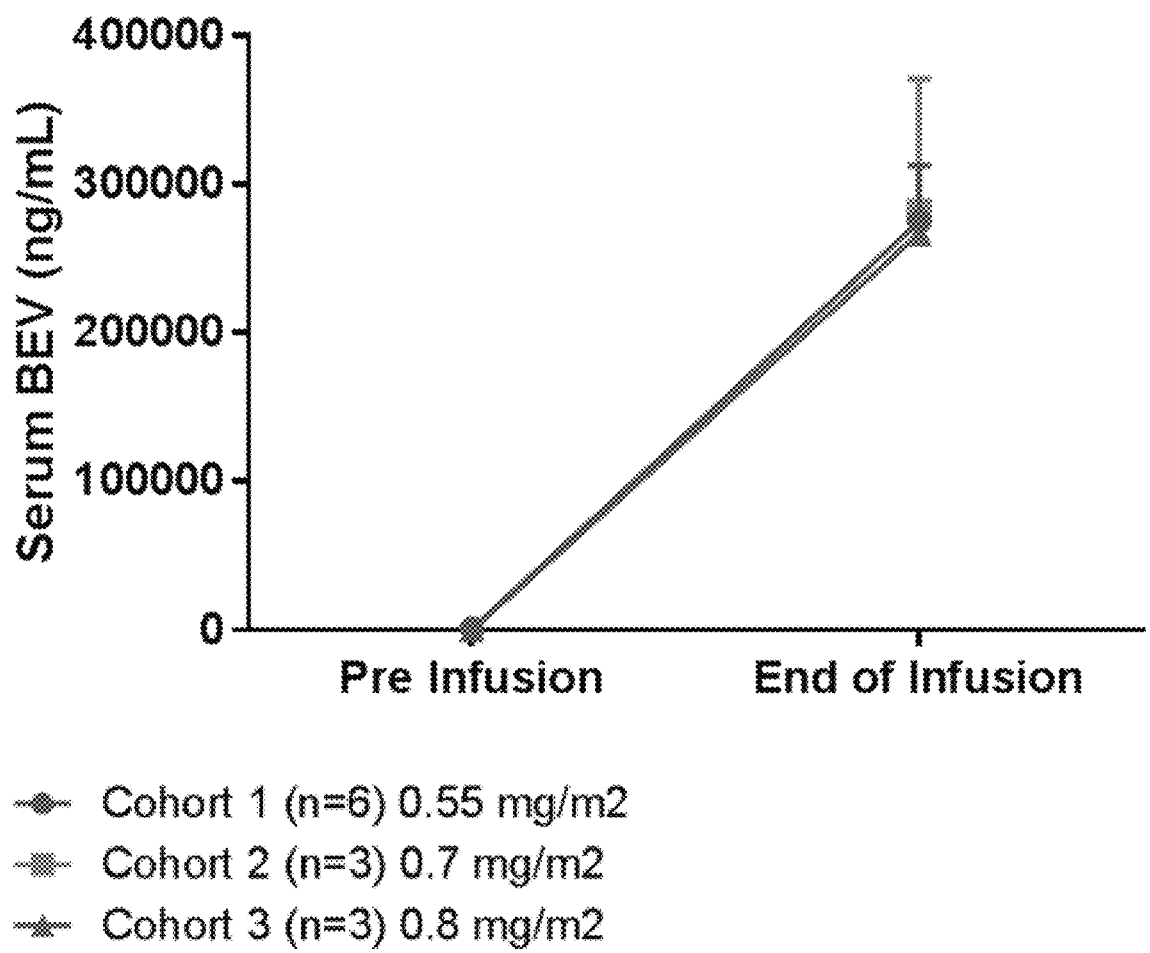
FIG. 75 shows the concentration of bevacizumab in the serum of a patient C1D1 pre- and post-infusion.
Figure 76:
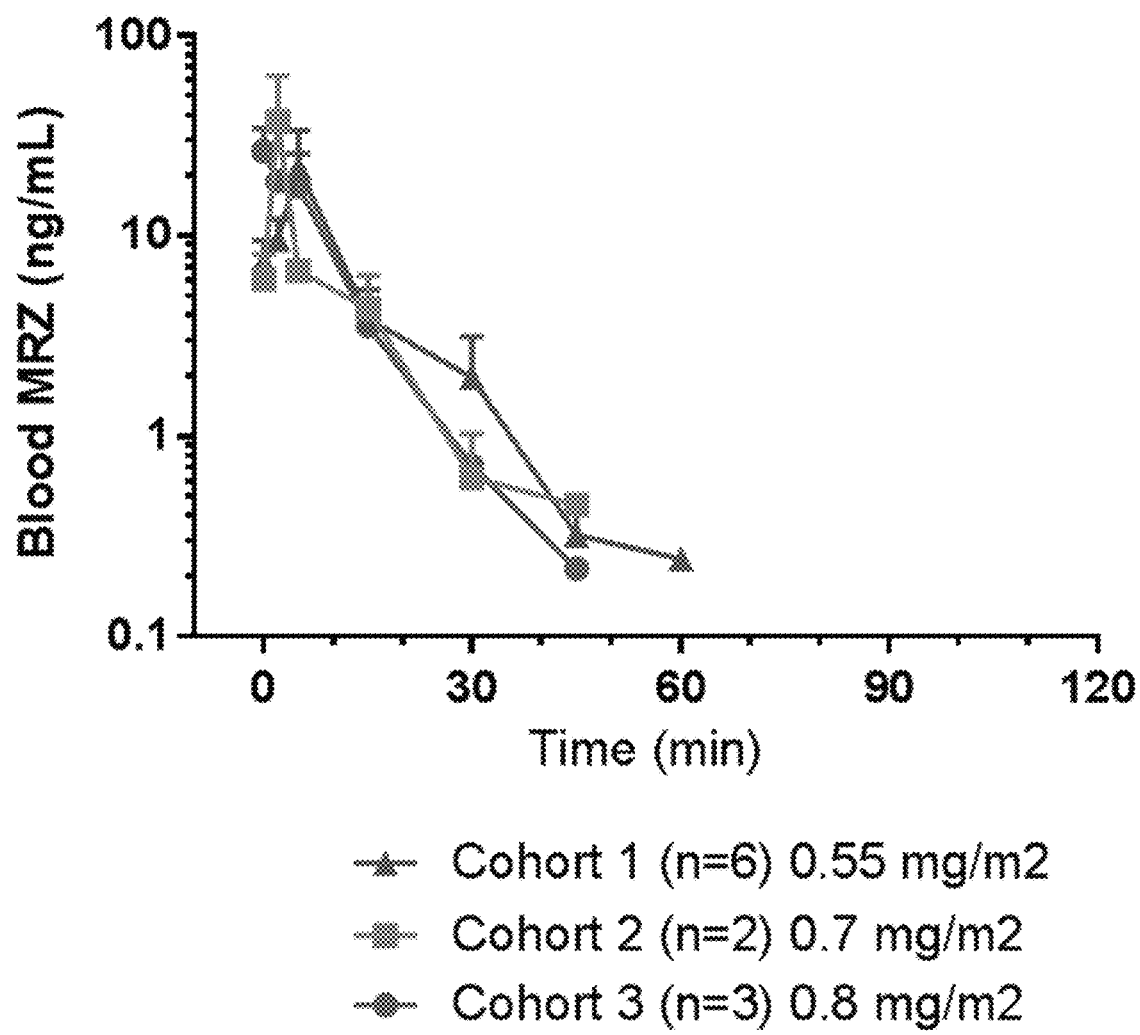
FIG. 76 shows the concentration of marizomib in the blood as a function of time on C1D8.
Figure 77:
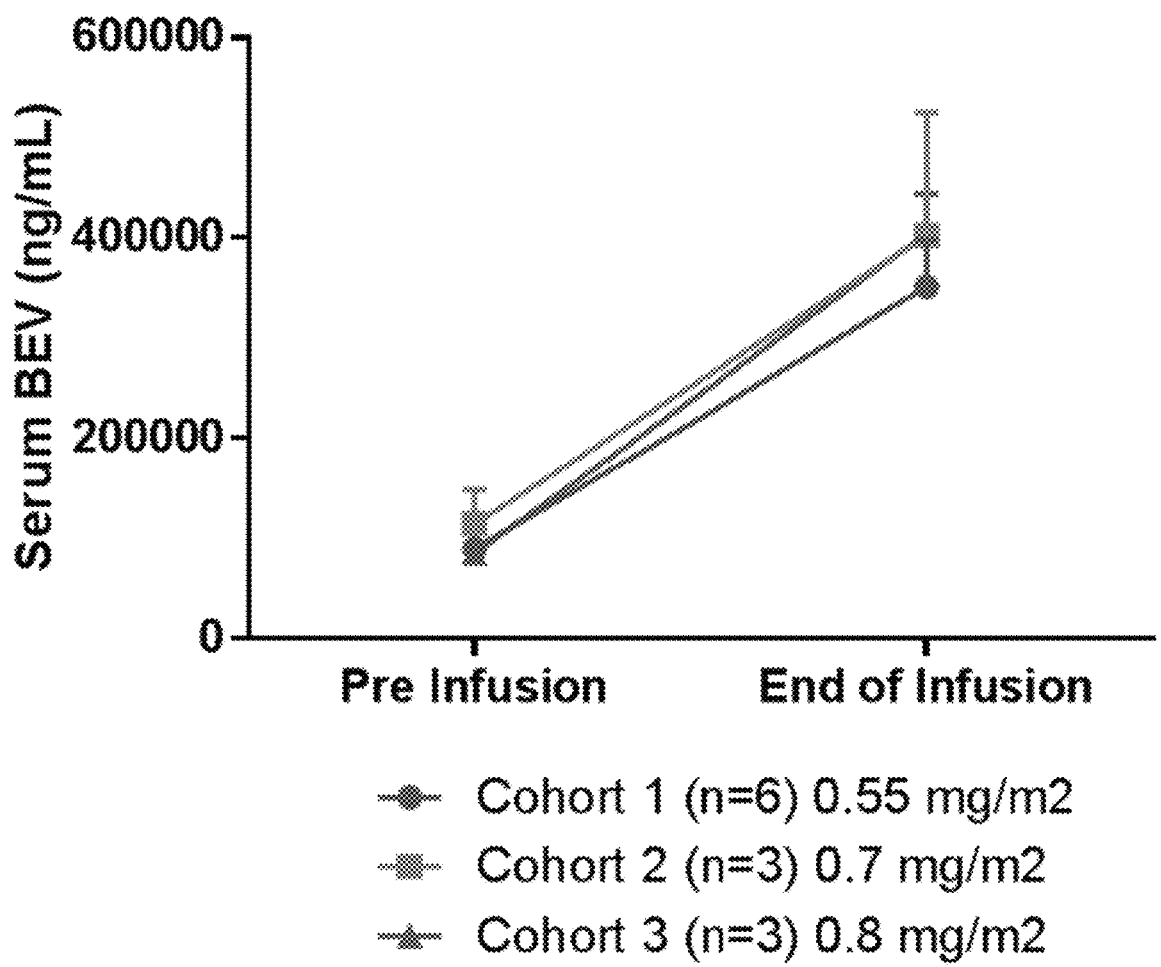
FIG. 77 shows concentration of bevacizumab in serum pre- and post-infusion for different cohorts on C1D15.

FIG. 74 shows the concentration of marizomib in the blood of patients on C1D1 pre- and post-infusion. FIG. 75 shows the concentration of bevacizumab in the serum of patients C1D1 pre- and post-infusion. FIG. 76 shows the concentration of marizomib in the blood as a function of time on C1D8. FIG. 77 shows concentration of bevacizumab in serum pre- and post-infusion for different cohorts on C1D15.

As set forth in FIGS. 74-77, the mean $C_{max}$ of bevacizumab across all dose cohorts was 275 µg/mL on Day 1; the mean $C_{min}$ of bevacizumab on Day 15 was 95 µg/mL; and the mean $C_{max}$ of bevacizumab on Day 1 was 379 µg/mL. The results agree with published literature precedent for $C_{max}$ of bevacizumab of 284 µg/mL at Day 0 for a 10 mg/kg dose (Gordon et al., 2001).

MRZ-108: Demographics

| | |
|---|---|
| Median age, years (range) | 55 (27-76) |
| Male, % | 64% (23/36) |
| Karnofsky Performance Status (KPS) (data not available for 1 P1 pt) | |
| 100 - Normal, no complaints | 9% (3/35) |
| 90 - Able to carry on normal activity | 37% (13/35) |
| 80 - Normal activity with effort | 45% (16/35) |
| 70 - Unable to carry on normal activity, cares for self | 9% (3/35) |
| Prior Therapies | |
| Surgery, Radiation/Temozolomide | 100% (36/36) |
| Immunotherapy | 14% (5/36) |
| Other Investigational Drug or Device | 8% (3/36) |
| Median months from last RT (range) | 7.8 (2.5-29.5) |
| Corticosteroid use at baseline | 31% (11/36) |
| Median months from last progression to C1D1 (range) | 0.8 (0.1-3.8) |

Treatment Related Grade ≥3 AEs by Patient

| | MRZ Dose | | | | | | TOTAL |
|---|---|---|---|---|---|---|---|
| | 0.55 mg/m² Cohort 1 (N = 6) | | 0.7 mg/m² Cohort 2 (N = 3) | | 0.8 mg/m² Cohorts 3 & 4 (N = 27) | | |
| Preferred Term | BEV | MRZ | BEV | MRZ | BEV | MRZ | (N = 36) |
| Ataxia | 0 | 0 | 0 | 0 | 0 | 1 | 1 |
| Confusional State | 0 | 1 | 0 | 0 | 0 | 0 | 1 |
| Delusion | 0 | 0 | 0 | 0 | 0 | 1 | 1 |
| Fatigue | 1 | 1 | 0 | 0 | 1 | 1 | 2 |
| Hallucination | 0 | 1 | 0 | 0 | 0 | 1 | 2 |
| Headache | 1 | 0 | 0 | 0 | 1 | 3 | 4 |
| Insomnia | 0 | 0 | 0 | 0 | 0 | 1 | 1 |
| Embolism | 0 | 0 | 0 | 0 | 1 | 0 | 1 |
| Hypertension | 0 | 0 | 1 | 0 | 5 | 0 | 6 |
| Intracranial Hemorrhage | 0 | 0 | 0 | 0 | 1 | 0 | 1 |
| Embolism | 0 | 0 | 0 | 0 | 1 | 0 | 1 |
| Optic Nerve Disorder | 0 | 0 | 0 | 0 | 1 | 0 | 1 |
| Proteinuria | 0 | 0 | 1 | 0 | 0 | 0 | 1 |
| Fall | 0 | 0 | 0 | 0 | 0 | 1 | 1 |
| Dyspnea | 0 | 0 | 0 | 0 | 1 | 1 | 1 |
| Hyponatremia | 0 | 0 | 0 | 0 | 0 | 1 | 1 |

MRZ+BEV PFS and OS by MGMT Promoter Methylation Status

| | | 6 mo PFS | | | 9 mo PFS | | |
|---|---|---|---|---|---|---|---|
| Study | Treatment | All Pts | Unmethylated | Methylated | All Pts | Unmethylated | Methylated |
| MRZ-108 | MRZ + BEV | 34% | 34% | 29% | 22% | 23% | TBD |

| | | 6 mo OS | | | 9 mo OS | | |
|---|---|---|---|---|---|---|---|
| Study | Treatment | All Pts | Unmethylated | Methylated | All Pts | Umethylated | Methylated |
| MRZ-108 | MRZ + BEV | 73% | 63% | 73% | 55% | 44% | 73% |

MRZ+BEV PFS and OS in Unmethylated MGMT Promoter Compared with Historical BEV Monotherapy Studies

| Study | Treatment | 6 mo PFS Unmethylated MGMT Promoter | 9 mo PFS Unmethylated MGMT Promoter |
|---|---|---|---|
| MRZ-108 | MRZ + BEV | 34% | 23% |
| Taal (BELOB) | BEV Monotherapy | 8% | 0% |
| Field (CABARET) | | NR | NR |
| Heiland (Freiburg, Germany) | | 10% | 0% |
| Wick (EORTC 26101 P2) | | 10% | 10% |

| Study | Treatment | 6 mo OS Unmethylated MGMT Promoter | 9 mo OS Unmethylated MGMT Promoter |
|---|---|---|---|
| MRZ-108 | MRZ + BEV | 63% | 44% |
| Taal (BELOB) | BEV Monotherapy | 50% | 12% |
| Field (CABARET) | | NR | NR |
| Heiland (Freiburg, Germany) | | 25% | 12% |

MRZ+BEV Improved PFS & OS at 6 and 9 Months Compared with Historical BEV Monotherapy Studies

| | | 6 mo PFS | | | 9 mo PFS | | |
|---|---|---|---|---|---|---|---|
| Study | Treatment | All Pts | Unmethylated | Methylated | All Pts | Unmethylated | Methylated |
| MRZ-108 | MRZ + BEV | 34% | 34% | 29% | 22% | 23% | TBD |
| Taal (BELOB) | BEV Monotherapy | 16% | 8% | 33% | 8% | 0% | 22% |
| Field (CABARET) | | 18% | NR | NR | 6% | NR | NR |
| Heiland (Freiburg, Germany) | | 12% | 10% | 38% | 0% | 0% | 22% |

-continued

| Study | Treatment | 6 mo OS | | | 9 mo OS | | |
|---|---|---|---|---|---|---|---|
| | | All Pts | Unmethylated | Methylated | All Pts | Unmethylated | Methylated |
| Wick (EORTC 26101 P2) | | 14% | 10% | 25% | 9% | 10% | 9% |
| MRZ-108 | MRZ + BEV | 73% | 63% | 73% | 55% | 44% | 73% |
| Taal (BELOB) | BEV Monotherapy | 62% | 50% | 83% | 45% | 12% | 67% |
| Field (CABARET) | | 61% | NR | NR | 39% | NR | NR |
| Heiland (Freiburg, Germany) | | 18% | 25% | 58% | 30% | 72% | 40% |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

Enumerated Embodiments

A1. A method of treating a CNS-cancer comprising administering to a subject in need thereof an effective amount of marizomib and bevacizumab.

A2. The method of claim A1, wherein the CNS-cancer is a glioma.

A3. The method of claim A2, wherein the glioma is grade IV malignant glioma.

A4. The method of claim A2, wherein the glioma is glioblastoma.

A5. The method of claim A1, wherein the glioma is newly diagnosed.

A6. The method of claim A1, wherein the glioma is relapsed or refractory.

A7. The method of claim A1, wherein the subject's $O^6$-methylguanine-DNA methyltransferase is unmethylated.

A8. The method of claim A7, wherein the subject's $O^6$-methylguanine-DNA methyltransferase is less than 8% methylated.

A9. The method of claim A1, wherein the subject's EGFR is normal.

A10. The method of claim A1, wherein the subject's EGFR is altered.

A11. The method of claim A10, wherein the subject's EGFR alteration is amplified EGFR, mutated EGFR, EGFRVII positive, or a combination thereof.

B1. A method of treating a CNS-cancer comprising administering to a subject in need thereof an effective amount of marizomib and temozolomide.

B2. The method of claim B1, wherein the CNS-cancer is a glioma.

B3. The method of claim B2, wherein the glioma is grade IV malignant glioma.

B4. The method of claim B2, wherein the glioma is glioblastoma.

B5. The method of claim B1, wherein the glioma is newly diagnosed.

B6. The method of claim B1, wherein the glioma is relapsed or refractory.

B7. The method of claim B1, further comprising administering to the subject radiotherapy.

B8. The method of claim B1, wherein the combination of marizomib and temozolomide is synergistic.

B'1. A method of treating a CNS-cancer comprising administering to a subject in need thereof an effective amount of marizomib, temozolomide and radiotherapy.

C1. A method of treating a central nervous system hematological cancer in a subject in need thereof, comprising administering to the subject an effective amount of marizomib.

C2. The method of claim C1, wherein the central nervous system cancer is newly diagnosed.

C3. The method of claim C1, wherein the central nervous system hematologic cancer is central nervous system multiple myeloma, central nervous system leukemia, central nervous system myelodysplastic syndrome or central nervous system lymphoma.

C4. The method of claim C1, wherein the central nervous system-hematologic cancer originates from the central nervous system.

C5. The method of claim C1, wherein the central nervous system-hematologic cancer originates in the blood and metastasizes to the central nervous system.

C6. The method of claim C1, wherein the subject suffers from relapsed or refractory central nervous system-hematologic cancer.

C7. The method of claim C1, wherein the central nervous system-hematologic cancer affects the meninges.

C8. The method of claim C1, further comprising administering to the subject an additional therapeutic agent.

C9. The method of claim C1, wherein the additional therapeutic agent can cross the blood-brain barrier.

C10. The method of claim C1, wherein the additional therapeutic agent is an anti-CD38 antibody, pomalidomide, or any combination thereof.

C11. The method of claim C1, wherein the anti-CD38 antibody is daratumumab.

C12. The method of claim C1, wherein the combination therapy with the additional therapeutic agent is synergistic.

C'1. A method of treating central nervous system multiple myeloma comprising administering to a subject in need thereof an effective amount of marizomib.

C'2. A method of treating a central nervous system multiple myeloma comprising administering to a subject in need thereof an effective amount of marizomib and daratumumab.

C'3. A method of treating a central nervous system multiple myeloma comprising administering to a subject in need thereof an effective amount of marizomib and pomalidomide.

D1. A pharmaceutical composition comprising marizomib for the treatment of central nervous system cancer.

D2. Use of marizomib in the manufacture of a medicament for the treatment of central nervous system cancer.

D3. Use of marizomib for the treatment of a central nervous system cancer.

What is claimed is:

1. A method of treating a central nervous system cancer (CNS-cancer) comprising administering to a subject in need thereof an effective amount of marizomib and bevacizumab;
   wherein the subject has a level of $O^6$-methylguanine-DNA methyltransferase (MGMT) promoter methylation of 8% or less; and
   wherein the epidermal growth factor receptor (EGFR) status of the subject is normal.

2. The method of claim 1, wherein the CNS-cancer is glioma.

3. The method of claim 1, wherein the patient has not received a prior treatment with an anti-angiogenic agent.

4. The method of claim 3, wherein the anti-angiogenic agent is selected from the group consisting of bevacizumab, sorafenib, sunitinib, axitinib, pazopanib, everolimus and cilengitide.

5. The method of claim 1, wherein the patient has not received a prior treatment with a proteasome inhibitor.

6. The method of claim 5, wherein the proteasome inhibitor is selected from the group consisting of marizomib, bortezomib, and carfilzomib.

7. The method of claim 1, wherein the patient has a level of MGMT promoter methylation of 7% or less, 6% or less, 5% or less, 4% or less, 3% or less, 2% or less, 1% or less, or substantially no MGMT promoter methylation.

8. The method of claim 1, wherein the patient has a pathophysiological marker selected from the group consisting of an intraparenchymal lesion, a solitary cerebral plasmocytoma, a CNS myelomatosis, a solitary or multiple intraparenchymal lesions and a leptomeningeal disease with the presence of monoclonal plasma cells in the cerebrospinal fluid in the patient.

* * * * *